(12) United States Patent
Lindsted et al.

(10) Patent No.: US 11,939,380 B2
(45) Date of Patent: Mar. 26, 2024

(54) COMBINATION THERAPIES TARGETING PD-1, TIM-3, AND LAG-3

(71) Applicant: SYMPHOGEN A/S, Ballerup (DK)

(72) Inventors: Trine Lindsted, Farum (DK); Michael Monrad Grandal, Ballerup (DK); Eva Maria Carlsen Melander, Malmö (SE); Camilla Fröhlich, København Ø (DK); Mikkel Wandahl Pedersen, Allerød (DK); Michael Kragh, Copenhagen N (DK); Johan Lantto, Lund (SE); Monika Gad, Allerød (DK); Ivan David Horak, West Orange, NJ (US)

(73) Assignee: LES LABORATOIRES SERVIER, Suresnes (FR)

( * ) Notice: Subject to any disclaimer, the term of this patent is extended or adjusted under 35 U.S.C. 154(b) by 782 days.

(21) Appl. No.: 16/500,918

(22) PCT Filed: Apr. 5, 2018

(86) PCT No.: PCT/EP2018/058752
§ 371 (c)(1),
(2) Date: Oct. 4, 2019

(87) PCT Pub. No.: WO2018/185232
PCT Pub. Date: Oct. 11, 2018

(65) Prior Publication Data
US 2020/0407444 A1    Dec. 31, 2020

Related U.S. Application Data

(60) Provisional application No. 62/481,973, filed on Apr. 5, 2017.

(51) Int. Cl.
| | | |
|---|---|---|
| *C07K 16/28* | (2006.01) | |
| *A61P 35/00* | (2006.01) | |
| *A61K 39/00* | (2006.01) | |
| *A61K 45/06* | (2006.01) | |

(52) U.S. Cl.
CPC .......... *C07K 16/2818* (2013.01); *A61P 35/00* (2018.01); *A61K 2039/507* (2013.01); *A61K 45/06* (2013.01); *C07K 2317/31* (2013.01); *C07K 2317/565* (2013.01); *C07K 2317/92* (2013.01)

(58) Field of Classification Search
CPC .......... C07K 16/2818; C07K 2317/31; C07K 2317/565; C07K 2317/92; C07K 2317/76; C07K 16/2803; A61P 35/00; A61P 35/02; A61K 45/06; A61K 2039/507; A61K 2039/505; A61K 39/3955; Y02A 50/30
See application file for complete search history.

(56) References Cited

U.S. PATENT DOCUMENTS

| | | |
|---|---|---|
| 8,354,509 B2 | 1/2013 | Carven et al. |
| 8,927,697 B2 | 1/2015 | Davis et al. |
| 10,550,181 B2 | 2/2020 | Takayanagi et al. |
| 11,034,765 B2 | 6/2021 | Galler et al. |
| 11,359,018 B2 | 6/2022 | Lantto et al. |
| 11,390,674 B2 | 7/2022 | Lindsted et al. |
| 11,390,676 B2 | 7/2022 | Grandal et al. |
| 2007/0071675 A1 | 3/2007 | Wu et al. |
| 2011/0059106 A1 | 3/2011 | Kuchroo et al. |
| 2011/0070238 A1 | 3/2011 | Triebel et al. |
| 2011/0229461 A1 | 9/2011 | Tyson et al. |
| 2012/0100131 A1 | 4/2012 | Takayanagi et al. |
| 2013/0022623 A1 | 1/2013 | Karsunky et al. |
| 2013/0156774 A1* | 6/2013 | Kuchroo ................. A61P 35/00 424/136.1 |
| 2014/0093511 A1 | 4/2014 | Lonberg et al. |
| 2014/0328833 A1 | 11/2014 | Korman et al. |
| 2015/0203579 A1 | 7/2015 | Papadopoulos et al. |
| 2015/0210769 A1 | 7/2015 | Freeman et al. |
| 2015/0218274 A1 | 8/2015 | Sabatos-Peyton et al. |
| 2019/0276531 A1 | 9/2019 | Lindsted et al. |
| 2019/0367616 A1 | 12/2019 | Lantto et al. |
| 2021/0284734 A1 | 9/2021 | Galler et al. |
| 2022/0056126 A1 | 2/2022 | Grandal et al. |
| 2022/0363757 A1 | 11/2022 | Grandal et al. |
| 2022/0380470 A1 | 12/2022 | Lindsted et al. |
| 2023/0105714 A1 | 4/2023 | Lindsted et al. |

FOREIGN PATENT DOCUMENTS

| | | |
|---|---|---|
| CN | 103936853 | 7/2014 |
| EP | 2581113 A1 | 4/2013 |
| EP | 3026062 A1 | 6/2016 |
| EP | 3081576 A1 | 10/2016 |

(Continued)

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
Levantakos et al. (BioDrugs, 30:397-405, 2016).*
U.S. Appl. No. 16/093,024, filed Oct. 11, 2018, Trine Lindsted.
U.S. Appl. No. 16/340,855, filed Apr. 10, 2019, Michael M. Grandal.
U.S. Appl. No. 16/461,957, filed May 17, 2019, Johan Lantto.
U.S. Appl. No. 17/324,508, filed May 19, 2021, Gunther Galler.
Anonymous, "Anti-LAG-3 or Urelumab Alone and in Combination with Nivolumab in Treating Patients with Recurrent Glioblastoma," ClinicalTrials.gov (2016).

(Continued)

*Primary Examiner* — Nelson B Moseley, II
(74) *Attorney, Agent, or Firm* — Steptoe LLP; Z. Ying Li; Wyan-Ching M. Lee

(57) ABSTRACT

This disclosure relates to combination therapies targeting two or all of PD-1, TIM-3, and LAG-3 using antibodies specific for these targets in patients who are in need of enhanced immunity. Also included in the disclosure are compositions useful in the therapies. The therapies are useful in treating diseases such as cancers.

16 Claims, 19 Drawing Sheets
Specification includes a Sequence Listing.

(56) References Cited

FOREIGN PATENT DOCUMENTS

| WO | WO 9530750 | | 12/1995 | | |
|---|---|---|---|---|---|
| WO | WO 0177342 | | 10/2001 | | |
| WO | WO 2006/029879 A1 | | 3/2006 | | |
| WO | WO 2008/019817 A1 | | 2/2008 | | |
| WO | WO 2008/132601 | | 11/2008 | | |
| WO | WO 2008/156712 A1 | | 12/2008 | | |
| WO | WO 2010/019570 A2 | | 2/2010 | | |
| WO | WO 2010/029434 A1 | | 3/2010 | | |
| WO | WO 2010/029435 A1 | | 3/2010 | | |
| WO | WO 2010/084999 | | 7/2010 | | |
| WO | WO 2011/110621 A1 | | 9/2011 | | |
| WO | WO 2011/159877 A2 | | 12/2011 | | |
| WO | WO 2012/135408 A1 | | 10/2012 | | |
| WO | WO 2014/008218 A1 | | 1/2014 | | |
| WO | 2014/121221 A1 | | 8/2014 | | |
| WO | WO 2014/140180 A1 | | 9/2014 | | |
| WO | 2014/206107 A1 | | 12/2014 | | |
| WO | WO 2015/035606 A1 | | 3/2015 | | |
| WO | WO 2015/042246 A1 | | 3/2015 | | |
| WO | WO 2015/048312 A1 | | 4/2015 | | |
| WO | 2015/085847 A1 | | 6/2015 | | |
| WO | WO 2015/117002 | | 8/2015 | | |
| WO | WO 2015/136541 | | 9/2015 | | |
| WO | WO 2015/138920 A1 | | 9/2015 | | |
| WO | WO 2015/175340 A1 | | 11/2015 | | |
| WO | WO 2016/014688 A2 | | 1/2016 | | |
| WO | WO 2016/028672 A1 | | 2/2016 | | |
| WO | 2016/106159 A1 | | 6/2016 | | |
| WO | WO 2016/092419 A1 | | 6/2016 | | |
| WO | WO 2016/111947 | | 7/2016 | | |
| WO | WO 2016/126858 A2 | | 8/2016 | | |
| WO | WO 2016/144803 A2 | | 9/2016 | | |
| WO | WO 2017/055547 | * | 9/2016 | ............. | C07K 16/28 |
| WO | WO 2016/200782 A1 | | 12/2016 | | |
| WO | WO 2017/019897 A1 | | 2/2017 | | |
| WO | WO 2017/031242 A1 | | 2/2017 | | |
| WO | WO 2017/055404 | | 4/2017 | | |
| WO | WO 2017/055547 | * | 4/2017 | ............. | C07K 16/28 |
| WO | WO 2017/055547 A1 | | 4/2017 | | |
| WO | WO 2017/178493 A1 | | 10/2017 | | |
| WO | WO 2017/198741 | | 11/2017 | | |
| WO | WO 2018/013818 | | 1/2018 | | |
| WO | WO 2018/039020 | | 3/2018 | | |
| WO | WO 2018/069500 | | 4/2018 | | |
| WO | WO 2018/106588 A2 | | 6/2018 | | |
| WO | WO 2018/185232 | | 10/2018 | | |
| WO | WO 2018/191074 | | 10/2018 | | |

OTHER PUBLICATIONS

Anonymous, "NCT02608268: Phase I-1b/II Open-label Multi-Center Study of the Safety and Efficacy of MBG453 as Single Agent and in Combination with PDR001 in Adult Patients with Advanced Malignancies," ClinicalTrials.gov (2017).
Anonymous, "NCT02817633: A Phase 1 Dose Escalation and Cohort Expansion Study of TSR-022, an Anti-TIM-3 Monoclonal Antibody, in Patients with Advanced Solid Tumors," ClinicalTrials.gov (2017).
Anonymous: "Naturally optimized human antibodies," 1-16 (2016). Retrieved from the Internet: URL:http://content.stockpr.eom/omniab/db/2 52/746/file/OmniAb.pdf [retrieved on Jan. 9, 2018].
Anderson et al., "Promotion of tissue inflammation by the immune receptor Tim-3 expressed on innate immune cells," Science 318:1141-1143 (2007).
Andrews et al., "LAG3 (CD223) as a cancer immunotherapy target," Immunol Rev 276(1):80-96 (2017).
Benjamini et al., "Immunology: A Short Course," 2nd edition, p. 40 only (1991).
Cheng et al., "Structure and interactions of the human programmed cell death 1 receptor," J Biol Chem 288(17):11771-85 (2013).
Chiba et al., "Tumor-infiltrating DCs suppress nucleic acid-mediated innate immune responses through interactions between the receptor TIM-3 and the alarmin HMGB1," Nat. Immunology 13(9):832-42 (2012).
Das et al., "Tim-3 and its role in regulating anti-tumor immunity," Immunol Rev. 276(1):97-111 (2017).
Da Silva et al., "Reversal of NK-cell exhaustion in advanced melanoma by Tim-3 blockade," Cancer Immunol Res 2:410-422 (2014).
Dekruyff et al., "T cell/transmembrane, Ig, and mucin-3 allelic variants differentially recognize phosphatidylserine and mediate phagocytosis of apoptotic cells," J Immunology 184(4):1918-30 (2010).
Fenwick et al., "Identification of novel antagonistic anti-PD-1 antibodies that are non-blocking of the PD-1 / PD-L1 interaction," Journal of Clinical Oncology 34:15_suppl (2016).
Freeman et al., "TIM genes: a family of cell surface phosphatidylserine receptors that regulate innate and adaptive immunity," Immunol Rev 235:172-89 (2010).
Hu et al., Abstract of "Preparation and characterization of a novel monoclonal antibody against human PD-1," Current Immunology, 30(1):24-29 (2010) (with English abstract).
Huard et al., "Characterization of the major histocompatibility complex class II binding site on LAG-3 protein," Proc Natl Acad Sci USA 94:5744-5749 (1997).
Jing et al., "Combined immune checkpoint protein blockade and low dose whole body irradiation as immunotherapy for myeloma," J Immunother Cancer 3(1):2 (2015).
Kehry, "Targeting PD-1, TIM-3 and LAG-3 in combination for improved Immunotherapy Combinations," Journal for Immunotherapy of Cancer, 1 page (2015). [Retrieved from Internet—URL: https://www.tesarobio.com/application/files/3014/7552/4272/AACRApr2015.pdf].
Kikushige et al., "TIM-3 as a novel therapeutic target for eradicating acute myelogenous leukemia stem cells," Int J Hematol 98(6):627-33 (2013).
Kuchroo et al., "New roles for TIM family members in immune regulation," Nat Rev Immunol 8:577-580 (2008).
Lee et al., "Structural basis of checkpoint blockade by monoclonal antibodies in cancer immunotherapy," Nature Communications 7:13354 (2016).
Li et al., "Tim-3/galectin-9 signaling pathway mediates T-cell dysfunction and predicts poor prognosis in patients with hepatitis B virus-associated hepatocellular carcinoma," Hepatology 56(4):1342-51 (2012).
Liu et al., "Targeting PD-1 and Tim-3 pathways to reverse CD8 T-cell exhaustion and enhance ex vivo T-cell responses to autologous dendritic/tumor vaccines," J Immunother 39(4):171-80 (2016).
Moon, "Abstract 1641: Dual antibody blockade of TIM3 and PD1 on NYES01 redirected human T cells leads to augmented control of lung cancer tumors," Cancer Research 77:1641(2017).
Na et al., "Structural basis for blocking PD-1-mediated immune suppression by therapeutic antibody pembrolizumab," Cell Res. 27(1):147-150 (2017).
Pan et al., "Blocking neuropilin-1 function has an additive effect with anti-VEGF to inhibit tumor growth," Cancer Cell 11(1):53-67 (2007).
Scapin et al., "Structure of full-length human anti-PD1 therapeutic IgG4 antibody pembrolizumab," Nat Struct Mol Biol 22(12):953-8 (2015).
Storz, "Intellectual property issues of immune checkpoint inhibitors," MAbs 8(1):10-26 (2016).
Triebel, "LAG-3: a regulator of T-cell and DC responses and its use in therapeutic vaccination," Trends Immunol 24(12):619-22 (2003).
Wang et al., "In vitro characterization of the anti-PD-1 antibody nivolumab, BMS-936558, and in vivo toxicology in non-human primates," Cancer Immunol Res 2(9):846-56 (2014).
Zak et al., "Structure of the complex of human programmed death 1, PD-1, and its ligand PD-L1," Structure 23(12):2341-2348 (2015).

(56) References Cited

OTHER PUBLICATIONS

Hlavacek et al., "Steric Effects on Multivalent Ligand-Receptor Binding: Exclusion of Ligand Sites by Bound Cell Surface Receptors," Biophys J. 76(6):3031-43 (1999).
Sakuishi et al., "Targeting Tim-3 and PD-1 pathways to reverse T cell exhaustion and restore anti-tumor immunity," J Exp Med. 207(10):2187-94 (2010).
U.S. Pat. No. 11,034,765, filed Apr. 2, 2018/Jun. 15, 2021, Galler et al.
U.S. Appl. No. 17/741,967, filed May 11, 2022, Lindsted et al.
U.S. Appl. No. 17/834,497, filed Jun. 7, 2022, Grandal et al.
U.S. Appl. No. 17/834,554, filed Jun. 7, 2022, Lindsted et al.
Liu et al., "Glycosylation-independent binding of monoclonal antibody toripalimab to FG loop of PD-1 for tumor immune checkpoint therapy," MAbs. 11(4): 681-690 (2019).
Liu et al., "N-glycosylation of PD-1 promotes binding of camrelizumab," EMBO Rep. 21(12): e51444 (2020).
Liu et al., "PD-1 N58-glycosylation-dependent binding of monoclonal antibody cemiplimab for immune checkpoint therapy," Front. Immunol. 13:826045 (2022).
WHO, International Nonproprietary Names for Pharmaceutical Substances (INN), WHO Drug Information, 31(1) List 77:74-75 (2017).
WHO, International Nonproprietary Names for Pharmaceutical Substances (INN), WHO Drug Information, 33(1) List 81:124-125 (2019).
WHO, International Nonproprietary Names for Pharmaceutical Substances (INN), WHO Drug Information, 33(1) List 81:57-58 (2019).
Murphy et al., "Enhancing recombinant antibody performance by optimally engineering its format," J Immunol Methods 463:127-133 (2018).
Anonymous: "Definition of lomvastomig—NCI Drug Dictionary—NCI," 1 page (2019). Retrieved from the Internet: URL: https://www.cancer.gov/publications/dictionaries/cancer-drug/def/lomvastomig [retrieved on Jun. 13, 2023].
Friedlaender et al., "New emerging targets in cancer immunotherapy: the role of TIM3," ESMO Open 4(Suppl 3): e000497 (2019).
Koyama et al., "Adaptive resistance to therapeutic PD-1 blockade is associated with upregulation of alternative immune checkpoints," Nat Commun. 7:10501 (2016).

* cited by examiner

ID NO: 397) which is
COMBINATION THERAPIES TARGETING PD-1, TIM-3, AND LAG-3

CROSS-REFERENCE TO RELATED APPLICATIONS

This application is a national stage application under 35 U.S.C. § 371 of International Patent Application No. PCT/EP2018/058752, filed Apr. 5, 2018, which claims priority from U.S. Provisional Patent Application 62/481,973, filed Apr. 5, 2017. The disclosures of those applications are incorporated by reference herein in their entirety.

SEQUENCE LISTING

The instant application contains a Sequence Listing which has been submitted electronically in ASCII format and is hereby incorporated by reference in its entirety. The electronic copy of the Sequence Listing, created on Mar. 23, 2018, is named 022675_WO058_SL.txt and is 232,360 bytes in size.

BACKGROUND OF THE INVENTION

PD-1, also known as Programmed Cell Death Protein 1 and CD279, is a 268 amino acid cell surface receptor that belongs to the immunoglobulin superfamily. PD-1 is a member of the CD28 family of T cell regulators and is expressed on T cells, B cells and macrophages. It binds ligands PD-L1 (also known as B7 homolog) and PD-L2 (also known as B7-DC). PD-1 is a type I membrane protein whose structure includes an extracellular IgV domain, a transmembrane region and an intracellular tail containing two phosphorylation sites. Known as an immune checkpoint protein, PD-1 functions as an inducible immune modulatory receptor, playing a role in, e.g., negative regulation of T cell responses to antigen stimulation.

PD-L1 is the predominant ligand for PD-1. Binding of PD-L1 to PD-1 inhibits T cell activity, reducing cytokine production and suppressing T cell proliferation. Cancer cells that express PD-L1 are able to exploit this mechanism to inactivate the anti-tumor activity of T cells via binding of PD-L1 to the PD-1 receptor. In view of its immune response regulatory properties, PD-1 has been investigated as a potential target for immunotherapy, including treatment of cancer and autoimmune diseases. Two anti-PD-1 antibodies, pembrolizumab and nivolumab, have been approved in the United States and Europe for treating certain cancers.

Other immune checkpoint proteins include TIM-3 (T-cell immunoglobulin and mucin-domain containing 3) and LAG-3 (lymphocyte-activation gene 3). TIM-3, also known as HAVCR2 (hepatitis A virus cellular receptor 2) or CD366, is a member of the T-cell immunoglobulin and mucin domain protein family. TIM-3 is encoded in humans by the Havcr2 gene and is a 33 kDa type I glycoprotein with a membrane distal IgV domain and a membrane proximal mucin-domain. It contains a conserved region of five Tyr residues in the intracellular domain, which are phosphorylated upon ligand binding. TIM-3 is expressed by a range of different cells originating from both the adaptive and innate arms of the immune system, including T-cells, dendritic cells, macrophages, and natural killer (NK) cells. TIM-3 expression is low on naïve T cells but becomes highly upregulated upon T cell activation. In contrast to T-cells, innate cells such as dendritic cells, NK cells and monocytes have high basal TIM-3 expression. TIM-3 has been associated with several, mostly promiscuous, ligands, including galectin-9, phosphatidylserine, CEACAM-1 and HMGB-1, but the exact roles of these ligands are currently unknown.

Although TIM-3 has been suggested to be a checkpoint inhibitor, there is relatively sparse evidence to support the idea that TIM-3 directly mediates suppression of T cell activation or cytokine secretion in a manner similar to, e.g., PD-1. Furthermore, and in contrast to PD-1, TIM-3 appears to play a role in regulation of cells of the innate system, and in particular dendritic cells. The majority of functional data related to TIM-3 and its role in tumor immunology comes from in vivo studies using various antibodies. In most of these studies, due to poor antibody validation, it is not clear whether the effects of the TIM-3 antibodies are mediated by inhibition of ligand binding or by an agonistic effect on the target. In view of its immune response regulatory properties, TIM-3 has been investigated as a potential target for immunotherapy, including for treatment of cancer and autoimmune diseases. A single anti-TIM-3 antibody is currently in clinical development, but there are currently no approved anti-TIM-3 antibodies.

LAG-3, also known as CD223, is an immunoglobulin superfamily protein that functions as an immune checkpoint receptor. The mature protein is a 503-amino acid type I transmembrane protein with four extracellular Ig-like domains. It is expressed on various types of cells including activated T cells, T regulatory (Treg) cells, natural killer cells, B cells and plasmacytoid dendritic cells. Information on sequence data, exon/intron organization, and the chromosomal localization of LAG-3 indicates that it is closely related to CD4. Similar to CD4, LAG-3 binds MHC class II molecules, although with a higher affinity and at a distinct site compared to CD4.

LAG-3 is a co-inhibitory receptor that is thought to regulate T cell proliferation, activation and homeostasis in a manner similar to CTLA-4 and PD-1. Upon ligand binding to the extracellular domain, LAG-3 exerts its effect through subsequent signaling via the cytoplasmic domain. The best characterized ligand for LAG-3 is MHC class II (MHCII), but other LAG-3 ligands have been described, including LSECtin. LAG-3 has no classical ITIM or ITSM motifs, but has a conserved KIEELE motif (SEQ ID NO: 397) which is thought to be indispensable for accomplishing its inhibitory effect on T-cell activity. The exact mechanism by which LAG-3 affects T-cell activity is poorly understood. LAG-3 inhibits T cell expansion by blocking entry of activated T-cells into the growth phase of the cell cycle, resulting in the accumulation of cells in the S-phase. LAG-3 is also thought to play a role in enhancing the suppressive activity of regulatory T-cells and in modulating dendritic cell function. Cancer cells have the ability to upregulate expression of MHCII, which binds LAG-3 on effector T-cells, thus inhibiting their activity and inducing tumor immune escape.

In view of the critical role of PD-1, LAG-3, and TIM-3 as immune modulators, there is a need for new and improved combination therapies that target these receptors to treat cancers and certain disorders of the immune system.

SUMMARY OF THE INVENTION

The present invention is based on the discovery that the immunity-enhancing efficacy of an anti-PD-1 antibody, such as those described herein, is significantly increased when the antibody is used in combination with an anti-TIM-3 antibody and/or an anti-LAG-3 antibody. The present inventors have found that the combination therapies of the present invention are particularly effective in treating cancer in a human patient by activating the patient's own anti-cancer immunity. Compared to currently available treatments for cancer, including antibody treatments, it is contemplated that the combination therapies of the invention may provide a superior clinical response.

Accordingly, the present invention provides a method of enhancing immunity in a human patient in need thereof, such as a cancer patient, by administering to the patient (1) an anti-PD-1 antibody, or an antigen-binding portion thereof, that competes for binding to human PD-1 with, or binds to the same epitope of human PD-1 as, an antibody selected from the group consisting of 12819.15384, 12748.15381, 12748.16124, 12865.15377, 12892.15378, 12796.15376, 12777.15382, 12760.15375 and 13112.15380; and (2) an anti-TIM-3 antibody or an antigen-binding portion thereof and/or an anti-LAG-3 antibody or an antigen-binding portion thereof. In certain embodiments, the method comprises administering the anti-PD-1 antibody or antigen-binding portion thereof, the anti-TIM-3 antibody or antigen-binding portion thereof, and the anti-LAG-3 antibody or antigen-binding portion thereof.

In some embodiments, the anti-PD-1 antibody binds to an epitope of human PD-1 comprising:
  a) residues V64, L128, P130, K131, and A132 of SEQ ID NO: 388;
  b) residues V44 and T145 of SEQ ID NO: 388;
  c) residues K131 and E136 of SEQ ID NO: 388; or
  d) residues V44 and T145 of SEQ ID NO: 388.

In some embodiments, the anti-PD-1 antibody binds to an epitope of human PD-1 comprising:
  a) residues 56-64, 69-90, and 122-140 of SEQ ID NO: 388;
  b) residues 69-90 and 122-140 of SEQ ID NO: 388;
  c) residues 69-75 of SEQ ID NO: 388;
  d) residues 136-140 of SEQ ID NO: 388; or
  e) residues 69-75 and 136-140 of SEQ ID NO: 388.

In some embodiments, the anti-PD-1 antibody has at least one of the following properties:
  a) binds to human PD-1 with a $K_D$ of 750 pM or less;
  b) binds to cynomolgus PD-1 with a $K_D$ of 7 nM or less;
  c) binds to mouse PD-1 with a $K_D$ of 1 nM or less;
  d) does not bind to rat PD-1,
  e) increases IL-2 secretion in a Staphylococcal enterotoxin B (SEB) whole blood assay;
  f) increases IFN-γ secretion in a one-way mixed lymphocyte reaction assay;
  g) inhibits the interaction of PD-1 with PD-L1 by at least 60% at a concentration of 10 μg/mL in a flow cytometric competition assay;
  h) blocks binding of PD-L1 and PD-L2 to PD-1 by at least 90% at a concentration of 10 μg/mL as determined by Bio-Layer Interferometry analysis; and
  i) inhibits tumor growth in vivo.

In certain embodiments, the anti-PD-1 antibody has all of said properties.

In some embodiments, the heavy chain complementarity-determining regions (H-CDR) 1-3 and light chain complementarity-determining regions (L-CDR) 1-3 of the anti-PD-1 antibody comprise the amino acid sequences of:
  a) SEQ ID NOs: 228-233, respectively;
  b) SEQ ID NOs: 238-243, respectively;
  c) SEQ ID NOs: 248-253, respectively;
  d) SEQ ID NOs: 258-263, respectively;
  e) SEQ ID NOs: 268-273, respectively;
  f) SEQ ID NOs: 278-283, respectively;
  g) SEQ ID NOs: 288-293, respectively; or
  h) SEQ ID NOs: 298-303, respectively.

In some embodiments, the heavy and light chain variable domains of the anti-PD-1 antibody comprise the amino acid sequences of:
  a) SEQ ID NOs: 226 and 227, respectively;
  b) SEQ ID NOs: 236 and 237, respectively;
  c) SEQ ID NOs: 236 and 392, respectively;
  d) SEQ ID NOs: 246 and 247, respectively;
  e) SEQ ID NOs: 256 and 257, respectively;
  f) SEQ ID NOs: 266 and 267, respectively;
  g) SEQ ID NOs: 276 and 277, respectively;
  h) SEQ ID NOs: 286 and 287, respectively; or
  i) SEQ ID NOs: 296 and 297, respectively.

In some embodiments, the anti-PD-1 antibody comprises:
  a) a heavy chain (HC) comprising the amino acid sequence of SEQ ID NO: 226 and the amino acid sequence of SEQ ID NO: 375, and a light chain (LC) comprising the amino acid sequence of SEQ ID NO: 227 and the amino acid sequence of SEQ ID NO: 379;
  b) an HC comprising the amino acid sequence of SEQ ID NO: 236 and the amino acid sequence of SEQ ID NO: 375, and an LC comprising the amino acid sequence of SEQ ID NO: 237 and the amino acid sequence of SEQ ID NO: 379;
  c) an HC comprising the amino acid sequence of SEQ ID NO: 236 and the amino acid sequence of SEQ ID NO: 375, and an LC comprising the amino acid sequence of SEQ ID NO: 392 and the amino acid sequence of SEQ ID NO: 379;
  d) an HC comprising the amino acid sequence of SEQ ID NO: 246 and the amino acid sequence of SEQ ID NO: 375, and an LC comprising the amino acid sequence of SEQ ID NO: 247 and the amino acid sequence of SEQ ID NO: 379;
  e) an HC comprising the amino acid sequence of SEQ ID NO: 256 and the amino acid sequence of SEQ ID NO: 375, and an LC comprising the amino acid sequence of SEQ ID NO: 257 and the amino acid sequence of SEQ ID NO: 379;
  f) an HC comprising the amino acid sequence of SEQ ID NO: 266 and the amino acid sequence of SEQ ID NO: 375, and an LC comprising the amino acid sequence of SEQ ID NO: 267 and the amino acid sequence of SEQ ID NO: 379;
  g) an HC comprising the amino acid sequence of SEQ ID NO: 276 and the amino acid sequence of SEQ ID NO: 375, and an LC comprising the amino acid sequence of SEQ ID NO: 277 and the amino acid sequence of SEQ ID NO: 379;
  h) an HC comprising the amino acid sequence of SEQ ID NO: 286 and the amino acid sequence of SEQ ID NO: 375, and an LC comprising the amino acid sequence of SEQ ID NO: 287 and the amino acid sequence of SEQ ID NO: 379; or
  i) an HC comprising the amino acid sequence of SEQ ID NO: 296 and the amino acid sequence of SEQ ID NO: 375, and an LC comprising the amino acid sequence of SEQ ID NO: 297 and the amino acid sequence of SEQ ID NO: 379.

In some embodiments, the anti-TIM-3 antibody competes for binding to human TIM-3 with, or binds to the same epitope of human TIM-3 as, an antibody selected from the group consisting of 15086.17145, 15086.15086, 15086.16837, 15086.17144, 20131, 20293, 15105, 15107, 15109, 15174, 15175, 15260, 15284, 15299, 15353, 15354, 17244, 17245, 19324, 19416, 19568, 20185, 20300, 20362, and 20621.

In some embodiments, the anti-TIM-3 antibody binds to an epitope of human TIM-3 comprising:
 a) residues P50, V60, F61, E62, G64, R69, I117, M118, and D120 of SEQ ID NO: 389;
 b) residues F61, R69, and I117 of SEQ ID NO: 389; or
 c) residues P50, F61, E62, I117, M118, and D120 of SEQ ID NO: 389.

In some embodiments, the anti-TIM-3 antibody binds to an epitope of human TIM-3 comprising:
 a) residues 62-67 of SEQ ID NO: 389; or
 b) residues 114-117 of SEQ ID NO: 389.

In some embodiments, the anti-TIM-3 antibody has at least one of the following properties:
 a) binds to human TIM-3 with a $K_D$ of 23 nM or less as measured by surface plasmon resonance;
 b) binds to cynomolgus TIM-3 with a $K_D$ of 22 nM or less as measured by surface plasmon resonance;
 c) binds to human TIM-3 with an EC50 of 1.2 nM or less as measured by ELISA;
 d) binds to cynomolgus TIM-3 with an EC50 of 46 nM or less as measured by ELISA;
 e) increases IFN-γ secretion in a one-way mixed lymphocyte reaction assay;
 f) increases IFN-γ secretion in a two-way mixed lymphocyte reaction assay;
 g) increases TNF-α secretion in a one-way mixed lymphocyte reaction assay;
 h) increases TNF-α secretion from dendritic cells; and
 i) inhibits interaction of TIM-3 with phosphatidylserine.

In certain embodiments, the anti-TIM-3 antibody has at least properties a), c), d), e), g), h), and i).

In some embodiments, the H-CDR1-3 and L-CDR1-3 of the anti-TIM-3 antibody comprise the amino acid sequences of:
 a) SEQ ID NOs: 8-13, respectively;
 b) SEQ ID NOs: 18-23, respectively;
 c) SEQ ID NOs: 28-33, respectively;
 d) SEQ ID NOs: 38-43, respectively;
 e) SEQ ID NOs: 48-53, respectively;
 f) SEQ ID NOs: 58-63, respectively;
 g) SEQ ID NOs: 68-73, respectively;
 h) SEQ ID NOs: 78-83, respectively;
 i) SEQ ID NOs: 88-93, respectively;
 j) SEQ ID NOs: 98-103, respectively;
 k) SEQ ID NOs: 108-113, respectively;
 l) SEQ ID NOs: 118-123, respectively;
 m) SEQ ID NOs: 128-133, respectively;
 n) SEQ ID NOs: 138-143, respectively;
 o) SEQ ID NOs: 148-153, respectively;
 p) SEQ ID NOs: 158-163, respectively;
 q) SEQ ID NOs: 168-173, respectively;
 r) SEQ ID NOs: 178-183, respectively;
 s) SEQ ID NOs: 188-193, respectively;
 t) SEQ ID NOs: 198-203, respectively;
 u) SEQ ID NOs: 208-213, respectively; or
 v) SEQ ID NOs: 218-223, respectively.

In some embodiments, the heavy and light chain variable domains of the anti-TIM-3 antibody comprise the amino acid sequences of:
 a) SEQ ID NOs: 7 and 4, respectively;
 b) SEQ ID NOs: 3 and 4, respectively;
 c) SEQ ID NOs: 16 and 17, respectively;
 d) SEQ ID NOs: 26 and 27, respectively;
 e) SEQ ID NOs: 36 and 37, respectively;
 f) SEQ ID NOs: 46 and 47, respectively;
 g) SEQ ID NOs: 56 and 57, respectively;
 h) SEQ ID NOs: 66 and 67, respectively;
 i) SEQ ID NOs: 76 and 77, respectively;
 j) SEQ ID NOs: 86 and 87, respectively;
 k) SEQ ID NOs: 96 and 97, respectively;
 l) SEQ ID NOs: 106 and 107, respectively;
 m) SEQ ID NOs: 116 and 117, respectively;
 n) SEQ ID NOs: 126 and 127, respectively;
 o) SEQ ID NOs: 136 and 137, respectively;
 p) SEQ ID NOs: 146 and 147, respectively;
 q) SEQ ID NOs: 156 and 157, respectively;
 r) SEQ ID NOs: 166 and 167, respectively;
 s) SEQ ID NOs: 176 and 177, respectively;
 t) SEQ ID NOs: 186 and 187, respectively;
 u) SEQ ID NOs: 196 and 197, respectively;
 v) SEQ ID NOs: 206 and 207, respectively; or
 w) SEQ ID NOs: 216 and 217, respectively.

In some embodiments, the anti-TIM-3 antibody comprises:
 a) an HC comprising the amino acid sequence of SEQ ID NO: 7 and the amino acid sequence of SEQ ID NO: 374, 375, 376, or 377, and an LC comprising the amino acid sequence of SEQ ID NO: 4 and the amino acid sequence of SEQ ID NO: 378;
 b) an HC comprising the amino acid sequence of SEQ ID NO: 3 and the amino acid sequence of SEQ ID NO: 374, 375, 376, or 377, and an LC comprising the amino acid sequence of SEQ ID NO: 4 and the amino acid sequence of SEQ ID NO: 378;
 c) an HC comprising the amino acid sequence of SEQ ID NO: 16 and the amino acid sequence of SEQ ID NO: 374, 375, 376, or 377, and an LC comprising the amino acid sequence of SEQ ID NO: 17 and the amino acid sequence of SEQ ID NO: 378;
 d) an HC comprising the amino acid sequence of SEQ ID NO: 26 and the amino acid sequence of SEQ ID NO: 374, 375, 376, or 377, and an LC comprising the amino acid sequence of SEQ ID NO: 27 and the amino acid sequence of SEQ ID NO: 378;
 e) an HC comprising the amino acid sequence of SEQ ID NO: 36 and the amino acid sequence of SEQ ID NO: 374, 375, 376, or 377, and an LC comprising the amino acid sequence of SEQ ID NO: 37 and the amino acid sequence of SEQ ID NO: 378;
 f) an HC comprising the amino acid sequence of SEQ ID NO: 46 and the amino acid sequence of SEQ ID NO: 374, 375, 376, or 377, and an LC comprising the amino acid sequence of SEQ ID NO: 47 and the amino acid sequence of SEQ ID NO: 378;
 g) an HC comprising the amino acid sequence of SEQ ID NO: 56 and the amino acid sequence of SEQ ID NO: 374, 375, 376, or 377, and an LC comprising the amino acid sequence of SEQ ID NO: 57 and the amino acid sequence of SEQ ID NO: 378;
 h) an HC comprising the amino acid sequence of SEQ ID NO: 66 and the amino acid sequence of SEQ ID NO: 374, 375, 376, or 377, and an LC comprising the amino acid sequence of SEQ ID NO: 67 and the amino acid sequence of SEQ ID NO: 378;
 i) an HC comprising the amino acid sequence of SEQ ID NO: 76 and the amino acid sequence of SEQ ID NO: 374, 375, 376, or 377, and an LC comprising the amino acid sequence of SEQ ID NO: 77 and the amino acid sequence of SEQ ID NO: 378;
 j) an HC comprising the amino acid sequence of SEQ ID NO: 86 and the amino acid sequence of SEQ ID NO: 374, 375, 376, or 377, and an LC comprising the amino acid sequence of SEQ ID NO: 87 and the amino acid sequence of SEQ ID NO: 378;

k) an HC comprising the amino acid sequence of SEQ ID NO: 96 and the amino acid sequence of SEQ ID NO: 374, 375, 376, or 377, and an LC comprising the amino acid sequence of SEQ ID NO: 97 and the amino acid sequence of SEQ ID NO: 378;
l) an HC comprising the amino acid sequence of SEQ ID NO: 106 and the amino acid sequence of SEQ ID NO: 374, 375, 376, or 377, and an LC comprising the amino acid sequence of SEQ ID NO: 107 and the amino acid sequence of SEQ ID NO: 378;
m) an HC comprising the amino acid sequence of SEQ ID NO: 116 and the amino acid sequence of SEQ ID NO: 374, 375, 376, or 377, and an LC comprising the amino acid sequence of SEQ ID NO: 117 and the amino acid sequence of SEQ ID NO: 378;
n) an HC comprising the amino acid sequence of SEQ ID NO: 126 and the amino acid sequence of SEQ ID NO: 374, 375, 376, or 377, and an LC comprising the amino acid sequence of SEQ ID NO: 127 and the amino acid sequence of SEQ ID NO: 378;
o) an HC comprising the amino acid sequence of SEQ ID NO: 136 and the amino acid sequence of SEQ ID NO: 374, 375, 376, or 377, and an LC comprising the amino acid sequence of SEQ ID NO: 137 and the amino acid sequence of SEQ ID NO: 378;
p) an HC comprising the amino acid sequence of SEQ ID NO: 146 and the amino acid sequence of SEQ ID NO: 374, 375, 376, or 377, and an LC comprising the amino acid sequence of SEQ ID NO: 147 and the amino acid sequence of SEQ ID NO: 378;
q) an HC comprising the amino acid sequence of SEQ ID NO: 156 and the amino acid sequence of SEQ ID NO: 374, 375, 376, or 377, and an LC comprising the amino acid sequence of SEQ ID NO: 157 and the amino acid sequence of SEQ ID NO: 378;
r) an HC comprising the amino acid sequence of SEQ ID NO: 166 and the amino acid sequence of SEQ ID NO: 374, 375, 376, or 377, and an LC comprising the amino acid sequence of SEQ ID NO: 167 and the amino acid sequence of SEQ ID NO: 378;
s) an HC comprising the amino acid sequence of SEQ ID NO: 176 and the amino acid sequence of SEQ ID NO: 374, 375, 376, or 377, and an LC comprising the amino acid sequence of SEQ ID NO: 177 and the amino acid sequence of SEQ ID NO: 378;
t) an HC comprising the amino acid sequence of SEQ ID NO: 186 and the amino acid sequence of SEQ ID NO: 374, 375, 376, or 377, and an LC comprising the amino acid sequence of SEQ ID NO: 187 and the amino acid sequence of SEQ ID NO: 378;
u) an HC comprising the amino acid sequence of SEQ ID NO: 196 and the amino acid sequence of SEQ ID NO: 374, 375, 376, or 377, and an LC comprising the amino acid sequence of SEQ ID NO: 197 and the amino acid sequence of SEQ ID NO: 378;
v) an HC comprising the amino acid sequence of SEQ ID NO: 206 and the amino acid sequence of SEQ ID NO: 374, 375, 376, or 377, and an LC comprising the amino acid sequence of SEQ ID NO: 207 and the amino acid sequence of SEQ ID NO: 378; or
w) an HC comprising the amino acid sequence of SEQ ID NO: 216 and the amino acid sequence of SEQ ID NO: 374, 375, 376, or 377, and an LC comprising the amino acid sequence of SEQ ID NO: 217 and the amino acid sequence of SEQ ID NO: 378.

In some embodiments, the anti-LAG-3 antibody competes for binding to human LAG-3 with, or binds to the same epitope of human LAG-3 as, an antibody selected from the group consisting of 15532, 15646, 15723, 15595, 15431, 15572, and 15011.

In some embodiments, the anti-LAG-3 antibody binds to an epitope of human LAG-3 comprising:
a) residues H85, P86, A87, P89, S91, W92, and G93 of SEQ ID NO: 68;
b) residues A40, Q41, P43, P46, P49, D52, T62, Q64, H65, Q66, P67, D68, G93, P94, P96, R98, Y99, T100, V101, P106, G107, R119, E124, R129, G130, D131, S133, R137, P138, D143, R148, and R163 of SEQ ID NO: 68;
c) residues A40, Q41, P43, P46, P49, D52, T62, Q64, H65, Q66, P67, D68, P96, Y99, T100, V101, P106, G107, R119, E124, R129, G130, D131, S133, R137, P138, D143, R148, and R163 of SEQ ID NO: 68; or
d) residues G107, L109, R110, and S111 of SEQ ID NO: 68.

In some embodiments, the anti-LAG-3 antibody binds to an epitope of human LAG-3 comprising:
a) residues 98-105 of SEQ ID NO: 68;
b) residues 78-105 and 123-131 of SEQ ID NO: 68;
c) residues 23-30, 40-66, 88-105, 123-137, and 148-152 of SEQ ID NO: 68; or
d) residues 23-30, 40-66, 98-105, 118-137, and 148-161 of SEQ ID NO: 68.

In some embodiments, the anti-LAG-3 antibody has at least one of the following properties:
a) at a concentration of 20 μg/mL, reduces the binding of human LAG-3 to human MHC class II on A375 cells by greater than 85% compared to a negative control antibody as determined by a flow cytometric competition assay;
b) at a concentration of 20 μg/mL, reduces the binding of human LAG-3 to human MHC class II on A375 cells to between 35% and 85% compared to a negative control antibody as determined by a flow cytometric competition assay;
c) blocks binding between human LAG-3 expressed on Jurkat cells and human MHC class II expressed on Raji cells;
d) binds to human LAG-3 with an EC50 of 0.1 nM or less as measured by flow cytometry;
e) binds to cynomolgus LAG-3 with an EC50 of 0.3 nM or less as measured by flow cytometry;
f) binds to human LAG-3 with a $K_D$ of 3.0×10-8 or less as measured by surface plasmon resonance;
g) binds to cynomolgus LAG-3 with a $K_D$ of 1.5×10-7 or less as measured by surface plasmon resonance;
h) binds to mouse LAG-3 with a $K_D$ of 3.5×10-8 or less as measured by surface plasmon resonance;
i) stimulates IL-2 production in Staphylococcal enterotoxin B (SEB) treated human peripheral blood mononuclear cells (PBMCs);
j) reduces cellular levels of LAG-3 in human T cells;
k) reduces soluble levels of LAG-3 in the culture of human T cells;
l) induces tumor growth regression in vivo;
m) delays tumor growth in vivo; and
n) does not bind to the same epitope of human LAG-3 as antibody 25F7-Lag3.5.

In certain embodiments, the anti-LAG-3 antibody has at least properties a), c), d), e), f), g), i), j), k), m), and n).

In some embodiments, the H-CDR1-3 and L-CDR1-3 of the anti-LAG-3 antibody comprise the amino acid sequences of:
  a) SEQ ID NOs: 318-323, respectively;
  b) SEQ ID NOs: 308-313, respectively;
  c) SEQ ID NOs: 328-333, respectively;
  d) SEQ ID NOs: 338-343, respectively;
  e) SEQ ID NOs: 348-353, respectively;
  f) SEQ ID NOs: 358-363, respectively; or
  g) SEQ ID NOs: 368-373, respectively.

In some embodiments, the heavy and light chain variable domains of the anti-LAG-3 antibody comprise the amino acid sequences of:
  a) SEQ ID NOs: 316 and 317, respectively;
  b) SEQ ID NOs: 306 and 307, respectively;
  c) SEQ ID NOs: 326 and 327, respectively;
  d) SEQ ID NOs: 336 and 337, respectively;
  e) SEQ ID NOs: 346 and 347, respectively;
  f) SEQ ID NOs: 356 and 357, respectively; or
  g) SEQ ID NOs: 366 and 367, respectively.

In some embodiments, the anti-LAG-3 antibody comprises:
  a) an HC comprising the amino acid sequence of SEQ ID NO: 316 and the amino acid sequence of SEQ ID NO: 375, and an LC comprising the amino acid sequence of SEQ ID NO: 317 and the amino acid sequence of SEQ ID NO: 378;
  b) an HC comprising the amino acid sequence of SEQ ID NO: 306 and the amino acid sequence of SEQ ID NO: 375, and an LC comprising the amino acid sequence of SEQ ID NO: 307 and the amino acid sequence of SEQ ID NO: 378;
  c) an HC comprising the amino acid sequence of SEQ ID NO: 326 and the amino acid sequence of SEQ ID NO: 375, and an LC comprising the amino acid sequence of SEQ ID NO: 327 and the amino acid sequence of SEQ ID NO: 378;
  d) an HC comprising the amino acid sequence of SEQ ID NO: 336 and the amino acid sequence of SEQ ID NO: 375, and an LC comprising the amino acid sequence of SEQ ID NO: 337 and the amino acid sequence of SEQ ID NO: 378;
  e) an HC comprising the amino acid sequence of SEQ ID NO: 346 and the amino acid sequence of SEQ ID NO: 375, and an LC comprising the amino acid sequence of SEQ ID NO: 347 and the amino acid sequence of SEQ ID NO: 378;
  f) an HC comprising the amino acid sequence of SEQ ID NO: 356 and the amino acid sequence of SEQ ID NO: 375, and an LC comprising the amino acid sequence of SEQ ID NO: 357 and the amino acid sequence of SEQ ID NO: 378; or
  g) an HC comprising the amino acid sequence of SEQ ID NO: 366 and the amino acid sequence of SEQ ID NO: 375, and an LC comprising the amino acid sequence of SEQ ID NO: 367 and the amino acid sequence of SEQ ID NO: 379.

In some embodiments, the method comprises administering to the patient:
  a) an anti-PD-1 antibody whose H-CDR1-3 and L-CDR1-3 comprise the amino acid sequences of SEQ ID NOs: 228-233, respectively; and an anti-TIM-3 antibody whose H-CDR1-3 and L-CDR1-3 comprise the amino acid sequences of SEQ ID NOs: 8-13, respectively;
  b) an anti-PD-1 antibody whose VH and VL comprise the amino acid sequences of SEQ ID NOs: 226 and 227, respectively; and an anti-TIM-3 antibody whose VH and VL comprise the amino acid sequences of SEQ ID NOs: 7 and 4, respectively; or
  c) an anti-PD-1 antibody comprising an HC that comprises the amino acid sequences of SEQ ID NOs: 226 and 375 and an LC that comprises the amino acid sequences of SEQ ID NOs: 227 and 379; and an anti-TIM-3 antibody comprising an HC that comprises the amino acid sequences of SEQ ID NOs: 7 and 377 and an LC that comprises the amino acid sequences of SEQ ID NOs: 4 and 378.

In some embodiments, the method comprises administering to the patient:
  a) an anti-PD-1 antibody whose H-CDR1-3 and L-CDR1-3 comprise the amino acid sequences of SEQ ID NOs: 228-233, respectively; and an anti-LAG-3 antibody whose H-CDR1-3 and L-CDR1-3 comprise the amino acid sequences of SEQ ID NOs: 318-323, respectively;
  b) an anti-PD-1 antibody whose VH and VL comprise the amino acid sequences of SEQ ID NOs: 226 and 227, respectively; and an anti-LAG-3 antibody whose VH and VL comprise the amino acid sequences of SEQ ID NOs: 316 and 317, respectively; or
  c) an anti-PD-1 antibody comprising an HC that comprises the amino acid sequences of SEQ ID NOs: 226 and 375 and an LC that comprises the amino acid sequences of SEQ ID NOs: 227 and 379; and an anti-LAG-3 antibody comprising an HC that comprises the amino acid sequences of SEQ ID NOs: 316 and 375 and an LC that comprises the amino acid sequences of SEQ ID NOs: 317 and 378.

In some embodiments, the method comprises administering to the patient:
  a) an anti-PD-1 antibody whose H-CDR1-3 and L-CDR1-3 comprise the amino acid sequences of SEQ ID NOs: 228-233, respectively; an anti-TIM-3 antibody whose H-CDR1-3 and L-CDR1-3 comprise the amino acid sequences of SEQ ID NOs: 8-13, respectively; and an anti-LAG-3 antibody whose H-CDR1-3 and L-CDR1-3 comprise the amino acid sequences of SEQ ID NOs: 318-323, respectively;
  b) an anti-PD-1 antibody whose VH and VL comprise the amino acid sequences of SEQ ID NOs: 226 and 227, respectively; an anti-TIM-3 antibody whose VH and VL comprise the amino acid sequences of SEQ ID NOs: 7 and 4, respectively; and an anti-LAG-3 antibody whose VH and VL comprise the amino acid sequences of SEQ ID NOs: 316 and 317, respectively; or
  c) an anti-PD-1 antibody comprising an HC that comprises the amino acid sequences of SEQ ID NOs: 226 and 375 and an LC that comprises the amino acid sequences of SEQ ID NOs: 227 and 379; an anti-TIM-3 antibody comprising an HC that comprises the amino acid sequences of SEQ ID NOs: 7 and 377 and an LC that comprises the amino acid sequences of SEQ ID NOs: 4 and 378; and an anti-LAG-3 antibody comprising an HC that comprises the amino acid sequences of SEQ ID NOs: 316 and 375 and an LC that comprises the amino acid sequences of SEQ ID NOs: 317 and 378.

The antibodies or antigen-binding portions may be administered to the patient concurrently (e.g., in a single pharmaceutical composition) or sequentially.

The therapies of the present invention are useful in treating a patient who has cancer, such as a hematological malignancy (e.g., leukemia, Hodgkin's lymphoma, or non-Hodgkin's lymphoma), or a solid tumor. In some embodiments, the patient may have melanoma, non-small cell lung cancer, bladder cancer, head and neck squamous cell carcinoma, ovarian cancer, colorectal cancer, renal cell carcinoma, Merkel-cell carcinoma, fibrosarcoma, gliosarcoma, or glioblastoma. The therapies of the present invention can additionally include radiation, or at least one of a chemotherapeutic agent, an anti-neoplastic agent, and an anti-angiogenic agent.

Also provided in the present invention is a multi-specific (e.g., bi-specific or tri-specific) antibody that specifically binds to: a) human PD-1 and human TIM-3; b) human PD-1 and human LAG-3; or c) human PD-1, human anti-TIM-3, and human LAG-3. In certain embodiments, the multi-specific antibody comprises an antigen-binding portion of an anti-PD-1 antibody as described herein, an antigen-binding portion of an anti-TIM-3 antibody as described herein, and/or an antigen-binding portion of an anti-LAG-3 antibody as described herein.

Also provided in the present invention is a pharmaceutical composition comprising (1) an anti-PD-1 antibody or an antigen-binding portion thereof as described herein, (2) an anti-TIM-3 antibody or an antigen-binding portion thereof and/or an anti-LAG-3 antibody or an antigen-binding portion thereof, and (3) a pharmaceutically acceptable excipient. The anti-TIM-3 antibody and the anti-LAG-3 antibody can be selected from those as described herein.

In some embodiments, the pharmaceutical composition comprises:
 a) an anti-PD-1 antibody whose H-CDR1-3 and L-CDR1-3 comprise the amino acid sequences of SEQ ID NOs: 228-233, respectively; an anti-TIM-3 antibody whose H-CDR1-3 and L-CDR1-3 comprise the amino acid sequences of SEQ ID NOs: 8-13, respectively; and an anti-LAG-3 antibody whose H-CDR1-3 and L-CDR1-3 comprise the amino acid sequences of SEQ ID NOs: 318-323, respectively;
 b) an anti-PD-1 antibody whose VH and VL comprise the amino acid sequences of SEQ ID NOs: 226 and 227, respectively; an anti-TIM-3 antibody whose VH and VL comprise the amino acid sequences of SEQ ID NOs: 7 and 4, respectively; and an anti-LAG-3 antibody whose VH and VL comprise the amino acid sequences of SEQ ID NOs: 316 and 317, respectively; or
 c) an anti-PD-1 antibody comprising an HC that comprises the amino acid sequences of SEQ ID NOs: 226 and 375 and an LC that comprises the amino acid sequences of SEQ ID NOs: 227 and 379; an anti-TIM-3 antibody comprising an HC that comprises the amino acid sequences of SEQ ID NOs: 7 and 377 and an LC that comprises the amino acid sequences of SEQ ID NOs: 4 and 378; and an anti-LAG-3 antibody comprising an HC that comprises the amino acid sequences of SEQ ID NOs: 316 and 375 and an LC that comprises the amino acid sequences of SEQ ID NOs: 317 and 378.

The antibodies in the composition may be present in equal amounts. In some embodiments, the pharmaceutical composition is for use in treating a human patient in a method described herein. In particular embodiments, the pharmaceutical composition is for use in enhancing immunity in a human patient in need thereof, e.g., for treating cancer.

The present invention also provides an anti-PD-1 antibody or an antigen-binding portion thereof as described herein for use in a treatment method described herein, e.g., enhancing immunity and/or treating cancer in a human patient in need thereof, in combination with an anti-TIM-3 antibody or an antigen-binding portion thereof and/or an anti-LAG-3 antibody or an antigen-binding portion thereof. The anti-TIM-3 antibody and the anti-LAG-3 antibody can be selected from those as described herein.

The present invention also provides an anti-PD-1 antibody or an antigen-binding portion thereof as described herein for use in treating a human patient in a method described herein.

The present invention also provides the use of an anti-PD-1 antibody or an antigen-binding portion thereof as described herein for the manufacture of a medicament for enhancing immunity and/or treating cancer in a patient in need thereof (e.g., a human patient), in combination with an anti-TIM-3 antibody or an antigen-binding portion thereof and/or an anti-LAG-3 antibody or an antigen-binding portion thereof. In some embodiments, the present invention provides the use of an anti-PD-1 antibody or an antigen-binding portion thereof as described herein, and an anti-TIM-3 antibody or an antigen-binding portion thereof and/or an anti-LAG-3 antibody or an antigen-binding portion thereof, for the manufacture of a medicament for enhancing immunity in a human patient in need thereof, e.g., for treating cancer. The anti-TIM-3 antibody and the anti-LAG-3 antibody can be selected from those as described herein.

The present invention also provides the use of an anti-PD-1 antibody or an antigen-binding portion thereof as described herein for the manufacture of a medicament for treating a human patient in a method described herein.

The present invention further provides an article of manufacture comprising an anti-PD-1 antibody or an antigen-binding portion thereof as described herein, in combination with an anti-TIM-3 antibody or an antigen-binding portion thereof and/or an anti-LAG-3 antibody or an antigen-binding portion thereof, wherein said article of manufacture is suitable for enhancing immunity and/or treating cancer in a patient (such as a human patient), e.g., in a treatment method described herein. The anti-TIM-3 antibody and the anti-LAG-3 antibody can be selected from those as described herein.

or with (Panel B) soluble anti-CD3 for 5 days prior to adding 1 µCi/well 3H-thymidine for an additional 18 hours. 3H-thymidine incorporation in the harvested cells was determined by liquid scintillation counting.

Figure 4:
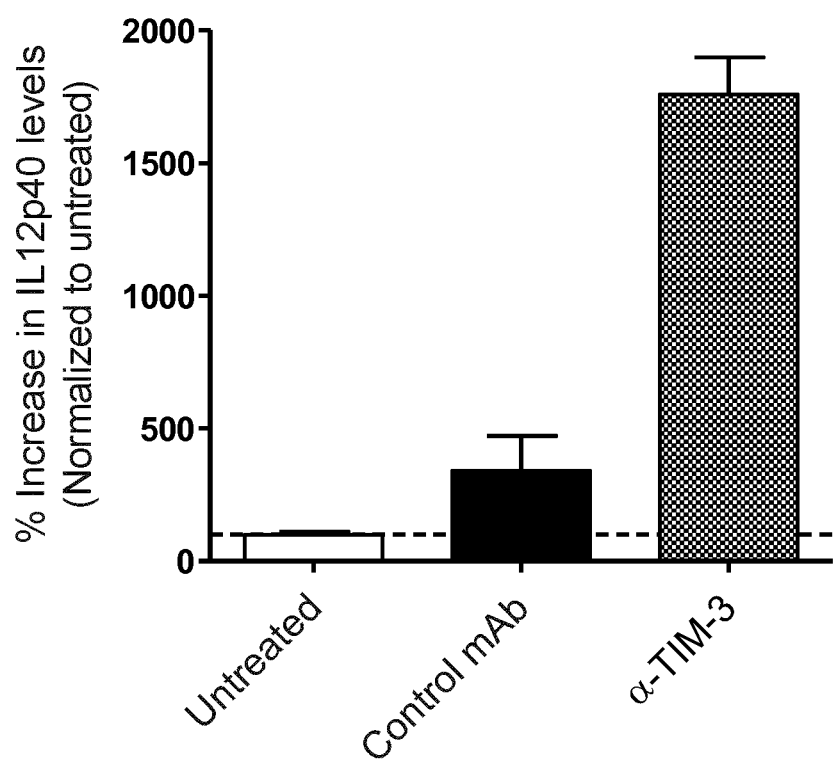

FIG. 4 is a graph showing the effect of anti-TIM-3 antibody 15086.17145 on IL-12p40 secretion from monocyte derived dendritic cells incubated for 5 days with 10 µg/mL of antibody. IL-12p40 levels in cell supernatants were determined using ELISA.

Figure 5:
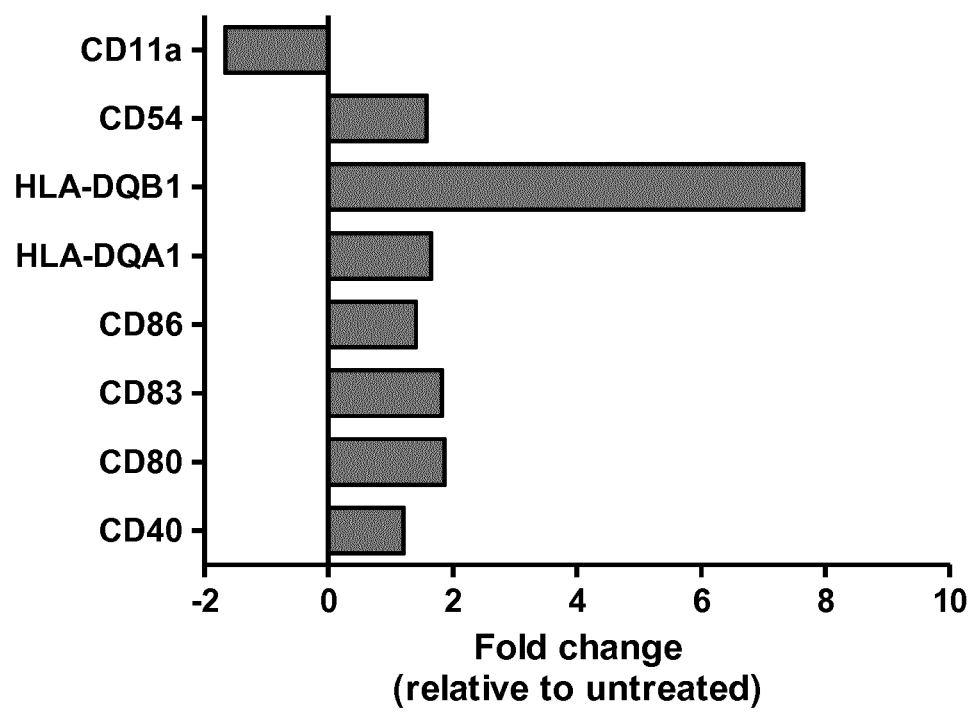
Figure 5:
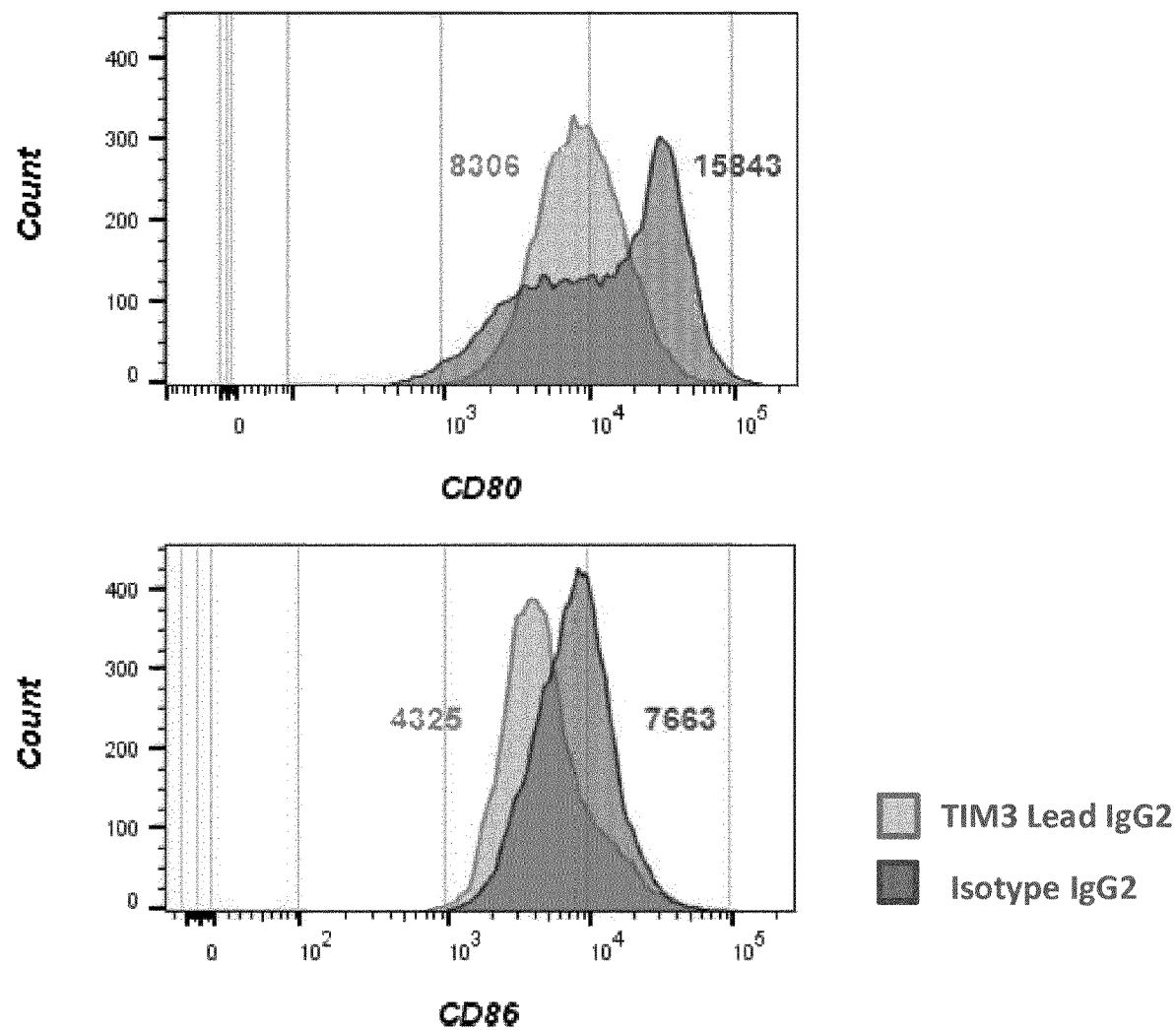

FIG. 5 is a pair of graphs showing expression levels of selected activation markers on monocyte derived dendritic cells after treatment with 25 µg/mL anti-TIM-3 antibody 15086.17145 for 24 hours. Panel A shows gene expression analysis of several activation markers and co-simulatory molecules. Panel B shows validation of increased CD80 and Cd86 levels using FACS. The histogram overlays shown are representative of CD11c+ dendritic cells, and numbers adjacent to the histograms denote MFI (mean fluorescence intensity) values.

Figure 6:
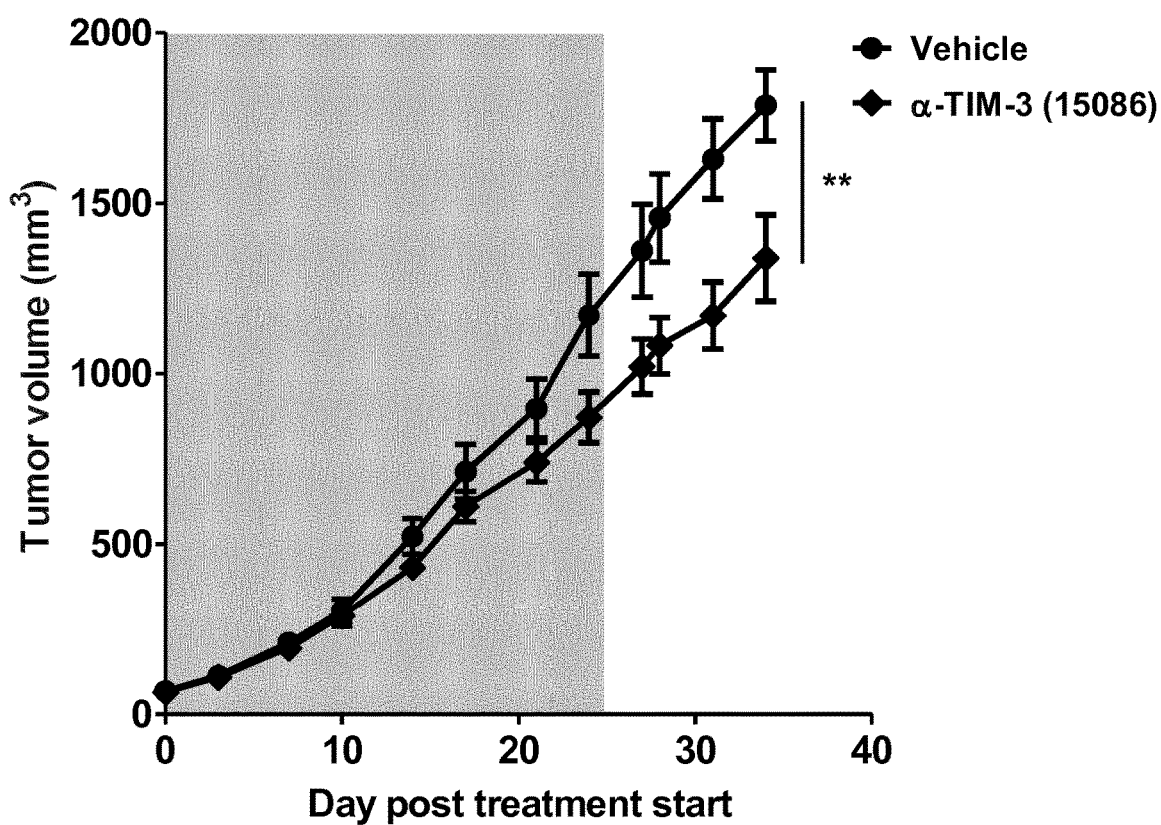

FIG. 6 is a graph showing the effect of TIM-3 targeting on tumor growth in a CD34+ humanized NSG-SGM3 mouse model engrafted with the human lung patient-derived xenograft (PDX) model LG1306. Mice were treated with anti-TIM-3 antibody 15086.17145 at an initial dose of 10 mg/kg followed by 5 mg/kg 5×QSD. The grey area denotes the treatment period. Data are presented as means±SEM. $**p<0.01$.

Figure 7:
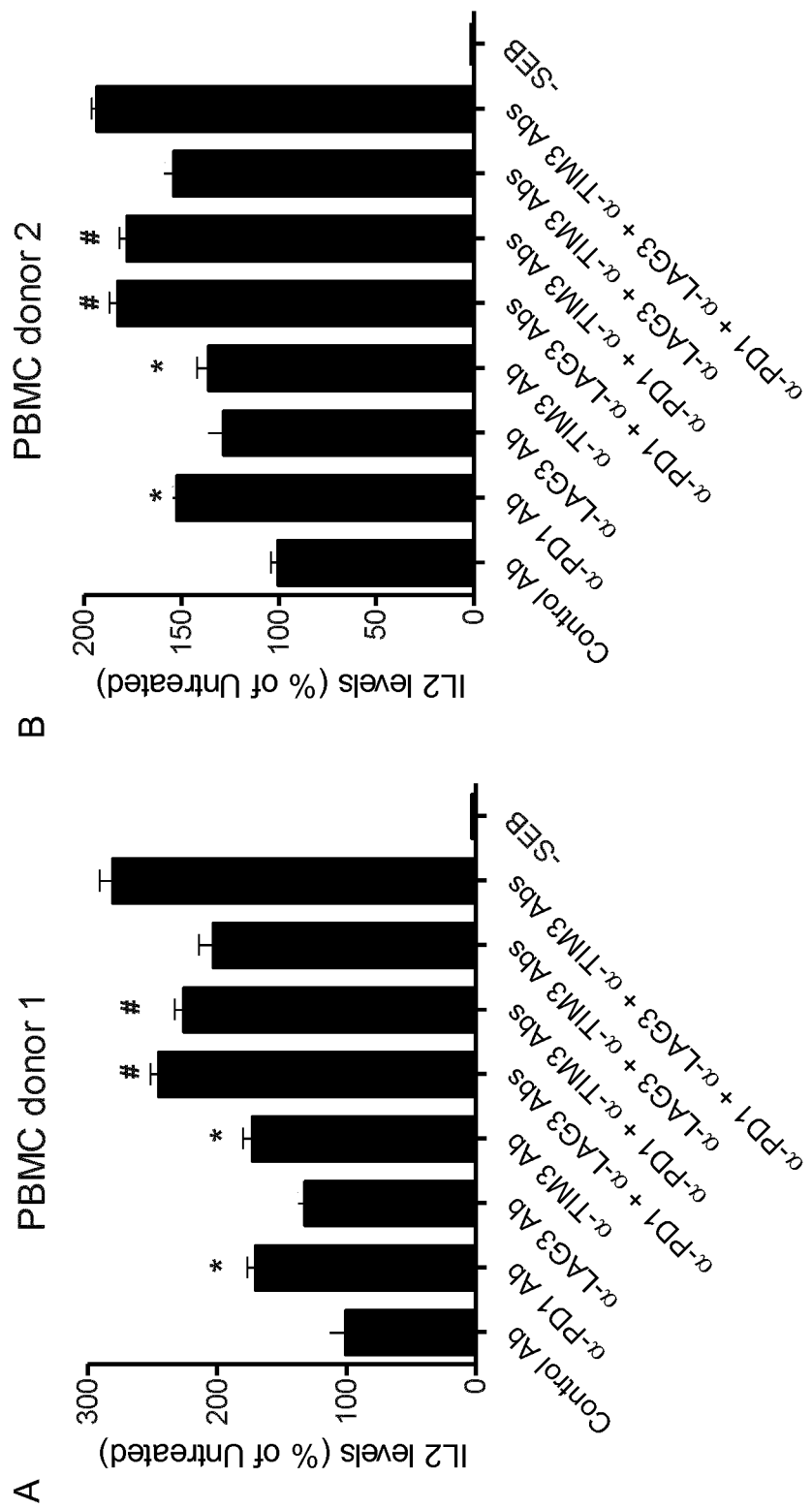

FIG. 7 is a pair of graphs showing the enhanced effect on IL-2 levels of combining anti-PD-1 antibody 12819 with anti-LAG-3 antibody 15532 and/or anti-TIM-3 antibody 15086.17145 in a SEB (Staphylococcal Enterotoxin B)+PBMC (peripheral blood mononuclear cell) assay for two donor pairs (Panels A and B). The bars indicate IL-2 secretion from PBMCs treated with 10 µg/mL of the indicated antibodies or antibody mixtures, and SEB, for 48 hours. Signs above the bars indicate single treatments that are significantly different ($p<0.05$) from control antibody (*) or mixtures of two antibodies that are significantly different from the constituent single antibody treatments (#).

Figure 8:
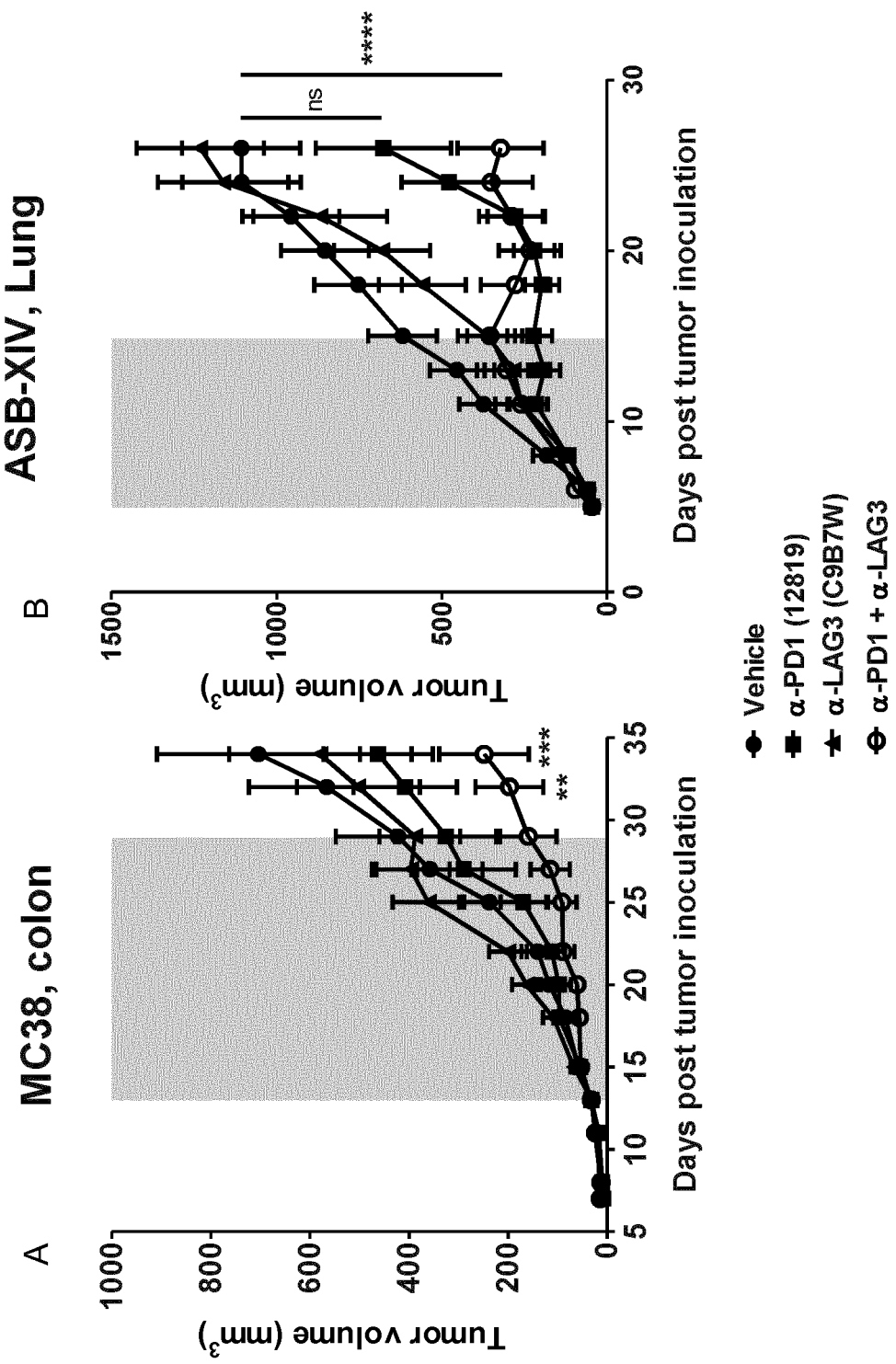

FIG. 8 is a pair of graphs showing the effect on tumor growth of 10 mg/kg of anti-PD-1 antibody 12819, anti-LAG-3 antibody C9B7W (which is reactive with mouse LAG-3), or the combination of anti-PD-1 and anti-LAG-3 antibodies, or vehicle treatment, in two syngeneic mouse tumor models: MC38 (colon cancer, Panel A) and ASB-XIV (lung cancer, Panel B). The grey area denotes the treatment period. Data are presented as means±SEM (standard error of the mean). $p<0.01$, $*p<0.001$, $****p<0.0001$.

Figure 9:
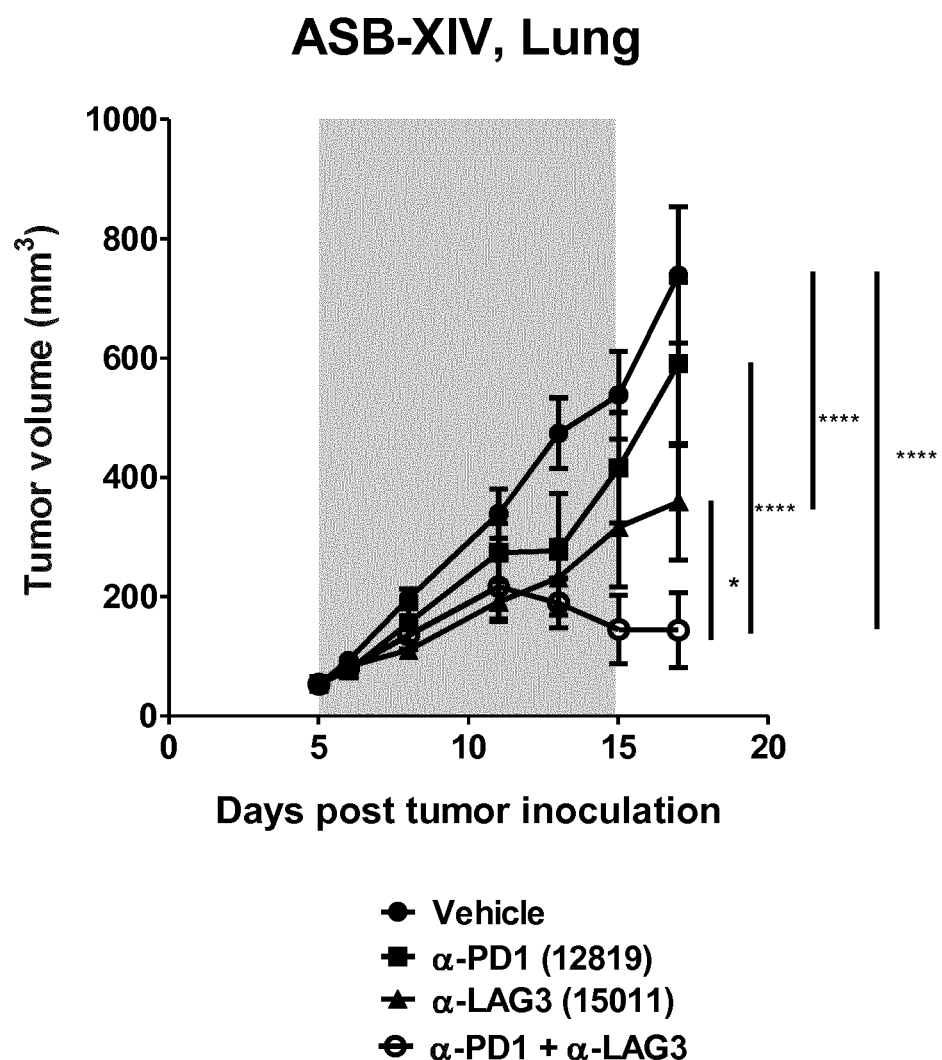

FIG. 9 is a graph showing the effect on tumor growth of 10 mg/kg of anti-PD-1 antibody 12819, anti-LAG-3 antibody 15011, or the combination of anti-PD-1 and anti-LAG-3 antibodies, or vehicle treatment, in the ASB-XIV syngeneic mouse tumor model. The grey area denotes the treatment period. Data are presented as means±SEM. $*p<0.05$, $****p<0.0001$.

Figure 10:
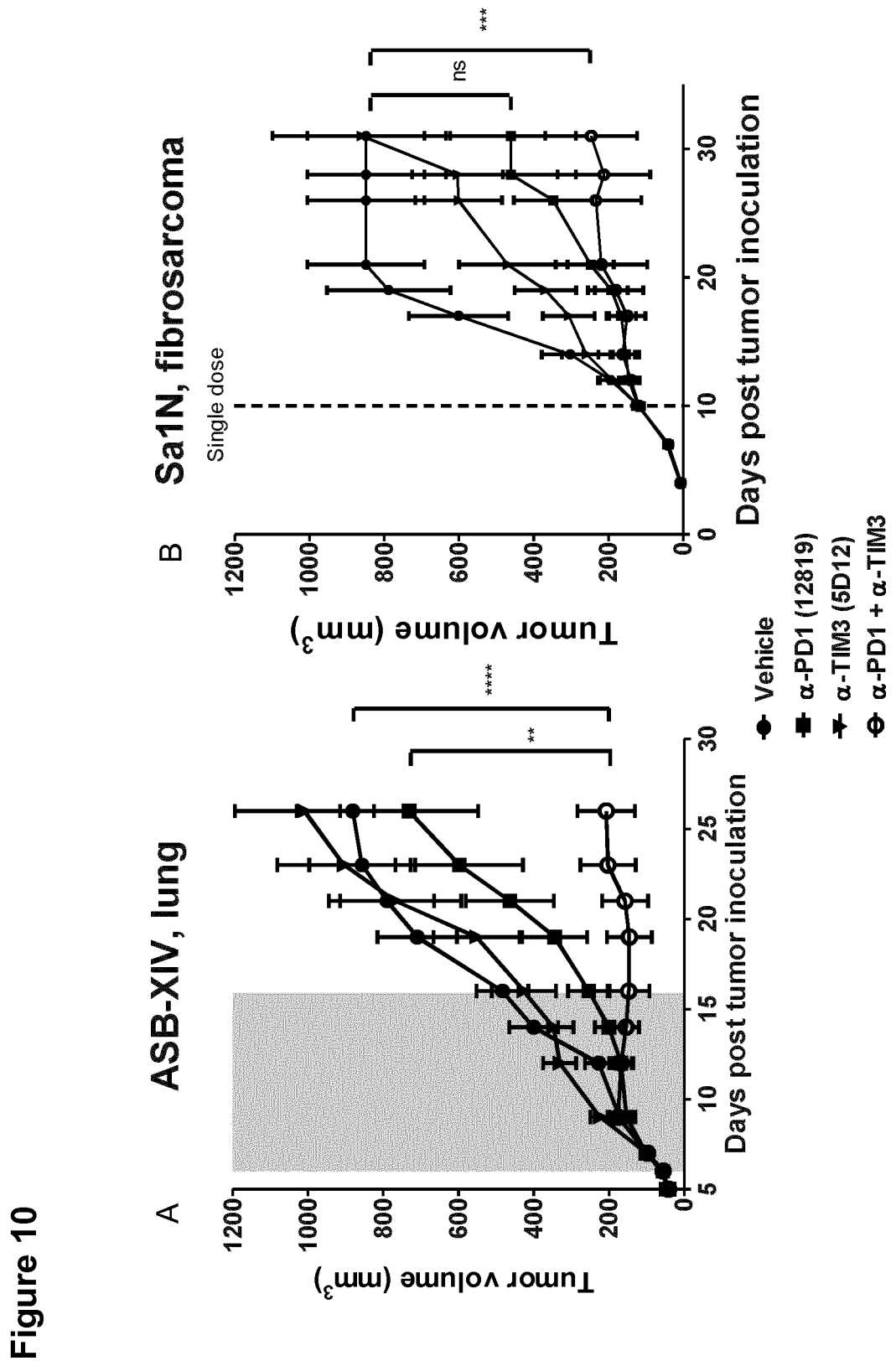

FIG. 10 is a pair of graphs showing the effect on tumor growth of anti-PD-1 antibody 12819, anti-TIM-3 antibody 5D12, or the combination of anti-PD-1 and anti-TIM-3 antibodies, or vehicle treatment, on tumor growth in two syngeneic mouse tumor models: ASB-XIV (lung cancer, Panel A) and Sa1N (fibrosarcoma, Panel B). The antibody treatments were administered at a dose of 10 mg/kg/target in mice with ASB-XIV tumors. Mice with Sa1N tumors were dosed with anti-PD-1 and anti-TIM-3 antibodies at 1 mg/kg and 10 mg/kg, respectively. The grey area denotes the treatment period. Data are presented as means±SEM. $p<0.01$, $*p<0.001$, and $****p<0.0001$.

Figure 11:
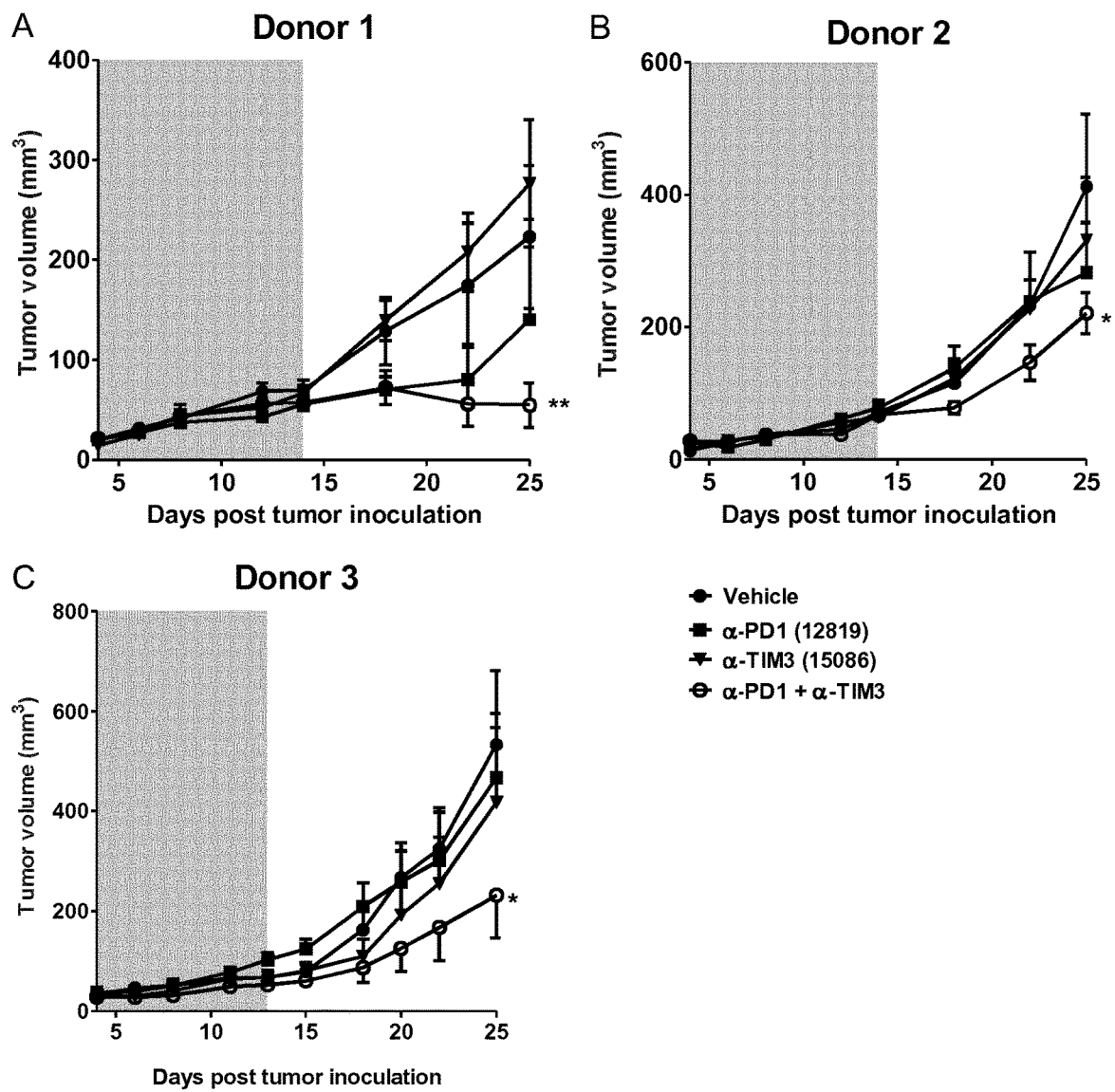

FIG. 11 is a set of graphs showing the effect on tumor growth of 10 mg/kg anti-PD-1 antibody 12819, anti-TIM-3 antibody 15086, or the combination of anti-PD-1 and anti-TIM-3 antibodies, or vehicle treatment, in a human xenograft tumor model, where the human melanoma cell line A375 was engrafted in mice reconstituted with human PBMC. One human PBMC donor was used in each experiment and the three graphs represent three different donors (Panels A-C). The grey area denotes the treatment period. Data are presented as means±SEM. $*p<0.05$ and $**p<0.01$.

Figure 12:
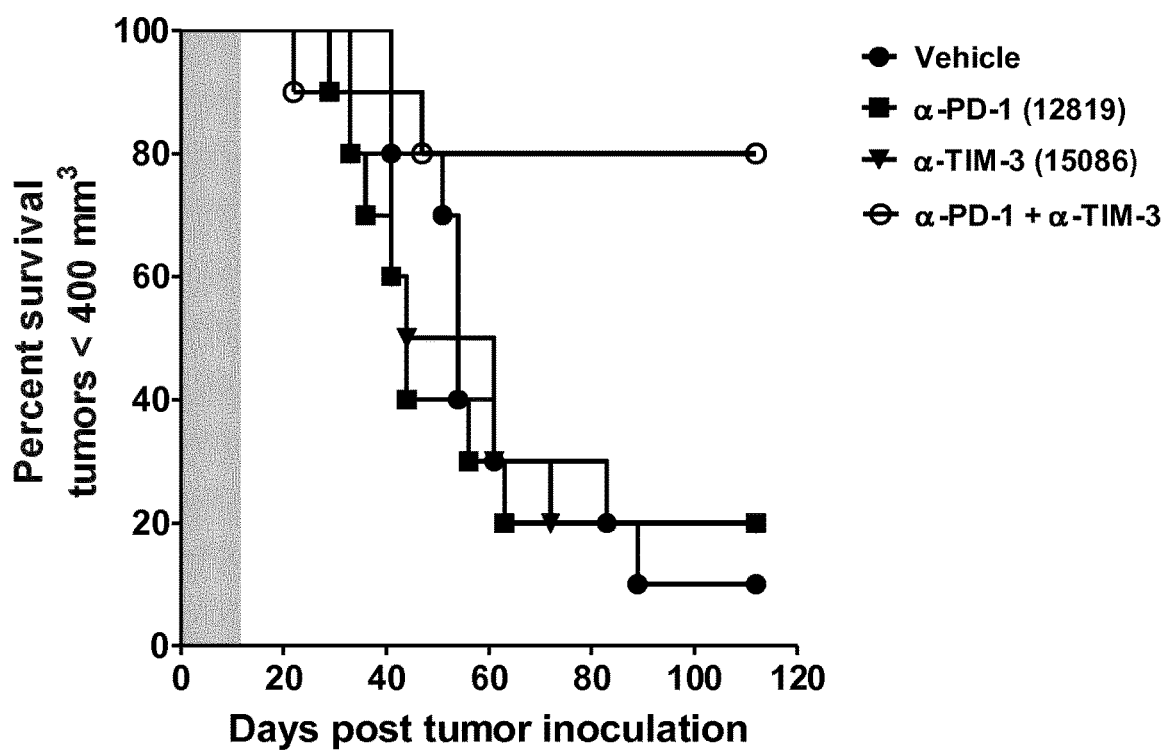
Figure 12:
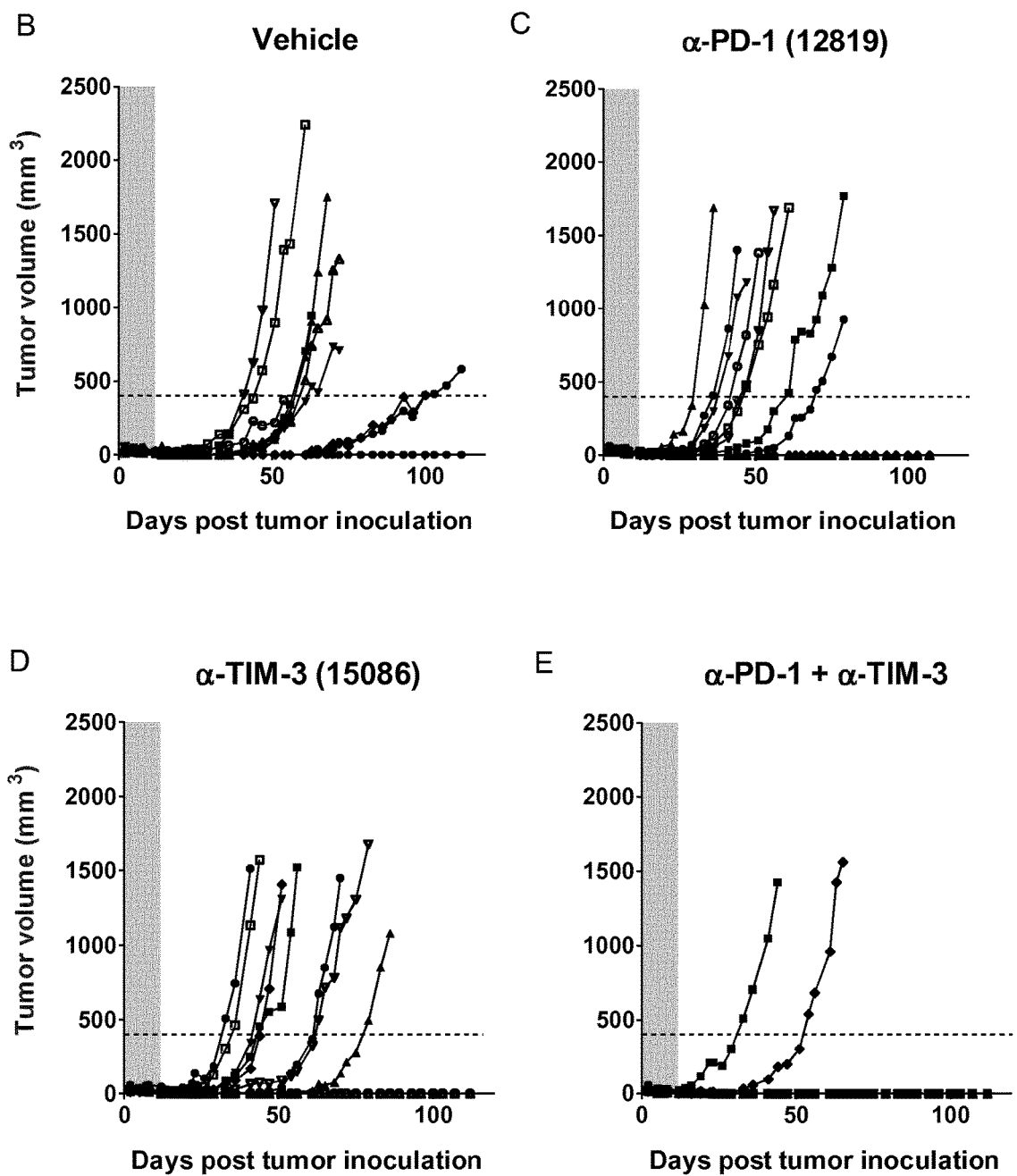

FIG. 12 is a set of graphs showing the effect of single and dual targeting of PD-1 and TIM-3 on percent survival (Panel A) and tumor growth (Panels B-E) in NOD-scid mice engrafted with a mixture of human PBMCs and A375 melanoma cells. The mice were treated with anti-PD-1 antibody 12819, anti-TIM-3 antibody 15086.17145, or a combination of the anti-PD-1 and anti-TIM-3 antibodies. The antibody treatments were administered at a dose of 10 mg/kg three times weekly for each antibody. The grey area denotes the treatment period. Data in Panel A are presented as percentage of mice with tumor size <400 mm$^3$ in each treatment group over time.

Figure 13:
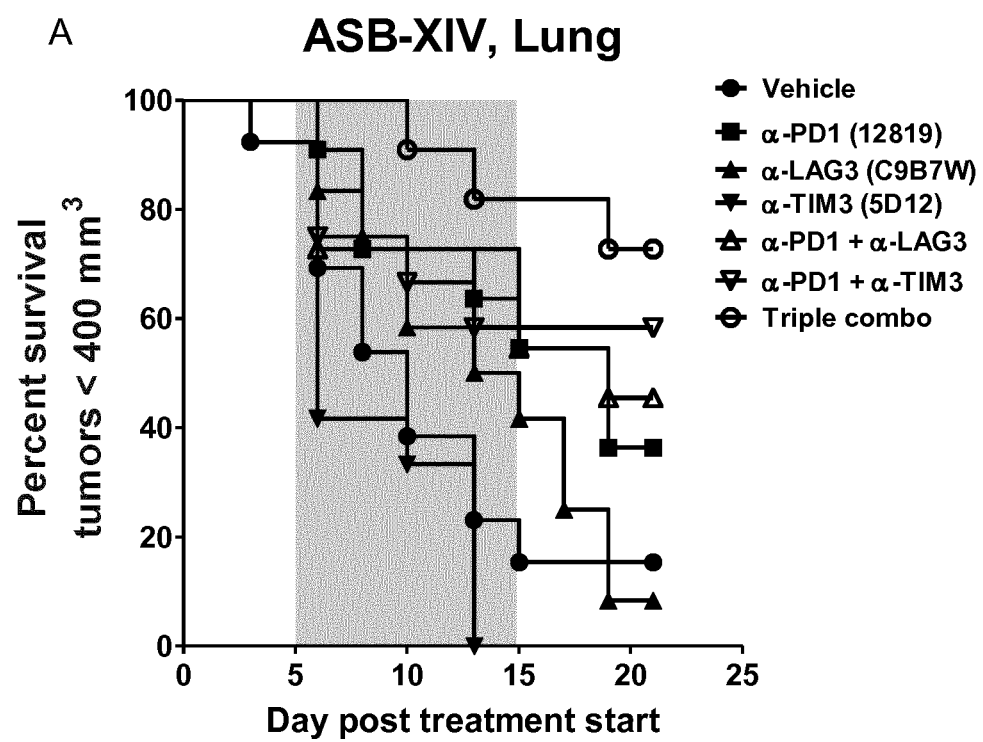
Figure 13:
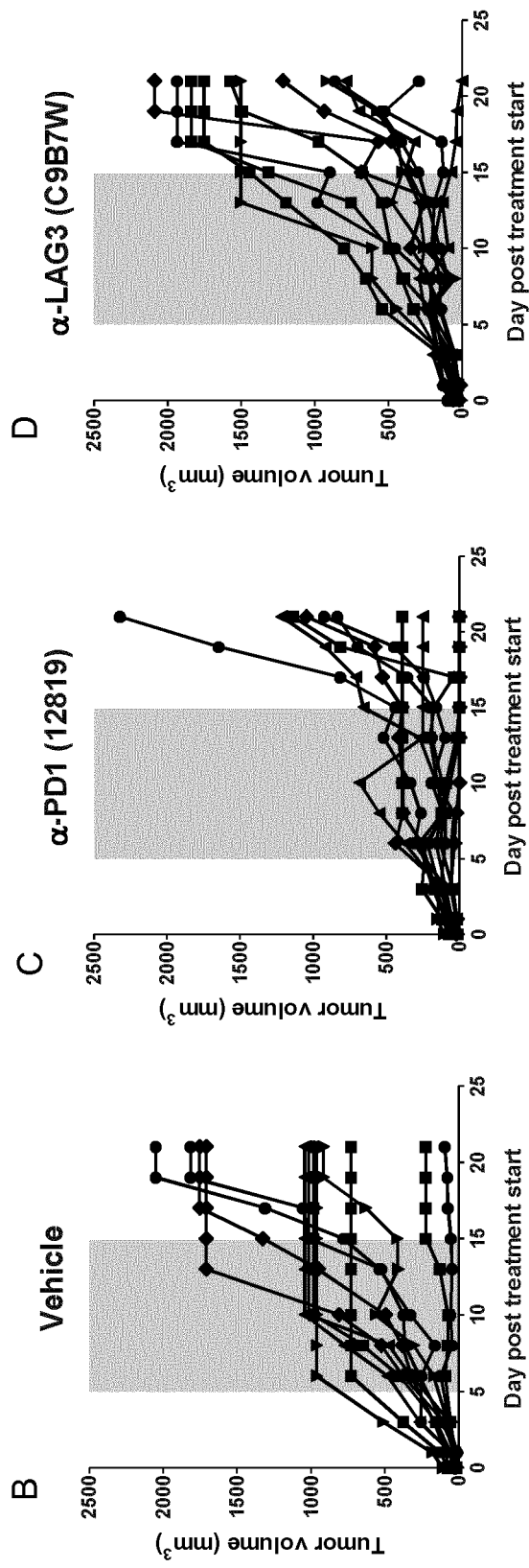
Figure 13:
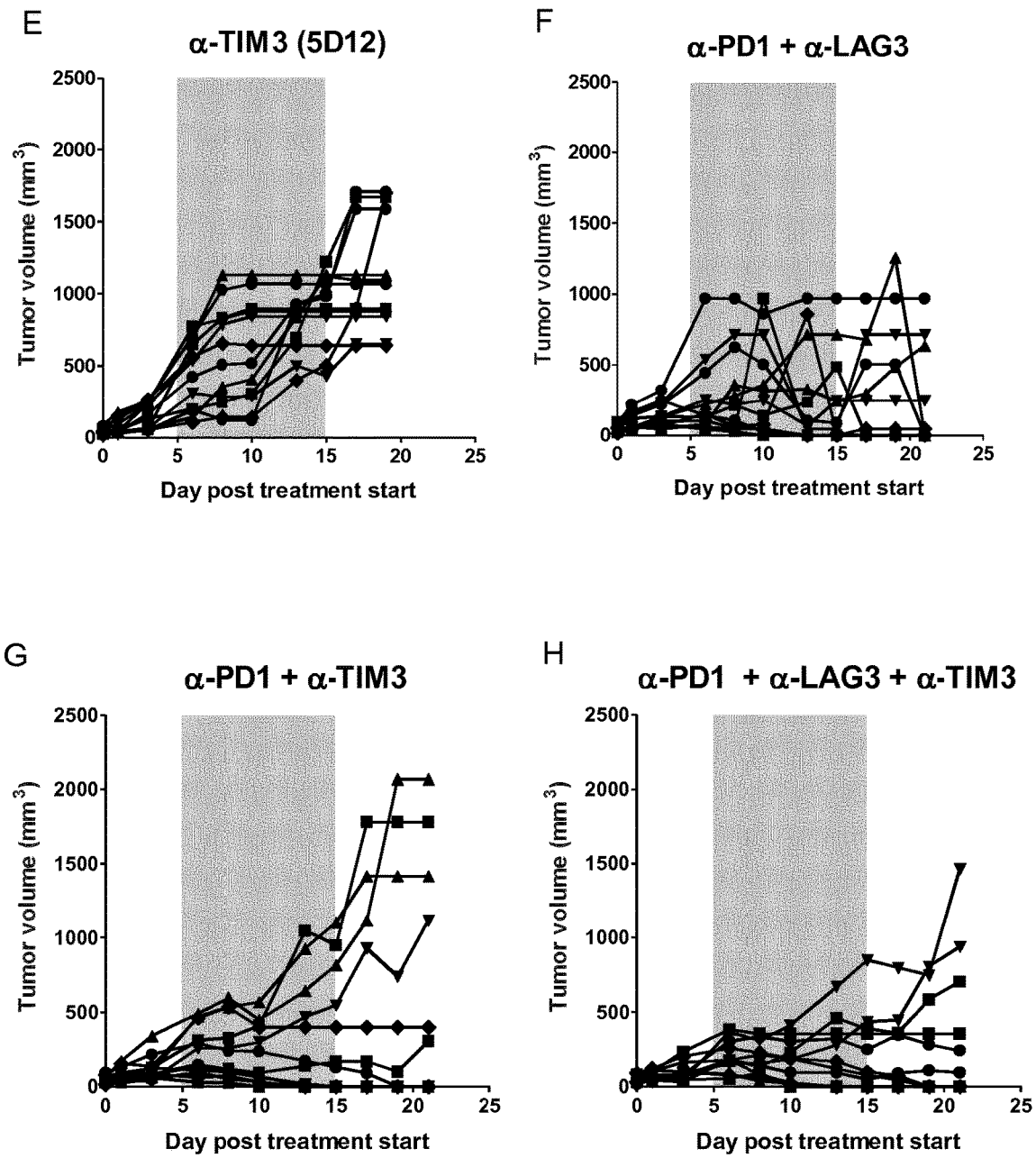

FIG. 13 is a set of graphs showing the effect of single, dual, and triple targeting of PD-1, LAG-3 and TIM-3 on percent survival (Panel A) and tumor growth (Panels B-H) in the ASB-XIV syngeneic tumor model using anti-PD-1 antibody 12819, anti-LAG-3 antibody C9B7W, anti-TIM-3 antibody 5D12, the combination of anti-PD1 and anti-LAG3 antibodies, the combination of anti-PD1 and anti-TIM-3 antibodies, or the "triple combo" (which refers to the combination of the anti-PD-1, anti-LAG-3, and anti-TIM-3 antibodies). The antibody treatments were administered at a dose of 10 mg/kg for each antibody. The grey area denotes the treatment period.

DETAILED DESCRIPTION OF THE INVENTION

The present invention provides new combination therapies and compositions that target human PD-1, human TIM-3, and/or human LAG-3 by using antibodies that bind these targets. The therapies and compositions can be used to enhance the immune system in a human patient, such as a cancer patient. Unless otherwise stated, as used herein, "PD-1" refers to human PD-1. A human PD-1 polypeptide sequence is available under Uniprot Accession No. Q15116, shown here as SEQ ID NO: 388. Unless otherwise stated, as used herein, "TIM-3" refers to human TIM-3. A human TIM-3 polypeptide sequence is available under Uniprot Accession No. Q8TDQ0, shown here as SEQ ID NO: 389. Unless otherwise stated, as used herein, "LAG-3" refers to human LAG-3. A human LAG-3 polypeptide sequence is available under Uniprot Accession No. P18627, shown here as SEQ ID NO: 390.

The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. Each heavy chain is comprised of a heavy chain variable domain (VH) and a heavy chain constant region (CH). Each light chain is composed of a light chain variable domain (VL) and a light chain constant region (CL). The VH and VL domains can be subdivided further into regions of hypervariability, termed "complementarity determining regions" (CDRs), interspersed with regions that are more conserved, termed "framework regions" (FRs). Each VH and VL is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. The assignment of amino acid numbers in the heavy or light chain may be in accordance with IMGT® definitions (Lefranc et al., *Dev Comp Immunol* 27(1):55-77 (2003)); or the definitions of Kabat, *Sequences of Proteins of Immunological Interest* (National Institutes of Health, Bethesda, MD (1987 and 1991)); Chothia & Lesk, *J. Mol. Biol.* 196:901-917 (1987); or Chothia et al., *Nature* 342:878-883 (1989). Unless otherwise indicated, all antibody amino acid residue numbers referred to in this disclosure are those under the IMGT® numbering scheme.

The term "recombinant antibody" refers to an antibody that is expressed from a cell or cell line comprising the nucleotide sequence(s) that encode the antibody, wherein said nucleotide sequence(s) are not naturally associated with the cell.

The term "isolated protein", "isolated polypeptide" or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, and/or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind to an antigen when the $K_D$ is 1 mM, preferably 100 nM. A $K_D$ binding affinity constant can be measured, e.g., by surface plasmon resonance (SPR) (BIAcore™) or Bio-Layer Interferometry, for example using the *IBIS* MX96 SPR system from *IBIS* Technologies, the ProteOn™ XPR36 SPR system from Bio-Rad, or the Octet™ system from ForteBio.

The term "$k_{off}$" refers to the dissociation rate constant of a particular antibody-antigen interaction. A $k_{off}$ dissociation rate constant can be measured, e.g., by Bio-Layer Interferometry, for example using one of the systems listed above.

The term "epitope" as used herein refers to a portion (determinant) of an antigen that specifically binds to an antibody or a related molecule such as a bi-specific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest or a relevant portion thereof, then screening for binding to the epitope.

One can determine whether an antibody binds to the same epitope as, or competes for binding with, an antibody as described herein by using methods known in the art, including, without limitation, competition assays, epitope binning, and alanine scanning. In some embodiments, the test antibody and an antibody as described herein bind to at least one common residue (e.g., at least two, three, four, five, six, seven, eight, or nine residues) on the target protein (i.e., TIM-3, PD-1, or LAG-3). In further embodiments, the contact residues on the target protein are completely identical between the test antibody and the antibody as described herein. In one embodiment, one allows the antibody as described herein to bind to the target protein under saturating conditions and then measures the ability of the test antibody to bind to the target protein. If the test antibody is able to bind to the target protein at the same time as the reference antibody, then the test antibody binds to a different epitope than the reference antibody. However, if the test antibody is not able to bind to the target protein at the same time, then the test antibody binds to the same epitope, an overlapping epitope, or an epitope that is in close proximity to the epitope bound by the antibody as described herein. This experiment can be performed using, e.g., ELISA, RIA, BIACORE™, SPR, Bio-Layer Interferometry or flow cytometry. To test whether an antibody cross-competes with another antibody, one may use the competition method described above in two directions, i.e., determining if the known antibody blocks the test antibody and vice versa. Such cross-competition experiments may be performed e.g. using an IBIS MX96 SPR instrument or the Octet™ system.

The term "chimeric antibody" refers in its broadest sense to an antibody that contains one or more regions from one antibody and one or more regions from one or more other antibodies, typically an antibody that is partially of human origin and partially of non-human origin, i.e., derived in part from a non-human animal, for example a mouse, rat or other rodent, or an avian such as a chicken. Chimeric antibodies are preferred over non-human antibodies in order to reduce the risk of a human anti-antibody response, e.g., a human anti-mouse antibody response in the case of a murine antibody. An example of a typical chimeric antibody is one in which the variable domain sequences are murine while the constant region sequences are human. In the case of a chimeric antibody, the non-human parts may be subjected to further alteration in order to humanize the antibody. The chimeric antibodies described herein have chicken variable domain sequences and human constant region sequences.

The term "humanize" refers to the fact that where an antibody is wholly or partially of non-human origin (for example, a murine or chicken antibody obtained from immunization of mice or chickens, respectively, with an antigen of interest, or a chimeric antibody based on such a murine or chicken antibody), it is possible to replace certain amino acids, in particular in the framework regions and constant regions of the heavy and light chains, in order to avoid or minimize an immune response in humans. Although it is not possible to precisely predict the immunogenicity and thereby the human anti-antibody response of a particular antibody, non-human antibodies tend to be more immunogenic in humans than human antibodies. Chimeric antibodies, where the foreign (e.g., rodent or avian) constant regions have been replaced with sequences of human origin, have been shown to be generally less immunogenic than antibodies of fully foreign origin, and the trend in therapeutic antibodies is towards humanized or fully human antibodies. Chimeric antibodies or other antibodies of non-human origin thus can be humanized to reduce the risk of a human anti-antibody response.

For chimeric antibodies, humanization typically involves modification of the framework regions of the variable domain sequences. Amino acid residues that are part of complementarity determining regions (CDRs) most often will not be altered in connection with humanization, although in certain cases it may be desirable to alter individual CDR amino acid residues, for example to remove a glycosylation site, a deamidation site, an aspartate isomerization site or an undesired cysteine or methionine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, preferably by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues.

Numerous methods for humanization of an antibody sequence are known in the art; see, e.g., the review by Almagro & Fransson, *Front Biosci.* 13:1619-1633 (2008). One commonly used method is CDR grafting, which for, e.g., a murine-derived chimeric antibody involves identification of human germline gene counterparts to the murine variable domain genes and grafting of the murine CDR sequences into this framework. The specificity of an antibody's interaction with a target antigen resides primarily in the amino acid residues located in the six CDRs of the heavy and light chain. The amino acid sequences within CDRs are therefore much more variable between individual antibodies than sequences outside of CDRs. Because CDR sequences are responsible for most antibody-antigen interactions, it is possible to express recombinant antibodies that mimic the properties of a specific naturally occurring antibody, or more generally any specific antibody with a given amino acid sequence, e.g., by constructing expression vectors that express CDR sequences from the specific antibody grafted into framework sequences from a different antibody. As a result, it is possible to "humanize" a non-human antibody and still substantially maintain the binding specificity and affinity of the original antibody. CDR grafting may be based on the Kabat CDR definitions, although a more recent publication (Magdelaine-Beuzelin et al., *Crit Rev. Oncol Hematol.* 64:210-225 (2007)) has suggested that the IMGT® definition (the international ImMunoGeneTics information System®, www.imgt.org) may improve the result of the humanization (see Lefranc et al., *Dev. Comp Immunol.* 27:55-77 (2003)).

In some cases, CDR grafting may reduce the binding specificity and affinity, and thus the biological activity, of a CDR-grafted non-human antibody as compared to the parent antibody from which the CDRs are obtained. Back mutations (sometimes referred to as "framework repair") may be introduced at selected positions of the CDR-grafted antibody, typically in the framework regions, in order to reestablish the binding specificity and affinity of the parent antibody. Positions for possible back mutations can be identified using information available in the literature and in antibody databases. Amino acid residues that are candidates for back mutations are typically those that are located at the surface of an antibody molecule, while residues that are buried or that have a low degree of surface exposure will not normally be altered.

An alternative humanization technique to CDR grafting and back mutation is resurfacing, in which non-surface exposed residues of non-human origin are retained, while surface residues are altered to human residues.

In certain cases, it may be desirable to alter one or more CDR amino acid residues in order to improve binding affinity to the target epitope. This is known as "affinity maturation." Various affinity maturation methods are known in the art, for example the in vitro scanning saturation mutagenesis method described by Burks et al., *Proc Natl Acad Sci USA,* 94:412-417 (1997), and the stepwise in vitro affinity maturation method of Wu et al., *Proc Natl Acad Sci USA* 95:6037-6042 (1998).

The term "human antibody" refers to an antibody in which the variable domain and constant region sequences are derived from human sequences. The term encompasses antibodies with sequences that are derived from human genes but have been modified, e.g., to decrease immunogenicity, increase affinity, and/or increase stability. Further, the term encompasses antibodies produced recombinantly using human-derived sequences in nonhuman cells, which may impart glycosylation not typical of human cells. The term also encompasses antibodies produced in transgenic nonhuman organisms with human antibody genes (e.g., OmniRat® rats).

The term "antigen-binding portion" of an antibody (or simply "antibody portion"), as used herein, refers to one or more portions or fragments of an antibody that retain the ability to specifically bind to an antigen (e.g., human TIM-3, human PD-1, or human LAG-3, or a portion thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the $V_L$, $V_H$, $C_L$ and $C_H 1$ domains; (ii) a $F(ab')_2$ fragment: a bivalent fragment comprising two Fab fragments linked by a disulfide bridge at the hinge region; (iii) an Fd fragment consisting of the $V_H$ and $C_H 1$ domains; (iv) a Fv fragment consisting of the VL and $V_H$ domains of a single arm of an antibody, (v) a dAb fragment, which consists of a $V_H$ domain; and (vi) an isolated complementarity determining region (CDR) capable of specifically binding to an antigen. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ domains pair to form monovalent molecules (known as single chain Fv (scFv)). Also within the invention are antigen-binding molecules comprising a $V_H$ and/or a $V_L$. In the case of a $V_H$, the molecule may also comprise one or more of a CH1, hinge, CH2, or CH3 region. Such single chain antibodies are also intended to be encompassed within the term "antigen-binding portion" of an antibody. Other forms of single chain antibodies, such as diabodies, are also encompassed. Diabodies are bivalent, bi-specific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and F(ab')$_2$ fragments, can be prepared from whole antibodies using conventional techniques, such as papain or pepsin digestion of whole antibodies. Moreover, antibodies, antibody portions and immunoadhesion molecules can be obtained using standard recombinant DNA techniques, e.g., as described herein.

The class (isotype) and subclass of antibodies described herein may be determined by any method known in the art. In general, the class and subclass of an antibody may be determined using antibodies that are specific for a particular class and subclass of antibody. Such antibodies are available commercially. The class and subclass can be determined by ELISA and Western Blot as well as other techniques. Alternatively, the class and subclass may be determined by sequencing all or a portion of the constant regions of the heavy and/or light chains of the antibodies, comparing their amino acid sequences to the known amino acid sequences of various classes and subclasses of immunoglobulins, and determining the class and subclass of the antibodies. A preferred isotype of the present invention is an IgG isotype.

When referring to particular amino acid residues in a given position of an antibody sequence, an indication of, e.g., "35S" refers to the position and residue, i.e., in this case indicating that a serine residue (S) is present in position 35 of the sequence. Similarly, an indication of, e.g., "13Q+35S" refers to the two residues in the respective positions. Unless otherwise indicated, all antibody amino acid residue numbers referred to in this disclosure are those under the IMGT® numbering scheme.

Anti-PD-1 Antibodies

In some embodiments, the anti-PD-1 antibodies disclosed herein may be chimeric, with variable domains derived from chickens and human constant regions, or may be humanized.

The anti-PD-1 antibodies disclosed herein may be referred to by either a 5-digit number, e.g., "12819," or by a 10-digit number, e.g., "12819.15384." As used herein, the 5-digit number refers to all antibodies having the heavy and light chain CDR1-3 sequences shown for that number, whereas the use of a 10-digit number refers to a particular humanized variant. For example, 12819.15384 is a particular humanized variant having the CDR sequences of a 12819 antibody. The 5-digit number encompasses, for example, 10-digit variants that are identical except for some changes in the FRs (e.g., lacking residues SY at the N-terminus of the mature light chain, or having residues SS in lieu of SY). These modifications do not change the functional (e.g., antigen-binding) properties of the antibodies.

In some embodiments, the combination therapy or composition comprises an anti-PD-1 antibody or an antigen-binding portion thereof, wherein the anti-PD-1 antibody is the antibody referred to herein as antibody 12819.15384, 12748.15381, 12748.16124, 12865.15377, 12892.15378, 12796.15376, 12777.15382, 12760.15375 or 13112.15380 or a variant of any of these, where the variant may, e.g., contain certain minimum amino acid changes relative to said antibody (e.g., 1, 2, 3, 4, 5, 6, 7, 8, 9, or 10 amino acid changes, which may be, e.g., in the framework regions) without losing the antigen-binding specificity of the antibody.

In some embodiments, the anti-PD-1 antibody competes for binding to human PD-1 with, or binds to the same epitope of human PD-1 as, any one of antibodies 12819.15384, 12748.15381, 12748.16124, 12865.15377, 12892.15378, 12796.15376, 12777.15382, 12760.15375 and 13112.15380.

In some embodiments, any of the anti-PD-1 antibodies or antigen-binding portions described herein may compete or cross-compete for binding to PD-1 with 12865, 12892, and 12777 antibodies (e.g., antibodies 12865.15377, 12892.15378, and 12777.15382). In some embodiments, any of the anti-PD-1 antibodies or antigen-binding portions described herein may compete or cross-compete for binding to PD-1 with a 12819 antibody (e.g., antibody 12819.15384). In some embodiments, any of the anti-PD-1 antibodies or antigen-binding portions described herein may compete or cross-compete for binding to PD-1 with 12760 and 13112 antibodies (e.g., antibodies 12760.15375 and 13112.15380). In some embodiments, the antibody has an IgG1 or IgG2 format. In certain embodiments, the antibody has an IgG1 format.

In some embodiments, the anti-PD-1 antibody competes or cross-competes for binding to human PD-1 with, or binds to the same epitope of human PD-1 as, an antibody whose heavy chain (H) CDR1-3 and light chain (L) CDR1-3 comprise, respectively, SEQ ID NOs: 228-233, 238-243, 248-253, 258-263, 268-273, 278-283, 288-293, or 298-303.

In some embodiments, the anti-PD-1 antibody comprises an H-CDR3 comprising the H-CDR3 amino acid sequence of SEQ ID NO: 230, 240, 250, 260, 270, 280, 290, or 300.

In some embodiments, the anti-PD-1 antibody comprises H-CDR1-3 comprising the H-CDR1-3 amino acid sequences, respectively, of SEQ ID NOs: 228-230, 238-240, 248-250, 258-260, 268-270, 278-280, 288-290, or 298-300.

In some embodiments, the anti-PD-1 antibody has a VH that is at least 90% (e.g., at least 92%, at least 95%, at least 96%, at least 97%, at least 98%, or at least 99%) identical in amino acid sequence to SEQ ID NO: 226, 236, 246, 256, 266, 276, 286, or 296.

In some embodiments, the anti-PD-1 antibody has a VH that comprises SEQ ID NO: 226, 236, 246, 256, 266, 276, 286, or 296.

In some embodiments, the anti-PD-1 antibody has a VH that is at least 90% (e.g., at least 92%, at least 95%, at least 96%, at least 97%, at least 98%, or at least 99%) identical in sequence to SEQ ID NO: 226, 236, 246, 256, 266, 276, 286, or 296; and a CH that is at least 90% (e.g., at least 92%, at least 95%, at least 96%, at least 97%, at least 98%, or at least 99%) identical in sequence to SEQ ID NO: 375.

In some embodiments, the anti-PD-1 antibody has an HC that comprises the VH amino acid sequence of SEQ ID NO: 226, 236, 246, 256, 266, 276, 286, or 296 and the CH amino acid sequence of SEQ ID NO: 375.

In some embodiments, the anti-PD-1 antibody has an L-CDR3 comprising the L-CDR3 amino acid sequence of SEQ ID NO: 233, 243, 253, 263, 273, 283, 293, or 303.

In some embodiments, the anti-PD-1 antibody comprises L-CDR1-3 comprising the L-CDR1-3 amino acid sequences, respectively, of SEQ ID NOs: 231-233, 241-243, 251-253, 261-263, 271-273, 281-283, 291-293, or 301-303.

In some embodiments, the anti-PD-1 antibody has a VL that is at least 90% (e.g., at least 92%, at least 95%, at least 96%, at least 97%, at least 98%, or at least 99%) identical in sequence to the VL amino acid sequence of SEQ ID NO: 227, 237, 247, 257, 267, 277, 287, 297, or 392.

In some embodiments, the anti-PD-1 antibody has a VL that comprises the VL amino acid sequence of SEQ ID NO: 227, 237, 247, 257, 267, 277, 287, 297, or 392.

In some embodiments, the anti-PD-1 antibody has a VL that is at least 90% (e.g., at least 92%, at least 95%, at least 96%, at least 97%, at least 98%, or at least 99%) identical in sequence to the VL amino acid sequence of SEQ ID NO: 227, 237, 247, 257, 267, 277, 287, 297, or 392; and a CL that is at least 90% (e.g., at least 92%, at least 95%, at least 96%, at least 97%, at least 98%, or at least 99%) identical in sequence to SEQ ID NO: 379.

In some embodiments, the anti-PD-1 antibody has a LC that comprises the VL amino acid sequence of SEQ ID NO: 227, 237, 247, 257, 267, 277, 287, 297, or 392 and the CL amino acid sequence of SEQ ID NO: 379.

In some embodiments, the anti-PD-1 antibody comprises any of the above heavy chain sequences and any of the above light chain sequences.

In some embodiments, the anti-PD-1 antibody comprises an H-CDR3 and L-CDR3 comprising the H-CDR3 and L-CDR3 amino acid sequences, respectively, of SEQ ID NOs: 230 and 233, 240 and 243, 250 and 253, 260 and 263, 270 and 273, 280 and 283, 290 and 293, or 300 and 303.

In some embodiments, the anti-PD-1 antibody comprises H-CDR1-3 and L-CDR1-3 comprising the H-CDR1-3 and L-CDR1-3 sequences, respectively, of SEQ ID NOs: 228-233, 238-243, 248-253, 258-263, 268-273, 278-283, 288-293, or 298-303.

In some embodiments, the anti-PD-1 antibody comprises a VH that is at least 90% (e.g., at least 92%, at least 95%, at least 96%, at least 97%, at least 98%, or at least 99%) identical in sequence to the amino acid sequence of SEQ ID NO: 226, 236, 246, 256, 266, 276, 286, or 296, and a VL that is at least 90% (e.g., at least 92%, at least 95%, at least 96%, at least 97%, at least 98%, or at least 99%) identical in sequence to the amino acid sequence of SEQ ID NO: 227, 237, 247, 257, 267, 277, 287, 297, or 392.

In some embodiments, the anti-PD-1 antibody has a VH that comprises the amino acid sequence of SEQ ID NO: 226, 236, 246, 256, 266, 276, 286, or 296, and a VL that comprises the amino acid sequence of SEQ ID NO: 227, 237, 247, 257, 267, 277, 287, 297, or 392.

In some embodiments, the anti-PD-1 antibody has an HC that comprises the amino acid sequence of SEQ ID NO: 226, 236, 246, 256, 266, 276, 286, or 296 and the amino acid sequence of SEQ ID NO: 375; and an LC that comprises the amino acid sequence of SEQ ID NO: 227, 237, 247, 257, 267, 277, 287, 297, or 392 and the amino acid sequence of SEQ ID NO: 379.

In some embodiments, the anti-PD-1 antibody comprises the H-CDR1-3 and L-CDR1-3 amino acid sequences of:
  a) SEQ ID NOs: 228-233, respectively;
  b) SEQ ID NOs: 238-243, respectively;
  c) SEQ ID NOs: 248-253, respectively;
  d) SEQ ID NOs: 258-263, respectively;
  e) SEQ ID NOs: 268-273, respectively;
  f) SEQ ID NOs: 278-283, respectively;
  g) SEQ ID NOs: 288-293, respectively; or
  h) SEQ ID NOs: 298-303, respectively.

In some embodiments, the anti-PD-1 antibody comprises a VH and a VL having the amino acid sequences of:
  a) SEQ ID NOs: 226 and 227, respectively;
  b) SEQ ID NOs: 236 and 237, respectively;
  c) SEQ ID NOs: 236 and 392, respectively;
  d) SEQ ID NOs: 246 and 247, respectively;
  e) SEQ ID NOs: 256 and 257, respectively;
  f) SEQ ID NOs: 266 and 267, respectively;
  g) SEQ ID NOs: 276 and 277, respectively;
  h) SEQ ID NOs: 286 and 287, respectively; or
  i) SEQ ID NOs: 296 and 297, respectively.

In some embodiments, the anti-PD-1 antibody comprises:
  a) an HC comprising the amino acid sequence of SEQ ID NO: 226 and the amino acid sequence of SEQ ID NO: 375, and an LC comprising the amino acid sequence of SEQ ID NO: 227 and the amino acid sequence of SEQ ID NO: 379;
  b) an HC comprising the amino acid sequence of SEQ ID NO: 236 and the amino acid sequence of SEQ ID NO: 375, and an LC comprising the amino acid sequence of SEQ ID NO: 237 and the amino acid sequence of SEQ ID NO: 379;
  c) an HC comprising the amino acid sequence of SEQ ID NO: 236 and the amino acid sequence of SEQ ID NO: 375, and an LC comprising the amino acid sequence of SEQ ID NO: 392 and the amino acid sequence of SEQ ID NO: 379;
  d) an HC comprising the amino acid sequence of SEQ ID NO: 246 and the amino acid sequence of SEQ ID NO: 375, and an LC comprising the amino acid sequence of SEQ ID NO: 247 and the amino acid sequence of SEQ ID NO: 379;
  e) an HC comprising the amino acid sequence of SEQ ID NO: 256 and the amino acid sequence of SEQ ID NO: 375, and an LC comprising the amino acid sequence of SEQ ID NO: 257 and the amino acid sequence of SEQ ID NO: 379;
  f) an HC comprising the amino acid sequence of SEQ ID NO: 266 and the amino acid sequence of SEQ ID NO: 375, and an LC comprising the amino acid sequence of SEQ ID NO: 267 and the amino acid sequence of SEQ ID NO: 379;
  g) an HC comprising the amino acid sequence of SEQ ID NO: 276 and the amino acid sequence of SEQ ID NO: 375, and an LC comprising the amino acid sequence of SEQ ID NO: 277 and the amino acid sequence of SEQ ID NO: 379;
  h) an HC comprising the amino acid sequence of SEQ ID NO: 286 and the amino acid sequence of SEQ ID NO: 375, and an LC comprising the amino acid sequence of SEQ ID NO: 287 and the amino acid sequence of SEQ ID NO: 379; or
  i) an HC comprising the amino acid sequence of SEQ ID NO: 296 and the amino acid sequence of SEQ ID NO: 375, and an LC comprising the amino acid sequence of SEQ ID NO: 297 and the amino acid sequence of SEQ ID NO: 379.

In some embodiments, the anti-PD-1 antibody is selected from the group consisting of:
  a) an antibody whose H-CDR1-3 comprise the amino acid sequences of SEQ ID NOs: 228-230, respectively;
  b) an antibody whose VH is at least 90% identical in sequence to the amino acid sequence of SEQ ID NO: 226;
  c) an antibody whose VH comprises the amino acid sequence of SEQ ID NO: 226;
  d) an antibody whose HC comprises the amino acid sequences of SEQ ID NOs: 226 and 375;
  e) an antibody whose L-CDR1-3 comprise the amino acid sequences of SEQ ID NOs: 231-233, respectively;
  f) an antibody whose VL is at least 90% identical in sequence to the amino acid sequence of SEQ ID NO: 227;
  g) an antibody whose VL comprises the amino acid sequence of SEQ ID NO: 227;

h) an antibody whose LC comprises the amino acid sequences of SEQ ID NOs: 227 and 379;
i) an antibody whose H-CDR1-3 and L-CDR1-3 comprise the amino acid sequences of SEQ ID NOs: 228-233, respectively;
j) an antibody whose VH is at least 90% identical in sequence to the amino acid sequence of SEQ ID NO: 226 and whose VL is at least 90% identical in sequence to the amino acid sequence of SEQ ID NO: 227;
k) an antibody whose VH comprises the amino acid sequence of SEQ ID NO: 226 and whose VL comprises the amino acid sequence of SEQ ID NO: 227; and
l) an antibody whose HC comprises the amino acid sequence of SEQ ID NO: 226 and the amino acid sequence of SEQ ID NO: 375; and whose LC comprises the amino acid sequences of SEQ ID NOs: 227 and 379.

In some embodiments, the anti-PD-1 antibody is selected from the group consisting of:
a) an antibody whose H-CDR1-3 comprise the amino acid sequences of SEQ ID NOs: 238-240, respectively;
b) an antibody whose VH is at least 90% identical in sequence to the amino acid sequence of SEQ ID NO: 236;
c) an antibody whose VH comprises the amino acid sequence of SEQ ID NO: 236;
d) an antibody whose HC comprises the amino acid sequences of SEQ ID NOs: 236 and 375;
e) an antibody whose L-CDR1-3 comprise the amino acid sequences of SEQ ID NOs: 241-243, respectively;
f) an antibody whose VL is at least 90% identical in sequence to the amino acid sequence of SEQ ID NO: 237;
g) an antibody whose VL comprises the amino acid sequence of SEQ ID NO: 237;
h) an antibody whose LC comprises the amino acid sequences of SEQ ID NOs: 237 and 379;
i) an antibody whose H-CDR1-3 and L-CDR1-3 comprise the amino acid sequences of SEQ ID NOs: 238-243, respectively;
j) an antibody whose VH is at least 90% identical in sequence to the amino acid sequence of SEQ ID NO: 236 and whose VL is at least 90% identical in sequence to the amino acid sequence of SEQ ID NO: 237;
k) an antibody whose VH comprises the amino acid sequence of SEQ ID NO: 236 and whose VL comprises the amino acid sequence of SEQ ID NO: 237; and
l) an antibody whose HC comprises the amino acid sequence of SEQ ID NO: 236 and the amino acid sequence of SEQ ID NO: 375; and whose LC comprises the amino acid sequences of SEQ ID NOs: 237 and 379.

In some embodiments, the anti-PD-1 antibody is selected from the group consisting of:
a) an antibody whose H-CDR1-3 comprise the amino acid sequences of SEQ ID NOs: 238-240, respectively;
b) an antibody whose VH is at least 90% identical in sequence to the amino acid sequence of SEQ ID NO: 236;
c) an antibody whose VH comprises the amino acid sequence of SEQ ID NO: 236;
d) an antibody whose HC comprises the amino acid sequences of SEQ ID NOs: 236 and 375;
e) an antibody whose L-CDR1-3 comprise the amino acid sequences of SEQ ID NOs: 241-243, respectively;
f) an antibody whose VL is at least 90% identical in sequence to the amino acid sequence of SEQ ID NO: 392;
g) an antibody whose VL comprises the amino acid sequence of SEQ ID NO: 392;
h) an antibody whose LC comprises the amino acid sequences of SEQ ID NOs: 392 and 379;
i) an antibody whose H-CDR1-3 and L-CDR1-3 comprise the amino acid sequences of SEQ ID NOs: 238-243, respectively;
j) an antibody whose VH is at least 90% identical in sequence to the amino acid sequence of SEQ ID NO: 236 and whose VL is at least 90% identical in sequence to the amino acid sequence of SEQ ID NO: 392;
k) an antibody whose VH comprises the amino acid sequence of SEQ ID NO: 236 and whose VL comprises the amino acid sequence of SEQ ID NO: 392; and
l) an antibody whose HC comprises the amino acid sequence of SEQ ID NO: 236 and the amino acid sequence of SEQ ID NO: 375; and whose LC comprises the amino acid sequences of SEQ ID NOs: 392 and 379.

In some embodiments, the anti-PD-1 antibody is selected from the group consisting of:
a) an antibody whose H-CDR1-3 comprise the amino acid sequences of SEQ ID NOs: 248-250, respectively;
b) an antibody whose VH is at least 90% identical in sequence to the amino acid sequence of SEQ ID NO: 246;
c) an antibody whose VH comprises the amino acid sequence of SEQ ID NO: 246;
d) an antibody whose HC comprises the amino acid sequences of SEQ ID NOs: 246 and 375;
e) an antibody whose L-CDR1-3 comprise the amino acid sequences of SEQ ID NOs: 251-253, respectively;
f) an antibody whose VL is at least 90% identical in sequence to the amino acid sequence of SEQ ID NO: 247;
g) an antibody whose VL comprises the amino acid sequence of SEQ ID NO: 247;
h) an antibody whose LC comprises the amino acid sequences of SEQ ID NOs: 247 and 379;
i) an antibody whose H-CDR1-3 and L-CDR1-3 comprise the amino acid sequences of SEQ ID NOs: 248-253, respectively;
j) an antibody whose VH is at least 90% identical in sequence to the amino acid sequence of SEQ ID NO: 246 and whose VL is at least 90% identical in sequence to the amino acid sequence of SEQ ID NO: 247;
k) an antibody whose VH comprises the amino acid sequence of SEQ ID NO: 246 and whose VL comprises the amino acid sequence of SEQ ID NO: 247; and
l) an antibody whose HC comprises the amino acid sequence of SEQ ID NO: 246 and the amino acid sequence of SEQ ID NO: 375; and whose LC comprises the amino acid sequences of SEQ ID NOs: 247 and 379.

In some embodiments, the anti-PD-1 antibody is selected from the group consisting of:
a) an antibody whose H-CDR1-3 comprise the amino acid sequences of SEQ ID NOs: 258-260, respectively;
b) an antibody whose VH is at least 90% identical in sequence to the amino acid sequence of SEQ ID NO: 256;
c) an antibody whose VH comprises the amino acid sequence of SEQ ID NO: 256;

d) an antibody whose HC comprises the amino acid sequences of SEQ ID NOs: 256 and 375;
e) an antibody whose L-CDR1-3 comprise the amino acid sequences of SEQ ID NOs: 261-263, respectively;
f) an antibody whose VL is at least 90% identical in sequence to the amino acid sequence of SEQ ID NO: 257;
g) an antibody whose VL comprises the amino acid sequence of SEQ ID NO: 257;
h) an antibody whose LC comprises the amino acid sequences of SEQ ID NOs: 257 and 379;
i) an antibody whose H-CDR1-3 and L-CDR1-3 comprise the amino acid sequences of SEQ ID NOs: 258-263, respectively;
j) an antibody whose VH is at least 90% identical in sequence to the amino acid sequence of SEQ ID NO: 256 and whose VL is at least 90% identical in sequence to the amino acid sequence of SEQ ID NO: 257;
k) an antibody whose VH comprises the amino acid sequence of SEQ ID NO: 256 and whose VL comprises the amino acid sequence of SEQ ID NO: 257; and
l) an antibody whose HC comprises the amino acid sequence of SEQ ID NO: 256 and the amino acid sequence of SEQ ID NO: 375; and whose LC comprises the amino acid sequences of SEQ ID NOs: 257 and 379.

In some embodiments, the anti-PD-1 antibody is selected from the group consisting of:
a) an antibody whose H-CDR1-3 comprise the amino acid sequences of SEQ ID NOs: 268-270, respectively;
b) an antibody whose VH is at least 90% identical in sequence to the amino acid sequence of SEQ ID NO: 266;
c) an antibody whose VH comprises the amino acid sequence of SEQ ID NO: 266;
d) an antibody whose HC comprises the amino acid sequences of SEQ ID NOs: 266 and 375;
e) an antibody whose L-CDR1-3 comprise the amino acid sequences of SEQ ID NOs: 271-273, respectively;
f) an antibody whose VL is at least 90% identical in sequence to the amino acid sequence of SEQ ID NO: 267;
g) an antibody whose VL comprises the amino acid sequence of SEQ ID NO: 267;
h) an antibody whose LC comprises the amino acid sequences of SEQ ID NOs: 267 and 379;
i) an antibody whose H-CDR1-3 and L-CDR1-3 comprise the amino acid sequences of SEQ ID NOs: 268-273, respectively;
j) an antibody whose VH is at least 90% identical in sequence to the amino acid sequence of SEQ ID NO: 266 and whose VL is at least 90% identical in sequence to the amino acid sequence of SEQ ID NO: 267;
k) an antibody whose VH comprises the amino acid sequence of SEQ ID NO: 266 and whose VL comprises the amino acid sequence of SEQ ID NO: 267; and
l) an antibody whose HC comprises the amino acid sequence of SEQ ID NO: 266 and the amino acid sequence of SEQ ID NO: 375; and whose LC comprises the amino acid sequences of SEQ ID NOs: 267 and 379.

In some embodiments, the anti-PD-1 antibody is selected from the group consisting of:
a) an antibody whose H-CDR1-3 comprise the amino acid sequences of SEQ ID NOs: 278-280, respectively;
b) an antibody whose VH is at least 90% identical in sequence to the amino acid sequence of SEQ ID NO: 276;
c) an antibody whose VH comprises the amino acid sequence of SEQ ID NO: 276;
d) an antibody whose HC comprises the amino acid sequences of SEQ ID NOs: 276 and 375;
e) an antibody whose L-CDR1-3 comprise the amino acid sequences of SEQ ID NOs: 281-283, respectively;
f) an antibody whose VL is at least 90% identical in sequence to the amino acid sequence of SEQ ID NO: 277;
g) an antibody whose VL comprises the amino acid sequence of SEQ ID NO: 277;
h) an antibody whose LC comprises the amino acid sequences of SEQ ID NOs: 277 and 379;
i) an antibody whose H-CDR1-3 and L-CDR1-3 comprise the amino acid sequences of SEQ ID NOs: 278-283, respectively;
j) an antibody whose VH is at least 90% identical in sequence to the amino acid sequence of SEQ ID NO: 276 and whose VL is at least 90% identical in sequence to the amino acid sequence of SEQ ID NO: 277;
k) an antibody whose VH comprises the amino acid sequence of SEQ ID NO: 276 and whose VL comprises the amino acid sequence of SEQ ID NO: 277; and
l) an antibody whose HC comprises the amino acid sequence of SEQ ID NO: 276 and the amino acid sequence of SEQ ID NO: 375; and whose LC comprises the amino acid sequences of SEQ ID NOs: 277 and 379.

In some embodiments, the anti-PD-1 antibody is selected from the group consisting of:
a) an antibody whose H-CDR1-3 comprise the amino acid sequences of SEQ ID NOs: 288-290, respectively;
b) an antibody whose VH is at least 90% identical in sequence to the amino acid sequence of SEQ ID NO: 286;
c) an antibody whose VH comprises the amino acid sequence of SEQ ID NO: 286;
d) an antibody whose HC comprises the amino acid sequences of SEQ ID NOs: 286 and 375;
e) an antibody whose L-CDR1-3 comprise the amino acid sequences of SEQ ID NOs: 291-293, respectively;
f) an antibody whose VL is at least 90% identical in sequence to the amino acid sequence of SEQ ID NO: 287;
g) an antibody whose VL comprises the amino acid sequence of SEQ ID NO: 287;
h) an antibody whose LC comprises the amino acid sequences of SEQ ID NOs: 287 and 379;
i) an antibody whose H-CDR1-3 and L-CDR1-3 comprise the amino acid sequences of SEQ ID NOs: 288-293, respectively;
j) an antibody whose VH is at least 90% identical in sequence to the amino acid sequence of SEQ ID NO: 286 and whose VL is at least 90% identical in sequence to the amino acid sequence of SEQ ID NO: 287;
k) an antibody whose VH comprises the amino acid sequence of SEQ ID NO: 286 and whose VL comprises the amino acid sequence of SEQ ID NO: 287; and
l) an antibody whose HC comprises the amino acid sequence of SEQ ID NO: 286 and the amino acid sequence of SEQ ID NO: 375; and whose LC comprises the amino acid sequences of SEQ ID NOs: 287 and 379.

In some embodiments, the anti-PD-1 antibody is selected from the group consisting of:
  a) an antibody whose H-CDR1-3 comprise the amino acid sequences of SEQ ID NOs: 298-300, respectively;
  b) an antibody whose VH is at least 90% identical in sequence to the amino acid sequence of SEQ ID NO: 296;
  c) an antibody whose VH comprises the amino acid sequence of SEQ ID NO: 296;
  d) an antibody whose HC comprises the amino acid sequences of SEQ ID NOs: 296 and 375;
  e) an antibody whose L-CDR1-3 comprise the amino acid sequences of SEQ ID NOs: 301-303, respectively;
  f) an antibody whose VL is at least 90% identical in sequence to the amino acid sequence of SEQ ID NO: 297;
  g) an antibody whose VL comprises the amino acid sequence of SEQ ID NO: 297;
  h) an antibody whose LC comprises the amino acid sequences of SEQ ID NOs: 297 and 379;
  i) an antibody whose H-CDR1-3 and L-CDR1-3 comprise the amino acid sequences of SEQ ID NOs: 298-303, respectively;
  j) an antibody whose VH is at least 90% identical in sequence to the amino acid sequence of SEQ ID NO: 296 and whose VL is at least 90% identical in sequence to the amino acid sequence of SEQ ID NO: 297;
  k) an antibody whose VH comprises the amino acid sequence of SEQ ID NO: 296 and whose VL comprises the amino acid sequence of SEQ ID NO: 297; and
  l) an antibody whose HC comprises the amino acid sequence of SEQ ID NO: 296 and the amino acid sequence of SEQ ID NO: 375; and whose LC comprises the amino acid sequences of SEQ ID NOs: 297 and 379.

In some embodiments, any of the anti-PD-1 antibodies or antigen-binding portions described herein may bind to human PD-1 with a $K_D$ of at least 900, at least 850, at least 800, at least 750, at least 700, at least 650, at least 600, at least 550, at least 500, at least 450, at least 400, at least 350, at least 300, at least 250, at least 200, at least 150, at least 100, at least 50, at least 40, at least 30, or at least 20 pM. In certain embodiments, the $K_D$ is determined using surface plasmon resonance. In particular embodiments, the anti-PD-1 antibodies or antigen-binding portions bind to human PD-1 with a higher affinity than nivolumab, pembrolizumab, or both.

In some embodiments, any of the anti-PD-1 antibodies or antigen-binding portions described herein may bind to cynomolgus PD-1 with a $K_D$ of at least 9000, at least 8000, at least 7000, at least 6000, at least 5000, at least 4000, at least 3000, at least 2500, at least 2000, at least 1500, at least 1000, at least 900, at least 800, at least 700, at least 600, at least 500, at least 400, at least 300, at least 200, at least 100, at least 75, at least 50, at least 25, at least 20, at least 15, at least 10, or at least 5 pM. In certain embodiments, the $K_D$ is determined using surface plasmon resonance.

In some embodiments, any of the anti-PD-1 antibodies or antigen-binding portions described herein may bind to mouse PD-1 with a $K_D$ of at least 1000, at least 950, at least 900, or at least 850 pM. In certain embodiments, the $K_D$ is determined using surface plasmon resonance.

In some embodiments, any of the anti-PD-1 antibodies or antigen-binding portions described herein may inhibit the interaction of PD-1 with PD-L1 by at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% at a concentration of 10 μg/mL in a flow cytometric competition assay. In certain embodiments, the anti-PD-1 antibodies or antigen-binding portions may inhibit the interaction of PD-1 with PD-L1 by at least 83%.

In some embodiments, any of the anti-PD-1 antibodies or antigen-binding portions described herein may block binding of PD-L1 and PD-L2 to PD-1 by at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% at a concentration of 10 μg/mL as determined by Bio-Layer Interferometry analysis. In certain embodiments, the anti-PD-1 antibodies or antigen-binding portions block binding of PD-L1 and PD-L2 to PD-1 by at least 90%.

In some embodiments, the anti-PD-1 antibody or antigen-binding portion described herein has at least one of the following properties:
  a) binds to human PD-1 with a $K_D$ of 750 pM or less;
  b) binds to cynomolgus PD-1 with a $K_D$ of 7 nM or less;
  c) binds to mouse PD-1 with a $K_D$ of 1 nM or less;
  d) does not bind to rat PD-1,
  e) increases IL-2 secretion in an SEB whole blood assay;
  f) increases IFN-γ secretion in a one-way mixed lymphocyte reaction assay;
  g) inhibits the interaction of PD-1 with PD-L1 by at least 60% at a concentration of 10 μg/mL in a flow cytometric competition assay;
  h) blocks binding of PD-L1 and PD-L2 to PD-1 by at least 90% at a concentration of 10 μg/mL as determined by Bio-Layer Interferometry analysis; and
  i) inhibits tumor growth in vivo.

Examples of such an antibody include, without limitation, a 12819 antibody (having properties a-i); 12748, 12892, and 12777 antibodies (having at least properties a, b, and e-h), 12865 and 12796 antibodies (having at least properties a, b, e, f, and h), and 12760 and 13112 antibodies (having at least properties a, b, e, and f). In some embodiments, the anti-PD-1 antibody or antigen-binding portion has all of said properties. In some embodiments, the anti-PD-1 antibody or antigen-binding portion has at least properties a, b, and e-h. In some embodiments, the anti-PD-1 antibody or antigen-binding portion has at least properties a, b, e, f, and h. In some embodiments, the anti-PD-1 antibody or antigen-binding portion has at least properties a, b, e, and f.

In some embodiments, an anti-PD-1 antibody or an antigen-binding portion thereof as described herein binds to an epitope of PD-1 that includes at least one (e.g., at least one, at least two, at least three, at least four, or at least five) of the following residues of SEQ ID NO: 388: V44, V64, L128, P130, K131, A132, E136, and T145. In certain embodiments, the antibody or antigen-binding portion binds to an epitope of PD-1 that includes residues V64, L128, P130, K131, and A132 of SEQ ID NO: 388 (such as a 12819 antibody, e.g., antibody 12819.15384). In certain embodiments, the antibody or antigen-binding portion binds to an epitope of PD-1 that includes residues K131 and E136 of SEQ ID NO: 388 (such as a 12865 antibody, e.g., antibody 12865.15377). In certain embodiments, the antibody or antigen-binding portion binds to an epitope of PD-1 that includes residues V44 and T145 of SEQ ID NO: 388 (such as a 13112 antibody, e.g., antibody 13112.15380).

In some embodiments, the combination therapy or composition comprises an anti-PD-1 antibody or an antigen-binding portion thereof that binds to an epitope of PD-1 comprising amino acid residue K131 of SEQ ID NO: 388 (e.g., a 12819 or 12865 antibody). In some embodiments, the epitope further comprises amino acid residues P130 and A132, and may additionally comprise amino acid residues V64 and L128 (e.g., a 12819 antibody). In some embodiments, the epitope further comprises amino acid residue E136 (e.g., a 12865 antibody).

In some embodiments, an anti-PD-1 antibody or an antigen-binding portion thereof as described herein binds to an epitope of PD-1 that comprises residues 56-64, 69-90, and/or 122-140 of SEQ ID NO: 388. In certain embodiments, the antibody or antigen-binding portion binds to an epitope of PD-1 that comprises residues 69-90 and 122-140 of SEQ ID NO: 388 (such as 12819 and 12865 antibodies, e.g., antibodies 12819.15384 and 12865.15377). In certain embodiments, the antibody or antigen-binding portion binds to an epitope of PD-1 that comprises residues 56-64, 69-90, and 122-140 of SEQ ID NO: 388 (e.g., a 12819 antibody). In certain embodiments, the antibody or antigen-binding portion binds to an epitope of PD-1 that comprises residues 69-90 and 122-140 of SEQ ID NO: 388 (e.g., a 12865 antibody). In some embodiments, the antibody or portion binds to residues 69-75 (or a fragment thereof, such as a one, two, three, four, five, or six residue fragment), of SEQ ID NO: 388 (such as 12819 and 12865 antibodies, e.g., antibodies 12819.15384 and 12865.15377). In some embodiments, the antibody or portion binds to residues 136-140 (or a fragment thereof, such as a one, two, three, or four residue fragment) of SEQ ID NO: 388 (such as 12819 and 12865 antibodies, e.g., antibodies 12819.15384 and 12865.15377). In some embodiments, the antibody or portion binds to residues 69-75 (or a fragment thereof) and residues 136-140 (or a fragment thereof) of SEQ ID NO: 388, (such as 12819 and 12865 antibodies, e.g., antibodies 12819.15384 and 12865.15377). An epitope with any combination of the above residues is also contemplated.

In some embodiments, an anti-PD-1 antibody or an antigen-binding portion thereof as described herein is an anti-PD-1 antibody or antigen-binding portion described in PCT Patent Publication WO 2017/055547 or PCT Patent Application PCT/EP2017/079615, which are incorporated by reference in their entirety herein.

Anti-TIM-3 Antibodies

In a particular embodiment, the anti-TIM-3 antibodies disclosed herein are human antibodies generated from transgenic rats that are able to generate antibodies with human idiotypes.

The anti-TIM-3 antibodies disclosed herein may be referred to by either a 5-digit number, e.g. "20131", or by a 10-digit number, e.g. "15086.16837". 10-digit numbers with the same first five digits are derived from the same parent antibody, as in the case of antibodies 15086.15086, 15086.16837, 15086.17145, 15086.17144. Such antibodies, which share the same six CDRs, are expected to have the same or substantially the same target binding properties. As will be apparent from the protein and DNA sequences provided herein, the 15086.16837, 15086.17145, and 15086.17144 variants have only a single amino acid difference in the VH sequence compared to the parent 15086 antibody ("15086.15086"), namely E, rather than Q, in position 6, whereas the VL amino acid sequences are identical. It will also be apparent that these variants differ primarily by their antibody format/subclass, i.e.:

15086.15086: IgG1
15086.16837: IgG1 LALA
15086.17145: IgG2
15086.17144: IgG4

The VH sequence of the IgG2 and IgG4 subclass antibodies is the same as that of the IgG1 LALA variant. The VL sequence is the same for all four of the antibody subclasses.

In some embodiments, the combination therapy or composition comprises an anti-TIM-3 antibody or an antigen-binding portion thereof, wherein the anti-TIM-3 antibody is the antibody referred to herein as antibody 15086.17145, 15086.15086, 15086.16837, 15086.17144, 20131, 20293, 15105, 15107, 15109, 15174, 15175, 15260, 15284, 15299, 15353, 15354, 17244, 17245, 19324, 19416, 19568, 20185, 20300, 20362, or 20621 or a variant of any of these, where the variant may, e.g., contain certain minimum amino acid changes relative to said antibody (e.g., 1, 2, 3, 4, 5, 6, 7, 8, 9, or 10 amino acid changes, which may be, e.g., in the framework regions) without losing the antigen-binding specificity of antibody.

In some embodiments, the anti-TIM-3 antibody competes or cross-competes for binding to human TIM-3 with, or binds to the same epitope of human TIM-3 as, antibody 15086.15086 having the IgG1 format, antibody 15086.16837 having the IgG1 LALA format, antibody 15086.17145 having the IgG2 format, or antibody 15086.17144 having the IgG4 format. In some embodiments, the antibody has an IgG1 or IgG2 format. In certain embodiments, the antibody has an IgG2 format.

In some embodiments, the anti-TIM-3 antibody competes or cross-competes for binding to human TIM-3 with, or binds to the same epitope of human TIM-3 as, antibody 20131, 20293, 15105, 15107, 15109, 15174, 15175, 15260, 15284, 15299, 15353, 15354, 17244, 17245, 19324, 19416, 19568, 20185, 20300, 20362, or 20621. In some embodiments, the antibody has an IgG1 or IgG2 format. In certain embodiments, the antibody has an IgG2 format.

In some embodiments, the anti-TIM-3 antibody competes or cross-competes for binding to human TIM-3 with, or binds to the same epitope of human TIM-3 as, an antibody whose heavy chain (H) CDR1-3 and light chain (L) CDR1-3 comprise, respectively, SEQ ID NOs: 8-13, 18-23, 28-33, 38-43, 48-53, 58-63, 68-73, 78-83, 88-93, 98-103, 108-113, 118-123, 128-133, 138-143, 148-153, 158-163, 168-173, 178-183, 188-193, 198-203, 208-213, or 218-223.

In some embodiments, the anti-TIM-3 antibody comprises an H-CDR3 comprising the H-CDR3 amino acid sequence of SEQ ID NO: 10, 20, 30, 40, 50, 60, 70, 80, 90, 100, 110, 120, 130, 140, 150, 160, 170, 180, 190, 200, 210, or 220.

In some embodiments, the anti-TIM-3 antibody comprises H-CDR1-3 comprising the H-CDR1-3 amino acid sequences, respectively, of SEQ ID NOs: 8-10, 18-20, 28-30, 38-40, 48-50, 58-60, 68-70, 78-80, 88-90, 98-100, 108-110, 118-120, 128-130, 138-140, 148-150, 158-160, 168-170, 178-180, 188-190, 198-200, 208-210, or 218-220.

In some embodiments, the anti-TIM-3 antibody has a VH that is at least 90% (e.g., at least 92%, at least 95%, at least 96%, at least 97%, at least 98%, or at least 99%) identical in amino acid sequence to SEQ ID NO: 3, 7, 16, 26, 36, 46, 56, 66, 76, 86, 96, 106, 116, 126, 136, 146, 156, 166, 176, 186, 196, 206, or 216.

In some embodiments, the anti-TIM-3 antibody has a VH that comprises SEQ ID NO: 3, 7, 16, 26, 36, 46, 56, 66, 76, 86, 96, 106, 116, 126, 136, 146, 156, 166, 176, 186, 196, 206, or 216.

In some embodiments, the anti-TIM-3 antibody has a VH that is at least 90% (e.g., at least 92%, at least 95%, at least 96%, at least 97%, at least 98%, or at least 99%) identical in sequence to SEQ ID NO: 3, 16, 26, 36, 46, 56, 66, 76, 86, 96, 106, 116, 126, 136, 146, 156, 166, 176, 186, 196, 206, or 216; and a CH that is at least 90% (e.g., at least 92%, at least 95%, at least 96%, at least 97%, at least 98%, or at least 99%) identical in sequence to SEQ ID NO: 374.

In some embodiments, the anti-TIM-3 antibody has an HC that comprises the VH amino acid sequence of SEQ ID NO: 3, 16, 26, 36, 46, 56, 66, 76, 86, 96, 106, 116, 126, 136, 146, 156, 166, 176, 186, 196, 206, or 216 and the CH amino acid sequence of SEQ ID NO: 374.

In some embodiments, the anti-TIM-3 antibody has a VH that is at least 90% (e.g., at least 92%, at least 95%, at least 96%, at least 97%, at least 98%, or at least 99%) identical in sequence to SEQ ID NO: 7, 16, 26, 36, 46, 56, 66, 76, 86, 96, 106, 116, 126, 136, 146, 156, 166, 176, 186, 196, 206, or 216; and a CH that is at least 90% (e.g., at least 92%, at least 95%, at least 96%, at least 97%, at least 98%, or at least 99%) identical in sequence to SEQ ID NO: 375, 376, or 377.

In some embodiments, the anti-TIM-3 antibody has a HC that comprises the VH amino acid sequence of SEQ ID NO: 7, 16, 26, 36, 46, 56, 66, 76, 86, 96, 106, 116, 126, 136, 146, 156, 166, 176, 186, 196, 206, or 216 and the CH amino acid sequence of SEQ ID NO: 375, 376, or 377. In certain embodiments, the CH amino acid sequence is SEQ ID NO: 377.

In some embodiments, the anti-TIM-3 antibody comprises an L-CDR3 comprising the L-CDR3 amino acid sequence of SEQ ID NO: 13, 23, 33, 43, 53, 63, 73, 83, 93, 103, 113, 123, 133, 143, 153, 163, 173, 183, 193, 203, 213, or 223.

In some embodiments, the anti-TIM-3 antibody comprises L-CDR1-3 comprising the L-CDR1-3 amino acid sequences, respectively, of SEQ ID NOs: 11-13, 21-23, 31-33, 41-43, 51-53, 61-63, 71-73, 81-83, 91-93, 101-103, 111-113, 121-123, 131-133, 141-143, 151-153, 161-163, 171-173, 181-183, 191-193, 201-203, 211-213, or 221-223.

In some embodiments, the anti-TIM-3 antibody has a VL that is at least 90% (e.g., at least 92%, at least 95%, at least 96%, at least 97%, at least 98%, or at least 99%) identical in sequence to the VL amino acid sequence of SEQ ID NO: 4, 17, 27, 37, 47, 57, 67, 77, 87, 97, 107, 117, 127, 137, 147, 157, 167, 177, 187, 197, 207, or 217.

In some embodiments, the anti-TIM-3 antibody has a VL that comprises the VL amino acid sequence of SEQ ID NO: 4, 17, 27, 37, 47, 57, 67, 77, 87, 97, 107, 117, 127, 137, 147, 157, 167, 177, 187, 197, 207, or 217.

In some embodiments, the anti-TIM-3 antibody has a VL that is at least 90% (e.g., at least 92%, at least 95%, at least 96%, at least 97%, at least 98%, or at least 99%) identical in sequence to the VL amino acid sequence of SEQ ID NO: 4, 17, 27, 37, 47, 57, 67, 77, 87, 97, 107, 117, 127, 137, 147, 157, 167, 177, 187, 197, 207, or 217; and a CL that is at least 90% (e.g., at least 92%, at least 95%, at least 96%, at least 97%, at least 98%, or at least 99%) identical in sequence to SEQ ID NO: 378.

In some embodiments, the anti-TIM-3 antibody has a LC that comprises the VL amino acid sequence of SEQ ID NO: 4, 17, 27, 37, 47, 57, 67, 77, 87, 97, 107, 117, 127, 137, 147, 157, 167, 177, 187, 197, 207, or 217 and the CL amino acid sequence of SEQ ID NO: 378.

In some embodiments, the anti-TIM-3 antibody comprises any of the above heavy chain sequences and any of the above light chain sequences.

In some embodiments, the anti-TIM-3 antibody comprises an H-CDR3 and L-CDR3 comprising the H-CDR3 and L-CDR3 amino acid sequences, respectively, of SEQ ID NOs: 10 and 13, 20 and 23, 30 and 33, 40 and 43, 50 and 53, 60 and 63, 70 and 73, 80 and 83, 90 and 93, 100 and 103, 110 and 113, 120 and 123, 130 and 133, 140 and 143, 150 and 153, 160 and 163, 170 and 173, 180 and 183, 190 and 193, 200 and 203, 210 and 213, or 220 and 223.

In some embodiments, the anti-TIM-3 antibody comprises H-CDR1-3 and L-CDR1-3 comprising the H-CDR1-3 and L-CDR1-3 sequences, respectively, of SEQ ID NOs: 8-13, 18-23, 28-33, 38-43, 48-53, 58-63, 68-73, 78-83, 88-93, 98-103, 108-113, 118-123, 128-133, 138-143, 148-153, 158-163, 168-173, 178-183, 188-193, 198-203, 208-213, or 218-223.

In some embodiments, the anti-TIM-3 antibody has a VH that is at least 90% (e.g., at least 92%, at least 95%, at least 96%, at least 97%, at least 98%, or at least 99%) identical in sequence to the amino acid sequence of SEQ ID NO: 3, 7, 16, 26, 36, 46, 56, 66, 76, 86, 96, 106, 116, 126, 136, 146, 156, 166, 176, 186, 196, 206, or 216, and a VL that is at least 90% (e.g., at least 92%, at least 95%, at least 96%, at least 97%, at least 98%, or at least 99%) identical in sequence to the amino acid sequence of SEQ ID NO: 4, 17, 27, 37, 47, 57, 67, 77, 87, 97, 107, 117, 127, 137, 147, 157, 167, 177, 187, 197, 207, or 217.

In some embodiments, the anti-TIM-3 antibody has a VH that comprises the amino acid sequence of SEQ ID NO: 3, 7, 16, 26, 36, 46, 56, 66, 76, 86, 96, 106, 116, 126, 136, 146, 156, 166, 176, 186, 196, 206, or 216, and a VL that comprises the amino acid sequence of SEQ ID NO: 4, 17, 27, 37, 47, 57, 67, 77, 87, 97, 107, 117, 127, 137, 147, 157, 167, 177, 187, 197, 207, or 217.

In some embodiments, the anti-TIM-3 antibody has an HC that comprises the amino acid sequence of SEQ ID NO: 3, 7, 16, 26, 36, 46, 56, 66, 76, 86, 96, 106, 116, 126, 136, 146, 156, 166, 176, 186, 196, 206, or 216 and the amino acid sequence of SEQ ID NO: 378; and an LC that comprises the amino acid sequence of SEQ ID NO: 4, 17, 27, 37, 47, 57, 67, 77, 87, 97, 107, 117, 127, 137, 147, 157, 167, 177, 187, 197, 207, or 217 and the amino acid sequence of SEQ ID NO: 374, 375, 376, or 377.

In some embodiments, the anti-TIM-3 antibody comprises the H-CDR1-3 and L-CDR1-3 amino acid sequences of:
  a) SEQ ID NOs: 8-13, respectively;
  b) SEQ ID NOs: 18-23, respectively;
  c) SEQ ID NOs: 28-33, respectively;
  d) SEQ ID NOs: 38-43, respectively;
  e) SEQ ID NOs: 48-53, respectively;
  f) SEQ ID NOs: 58-63, respectively;
  g) SEQ ID NOs: 68-73, respectively;
  h) SEQ ID NOs: 78-83, respectively;
  i) SEQ ID NOs: 88-93, respectively;
  j) SEQ ID NOs: 98-103, respectively;
  k) SEQ ID NOs: 108-113, respectively;
  l) SEQ ID NOs: 118-123, respectively;
  m) SEQ ID NOs: 128-133, respectively;
  n) SEQ ID NOs: 138-143, respectively;
  o) SEQ ID NOs: 148-153, respectively;
  p) SEQ ID NOs: 158-163, respectively;
  q) SEQ ID NOs: 168-173, respectively;
  r) SEQ ID NOs: 178-183, respectively;
  s) SEQ ID NOs: 188-193, respectively;
  t) SEQ ID NOs: 198-203, respectively;
  u) SEQ ID NOs: 208-213, respectively; or
  v) SEQ ID NOs: 218-223, respectively.

In some embodiments, the anti-TIM-3 antibody comprises a heavy chain variable domain and a light chain variable domain having the amino acid sequences of:
  a) SEQ ID NOs: 7 and 4, respectively;
  b) SEQ ID NOs: 3 and 4, respectively;

c) SEQ ID NOs: 16 and 17, respectively;
d) SEQ ID NOs: 26 and 27, respectively;
e) SEQ ID NOs: 36 and 37, respectively;
f) SEQ ID NOs: 46 and 47, respectively;
g) SEQ ID NOs: 56 and 57, respectively;
h) SEQ ID NOs: 66 and 67, respectively;
i) SEQ ID NOs: 76 and 77, respectively;
j) SEQ ID NOs: 86 and 87, respectively;
k) SEQ ID NOs: 96 and 97, respectively;
l) SEQ ID NOs: 106 and 107, respectively;
m) SEQ ID NOs: 116 and 117, respectively;
n) SEQ ID NOs: 126 and 127, respectively;
o) SEQ ID NOs: 136 and 137, respectively;
p) SEQ ID NOs: 146 and 147, respectively;
q) SEQ ID NOs: 156 and 157, respectively;
r) SEQ ID NOs: 166 and 167, respectively;
s) SEQ ID NOs: 176 and 177, respectively;
t) SEQ ID NOs: 186 and 187, respectively;
u) SEQ ID NOs: 196 and 197, respectively;
v) SEQ ID NOs: 206 and 207, respectively; or
w) SEQ ID NOs: 216 and 217, respectively.

In some embodiments, the anti-TIM-3 antibody comprises:

a) an HC comprising the amino acid sequence of SEQ ID NO: 7 and the amino acid sequence of SEQ ID NO: 374, 375, 376, or 377, and an LC comprising the amino acid sequence of SEQ ID NO: 4 and the amino acid sequence of SEQ ID NO: 378;

b) an HC comprising the amino acid sequence of SEQ ID NO: 3 and the amino acid sequence of SEQ ID NO: 374, 375, 376, or 377, and an LC comprising the amino acid sequence of SEQ ID NO: 4 and the amino acid sequence of SEQ ID NO: 378;

c) an HC comprising the amino acid sequence of SEQ ID NO: 16 and the amino acid sequence of SEQ ID NO: 374, 375, 376, or 377, and an LC comprising the amino acid sequence of SEQ ID NO: 17 and the amino acid sequence of SEQ ID NO: 378;

d) an HC comprising the amino acid sequence of SEQ ID NO: 26 and the amino acid sequence of SEQ ID NO: 374, 375, 376, or 377, and an LC comprising the amino acid sequence of SEQ ID NO: 27 and the amino acid sequence of SEQ ID NO: 378;

e) an HC comprising the amino acid sequence of SEQ ID NO: 36 and the amino acid sequence of SEQ ID NO: 374, 375, 376, or 377, and an LC comprising the amino acid sequence of SEQ ID NO: 37 and the amino acid sequence of SEQ ID NO: 378;

f) an HC comprising the amino acid sequence of SEQ ID NO: 46 and the amino acid sequence of SEQ ID NO: 374, 375, 376, or 377, and an LC comprising the amino acid sequence of SEQ ID NO: 47 and the amino acid sequence of SEQ ID NO: 378;

g) an HC comprising the amino acid sequence of SEQ ID NO: 56 and the amino acid sequence of SEQ ID NO: 374, 375, 376, or 377, and an LC comprising the amino acid sequence of SEQ ID NO: 57 and the amino acid sequence of SEQ ID NO: 378;

h) an HC comprising the amino acid sequence of SEQ ID NO: 66 and the amino acid sequence of SEQ ID NO: 374, 375, 376, or 377, and an LC comprising the amino acid sequence of SEQ ID NO: 67 and the amino acid sequence of SEQ ID NO: 378;

i) an HC comprising the amino acid sequence of SEQ ID NO: 76 and the amino acid sequence of SEQ ID NO: 374, 375, 376, or 377, and an LC comprising the amino acid sequence of SEQ ID NO: 77 and the amino acid sequence of SEQ ID NO: 378;

j) an HC comprising the amino acid sequence of SEQ ID NO: 86 and the amino acid sequence of SEQ ID NO: 374, 375, 376, or 377, and an LC comprising the amino acid sequence of SEQ ID NO: 87 and the amino acid sequence of SEQ ID NO: 378;

k) an HC comprising the amino acid sequence of SEQ ID NO: 96 and the amino acid sequence of SEQ ID NO: 374, 375, 376, or 377, and an LC comprising the amino acid sequence of SEQ ID NO: 97 and the amino acid sequence of SEQ ID NO: 378;

l) an HC comprising the amino acid sequence of SEQ ID NO: 106 and the amino acid sequence of SEQ ID NO: 374, 375, 376, or 377, and an LC comprising the amino acid sequence of SEQ ID NO: 107 and the amino acid sequence of SEQ ID NO: 378;

m) an HC comprising the amino acid sequence of SEQ ID NO: 116 and the amino acid sequence of SEQ ID NO: 374, 375, 376, or 377, and an LC comprising the amino acid sequence of SEQ ID NO: 117 and the amino acid sequence of SEQ ID NO: 378;

n) an HC comprising the amino acid sequence of SEQ ID NO: 126 and the amino acid sequence of SEQ ID NO: 374, 375, 376, or 377, and an LC comprising the amino acid sequence of SEQ ID NO: 127 and the amino acid sequence of SEQ ID NO: 378;

o) an HC comprising the amino acid sequence of SEQ ID NO: 136 and the amino acid sequence of SEQ ID NO: 374, 375, 376, or 377, and an LC comprising the amino acid sequence of SEQ ID NO: 137 and the amino acid sequence of SEQ ID NO: 378;

p) an HC comprising the amino acid sequence of SEQ ID NO: 146 and the amino acid sequence of SEQ ID NO: 374, 375, 376, or 377, and an LC comprising the amino acid sequence of SEQ ID NO: 147 and the amino acid sequence of SEQ ID NO: 378;

q) an HC comprising the amino acid sequence of SEQ ID NO: 156 and the amino acid sequence of SEQ ID NO: 374, 375, 376, or 377, and an LC comprising the amino acid sequence of SEQ ID NO: 157 and the amino acid sequence of SEQ ID NO: 378;

r) an HC comprising the amino acid sequence of SEQ ID NO: 166 and the amino acid sequence of SEQ ID NO: 374, 375, 376, or 377, and an LC comprising the amino acid sequence of SEQ ID NO: 167 and the amino acid sequence of SEQ ID NO: 378;

s) an HC comprising the amino acid sequence of SEQ ID NO: 176 and the amino acid sequence of SEQ ID NO: 374, 375, 376, or 377, and an LC comprising the amino acid sequence of SEQ ID NO: 177 and the amino acid sequence of SEQ ID NO: 378;

t) an HC comprising the amino acid sequence of SEQ ID NO: 186 and the amino acid sequence of SEQ ID NO: 374, 375, 376, or 377, and an LC comprising the amino acid sequence of SEQ ID NO: 187 and the amino acid sequence of SEQ ID NO: 378;

u) an HC comprising the amino acid sequence of SEQ ID NO: 196 and the amino acid sequence of SEQ ID NO: 374, 375, 376, or 377, and an LC comprising the amino acid sequence of SEQ ID NO: 197 and the amino acid sequence of SEQ ID NO: 378;

v) an HC comprising the amino acid sequence of SEQ ID NO: 206 and the amino acid sequence of SEQ ID NO: 374, 375, 376, or 377, and an LC comprising the amino acid sequence of SEQ ID NO: 207 and the amino acid sequence of SEQ ID NO: 378; or w) an HC comprising the amino acid sequence of SEQ ID NO: 216 and the amino acid sequence of SEQ ID NO: 374, 375, 376, or 377, and an LC comprising the amino acid sequence of SEQ ID NO: 217 and the amino acid sequence of SEQ ID NO: 378.

In some embodiments, the anti-TIM-3 antibody is selected from the group consisting of:
  a) an antibody whose H-CDR1-3 comprise the amino acid sequences of SEQ ID NOs: 8-10, respectively;
  b) an antibody whose VH is at least 90% identical in sequence to the amino acid sequence of SEQ ID NO: 3 or 7;
  c) an antibody whose VH comprises the amino acid sequence of SEQ ID NO: 3 or 7;
  d) an antibody whose HC comprises the amino acid sequences of SEQ ID NOs: 3 and 374, or the amino acid sequence of SEQ ID NO: 7 and the amino acid sequence of SEQ ID NO: 375, 376, or 377;
  e) an antibody whose L-CDR1-3 comprise the amino acid sequences of SEQ ID NOs: 11-13, respectively;
  f) an antibody whose VL is at least 90% identical in sequence to the amino acid sequence of SEQ ID NO: 4;
  g) an antibody whose VL comprises the amino acid sequence of SEQ ID NO: 4; h) an antibody whose LC comprises the amino acid sequences of SEQ ID NOs: 4 and 378;
  i) an antibody whose H-CDR1-3 and L-CDR1-3 comprise the amino acid sequences of SEQ ID NOs: 8-13, respectively;
  j) an antibody whose VH is at least 90% identical in sequence to the amino acid sequence of SEQ ID NO: 3 or 7 and whose VL is at least 90% identical in sequence to the amino acid sequence of SEQ ID NO: 4;
  k) an antibody whose VH comprises the amino acid sequence of SEQ ID NO: 3 or 15 and whose VL comprises the amino acid sequence of SEQ ID NO: 4; and
  l) an antibody whose HC comprises the amino acid sequences of SEQ ID NOs: 3 and 374, or the amino acid sequence of SEQ ID NO: 7 and the amino acid sequence of SEQ ID NO: 375, 376, or 377; and whose LC comprises the amino acid sequences of SEQ ID NOs: 4 and 378.

In some embodiments, the anti-TIM-3 antibody is selected from the group consisting of:
  a) an antibody whose H-CDR1-3 comprise the amino acid sequences of SEQ ID NOs: 18-20, respectively;
  b) an antibody whose VH is at least 90% identical in sequence to the amino acid sequence of SEQ ID NO: 16;
  c) an antibody whose VH comprises the amino acid sequence of SEQ ID NO: 16;
  d) an antibody whose HC comprises the amino acid sequences of SEQ ID NO: 16 and SEQ ID NO: 374, 375, 376, or 377;
  e) an antibody whose L-CDR1-3 comprise the amino acid sequences of SEQ ID NOs: 21-23, respectively;
  f) an antibody whose VL is at least 90% identical in sequence to the amino acid sequence of SEQ ID NO: 17;
  g) an antibody whose VL comprises the amino acid sequence of SEQ ID NO: 17;
  h) an antibody whose LC comprises the amino acid sequences of SEQ ID NOs: 17 and 378;
  i) an antibody whose H-CDR1-3 and L-CDR1-3 comprise the amino acid sequences of SEQ ID NOs: 18-23, respectively;
  j) an antibody whose VH is at least 90% identical in sequence to the amino acid sequence of SEQ ID NO: 16 and whose VL is at least 90% identical in sequence to the amino acid sequence of SEQ ID NO: 17;
  k) an antibody whose VH comprises the amino acid sequence of SEQ ID NO: 16 and whose VL comprises the amino acid sequence of SEQ ID NO: 17; and
  l) an antibody whose HC comprises the amino acid sequence of SEQ ID NO: 16 and the amino acid sequence of SEQ ID NO: 374, 375, 376, or 377; and whose LC comprises the amino acid sequences of SEQ ID NOs: 17 and 378.

In some embodiments, the anti-TIM-3 antibody is selected from the group consisting of:
  a) an antibody whose H-CDR1-3 comprise the amino acid sequences of SEQ ID NOs: 28-30, respectively;
  b) an antibody whose VH is at least 90% identical in sequence to the amino acid sequence of SEQ ID NO: 26;
  c) an antibody whose VH comprises the amino acid sequence of SEQ ID NO: 26;
  d) an antibody whose HC comprises the amino acid sequences of SEQ ID NO: 26 and SEQ ID NO: 374, 375, 376, or 377;
  e) an antibody whose L-CDR1-3 comprise the amino acid sequences of SEQ ID NOs: 31-33, respectively;
  f) an antibody whose VL is at least 90% identical in sequence to the amino acid sequence of SEQ ID NO: 27;
  g) an antibody whose VL comprises the amino acid sequence of SEQ ID NO: 27;
  h) an antibody whose LC comprises the amino acid sequences of SEQ ID NOs: 27 and 378;
  i) an antibody whose H-CDR1-3 and L-CDR1-3 comprise the amino acid sequences of SEQ ID NOs: 28-33, respectively;
  j) an antibody whose VH is at least 90% identical in sequence to the amino acid sequence of SEQ ID NO: 26 and whose VL is at least 90% identical in sequence to the amino acid sequence of SEQ ID NO: 27;
  k) an antibody whose VH comprises the amino acid sequence of SEQ ID NO: 26 and whose VL comprises the amino acid sequence of SEQ ID NO: 27; and
  l) an antibody whose HC comprises the amino acid sequence of SEQ ID NO: 26 and the amino acid sequence of SEQ ID NO: 374, 375, 376, or 377; and whose LC comprises the amino acid sequences of SEQ ID NOs: 27 and 378.

In some embodiments, the anti-TIM-3 antibody is selected from the group consisting of:
  a) an antibody whose H-CDR1-3 comprise the amino acid sequences of SEQ ID NOs: 38-40, respectively;
  b) an antibody whose VH is at least 90% identical in sequence to the amino acid sequence of SEQ ID NO: 36;
  c) an antibody whose VH comprises the amino acid sequence of SEQ ID NO: 36;
  d) an antibody whose HC comprises the amino acid sequences of SEQ ID NO: 36 and SEQ ID NO: 374, 375, 376, or 377;
  e) an antibody whose L-CDR1-3 comprise the amino acid sequences of SEQ ID NOs: 41-43, respectively;
  f) an antibody whose VL is at least 90% identical in sequence to the amino acid sequence of SEQ ID NO: 37;
  g) an antibody whose VL comprises the amino acid sequence of SEQ ID NO: 37;

h) an antibody whose LC comprises the amino acid sequences of SEQ ID NOs: 37 and 378;
i) an antibody whose H-CDR1-3 and L-CDR1-3 comprise the amino acid sequences of SEQ ID NOs: 38-43, respectively;
j) an antibody whose VH is at least 90% identical in sequence to the amino acid sequence of SEQ ID NO: 36 and whose VL is at least 90% identical in sequence to the amino acid sequence of SEQ ID NO: 37;
k) an antibody whose VH comprises the amino acid sequence of SEQ ID NO: 36 and whose VL comprises the amino acid sequence of SEQ ID NO: 37; and
l) an antibody whose HC comprises the amino acid sequence of SEQ ID NO: 36 and the amino acid sequence of SEQ ID NO: 374, 375, 376, or 377; and whose LC comprises the amino acid sequences of SEQ ID NOs: 37 and 378.

In some embodiments, the anti-TIM-3 antibody is selected from the group consisting of:
a) an antibody whose H-CDR1-3 comprise the amino acid sequences of SEQ ID NOs: 48-50, respectively;
b) an antibody whose VH is at least 90% identical in sequence to the amino acid sequence of SEQ ID NO: 46;
c) an antibody whose VH comprises the amino acid sequence of SEQ ID NO: 46;
d) an antibody whose HC comprises the amino acid sequences of SEQ ID NO: 46 and SEQ ID NO: 374, 375, 376, or 377;
e) an antibody whose L-CDR1-3 comprise the amino acid sequences of SEQ ID NOs: 51-53, respectively;
f) an antibody whose VL is at least 90% identical in sequence to the amino acid sequence of SEQ ID NO: 47;
g) an antibody whose VL comprises the amino acid sequence of SEQ ID NO: 47; h) an antibody whose LC comprises the amino acid sequences of SEQ ID NOs: 47 and 378;
i) an antibody whose H-CDR1-3 and L-CDR1-3 comprise the amino acid sequences of SEQ ID NOs: 48-53, respectively;
j) an antibody whose VH is at least 90% identical in sequence to the amino acid sequence of SEQ ID NO: 46 and whose VL is at least 90% identical in sequence to the amino acid sequence of SEQ ID NO: 47;
k) an antibody whose VH comprises the amino acid sequence of SEQ ID NO: 46 and whose VL comprises the amino acid sequence of SEQ ID NO: 47; and
l) an antibody whose HC comprises the amino acid sequence of SEQ ID NO: 46 and the amino acid sequence of SEQ ID NO: 374, 375, 376, or 377; and whose LC comprises the amino acid sequences of SEQ ID NOs: 47 and 378.

In some embodiments, the anti-TIM-3 antibody is selected from the group consisting of:
a) an antibody whose H-CDR1-3 comprise the amino acid sequences of SEQ ID NOs: 58-60, respectively;
b) an antibody whose VH is at least 90% identical in sequence to the amino acid sequence of SEQ ID NO: 56;
c) an antibody whose VH comprises the amino acid sequence of SEQ ID NO: 56;
d) an antibody whose HC comprises the amino acid sequences of SEQ ID NO: 56 and SEQ ID NO: 374, 375, 376, or 377;
e) an antibody whose L-CDR1-3 comprise the amino acid sequences of SEQ ID NOs: 61-63, respectively;
f) an antibody whose VL is at least 90% identical in sequence to the amino acid sequence of SEQ ID NO: 57;
g) an antibody whose VL comprises the amino acid sequence of SEQ ID NO: 57; h) an antibody whose LC comprises the amino acid sequences of SEQ ID NOs: 57 and 378;
i) an antibody whose H-CDR1-3 and L-CDR1-3 comprise the amino acid sequences of SEQ ID NOs: 58-63, respectively;
j) an antibody whose VH is at least 90% identical in sequence to the amino acid sequence of SEQ ID NO: 56 and whose VL is at least 90% identical in sequence to the amino acid sequence of SEQ ID NO: 57;
k) an antibody whose VH comprises the amino acid sequence of SEQ ID NO: 56 and whose VL comprises the amino acid sequence of SEQ ID NO: 57; and
l) an antibody whose HC comprises the amino acid sequence of SEQ ID NO: 56 and the amino acid sequence of SEQ ID NO: 374, 375, 376, or 377; and whose LC comprises the amino acid sequences of SEQ ID NOs: 57 and 378.

In some embodiments, the anti-TIM-3 antibody is selected from the group consisting of:
a) an antibody whose H-CDR1-3 comprise the amino acid sequences of SEQ ID NOs: 68-70, respectively;
b) an antibody whose VH is at least 90% identical in sequence to the amino acid sequence of SEQ ID NO: 66;
c) an antibody whose VH comprises the amino acid sequence of SEQ ID NO: 66;
d) an antibody whose HC comprises the amino acid sequences of SEQ ID NO: 66 and SEQ ID NO: 374, 375, 376, or 377;
e) an antibody whose L-CDR1-3 comprise the amino acid sequences of SEQ ID NOs: 71-73, respectively;
f) an antibody whose VL is at least 90% identical in sequence to the amino acid sequence of SEQ ID NO: 67;
g) an antibody whose VL comprises the amino acid sequence of SEQ ID NO: 67; h) an antibody whose LC comprises the amino acid sequences of SEQ ID NOs: 67 and 378;
i) an antibody whose H-CDR1-3 and L-CDR1-3 comprise the amino acid sequences of SEQ ID NOs: 68-73, respectively;
j) an antibody whose VH is at least 90% identical in sequence to the amino acid sequence of SEQ ID NO: 66 and whose VL is at least 90% identical in sequence to the amino acid sequence of SEQ ID NO: 67;
k) an antibody whose VH comprises the amino acid sequence of SEQ ID NO: 66 and whose VL comprises the amino acid sequence of SEQ ID NO: 67; and
l) an antibody whose HC comprises the amino acid sequence of SEQ ID NO: 66 and the amino acid sequence of SEQ ID NO: 374, 375, 376, or 377; and whose LC comprises the amino acid sequences of SEQ ID NOs: 67 and 378.

In some embodiments, the anti-TIM-3 antibody is selected from the group consisting of:
a) an antibody whose H-CDR1-3 comprise the amino acid sequences of SEQ ID NOs: 78-80, respectively;
b) an antibody whose VH is at least 90% identical in sequence to the amino acid sequence of SEQ ID NO: 76;
c) an antibody whose VH comprises the amino acid sequence of SEQ ID NO: 76;

d) an antibody whose HC comprises the amino acid sequences of SEQ ID NO: 76 and SEQ ID NO: 374, 375, 376, or 377;
e) an antibody whose L-CDR1-3 comprise the amino acid sequences of SEQ ID NOs: 81-83, respectively;
f) an antibody whose VL is at least 90% identical in sequence to the amino acid sequence of SEQ ID NO: 77;
g) an antibody whose VL comprises the amino acid sequence of SEQ ID NO: 77;
h) an antibody whose LC comprises the amino acid sequences of SEQ ID NOs: 77 and 378;
i) an antibody whose H-CDR1-3 and L-CDR1-3 comprise the amino acid sequences of SEQ ID NOs: 78-83, respectively;
j) an antibody whose VH is at least 90% identical in sequence to the amino acid sequence of SEQ ID NO: 76 and whose VL is at least 90% identical in sequence to the amino acid sequence of SEQ ID NO: 77;
k) an antibody whose VH comprises the amino acid sequence of SEQ ID NO: 76 and whose VL comprises the amino acid sequence of SEQ ID NO: 77; and
l) an antibody whose HC comprises the amino acid sequence of SEQ ID NO: 76 and the amino acid sequence of SEQ ID NO: 374, 375, 376, or 377; and whose LC comprises the amino acid sequences of SEQ ID NOs: 77 and 378.

In some embodiments, the anti-TIM-3 antibody is selected from the group consisting of:
a) an antibody whose H-CDR1-3 comprise the amino acid sequences of SEQ ID NOs: 88-90, respectively;
b) an antibody whose VH is at least 90% identical in sequence to the amino acid sequence of SEQ ID NO: 86;
c) an antibody whose VH comprises the amino acid sequence of SEQ ID NO: 86;
d) an antibody whose HC comprises the amino acid sequences of SEQ ID NO: 86 and SEQ ID NO: 374, 375, 376, or 377;
e) an antibody whose L-CDR1-3 comprise the amino acid sequences of SEQ ID NOs: 91-93, respectively;
f) an antibody whose VL is at least 90% identical in sequence to the amino acid sequence of SEQ ID NO: 87;
g) an antibody whose VL comprises the amino acid sequence of SEQ ID NO: 87;
h) an antibody whose LC comprises the amino acid sequences of SEQ ID NOs: 87 and 378;
i) an antibody whose H-CDR1-3 and L-CDR1-3 comprise the amino acid sequences of SEQ ID NOs: 88-93, respectively;
j) an antibody whose VH is at least 90% identical in sequence to the amino acid sequence of SEQ ID NO: 86 and whose VL is at least 90% identical in sequence to the amino acid sequence of SEQ ID NO: 87;
k) an antibody whose VH comprises the amino acid sequence of SEQ ID NO: 86 and whose VL comprises the amino acid sequence of SEQ ID NO: 87; and
l) an antibody whose HC comprises the amino acid sequence of SEQ ID NO: 86 and the amino acid sequence of SEQ ID NO: 374, 375, 376, or 377; and whose LC comprises the amino acid sequences of SEQ ID NOs: 87 and 378.

In some embodiments, the anti-TIM-3 antibody is selected from the group consisting of:
a) an antibody whose H-CDR1-3 comprise the amino acid sequences of SEQ ID NOs: 98-100, respectively;
b) an antibody whose VH is at least 90% identical in sequence to the amino acid sequence of SEQ ID NO: 96;
c) an antibody whose VH comprises the amino acid sequence of SEQ ID NO: 96;
d) an antibody whose HC comprises the amino acid sequences of SEQ ID NO: 96 and SEQ ID NO: 374, 375, 376, or 377;
e) an antibody whose L-CDR1-3 comprise the amino acid sequences of SEQ ID NOs: 101-103, respectively;
f) an antibody whose VL is at least 90% identical in sequence to the amino acid sequence of SEQ ID NO: 97;
g) an antibody whose VL comprises the amino acid sequence of SEQ ID NO: 97;
h) an antibody whose LC comprises the amino acid sequences of SEQ ID NOs: 97 and 378;
i) an antibody whose H-CDR1-3 and L-CDR1-3 comprise the amino acid sequences of SEQ ID NOs: 98-103, respectively;
j) an antibody whose VH is at least 90% identical in sequence to the amino acid sequence of SEQ ID NO: 96 and whose VL is at least 90% identical in sequence to the amino acid sequence of SEQ ID NO: 97;
k) an antibody whose VH comprises the amino acid sequence of SEQ ID NO: 96 and whose VL comprises the amino acid sequence of SEQ ID NO: 97; and
l) an antibody whose HC comprises the amino acid sequence of SEQ ID NO: 96 and the amino acid sequence of SEQ ID NO: 374, 375, 376, or 377; and whose LC comprises the amino acid sequences of SEQ ID NOs: 97 and 378.

In some embodiments, the anti-TIM-3 antibody is selected from the group consisting of:
a) an antibody whose H-CDR1-3 comprise the amino acid sequences of SEQ ID NOs: 108-110, respectively;
b) an antibody whose VH is at least 90% identical in sequence to the amino acid sequence of SEQ ID NO: 106;
c) an antibody whose VH comprises the amino acid sequence of SEQ ID NO: 106;
d) an antibody whose HC comprises the amino acid sequences of SEQ ID NO: 106 and SEQ ID NO: 374, 375, 376, or 377;
e) an antibody whose L-CDR1-3 comprise the amino acid sequences of SEQ ID NOs: 111-113, respectively;
f) an antibody whose VL is at least 90% identical in sequence to the amino acid sequence of SEQ ID NO: 107;
g) an antibody whose VL comprises the amino acid sequence of SEQ ID NO: 107;
h) an antibody whose LC comprises the amino acid sequences of SEQ ID NOs: 107 and 378;
i) an antibody whose H-CDR1-3 and L-CDR1-3 comprise the amino acid sequences of SEQ ID NOs: 108-113, respectively;
j) an antibody whose VH is at least 90% identical in sequence to the amino acid sequence of SEQ ID NO: 106 and whose VL is at least 90% identical in sequence to the amino acid sequence of SEQ ID NO: 107;
k) an antibody whose VH comprises the amino acid sequence of SEQ ID NO: 106 and whose VL comprises the amino acid sequence of SEQ ID NO: 107; and
l) an antibody whose HC comprises the amino acid sequence of SEQ ID NO: 106 and the amino acid sequence of SEQ ID NO: 374, 375, 376, or 377; and whose LC comprises the amino acid sequences of SEQ ID NOs: 107 and 378.

In some embodiments, the anti-TIM-3 antibody is selected from the group consisting of:
a) an antibody whose H-CDR1-3 comprise the amino acid sequences of SEQ ID NOs: 118-120, respectively;
b) an antibody whose VH is at least 90% identical in sequence to the amino acid sequence of SEQ ID NO: 116;
c) an antibody whose VH comprises the amino acid sequence of SEQ ID NO: 116;
d) an antibody whose HC comprises the amino acid sequences of SEQ ID NO: 116 and SEQ ID NO: 374, 375, 376, or 377;
e) an antibody whose L-CDR1-3 comprise the amino acid sequences of SEQ ID NOs: 121-123, respectively;
f) an antibody whose VL is at least 90% identical in sequence to the amino acid sequence of SEQ ID NO: 117;
g) an antibody whose VL comprises the amino acid sequence of SEQ ID NO: 117;
h) an antibody whose LC comprises the amino acid sequences of SEQ ID NOs: 117 and 378;
i) an antibody whose H-CDR1-3 and L-CDR1-3 comprise the amino acid sequences of SEQ ID NOs: 118-123, respectively;
j) an antibody whose VH is at least 90% identical in sequence to the amino acid sequence of SEQ ID NO: 116 and whose VL is at least 90% identical in sequence to the amino acid sequence of SEQ ID NO: 117;
k) an antibody whose VH comprises the amino acid sequence of SEQ ID NO: 116 and whose VL comprises the amino acid sequence of SEQ ID NO: 117; and
l) an antibody whose HC comprises the amino acid sequence of SEQ ID NO: 116 and the amino acid sequence of SEQ ID NO: 374, 375, 376, or 377; and whose LC comprises the amino acid sequences of SEQ ID NOs: 117 and 378.

In some embodiments, the anti-TIM-3 antibody is selected from the group consisting of:
a) an antibody whose H-CDR1-3 comprise the amino acid sequences of SEQ ID NOs: 128-130, respectively;
b) an antibody whose VH is at least 90% identical in sequence to the amino acid sequence of SEQ ID NO: 126;
c) an antibody whose VH comprises the amino acid sequence of SEQ ID NO: 126;
d) an antibody whose HC comprises the amino acid sequences of SEQ ID NO: 126 and SEQ ID NO: 374, 375, 376, or 377;
e) an antibody whose L-CDR1-3 comprise the amino acid sequences of SEQ ID NOs: 131-133, respectively;
f) an antibody whose VL is at least 90% identical in sequence to the amino acid sequence of SEQ ID NO: 127;
g) an antibody whose VL comprises the amino acid sequence of SEQ ID NO: 127;
h) an antibody whose LC comprises the amino acid sequences of SEQ ID NOs: 127 and 378;
i) an antibody whose H-CDR1-3 and L-CDR1-3 comprise the amino acid sequences of SEQ ID NOs: 128-133, respectively;
j) an antibody whose VH is at least 90% identical in sequence to the amino acid sequence of SEQ ID NO: 126 and whose VL is at least 90% identical in sequence to the amino acid sequence of SEQ ID NO: 127;
k) an antibody whose VH comprises the amino acid sequence of SEQ ID NO: 126 and whose VL comprises the amino acid sequence of SEQ ID NO: 127; and
l) an antibody whose HC comprises the amino acid sequence of SEQ ID NO: 126 and the amino acid sequence of SEQ ID NO: 374, 375, 376, or 377; and whose LC comprises the amino acid sequences of SEQ ID NOs: 127 and 378.

In some embodiments, the anti-TIM-3 antibody is selected from the group consisting of:
a) an antibody whose H-CDR1-3 comprise the amino acid sequences of SEQ ID NOs: 138-140, respectively;
b) an antibody whose VH is at least 90% identical in sequence to the amino acid sequence of SEQ ID NO: 136;
c) an antibody whose VH comprises the amino acid sequence of SEQ ID NO: 136;
d) an antibody whose HC comprises the amino acid sequences of SEQ ID NO: 136 and SEQ ID NO: 374, 375, 376, or 377;
e) an antibody whose L-CDR1-3 comprise the amino acid sequences of SEQ ID NOs: 141-143, respectively;
f) an antibody whose VL is at least 90% identical in sequence to the amino acid sequence of SEQ ID NO: 137;
g) an antibody whose VL comprises the amino acid sequence of SEQ ID NO: 137;
h) an antibody whose LC comprises the amino acid sequences of SEQ ID NOs: 137 and 378;
i) an antibody whose H-CDR1-3 and L-CDR1-3 comprise the amino acid sequences of SEQ ID NOs: 138-143, respectively;
j) an antibody whose VH is at least 90% identical in sequence to the amino acid sequence of SEQ ID NO: 136 and whose VL is at least 90% identical in sequence to the amino acid sequence of SEQ ID NO: 137;
k) an antibody whose VH comprises the amino acid sequence of SEQ ID NO: 136 and whose VL comprises the amino acid sequence of SEQ ID NO: 137; and
l) an antibody whose HC comprises the amino acid sequence of SEQ ID NO: 136 and the amino acid sequence of SEQ ID NO: 374, 375, 376, or 377; and whose LC comprises the amino acid sequences of SEQ ID NOs: 137 and 378.

In some embodiments, the anti-TIM-3 antibody is selected from the group consisting of:
a) an antibody whose H-CDR1-3 comprise the amino acid sequences of SEQ ID NOs: 148-150, respectively;
b) an antibody whose VH is at least 90% identical in sequence to the amino acid sequence of SEQ ID NO: 146;
c) an antibody whose VH comprises the amino acid sequence of SEQ ID NO: 146;
d) an antibody whose HC comprises the amino acid sequences of SEQ ID NO: 146 and SEQ ID NO: 374, 375, 376, or 377;
e) an antibody whose L-CDR1-3 comprise the amino acid sequences of SEQ ID NOs: 151-153, respectively;
f) an antibody whose VL is at least 90% identical in sequence to the amino acid sequence of SEQ ID NO: 147;
g) an antibody whose VL comprises the amino acid sequence of SEQ ID NO: 147;
h) an antibody whose LC comprises the amino acid sequences of SEQ ID NOs: 147 and 378;

i) an antibody whose H-CDR1-3 and L-CDR1-3 comprise the amino acid sequences of SEQ ID NOs: 148-53, respectively;
j) an antibody whose VH is at least 90% identical in sequence to the amino acid sequence of SEQ ID NO: 146 and whose VL is at least 90% identical in sequence to the amino acid sequence of SEQ ID NO: 147;
k) an antibody whose VH comprises the amino acid sequence of SEQ ID NO: 146 and whose VL comprises the amino acid sequence of SEQ ID NO: 147; and
l) an antibody whose HC comprises the amino acid sequence of SEQ ID NO: 146 and the amino acid sequence of SEQ ID NO: 374, 375, 376, or 377; and whose LC comprises the amino acid sequences of SEQ ID NOs: 147 and 378.

In some embodiments, the anti-TIM-3 antibody is selected from the group consisting of:
a) an antibody whose H-CDR1-3 comprise the amino acid sequences of SEQ ID NOs: 158-160, respectively;
b) an antibody whose VH is at least 90% identical in sequence to the amino acid sequence of SEQ ID NO: 156;
c) an antibody whose VH comprises the amino acid sequence of SEQ ID NO: 156;
d) an antibody whose HC comprises the amino acid sequences of SEQ ID NO: 156 and SEQ ID NO: 374, 375, 376, or 377;
e) an antibody whose L-CDR1-3 comprise the amino acid sequences of SEQ ID NOs: 161-163, respectively;
f) an antibody whose VL is at least 90% identical in sequence to the amino acid sequence of SEQ ID NO: 157;
g) an antibody whose VL comprises the amino acid sequence of SEQ ID NO: 157;
h) an antibody whose LC comprises the amino acid sequences of SEQ ID NOs: 157 and 378;
i) an antibody whose H-CDR1-3 and L-CDR1-3 comprise the amino acid sequences of SEQ ID NOs: 158-163, respectively;
j) an antibody whose VH is at least 90% identical in sequence to the amino acid sequence of SEQ ID NO: 156 and whose VL is at least 90% identical in sequence to the amino acid sequence of SEQ ID NO: 157;
k) an antibody whose VH comprises the amino acid sequence of SEQ ID NO: 156 and whose VL comprises the amino acid sequence of SEQ ID NO: 157; and
l) an antibody whose HC comprises the amino acid sequence of SEQ ID NO: 156 and the amino acid sequence of SEQ ID NO: 374, 375, 376, or 377; and whose LC comprises the amino acid sequences of SEQ ID NOs: 157 and 378.

In some embodiments, the anti-TIM-3 antibody is selected from the group consisting of:
a) an antibody whose H-CDR1-3 comprise the amino acid sequences of SEQ ID NOs: 168-170, respectively;
b) an antibody whose VH is at least 90% identical in sequence to the amino acid sequence of SEQ ID NO: 166;
c) an antibody whose VH comprises the amino acid sequence of SEQ ID NO: 166;
d) an antibody whose HC comprises the amino acid sequences of SEQ ID NO: 166 and SEQ ID NO: 374, 375, 376, or 377;
e) an antibody whose L-CDR1-3 comprise the amino acid sequences of SEQ ID NOs: 171-173, respectively;
f) an antibody whose VL is at least 90% identical in sequence to the amino acid sequence of SEQ ID NO: 167;
g) an antibody whose VL comprises the amino acid sequence of SEQ ID NO: 167;
h) an antibody whose LC comprises the amino acid sequences of SEQ ID NOs: 167 and 378;
i) an antibody whose H-CDR1-3 and L-CDR1-3 comprise the amino acid sequences of SEQ ID NOs: 168-173, respectively;
j) an antibody whose VH is at least 90% identical in sequence to the amino acid sequence of SEQ ID NO: 166 and whose VL is at least 90% identical in sequence to the amino acid sequence of SEQ ID NO: 167;
k) an antibody whose VH comprises the amino acid sequence of SEQ ID NO: 166 and whose VL comprises the amino acid sequence of SEQ ID NO: 167; and
l) an antibody whose HC comprises the amino acid sequence of SEQ ID NO: 166 and the amino acid sequence of SEQ ID NO: 374, 375, 376, or 377; and whose LC comprises the amino acid sequences of SEQ ID NOs: 167 and 378.

In some embodiments, the anti-TIM-3 antibody is selected from the group consisting of:
a) an antibody whose H-CDR1-3 comprise the amino acid sequences of SEQ ID NOs: 178-80, respectively;
b) an antibody whose VH is at least 90% identical in sequence to the amino acid sequence of SEQ ID NO: 176;
c) an antibody whose VH comprises the amino acid sequence of SEQ ID NO: 176;
d) an antibody whose HC comprises the amino acid sequences of SEQ ID NO: 176 and SEQ ID NO: 374, 375, 376, or 377;
e) an antibody whose L-CDR1-3 comprise the amino acid sequences of SEQ ID NOs: 181-183, respectively;
f) an antibody whose VL is at least 90% identical in sequence to the amino acid sequence of SEQ ID NO: 177;
g) an antibody whose VL comprises the amino acid sequence of SEQ ID NO: 177;
h) an antibody whose LC comprises the amino acid sequences of SEQ ID NOs: 177 and 378;
i) an antibody whose H-CDR1-3 and L-CDR1-3 comprise the amino acid sequences of SEQ ID NOs: 178-183, respectively;
j) an antibody whose VH is at least 90% identical in sequence to the amino acid sequence of SEQ ID NO: 176 and whose VL is at least 90% identical in sequence to the amino acid sequence of SEQ ID NO: 177;
k) an antibody whose VH comprises the amino acid sequence of SEQ ID NO: 176 and whose VL comprises the amino acid sequence of SEQ ID NO: 177; and
l) an antibody whose HC comprises the amino acid sequence of SEQ ID NO: 176 and the amino acid sequence of SEQ ID NO: 374, 375, 376, or 377; and whose LC comprises the amino acid sequences of SEQ ID NOs: 177 and 378.

In some embodiments, the anti-TIM-3 antibody is selected from the group consisting of:
a) an antibody whose H-CDR1-3 comprise the amino acid sequences of SEQ ID NOs: 188-190, respectively;
b) an antibody whose VH is at least 90% identical in sequence to the amino acid sequence of SEQ ID NO: 186;
c) an antibody whose VH comprises the amino acid sequence of SEQ ID NO: 186;

d) an antibody whose HC comprises the amino acid sequences of SEQ ID NO: 186 and SEQ ID NO: 374, 375, 376, or 377;
e) an antibody whose L-CDR1-3 comprise the amino acid sequences of SEQ ID NOs: 191-193, respectively;
f) an antibody whose VL is at least 90% identical in sequence to the amino acid sequence of SEQ ID NO: 187;
g) an antibody whose VL comprises the amino acid sequence of SEQ ID NO: 187;
h) an antibody whose LC comprises the amino acid sequences of SEQ ID NOs: 187 and 378;
i) an antibody whose H-CDR1-3 and L-CDR1-3 comprise the amino acid sequences of SEQ ID NOs: 188-193, respectively;
j) an antibody whose VH is at least 90% identical in sequence to the amino acid sequence of SEQ ID NO: 186 and whose VL is at least 90% identical in sequence to the amino acid sequence of SEQ ID NO: 187;
k) an antibody whose VH comprises the amino acid sequence of SEQ ID NO: 186 and whose VL comprises the amino acid sequence of SEQ ID NO: 187; and
l) an antibody whose HC comprises the amino acid sequence of SEQ ID NO: 186 and the amino acid sequence of SEQ ID NO: 374, 375, 376, or 377; and whose LC comprises the amino acid sequences of SEQ ID NOs: 187 and 378.

In some embodiments, the anti-TIM-3 antibody is selected from the group consisting of:
a) an antibody whose H-CDR1-3 comprise the amino acid sequences of SEQ ID NOs: 198-200, respectively;
b) an antibody whose VH is at least 90% identical in sequence to the amino acid sequence of SEQ ID NO: 196;
c) an antibody whose VH comprises the amino acid sequence of SEQ ID NO: 196;
d) an antibody whose HC comprises the amino acid sequences of SEQ ID NO: 196 and SEQ ID NO: 374, 375, 376, or 377;
e) an antibody whose L-CDR1-3 comprise the amino acid sequences of SEQ ID NOs: 201-203, respectively;
f) an antibody whose VL is at least 90% identical in sequence to the amino acid sequence of SEQ ID NO: 197;
g) an antibody whose VL comprises the amino acid sequence of SEQ ID NO: 197;
h) an antibody whose LC comprises the amino acid sequences of SEQ ID NOs: 197 and 378;
i) an antibody whose H-CDR1-3 and L-CDR1-3 comprise the amino acid sequences of SEQ ID NOs: 198-203, respectively;
j) an antibody whose VH is at least 90% identical in sequence to the amino acid sequence of SEQ ID NO: 196 and whose VL is at least 90% identical in sequence to the amino acid sequence of SEQ ID NO: 197;
k) an antibody whose VH comprises the amino acid sequence of SEQ ID NO: 196 and whose VL comprises the amino acid sequence of SEQ ID NO: 197; and
l) an antibody whose HC comprises the amino acid sequence of SEQ ID NO: 196 and the amino acid sequence of SEQ ID NO: 374, 375, 376, or 377; and whose LC comprises the amino acid sequences of SEQ ID NOs: 197 and 378.

In some embodiments, the anti-TIM-3 antibody is selected from the group consisting of:
a) an antibody whose H-CDR1-3 comprise the amino acid sequences of SEQ ID NOs: 208-210, respectively;
b) an antibody whose VH is at least 90% identical in sequence to the amino acid sequence of SEQ ID NO: 206;
c) an antibody whose VH comprises the amino acid sequence of SEQ ID NO: 206;
d) an antibody whose HC comprises the amino acid sequences of SEQ ID NO: 206 and SEQ ID NO: 374, 375, 376, or 377;
e) an antibody whose L-CDR1-3 comprise the amino acid sequences of SEQ ID NOs: 211-213, respectively;
f) an antibody whose VL is at least 90% identical in sequence to the amino acid sequence of SEQ ID NO: 207;
g) an antibody whose VL comprises the amino acid sequence of SEQ ID NO: 207;
h) an antibody whose LC comprises the amino acid sequences of SEQ ID NOs: 207 and 378;
i) an antibody whose H-CDR1-3 and L-CDR1-3 comprise the amino acid sequences of SEQ ID NOs: 208-213, respectively;
j) an antibody whose VH is at least 90% identical in sequence to the amino acid sequence of SEQ ID NO: 206 and whose VL is at least 90% identical in sequence to the amino acid sequence of SEQ ID NO: 207;
k) an antibody whose VH comprises the amino acid sequence of SEQ ID NO: 206 and whose VL comprises the amino acid sequence of SEQ ID NO: 207; and
l) an antibody whose HC comprises the amino acid sequence of SEQ ID NO: 206 and the amino acid sequence of SEQ ID NO: 374, 375, 376, or 377; and whose LC comprises the amino acid sequences of SEQ ID NOs: 207 and 378.

In some embodiments, the anti-TIM-3 antibody is selected from the group consisting of:
a) an antibody whose H-CDR1-3 comprise the amino acid sequences of SEQ ID NOs: 218-220, respectively;
b) an antibody whose VH is at least 90% identical in sequence to the amino acid sequence of SEQ ID NO: 216;
c) an antibody whose VH comprises the amino acid sequence of SEQ ID NO: 216;
d) an antibody whose HC comprises the amino acid sequences of SEQ ID NO: 216 and SEQ ID NO: 374, 375, 376, or 377;
e) an antibody whose L-CDR1-3 comprise the amino acid sequences of SEQ ID NOs: 221-223, respectively;
f) an antibody whose VL is at least 90% identical in sequence to the amino acid sequence of SEQ ID NO: 217;
g) an antibody whose VL comprises the amino acid sequence of SEQ ID NO: 217;
h) an antibody whose LC comprises the amino acid sequences of SEQ ID NOs: 217 and 378;
i) an antibody whose H-CDR1-3 and L-CDR1-3 comprise the amino acid sequences of SEQ ID NOs: 218-223, respectively;
j) an antibody whose VH is at least 90% identical in sequence to the amino acid sequence of SEQ ID NO: 216 and whose VL is at least 90% identical in sequence to the amino acid sequence of SEQ ID NO: 217;
k) an antibody whose VH comprises the amino acid sequence of SEQ ID NO: 216 and whose VL comprises the amino acid sequence of SEQ ID NO: 217; and
l) an antibody whose HC comprises the amino acid sequence of SEQ ID NO: 216 and the amino acid sequence of SEQ ID NO: 374, 375, 376, or 377; and whose LC comprises the amino acid sequences of SEQ ID NOs: 217 and 378.

In some embodiments, any of the anti-TIM-3 antibodies or antigen-binding portions described herein may inhibit binding of ligands such as galectin-9, CEACAM1, HMGB-1, and phosphatidylserine to TIM-3.

In some embodiments, any of the anti-TIM-3 antibodies or antigen-binding portions described herein may increase the activity of NK cells. In some embodiments, this activity can mediate ADCC.

In some embodiments, administration of an anti-TIM-3 antibody or an antigen-binding portion thereof as described herein may activate dendritic cells, causing their maturation and thereby their ability to stimulate T-cells. While not wishing to be bound by any particular theory, it is believed that the anti-TIM-3 antibodies described herein function as TIM-3 dendritic cell activators, whereby their effect on dendritic cells serves to stimulate T cells. In a tumor-related setting, the anti-TIM-3 antibodies thus would cause maturation and activation of tumor associated dendritic cells, resulting in activation of tumor specific T-cells.

In some embodiments, administration of an anti-TIM-3 antibody or an antigen-binding portion thereof as described herein may directly activate T cells.

In some embodiments, the anti-TIM-3 antibody or antigen-binding portion described herein has at least one of the following properties:
  a) binds to human TIM-3 with a $K_D$ of 23 nM or less as measured by surface plasmon resonance;
  b) binds to cynomolgus TIM-3 with a $K_D$ of 22 nM or less as measured by surface plasmon resonance;
  c) binds to human TIM-3 with an EC50 of 1.2 nM or less as measured by ELISA;
  d) binds to cynomolgus TIM-3 with an EC50 of 46 nM or less as measured by
  ELISA;
  e) increases IFN-γ secretion in a one-way mixed lymphocyte reaction assay;
  f) increases IFN-γ secretion in a two-way mixed lymphocyte reaction assay;
  g) increases TNF-α secretion in a one-way mixed lymphocyte reaction assay;
  h) increases TNF-α secretion from dendritic cells; and
  i) inhibits interaction of TIM-3 with phosphatidylserine.

Examples of such an antibody include, without limitation, antibody 15086.15086 (having at least properties a, c, d, e, g, and h); antibody 15086.17145 (having at least properties a, c, d, e, g, h, and i), antibody 15086.16837 or 15086.17144 (having at least properties a, c, and d), antibody 20293 or 20131 (having at least properties a, b, c, d, e, f, and h), antibody 20362 (having at least properties c, e, f, and h), and antibody 19324, 19416, 19568, 20185, 20300, or 20621 (having at least properties c, d, e, f, and h). In some embodiments, the anti-TIM-3 antibody or antigen-binding portion has all of said properties. In some embodiments, the anti-TIM-3 antibody or antigen-binding portion has at least properties a, c, d, e, g, and h. In some embodiments, the anti-TIM-3 antibody or antigen-binding portion has at least properties a, c, d, e, g, h, and i. In some embodiments, the anti-TIM-3 antibody or antigen-binding portion has at least properties a, c, and d. In some embodiments, the anti-TIM-3 antibody or antigen-binding portion has at least properties a, b, c, d, e, f, and h. In some embodiments, the anti-TIM-3 antibody or antigen-binding portion has at least properties c, e, f, and h. In some embodiments, the anti-TIM-3 antibody or antigen-binding portion has at least properties c, d, e, f, and h.

In some embodiments, an anti-TIM-3 antibody or an antigen-binding portion thereof as described herein binds to an epitope of TIM-3 that includes at least one (e.g., at least two, at least three, at least four, at least five, at least six, at least seven, at least eight, or at least nine) of the following residues of SEQ ID NO: 389: P50, V60, F61, E62, G64, R69, 1117, M118, and D120. In certain embodiments, the antibody or antigen-binding portion binds to an epitope of TIM-3 that includes residues P50, V60, F61, E62, G64, R69, 1117, M118, and D120 of SEQ ID NO: 389 (such as antibody 15086.15086, 15086.16837, 15086.17145, or 15086.17144). In certain embodiments, the antibody or antigen-binding portion binds to an epitope of TIM-3 that includes residues F61, R69, and 1117 of SEQ ID NO: 389 (such as antibody 20293). In certain embodiments, the antibody or antigen-binding portion binds to an epitope of TIM-3 that includes residues P50, F61, E62, 1117, M118, and D120 of SEQ ID NO: 389 (such as antibody 20131).

In some embodiments, the anti-TIM-3 antibody or antigen-binding portion thereof binds to an epitope of TIM-3 comprising amino acid residues F61 and 1117 of SEQ ID NO: 389 (e.g., antibody 15086.15086, 15086.16837, 15086.17145, 15086.17144, 20293, or 20131). In some embodiments, the epitope further comprises amino acid residue R69 (e.g., antibody 15086.15086, 15086.16837, 15086.17145, 15086.17144, or 20293). In some embodiments, the epitope further comprises P50, E62, M118, and D120 (e.g., antibody 15086.15086, 15086.16837, 15086.17145, 15086.17144, or 20131) and may additionally comprise amino acid residues V60 and G64 (e.g., antibody 15086.15086, 15086.16837, 15086.17145, or 15086.17144).

In some embodiments, an anti-TIM-3 antibody or an antigen-binding portion thereof as described herein binds to an epitope of TIM-3 that includes at least one (e.g., at least one, at least two, at least three, at least four, at least five, at least six, at least seven, at least eight, or at least nine) of the following residues of SEQ ID NO: 236: P50, V60, F61, E62, G64, R69, 1117, M118, and D120. An epitope with any combination of the above residues is contemplated.

In some embodiments, an anti-TIM-3 antibody or an antigen-binding portion thereof as described herein binds to an epitope of TIM-3 that comprises residues 62-67 and/or 114-117 of SEQ ID NO: 389. In some embodiments, the antibody or portion binds to residues 62-67 (or a fragment thereof, such as a one, two, three, four, or five residue fragment), of SEQ ID NO: 389 (e.g., antibodies 15086.15086, 15086.16837, 15086.17145, 15086.17144, and 20293). In some embodiments, the antibody or portion binds to residues 114-117 (or a fragment thereof, such as a one, two, or three residue fragment) of SEQ ID NO: 389 (e.g., antibody 20131). An epitope with any combination of the above residues is also contemplated.

In some embodiments, the anti-TIM-3 antibody or antigen-binding portion thereof does not compete for binding to TIM-3 with ABTIM3 (from PCT Patent Publication WO 2015/117002) and/or mAb15 (from PCT Patent Publication WO 2016/111947). In some embodiments, the anti-TIM-3 antibody or antigen-binding portion does not bind to the same epitope as ABTIM3 and/or mAB15; for example, the antibody or portion binds to one or more residues on TIM-3 that are not bound by ABTIM3 and/or mAb15.

In some embodiments, an anti-TIM-3 antibody or an antigen-binding portion thereof as described herein is an anti-TIM-3 antibody or antigen-binding portion described in PCT Patent Publication WO 2017/178493, which is incorporated by reference in its entirety herein.

Anti-LAG-3 Antibodies

In some embodiments, the anti-LAG-3 antibodies disclosed herein are human antibodies generated from transgenic rats that are able to generate antibodies with human idiotypes. In another embodiment, the antibodies are chicken-derived chimeric antibodies comprising chicken CDR sequences and human framework regions, where the framework regions have been subjected to humanization.

One advantage of the novel anti-LAG-3 antibodies described herein is that they are able to enhance activity of T-cells as measured by increased IL-2 production. While not wishing to be bound by any particular theory, it is believed that the anti-LAG-3 antibodies are able to block the interaction of LAG-3 with its putative ligands such as MHCII and LSECtin. The antibodies may accomplish this directly via blocking of the ligand binding region or via induction of LAG-3 internalization. Another potential advantage of the anti-LAG-3 antibodies described herein is a low level of secondary effector functions in antibodies having the "LALA" mutations (L234A/L235A), which hinder significant antibody binding to human FcgR (Fc gamma receptors) and hence depletion of effector T-cells.

In some embodiments, the combination therapy or composition comprises an anti-LAG-3 antibody or an antigen-binding portion thereof, wherein the anti-LAG-3 antibody is the antibody referred to herein as antibody 15646, 15532, 15723, 15595, 15431, 15572 or 15011 or a variant of any of these, where the variant may, e.g., contain certain minimum amino acid changes relative to said antibody (e.g., 1, 2, 3, 4, 5, 6, 7, 8, 9, or 10 amino acid changes, which may be, e.g., in the framework regions) without losing the antigen-binding specificity of antibody.

In some embodiments, the anti-LAG-3 antibody, or an antigen-binding portion thereof, competes or cross-competes for binding to human LAG-3 with, or binds to the same epitope of human LAG-3 as, antibody 15646, 15532, 15723, 15595, 15431, 15572 or 15011. In some embodiments, the antibody has an IgG1 or IgG2 format. In certain embodiments, the antibody has an IgG2 format.

In some embodiments, the anti-LAG-3 antibody competes or cross-competes for binding to human LAG-3 with, or binds to the same epitope of human LAG-3 as, an antibody whose heavy chain (H) CDR1-3 and light chain (L) CDR1-3 comprise, respectively, SEQ ID NOs: 308-313, 318-323, 328-333, 338-343, 348-353, 358-363, or 368-373.

In some embodiments, the anti-LAG-3 antibody comprises an H-CDR3 comprising the H-CDR3 amino acid sequence of SEQ ID NO: 310, 320, 330, 340, 350, 360, or 370.

In some embodiments, the anti-LAG-3 antibody comprises H-CDR1-3 comprising the H-CDR1-3 amino acid sequences, respectively, of SEQ ID NOs: 308-310, 318-320, 328-330, 338-340, 348-350, 358-360, or 368-370.

In some embodiments, the anti-LAG-3 antibody has a VH that is at least 90% (e.g., at least 92%, at least 95%, at least 96%, at least 97%, at least 98%, or at least 99%) identical in amino acid sequence to SEQ ID NO: 306, 316, 326, 336, 346, 356, or 366.

In some embodiments, the anti-LAG-3 antibody has a VH that comprises SEQ ID NO: 306, 316, 326, 336, 346, 356, or 366.

In some embodiments, the anti-LAG-3 antibody has a VH that is at least 90% (e.g., at least 92%, at least 95%, at least 96%, at least 97%, at least 98%, or at least 99%) identical in sequence to SEQ ID NO: 306, 316, 326, 336, 346, 356, or 366; and a CH that is at least 90% (e.g., at least 92%, at least 95%, at least 96%, at least 97%, at least 98%, or at least 99%) identical in sequence to SEQ ID NO: 375.

In some embodiments, the anti-LAG-3 antibody has a HC that comprises the VH amino acid sequence of SEQ ID NO: 306, 316, 326, 336, 346, 356, or 366 and the CH amino acid sequence of SEQ ID NO: 375.

In some embodiments, the anti-LAG-3 antibody comprises an L-CDR3 comprising the L-CDR3 amino acid sequence of SEQ ID NO: 313, 323, 333, 343, 353, 363, or 373.

In some embodiments, the anti-LAG-3 antibody comprises L-CDR1-3 comprising the L-CDR1-3 amino acid sequences, respectively, of SEQ ID NOs: 311-313, 321-323, 331-333, 341-343, 351-353, 361-363, or 371-373.

In some embodiments, the anti-LAG-3 antibody has a VL that is at least 90% (e.g., at least 92%, at least 95%, at least 96%, at least 97%, at least 98%, or at least 99%) identical in sequence to the VL amino acid sequence of SEQ ID NO: 307, 317, 327, 337, 347, 357, or 367.

In some embodiments, the anti-LAG-3 antibody has a VL that comprises the VL amino acid sequence of SEQ ID NO: 307, 317, 327, 337, 347, 357, or 367.

In some embodiments, the anti-LAG-3 antibody has a VL that is at least 90% (e.g., at least 92%, at least 95%, at least 96%, at least 97%, at least 98%, or at least 99%) identical in sequence to the VL amino acid sequence of SEQ ID NO: 307, 317, 327, 337, 347, or 357; and a CL that is at least 90% (e.g., at least 92%, at least 95%, at least 96%, at least 97%, at least 98%, or at least 99%) identical in sequence to SEQ ID NO: 378.

In some embodiments, the anti-LAG-3 antibody has a LC that comprises the VL amino acid sequence of SEQ ID NO: 307, 317, 327, 337, 347, or 357 and the CL amino acid sequence of SEQ ID NO: 378. In some embodiments, the anti-LAG-3 antibody has an LC that comprises the VL amino acid sequence of SEQ ID NO: 367 and the CL amino acid sequence of SEQ ID NO: 379.

In some embodiments, the anti-LAG-3 antibody comprises any of the above heavy chain sequences and any of the above light chain sequences.

In some embodiments, the anti-LAG-3 antibody comprises an H-CDR3 and L-CDR3 comprising the H-CDR3 and L-CDR3 amino acid sequences, respectively, of SEQ ID NOs: 310 and 313, 320 and 323, 330 and 333, 340 and 343, 350 and 353, 360 and 363, or 370 and 373.

In some embodiments, the anti-LAG-3 antibody comprises H-CDR1-3 and L-CDR1-3 comprising the H-CDR1-3 and L-CDR1-3 sequences, respectively, of SEQ ID NOs: 308-313, 318-323, 328-333, 338-343, 348-353, 358-363, or 368-373.

In some embodiments, the anti-LAG-3 antibody has a VH that is at least 90% (e.g., at least 92%, at least 95%, at least 98%, or at least 99%) identical in sequence to the amino acid sequence of SEQ ID NO: 306, 316, 326, 336, 346, 356, or 366, and a VL that is at least 90% (e.g., at least 92%, at least 95%, at least 98%, or at least 99%) identical in sequence to the amino acid sequence of SEQ ID NO: 307, 317, 327, 337, 347, 357, or 367.

In some embodiments, the anti-LAG-3 antibody has a VH that comprises the amino acid sequence of SEQ ID NO: 306, 316, 326, 336, 346, 356, or 366, and a VL that comprises the amino acid sequence of SEQ ID NO: 307, 317, 327, 337, 347, 357, or 367.

In some embodiments, the anti-LAG-3 antibody has an HC that comprises the amino acid sequence of SEQ ID NO: 306, 316, 326, 336, 346, 356, or 366 and the amino acid sequence of SEQ ID NO: 375; and an LC that comprises the amino acid sequence of SEQ ID NO: 307, 317, 327, 337, 347, or 357 and the amino acid sequence of SEQ ID NO: 378.

In some embodiments, the anti-LAG-3 antibody has an HC that comprises the amino acid sequence of SEQ ID NO: 306, 316, 326, 336, 346, 356, or 366 and the amino acid sequence of SEQ ID NO: 375; and an LC that comprises the amino acid sequence of SEQ ID NO: 367 and the amino acid sequence of SEQ ID NO: 379.

In some embodiments, the anti-LAG-3 antibody comprises the H-CDR1-3 and L-CDR1-3 amino acid sequences of:
 a) SEQ ID NOs: 308-313, respectively;
 b) SEQ ID NOs: 318-323, respectively;
 c) SEQ ID NOs: 328-333, respectively;
 d) SEQ ID NOs: 338-343, respectively;
 e) SEQ ID NOs: 348-353, respectively;
 f) SEQ ID NOs: 358-363, respectively; or
 g) SEQ ID NOs: 368-373, respectively.

In some embodiments, the anti-LAG-3 antibody comprises a heavy chain variable domain and a light chain variable domain having the amino acid sequences of:
 a) SEQ ID NOs: 306 and 307, respectively;
 b) SEQ ID NOs: 316 and 317, respectively;
 c) SEQ ID NOs: 326 and 327, respectively;
 d) SEQ ID NOs: 336 and 337, respectively;
 e) SEQ ID NOs: 346 and 347, respectively;
 f) SEQ ID NOs: 356 and 357, respectively; or
 g) SEQ ID NOs: 366 and 367, respectively.

In some embodiments, the anti-LAG-3 antibody comprises:
 a) an HC comprising the amino acid sequence of SEQ ID NO: 306 and the amino acid sequence of SEQ ID NO: 375, and an LC comprising the amino acid sequence of SEQ ID NO: 307 and the amino acid sequence of SEQ ID NO: 378;
 b) an HC comprising the amino acid sequence of SEQ ID NO: 316 and the amino acid sequence of SEQ ID NO: 375, and an LC comprising the amino acid sequence of SEQ ID NO: 317 and the amino acid sequence of SEQ ID NO: 378;
 c) an HC comprising the amino acid sequence of SEQ ID NO: 326 and the amino acid sequence of SEQ ID NO: 375, and an LC comprising the amino acid sequence of SEQ ID NO: 327 and the amino acid sequence of SEQ ID NO: 378;
 d) an HC comprising the amino acid sequence of SEQ ID NO: 336 and the amino acid sequence of SEQ ID NO: 375, and an LC comprising the amino acid sequence of SEQ ID NO: 337 and the amino acid sequence of SEQ ID NO: 378;
 e) an HC comprising the amino acid sequence of SEQ ID NO: 346 and the amino acid sequence of SEQ ID NO: 375, and an LC comprising the amino acid sequence of SEQ ID NO: 347 and the amino acid sequence of SEQ ID NO: 378;
 f) an HC comprising the amino acid sequence of SEQ ID NO: 356 and the amino acid sequence of SEQ ID NO: 375, and an LC comprising the amino acid sequence of SEQ ID NO: 357 and the amino acid sequence of SEQ ID NO: 378; or
 g) an HC comprising the amino acid sequence of SEQ ID NO: 366 and the amino acid sequence of SEQ ID NO: 375, and an LC comprising the amino acid sequence of SEQ ID NO: 367 and the amino acid sequence of SEQ ID NO: 379.

In some embodiments, the anti-LAG-3 antibody is selected from the group consisting of:
 a) an antibody whose H-CDR1-3 comprise the amino acid sequences of SEQ ID NOs: 308-310, respectively;
 b) an antibody whose VH is at least 90% identical in sequence to the amino acid sequence of SEQ ID NO: 306;
 c) an antibody whose VH comprises the amino acid sequence of SEQ ID NO: 306;
 d) an antibody whose HC comprises the amino acid sequences of SEQ ID NOs: 306 and 375;
 e) an antibody whose L-CDR1-3 comprise the amino acid sequences of SEQ ID NOs: 311-313, respectively;
 f) an antibody whose VL is at least 90% identical in sequence to the amino acid sequence of SEQ ID NO: 307;
 g) an antibody whose VL comprises the amino acid sequence of SEQ ID NO: 307;
 h) an antibody whose LC comprises the amino acid sequences of SEQ ID NOs: 307 and 378;
 i) an antibody whose H-CDR1-3 and L-CDR1-3 comprise the amino acid sequences of SEQ ID NOs: 308-313, respectively;
 j) an antibody whose VH is at least 90% identical in sequence to the amino acid sequence of SEQ ID NO: 306 and whose VL is at least 90% identical in sequence to the amino acid sequence of SEQ ID NO: 307;
 k) an antibody whose VH comprises the amino acid sequence of SEQ ID NO: 306 and whose VL comprises the amino acid sequence of SEQ ID NO: 307; and
 l) an antibody whose HC comprises the amino acid sequences of SEQ ID NOs: 306 and 375; and whose LC comprises the amino acid sequences of SEQ ID NOs: 307 and 378.

In some embodiments, the anti-LAG-3 antibody is selected from the group consisting of:
 a) an antibody whose H-CDR1-3 comprise the amino acid sequences of SEQ ID NOs: 318-320, respectively;
 b) an antibody whose VH is at least 90% identical in sequence to the amino acid sequence of SEQ ID NO: 316;
 c) an antibody whose VH comprises the amino acid sequence of SEQ ID NO: 316;
 d) an antibody whose HC comprises the amino acid sequences of SEQ ID NOs: 316 and 375;
 e) an antibody whose L-CDR1-3 comprise the amino acid sequences of SEQ ID NOs: 321-323, respectively;
 f) an antibody whose VL is at least 90% identical in sequence to the amino acid sequence of SEQ ID NO: 317;
 g) an antibody whose VL comprises the amino acid sequence of SEQ ID NO: 317;
 h) an antibody whose LC comprises the amino acid sequences of SEQ ID NOs: 317 and 378;
 i) an antibody whose H-CDR1-3 and L-CDR1-3 comprise the amino acid sequences of SEQ ID NOs: 318-323, respectively;
 j) an antibody whose VH is at least 90% identical in sequence to the amino acid sequence of SEQ ID NO: 316 and whose VL is at least 90% identical in sequence to the amino acid sequence of SEQ ID NO: 317;
 k) an antibody whose VH comprises the amino acid sequence of SEQ ID NO: 316 and whose VL comprises the amino acid sequence of SEQ ID NO: 317; and l) an antibody whose HC comprises the amino acid sequences of SEQ ID NOs: 316 and 375; and whose LC comprises the amino acid sequences of SEQ ID NOs: 317 and 378.

In some embodiments, the anti-LAG-3 antibody is selected from the group consisting of:
a) an antibody whose H-CDR1-3 comprise the amino acid sequences of SEQ ID NOs: 328-330, respectively;
b) an antibody whose VH is at least 90% identical in sequence to the amino acid sequence of SEQ ID NO: 326;
c) an antibody whose VH comprises the amino acid sequence of SEQ ID NO: 326;
d) an antibody whose HC comprises the amino acid sequences of SEQ ID NOs: 326 and 375;
e) an antibody whose L-CDR1-3 comprise the amino acid sequences of SEQ ID NOs: 331-333, respectively;
f) an antibody whose VL is at least 90% identical in sequence to the amino acid sequence of SEQ ID NO: 327;
g) an antibody whose VL comprises the amino acid sequence of SEQ ID NO: 327;
h) an antibody whose LC comprises the amino acid sequences of SEQ ID NOs: 327 and 378;
i) an antibody whose H-CDR1-3 and L-CDR1-3 comprise the amino acid sequences of SEQ ID NOs: 328-333, respectively;
j) an antibody whose VH is at least 90% identical in sequence to the amino acid sequence of SEQ ID NO: 326 and whose VL is at least 90% identical in sequence to the amino acid sequence of SEQ ID NO: 327;
k) an antibody whose VH comprises the amino acid sequence of SEQ ID NO: 326 and whose VL comprises the amino acid sequence of SEQ ID NO: 327; and
l) an antibody whose HC comprises the amino acid sequences of SEQ ID NOs: 326 and 375; and whose LC comprises the amino acid sequences of SEQ ID NOs: 327 and 378.

In some embodiments, the anti-LAG-3 antibody is selected from the group consisting of:
a) an antibody whose H-CDR1-3 comprise the amino acid sequences of SEQ ID NOs: 338-340, respectively;
b) an antibody whose VH is at least 90% identical in sequence to the amino acid sequence of SEQ ID NO: 336;
c) an antibody whose VH comprises the amino acid sequence of SEQ ID NO: 336;
d) an antibody whose HC comprises the amino acid sequences of SEQ ID NOs: 336 and 375;
e) an antibody whose L-CDR1-3 comprise the amino acid sequences of SEQ ID NOs: 341-343, respectively;
f) an antibody whose VL is at least 90% identical in sequence to the amino acid sequence of SEQ ID NO: 337;
g) an antibody whose VL comprises the amino acid sequence of SEQ ID NO: 337;
h) an antibody whose LC comprises the amino acid sequences of SEQ ID NOs: 337 and 378;
i) an antibody whose H-CDR1-3 and L-CDR1-3 comprise the amino acid sequences of SEQ ID NOs: 338-343, respectively;
j) an antibody whose VH is at least 90% identical in sequence to the amino acid sequence of SEQ ID NO: 336 and whose VL is at least 90% identical in sequence to the amino acid sequence of SEQ ID NO: 337;
k) an antibody whose VH comprises the amino acid sequence of SEQ ID NO: 336 and whose VL comprises the amino acid sequence of SEQ ID NO: 337; and
l) an antibody whose HC comprises the amino acid sequences of SEQ ID NOs: 336 and 375; and whose LC comprises the amino acid sequences of SEQ ID NOs: 337 and 378.

In some embodiments, the anti-LAG-3 antibody is selected from the group consisting of:
a) an antibody whose H-CDR1-3 comprise the amino acid sequences of SEQ ID NOs: 348-350, respectively;
b) an antibody whose VH is at least 90% identical in sequence to the amino acid sequence of SEQ ID NO: 346;
c) an antibody whose VH comprises the amino acid sequence of SEQ ID NO: 346;
d) an antibody whose HC comprises the amino acid sequences of SEQ ID NOs: 346 and 375;
e) an antibody whose L-CDR1-3 comprise the amino acid sequences of SEQ ID NOs: 351-353, respectively;
f) an antibody whose VL is at least 90% identical in sequence to the amino acid sequence of SEQ ID NO: 347;
g) an antibody whose VL comprises the amino acid sequence of SEQ ID NO: 347;
h) an antibody whose LC comprises the amino acid sequences of SEQ ID NOs: 347 and 378;
i) an antibody whose H-CDR1-3 and L-CDR1-3 comprise the amino acid sequences of SEQ ID NOs: 348-353, respectively;
j) an antibody whose VH is at least 90% identical in sequence to the amino acid sequence of SEQ ID NO: 346 and whose VL is at least 90% identical in sequence to the amino acid sequence of SEQ ID NO: 347;
k) an antibody whose VH comprises the amino acid sequence of SEQ ID NO: 346 and whose VL comprises the amino acid sequence of SEQ ID NO: 347; and
l) an antibody whose HC comprises the amino acid sequences of SEQ ID NOs: 346 and 375; and whose LC comprises the amino acid sequences of SEQ ID NOs: 347 and 378.

In some embodiments, the anti-LAG-3 antibody is selected from the group consisting of:
a) an antibody whose H-CDR1-3 comprise the amino acid sequences of SEQ ID NOs: 358-360, respectively;
b) an antibody whose VH is at least 90% identical in sequence to the amino acid sequence of SEQ ID NO: 356;
c) an antibody whose VH comprises the amino acid sequence of SEQ ID NO: 356;
d) an antibody whose HC comprises the amino acid sequences of SEQ ID NOs: 356 and 375;
e) an antibody whose L-CDR1-3 comprise the amino acid sequences of SEQ ID NOs: 361-363, respectively;
f) an antibody whose VL is at least 90% identical in sequence to the amino acid sequence of SEQ ID NO: 357;
g) an antibody whose VL comprises the amino acid sequence of SEQ ID NO: 357;
h) an antibody whose LC comprises the amino acid sequences of SEQ ID NOs: 357 and 378;
i) an antibody whose H-CDR1-3 and L-CDR1-3 comprise the amino acid sequences of SEQ ID NOs: 358-363, respectively;
j) an antibody whose VH is at least 90% identical in sequence to the amino acid sequence of SEQ ID NO:

356 and whose VL is at least 90% identical in sequence to the amino acid sequence of SEQ ID NO: 357;
k) an antibody whose VH comprises the amino acid sequence of SEQ ID NO: 356 and whose VL comprises the amino acid sequence of SEQ ID NO: 357; and
l) an antibody whose HC comprises the amino acid sequences of SEQ ID NOs: 356 and 375; and whose LC comprises the amino acid sequences of SEQ ID NOs: 357 and 378.

In some embodiments, the anti-LAG-3 antibody is selected from the group consisting of:
a) an antibody whose H-CDR1-3 comprise the amino acid sequences of SEQ ID NOs: 368-370, respectively;
b) an antibody whose VH is at least 90% identical in sequence to the amino acid sequence of SEQ ID NO: 366;
c) an antibody whose VH comprises the amino acid sequence of SEQ ID NO: 366;
d) an antibody whose HC comprises the amino acid sequences of SEQ ID NOs: 366 and 375;
e) an antibody whose L-CDR1-3 comprise the amino acid sequences of SEQ ID NOs: 371-373, respectively;
f) an antibody whose VL is at least 90% identical in sequence to the amino acid sequence of SEQ ID NO: 367;
g) an antibody whose VL comprises the amino acid sequence of SEQ ID NO: 367;
h) an antibody whose LC comprises the amino acid sequences of SEQ ID NOs: 367 and 379;
i) an antibody whose H-CDR1-3 and L-CDR1-3 comprise the amino acid sequences of SEQ ID NOs: 368-373, respectively;
j) an antibody whose VH is at least 90% identical in sequence to the amino acid sequence of SEQ ID NO: 366 and whose VL is at least 90% identical in sequence to the amino acid sequence of SEQ ID NO: 367;
k) an antibody whose VH comprises the amino acid sequence of SEQ ID NO: 366 and whose VL comprises the amino acid sequence of SEQ ID NO: 367; and
l) an antibody whose HC comprises the amino acid sequences of SEQ ID NOs: 366 and 375; and whose LC comprises the amino acid sequences of SEQ ID NOs: 367 and 379.

In some embodiments, any of the anti-LAG-3 antibodies or antigen-binding portions described herein may bind to human LAG-3 with an EC50 of, for example, 0.2 nM or less, 0.15 nM or less, 0.1 nM or less, 0.09 nM or less, 0.08 nM or less, 0.07 nM or less, 0.06 nM or less, 0.05 nM or less, or 0.04 nM or less. In some embodiments, any of the anti-LAG-3 antibodies or antigen-binding portions described herein may bind to cynomolgus LAG-3 with, for example, an EC50 of 0.4 nM or less, 0.3 nM or less, 0.2 nM or less, 0.1 nM or less, 0.09 nM or less, 0.08 nM or less, 0.07 nM or less, 0.06 nM or less, 0.05 nM or less, 0.04 nM or less, or 0.03 nM or less. In particular embodiments, any of the anti-LAG-3 antibodies or antigen-binding portions described herein may bind to human LAG-3 with, for example, an EC50 of 0.1 nM or less and cynomolgus LAG-3 with, for example, an EC50 of 0.3 nM or less.

In some embodiments, any of the anti-LAG-3 antibodies or antigen-binding portions described herein may bind to human LAG-3 with an EC50 of, for example, 0.1 nM or less. In some embodiments, any of the anti-LAG-3 antibodies or antigen-binding portions described herein may bind to cynomolgus LAG-3 with, for example, an EC50 of 0.3 nM or less. In particular embodiments, any of the anti-LAG-3 antibodies or antigen-binding portions described herein may bind to human LAG-3 with, for example, an EC50 of 0.1 nM or less and cynomolgus LAG-3 with, for example, an EC50 of 0.3 nM or less.

In some embodiments, any of the anti-LAG-3 antibodies or antigen-binding portions described herein may inhibit binding of ligands such as MHC class II (MHCII) or LSECtin to LAG-3. For example, at 20 µg/mL, the anti-LAG-3 antibody or antigen-binding portion may reduce the binding of LAG-3 to MHCII by at least 35%, at least 40%, at least 45%, at least 50%, at least 55%, at least 60%, at least 65%, at least 70%, at least 75%, at least 80%, at least 85%, at least 89%, at least 90%, at least 91%, at least 92%, at least 93%, at least 94%, at least 95%, at least 96%, at least 97%, at least 98%, at least 99%, or 100% compared to binding in the presence of a negative control antibody. In one embodiment, the anti-LAG-3 antibody or antigen-binding protein may reduce the binding of LAG-3 to MHCII by greater than 85% compared to the negative control. In one embodiment, the anti-LAG-3 antibody or antigen-binding protein may reduce the binding of LAG-3 to MHCII by between about 25% and 95%, 30% and 90%, or 35% and 85%, compared to the negative control.

In some embodiments, any of the anti-LAG-3 antibodies or antigen-binding portions described herein may block binding between LAG-3 and MHC class II, e.g., human LAG-3 expressed on Jurkat cells and human MHC class II expressed on Raji cells (for example, at a concentration of 0.1 µg/mL, 0.5 µg/mL, 1 µg/mL, 5 µg/mL, 10 µg/mL, 20 µg/mL, 30 µg/mL, 40 µg/mL, or 50 µg/mL).

In some embodiments, any of the anti-LAG-3 antibodies or antigen-binding portions described herein may bind to human LAG-3 with a $K_D$ of $5.0 \times 10^{-8}$ or less, $4.0 \times 10^{-8}$ or less, $3.0 \times 10^{-8}$ or less, $2.0 \times 10^{-8}$ or less, $1.0 \times 10^{-8}$ or less, $9.0 \times 10^{-9}$ or less, $8.0 \times 10^{-9}$ or less, $7.0 \times 10^{-9}$ or less, $6.0 \times 10^{-9}$ or less, $5.0 \times 10^{-9}$ or less, $4.0 \times 10^{-9}$ or less, $3.0 \times 10^{-9}$ or less, $2.0 \times 10^{-9}$ or less, or $1.0 \times 10^{-9}$ or less, as measured by surface plasmon resonance.

In some embodiments, any of the anti-LAG-3 antibodies or antigen-binding portions described herein may bind to cynomolgus LAG-3 with a $K_D$ of $1.5 \times 10^{-7}$ or less, $1.0 \times 10^{-7}$ or less, $9.0 \times 10^{-8}$ or less, $8.0 \times 10^{-8}$ or less, $7.0 \times 10^{-8}$ or less, $6.0 \times 10^{-8}$ or less, $5.0 \times 10^{-8}$ or less, $4.0 \times 10^{-8}$ or less, $3.0 \times 10^{-8}$ or less, $2.0 \times 10^{-8}$ or less, or $1.0 \times 10^{-8}$ or less, as measured by surface plasmon resonance.

In some embodiments, any of the anti-LAG-3 antibodies or antigen-binding portions described herein may bind to mouse LAG-3 with a $K_D$ of $5.0 \times 10^{-8}$ or less, $4.5 \times 10^{-8}$ or less, $4.0 \times 10^{-8}$ or less, $3.5 \times 10^{-8}$ or less, or $3.0 \times 10^{-8}$ or less, as measured by surface plasmon resonance.

In some embodiments, any of the anti-LAG-3 antibodies or antigen-binding portions described herein may stimulate IL-2 production, e.g., from SEB-stimulated PBMCs.

In some embodiments, any of the anti-LAG-3 antibodies or antigen-binding portions described herein may reduce cellular and/or soluble levels of LAG-3, e.g., in a human T cell line (such as a human T cell line overexpressing LAG-3).

In some embodiments, any of the anti-LAG-3 antibodies or antigen-binding portions described herein may induce tumor growth regression and/or delay tumor growth in vivo.

In some embodiments, any of the anti-LAG-3 antibodies or antigen-binding portions described herein may bind to a different epitope of human LAG-3 than antibody 25F7-Lag3.5.

In some embodiments, any of the anti-LAG-3 antibodies or antigen-binding portions described herein may activate T-cells, causing enhanced anti-tumor activity.

In some embodiments, the anti-LAG-3 antibody or antigen-binding portion described herein has at least one of the following properties:
a) at a concentration of 20 µg/mL, reduces the binding of human LAG-3 to human MHC class II on A375 cells by greater than 85% compared to a negative control antibody as determined by a flow cytometric competition assay;
b) at a concentration of 20 µg/mL, reduces the binding of human LAG-3 to human MHC class II on A375 cells to between 35% and 85% compared to a negative control antibody as determined by a flow cytometric competition assay;
c) blocks binding between human LAG-3 expressed on Jurkat cells and human MHC class II expressed on Raji cells;
d) binds to human LAG-3 with an EC50 of 0.1 nM or less as measured by flow cytometry;
e) binds to cynomolgus LAG-3 with an EC50 of 0.3 nM or less as measured by flow cytometry;
f) binds to human LAG-3 with a $K_D$ of 3.0×10-8 or less as measured by surface plasmon resonance;
g) binds to cynomolgus LAG-3 with a $K_D$ of 1.5×10-7 or less as measured by surface plasmon resonance;
h) binds to mouse LAG-3 with a $K_D$ of 3.5×10-8 or less as measured by surface plasmon resonance;
i) stimulates IL-2 production in Staphylococcal enterotoxin B (SEB) treated human peripheral blood mononuclear cells (PBMCs);
j) reduces cellular levels of LAG-3 in human T cells;
k) reduces soluble levels of LAG-3 in the culture of human T cells;
l) induces tumor growth regression in vivo;
m) delays tumor growth in vivo; and
n) does not bind to the same epitope of human LAG-3 as antibody 25F7-Lag3.5.

Examples of such an antibody include, without limitation, antibody 15646 (having at least properties b, c, d, e, i, and n), antibody 15532 (having at least properties a, c, d, e, f, g, i, j, k, m, and n), antibody 15723 (having at least properties b, c, d, e, i, and n), antibody 15595 (having at least properties a, c, d, e, i, and n), antibody 15431 (having at least properties a, c, d, e, f, g, i, and n), antibody 15572 (having at least properties b, c, d, e, f, g, i, and n), and antibody 15011 (having at least properties a, c, d, e, f, g, h, i, j, k, I, m, and n). In some embodiments, the anti-TIM-3 antibody or antigen-binding portion of the invention has at least 13, 12, 11, 10, 9, 8, 7, 6, 5, 4, 3, 2, or 1 of said properties. In some embodiments, the anti-TIM-3 antibody or antigen-binding portion of the invention has at least properties b, c, d, e, i, and n; at least properties a, c, d, e, f, g, i, j, k, m, and n; at least properties a, c, d, e, i, and n; at least properties a, c, d, e, f, g, i, and n; at least properties b, c, d, e, f, g, i, and n; or at least properties a, c, d, e, f, g, h, i, j, k, I, m, and n.

In some embodiments, the anti-LAG-3 antibody or antigen-binding portion of the invention competes for binding to human LAG-3 with antibody 15011, 15572, and/or 15431.

In some embodiments, the anti-LAG-3 antibody or antigen-binding portion of the invention binds to an epitope of human LAG-3 having:
a) amino acid residues H85, P86, A87, P89, S91, W92, and G93 of SEQ ID NO: 68;
b) amino acid residues A40, Q41, P43, P46, P49, D52, T62, Q64, H65, Q66, P67, D68, G93, P94, R98, Y99, T100, V101, P106, G107, R119, E124, R129, G130, D131, S133, R137, P138, D143, R148, and R163 of SEQ ID NO: 68;
c) amino acid residues A40, Q41, P43, P46, P49, D52, T62, Q64, H65, Q66, P67, D68, P96, Y99, T100, V101, P106, G107, R119, E124, R129, G130, D131, S133, R137, P138, D143, R148, and R163 of SEQ ID NO: 68; or
d) amino acid residues G107, L109, R110, and S111 of SEQ ID NO: 68.

In some embodiments, the anti-LAG-3 antibody or antigen-binding portion of the invention binds to an epitope having amino acid residues 98-105 of SEQ ID NO: 68. Examples of such an antibody include, without limitation, antibodies 15532, 15431, 15572, and 15011.

In some embodiments, the anti-LAG-3 antibody or antigen-binding portion of the invention binds to an epitope having:
a) amino acid residues 78-105 and 123-131 of SEQ ID NO: 68;
b) amino acid residues 23-30, 40-66, 88-105, 123-137, and 148-152 of SEQ ID NO: 68; or
c) amino acid residues 23-30, 40-66, 98-105, 118-137, and 148-161 of SEQ ID NO: 68

In some embodiments, an anti-LAG-3 antibody or an antigen-binding portion thereof as described herein is an anti-LAG-3 antibody or antigen-binding portion described in PCT Patent Application PCT/EP2017/076188, which is incorporated by reference in its entirety herein.

The class of an antibody described herein may be changed or switched with another class or subclass. In one aspect, a nucleic acid molecule encoding VL or VH is isolated using methods well-known in the art such that it does not include nucleic acid sequences encoding CL or CH. The nucleic acid molecules encoding VL or VH then are operatively linked to a nucleic acid sequence encoding a CL or CH, respectively, from a different class of immunoglobulin molecule. This may be achieved using a vector or nucleic acid molecule that comprises a CL or CH chain, as described above. For example, an antibody that was originally IgM may be class switched to IgG. Further, the class switching may be used to convert one IgG subclass to another, e.g., from IgG1 to IgG2. A K light chain constant region can be changed, e.g., to a λ light chain constant region. A preferred method for producing an antibody as described herein with a desired Ig isotype comprises the steps of isolating a nucleic acid molecule encoding the heavy chain of an antibody and a nucleic acid molecule encoding the light chain of an antibody, obtaining the variable domain of the heavy chain, ligating the variable domain of the heavy chain with the constant region of a heavy chain of the desired isotype, expressing the light chain and the ligated heavy chain in a cell, and collecting the antibody with the desired isotype.

An antibody described herein can be an IgG, an IgM, an IgE, an IgA, or an IgD molecule, but is typically of the IgG isotype, e.g. of IgG subclass IgG1, IgG2a or IgG2b, IgG3 or IgG4. In one embodiment, the antibody is an IgG1. In another embodiment, the antibody is an IgG2.

In one embodiment, the antibody may comprise at least one mutation in the Fc region. A number of different Fc mutations are known, where these mutations provide altered effector function. For example, in many cases it will be desirable to reduce or eliminate effector function, e.g., where ligand/receptor interactions are undesired or in the case of antibody-drug conjugates.

In one embodiment, the antibody comprises at least one mutation in the Fc region that reduces effector function. Fc region amino acid positions that may be advantageous to mutate in order to reduce effector function include one or more of positions 228, 233, 234 and 235, where amino acid positions are numbered according to the IMGT® numbering scheme.

In some embodiments, one or both of the amino acid residues at positions 234 and 235 may be mutated, for example, from Leu to Ala (L234A/L235A). These mutations reduce effector function of the Fc region of IgG1 antibodies. Additionally or alternatively, the amino acid residue at position 228 may be mutated, for example to Pro. In some embodiments, the amino acid residue at position 233 may be mutated, e.g., to Pro, the amino acid residue at position 234 may be mutated, e.g., to Val, and/or the amino acid residue at position 235 may be mutated, e.g., to Ala. The amino acid positions are numbered according to the IMGT® numbering scheme.

In some embodiments, where the antibody is of the IgG4 subclass, it may comprise the mutation S228P, i.e., having a proline in position 228, where the amino acid position is numbered according to the Eu IMGT® numbering scheme. This mutation is known to reduce undesired Fab arm exchange (Angal et al., *Mol Immunol.* 30:105-8 (1993)).

In certain embodiments, an antibody or antigen-binding portion thereof as described herein may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al., *Human Antibodies and Hybridomas* 6:93-101 (1995)) and use of a cysteine residue, a marker peptide and a C-terminal polyhistidine tag to make bivalent and biotinylated scFv molecules (Kipriyanov et al., *Mol. Immunol.* 31:1047-1058 (1994)). Other examples include where one or more CDRs from an antibody are incorporated into a molecule either covalently or noncovalently to make it an immunoadhesin that specifically binds to an antigen of interest. In such embodiments, the CDR(s) may be incorporated as part of a larger polypeptide chain, may be covalently linked to another polypeptide chain, or may be incorporated noncovalently.

In another embodiment, a fusion antibody or immunoadhesin may be made that comprises all or a portion of an antibody described herein linked to another polypeptide. In certain embodiments, only the variable domains of the antibody are linked to the polypeptide. In certain embodiments, the VH domain of an antibody is linked to a first polypeptide, while the VL domain of an antibody is linked to a second polypeptide that associates with the first polypeptide in a manner such that the VH and VL domains can interact with one another to form an antigen-binding site. In another preferred embodiment, the VH domain is separated from the VL domain by a linker such that the VH and VL domains can interact with one another (e.g., single-chain antibodies). The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bi-specific antibody.

To create a single chain antibody (scFv), the VH- and VL-encoding DNA fragments are operatively linked to another fragment encoding a flexible linker, e.g., encoding the amino acid sequence (Gly4-Ser)3 (SEQ ID NO: 396), such that the VH and VL sequences can be expressed as a contiguous single-chain protein, with the VL and VH domains joined by the flexible linker. See, e.g., Bird et al., *Science* 242:423-426 (1988); Huston et al., *Proc. Natl. Acad. Sci. USA* 85:5879-5883 (1988); and McCafferty et al., *Nature* 348:552-554 (1990). The single chain antibody may be monovalent, if only a single VH and VL are used; bivalent, if two VH and VL are used; or polyvalent, if more than two VH and VL are used. Bi-specific or polyvalent antibodies may be generated that bind specifically to human PD-1, TIM-3, or LAG-3 and to another molecule, for instance. In some embodiments, the bi-specific or polyvalent antibodies may bind to PD-1 and TIM-3, PD-1 and LAG-3, TIM-3 and LAG-3, or PD-1, TIM-3, and LAG-3.

In other embodiments, other modified antibodies may be prepared using antibody-encoding nucleic acid molecules. For instance, "kappa bodies" (Ill et al., *Protein Eng.* 10:949-57 (1997)), "minibodies" (Martin et al., *EMBO J.* 13:5303-9 (1994)), "diabodies" (Holliger et al., *Proc. Natl. Acad. Sci. USA* 90:6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

An antibody or antigen-binding portion as described herein can be derivatized or linked to another molecule (e.g., another peptide or protein). In general, the antibodies or portions thereof are derivatized such that antigen binding is not affected adversely by the derivatization or labeling. Accordingly, the antibodies and antibody portions that may be used in the combination therapies and compositions of the invention are intended to include both intact and modified forms of the antibodies described herein. For example, an antibody or antibody portion as described herein can be functionally linked (by chemical coupling, genetic fusion, noncovalent association or otherwise) to one or more other molecular entities, such as another antibody (e.g., a bi-specific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, e.g., to create bi-specific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available, e.g., from Pierce Chemical Company, Rockford, Il.

An antibody can also be derivatized with a chemical group such as polyethylene glycol (PEG), a methyl or ethyl group, or a carbohydrate group. These groups may be useful to improve the biological characteristics of the antibody, e.g., to increase serum half-life.

An antibody as described herein may also be labeled. As used herein, the terms "label" or "labeled" refer to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In certain embodiments, the antibodies described herein may be present in a neutral form (including zwitter ionic forms) or as a positively or negatively-charged species. In some embodiments, the antibodies may be complexed with a counterion to form a pharmaceutically acceptable salt.

The term "pharmaceutically acceptable salt" refers to a complex comprising one or more antibodies and one or more counterions, wherein the counterions are derived from pharmaceutically acceptable inorganic and organic acids and bases.

Combination Therapies

The present invention provides a combination therapy (e.g., a composition) that comprises any (e.g., any one) of the anti-PD-1 antibodies or antigen-binding portions thereof described herein and any (e.g., any one) of the anti-TIM-3 antibodies or antigen-binding portions thereof described herein. In some embodiments, the combination therapy comprises any (e.g., any one) of the anti-PD-1 antibodies or antigen-binding portions thereof described herein and any (e.g., any one) of the anti-LAG-3 antibodies or antigen-binding portions thereof described herein. In some embodiments, the combination therapy comprises any (e.g., any one) of the anti-TIM-3 antibodies or antigen-binding portions thereof described herein and any (e.g., any one) of the anti-LAG-3 antibodies or antigen-binding portions thereof described herein. In particular embodiments, the combination therapy comprises any (e.g., any one) of the anti-PD-1 antibodies or antigen-binding portions thereof described herein, any (e.g., any one) of the anti-TIM-3 antibodies or antigen-binding portions thereof described herein, and any (e.g., any one) of the anti-LAG-3 antibodies or antigen-binding portions thereof described herein. The combination therapy may take the form of, e.g., a method for treatment using said antibodies or antigen-binding portions or a pharmaceutical composition comprising said antibodies or antigen-binding portions.

In certain embodiments, the combination therapy or composition of the invention comprises anti-PD-1 antibody 12819 and anti-TIM-3 antibody 15086.17145. In certain embodiments, the combination therapy or composition of the invention comprises anti-PD-1 antibody 12819 and anti-LAG-3 antibody 15532.

In certain embodiments, the combination therapy or composition of the invention comprises anti-PD-1 antibody 12819, anti-TIM-3 antibody 15086.17145, and anti-LAG-3 antibody 15532.

In certain embodiments, the combination therapy or composition of the invention comprises:
  an anti-PD-1 antibody or an antigen-binding portion thereof comprising the H-CDR1-3 and L-CDR1-3 amino acid sequences of SEQ ID NOs: 228-233, respectively; and an anti-TIM-3 antibody or an antigen-binding portion thereof comprising the H-CDR1-3 and L-CDR1-3 amino acid sequences of SEQ ID NOs: 8-13, respectively;
  an anti-PD-1 antibody or an antigen-binding portion thereof comprising the VH and VL amino acid sequences of SEQ ID NOs: 226 and 227, respectively; and an anti-TIM-3 antibody or an antigen-binding portion thereof comprising the VH and VL amino acid sequences of SEQ ID NOs: 7 and 4, respectively; or
  an anti-PD-1 antibody comprising an HC that comprises the amino acid sequences of SEQ ID NOs: 226 and 375 and an LC that comprises the amino acid sequences of SEQ ID NOs: 227 and 379; and an anti-TIM-3 antibody comprising an HC that comprises the amino acid sequences of SEQ ID NOs: 7 and 377 and an LC that comprises the amino acid sequences of SEQ ID NOs: 4 and 378.

In certain embodiments, the combination therapy or composition of the invention comprises:
  an anti-PD-1 antibody or an antigen-binding portion thereof comprising the H-CDR1-3 and L-CDR1-3 amino acid sequences of SEQ ID NOs: 228-233, respectively; and an anti-LAG-3 antibody or an antigen-binding portion thereof comprising the H-CDR1-3 and L-CDR1-3 amino acid sequences of SEQ ID NOs: 318-323, respectively;
  an anti-PD-1 antibody or an antigen-binding portion thereof comprising the VH and VL amino acid sequences of SEQ ID NOs: 226 and 227, respectively; and an anti-LAG-3 antibody or an antigen-binding portion thereof comprising the VH and VL amino acid sequences of SEQ ID NOs: 316 and 317, respectively; or
  an anti-PD-1 antibody comprising an HC that comprises the amino acid sequences of SEQ ID NOs: 226 and 375 and an LC that comprises the amino acid sequences of SEQ ID NOs: 227 and 379; and an anti-LAG-3 antibody comprising an HC that comprises the amino acid sequences of SEQ ID NOs: 316 and 375 and an LC that comprises the amino acid sequences of SEQ ID NOs: 317 and 378.

In certain embodiments, the combination therapy or composition of the invention comprises:
  an anti-TIM-3 antibody or an antigen-binding portion thereof comprising the H-CDR1-3 and L-CDR1-3 amino acid sequences of SEQ ID NOs: 8-13, respectively; and an anti-LAG-3 antibody or an antigen-binding portion thereof comprising the H-CDR1-3 and L-CDR1-3 amino acid sequences of SEQ ID NOs: 318-323, respectively;
  an anti-TIM-3 antibody or an antigen-binding portion thereof comprising the VH and VL amino acid sequences of SEQ ID NOs: 7 and 4, respectively; and an anti-LAG-3 antibody or an antigen-binding portion thereof comprising the VH and VL amino acid sequences of SEQ ID NOs: 316 and 317, respectively; or
  an anti-TIM-3 antibody comprising an HC that comprises the amino acid sequences of SEQ ID NOs: 7 and 377 and an LC that comprises the amino acid sequences of SEQ ID NOs: 4 and 378; and an anti-LAG-3 antibody comprising an HC that comprises the amino acid sequences of SEQ ID NOs: 316 and 375 and an LC that comprises the amino acid sequences of SEQ ID NOs: 317 and 378.

In certain embodiments, the combination therapy or composition of the invention comprises:

an anti-PD-1 antibody or an antigen-binding portion thereof comprising the H-CDR1-3 and L-CDR1-3 amino acid sequences of SEQ ID NOs: 228-233, respectively; an anti-TIM-3 antibody or an antigen-binding portion thereof comprising the H-CDR1-3 and L-CDR1-3 amino acid sequences of SEQ ID NOs: 8-13, respectively; and an anti-TIM-3 antibody or an antigen-binding portion thereof comprising the H-CDR1-3 and L-CDR1-3 amino acid sequences of SEQ ID NOs: 318-323, respectively;

an anti-PD-1 antibody or an antigen-binding portion thereof comprising the VH and VL amino acid sequences of SEQ ID NOs: 226 and 227, respectively; an anti-TIM-3 antibody or an antigen-binding portion thereof comprising the VH and VL amino acid sequences of SEQ ID NOs: 7 and 4, respectively; and an anti-LAG-3 antibody or an antigen-binding portion thereof comprising the VH and VL amino acid sequences of SEQ ID NOs: 316 and 317, respectively; or an anti-PD-1 antibody comprising an HC that comprises the amino acid sequences of SEQ ID NOs: 226 and 375 and an LC that comprises the amino acid sequences of SEQ ID NOs: 227 and 379; an anti-TIM-3 antibody comprising an HC that comprises the amino acid sequences of SEQ ID NOs: 7 and 377 and an LC that comprises the amino acid sequences of SEQ ID NOs: 4 and 378; and an anti-LAG-3 antibody comprising an HC that comprises the amino acid sequences of SEQ ID NOs: 316 and 375 and an LC that comprises the amino acid sequences of SEQ ID NOs: 317 and 378.

In some embodiments, any or all of the antibodies in the combination therapy or composition may be an IgG, for example, IgG1 or IgG2.

Multi-Specific Binding Molecules

In a further aspect, the invention provides a multi-specific binding molecule having the binding specificity (e.g., comprising the antigen-binding portions, such as antigen-binding portions comprising the six CDRs) of:

an anti-PD-1 antibody as described herein and an anti-TIM-3 antibody as described herein;

an anti-PD-1 antibody as described herein and an anti-LAG-3 antibody as described herein; or an anti-TIM-3 antibody as described herein and an anti-LAG-3 antibody as described herein.

In some embodiments, the anti-PD-1 antibody, anti-TIM-3 antibody, and/or anti-LAG-3 antibody are selected from the antibodies described herein. In certain embodiments, the multi-specific binding molecule has the binding specificity of an anti-PD-1 antibody described herein, an anti-TIM-3 antibody described herein, and an anti-LAG-3 antibody described herein. Multi-specific binding molecules are known in the art, and examples of different types of multi-specific binding molecules are given elsewhere herein. Such multi-specific (e.g., bi-specific or trispecific) binding molecules are encompassed by the combination therapies of the invention.

In a further aspect, the invention provides combination therapy with two or more of a bi-specific binding molecule targeting PD-1, a bi-specific molecule targeting TIM-3, and a bi-specific binding molecule targeting LAG-3. A bi-specific binding molecule targeting PD-1, TIM-3, or LAG-3 may have the binding specificity of an antibody targeting said antigen as described herein and the binding specificity of another antibody targeting the same antigen (e.g., another antibody as described herein) or an antibody that targets a different protein, such as another immune checkpoint protein, a cancer antigen, or another cell surface molecule whose activity mediates a disease condition such as cancer. Such bi-specific binding molecules are known in the art, and examples of different types of bi-specific binding molecules are given elsewhere herein.

Nucleic Acid Molecules and Vectors

Also described are nucleic acid molecules and sequences encoding anti-PD-1, anti-TIM-3, and/or anti-LAG-3 antibodies or antigen-binding portions thereof described herein. In some embodiments, different nucleic acid molecules encode the heavy chain and light chain amino acid sequences of the anti-PD-1 antibody or antigen-binding portion thereof, anti-TIM-3 antibody or antigen-binding portion thereof, or anti-LAG-3 antibody or antigen-binding portion thereof. In other embodiments, the same nucleic acid molecule encodes the heavy chain and light chain amino acid sequences of the anti-PD-1 antibody or antigen-binding portion thereof, anti-TIM-3 antibody or antigen-binding portion thereof, or anti-LAG-3 antibody or antigen-binding portion thereof.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric form of nucleotides of at least 10 bases in length, either ribonucleotides or deoxynucleotides or a modified form of either type of nucleotide. The term includes single and double stranded forms.

In some embodiments, the nucleotide sequences are at least 70%, 75%, 80%, 85%, 90%, 95%, 97%, 98% or 99% identical to one or more nucleotide sequences recited herein, e.g., to a nucleotide sequence encoding an amino acid sequence selected from the group consisting of SEQ ID NOs: 1, 2, 5, 6, 14, 15, 24, 25, 34, 35, 44, 45, 54, 55, 64, 65, 74, 75, 84, 85, 94, 95, 104, 105, 114, 115, 124, 125, 134, 135, 144, 145, 154, 155, 164, 165, 174, 175, 184, 185, 194, 195, 204, 205, 214, 215, 224, 225, 234, 235, 244, 245, 254, 255, 264, 265, 274, 275, 284, 285, 294, 295, 304, 305, 314, 315, 324, 325, 334, 335, 344, 345, 354, 355, 364, 365 or 391. The term "percent sequence identity" in the context of nucleic acid sequences refers to the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wisconsin FASTA, which includes, e.g., the programs FASTA2 and FASTA3, provides alignments and percent sequence identity of the regions of the best overlap between the query and search sequences (see, e.g., Pearson, *Methods Enzymol.* 183:63-98 (1990); Pearson, *Methods Mol. Biol.* 132:185-219 (2000); Pearson, *Methods Enzymol.* 266:227-258 (1996); and Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In some embodiments, the nucleic acid molecule comprising one or more nucleotide sequences selected from the group consisting of SEQ ID NOs: 1, 2, 5, 6, 14, 15, 24, 25, 34, 35, 44, 45, 54, 55, 64, 65, 74, 75, 84, 85, 94, 95, 104, 105, 114, 115, 124, 125, 134, 135, 144, 145, 154, 155, 164, 165, 174, 175, 184, 185, 194, 195, 204, 205, 214, 215, 224, 225, 234, 235, 244, 245, 254, 255, 264, 265, 274, 275, 284, 285, 294, 295, 304, 305, 314, 315, 324, 325, 334, 335, 344, 345, 354, 355, 364, 365 or 391.

In any of the above embodiments, the nucleic acid molecules may be isolated. A nucleic acid molecule encoding the heavy and/or light chain of an antibody or antigen-binding portion thereof described herein can be isolated from any source that produces such an antibody or portion. In various embodiments, the nucleic acid molecules are isolated from B cells that express an antibody isolated from an animal immunized with a PD-1, TIM-3, or LAG-3 antigen, or from an immortalized cell produced from such a B cell. Methods of isolating nucleic acids encoding an antibody are well-known in the art. mRNA may be isolated and used to produce cDNA for use in polymerase chain reaction (PCR) or cDNA cloning of antibody genes. In certain embodiments, a nucleic acid molecule as described herein can be synthesized rather than isolated.

In some embodiments, a nucleic acid molecule as described herein can comprise a nucleotide sequence encoding a VH domain from an antibody or antigen-binding portion described herein joined in-frame to a nucleotide sequence encoding a heavy chain constant region from any source. Similarly, a nucleic acid molecule of as described herein can comprise a nucleotide sequence encoding a VL domain from an antibody or antigen-binding portion described herein joined in-frame to a nucleotide sequence encoding a light chain constant region from any source.

In a further aspect, nucleic acid molecules encoding the variable domain of the heavy (VH) and/or light (VL) chains may be "converted" to full-length antibody genes. In one embodiment, nucleic acid molecules encoding the VH or VL domains are converted to full-length antibody genes by insertion into an expression vector already encoding heavy chain constant (CH) or light chain constant (CL) regions, respectively, such that the VH segment is operatively linked to the CH segment(s) within the vector, and/or the VL segment is operatively linked to the CL segment within the vector. In another embodiment, nucleic acid molecules encoding the VH and/or VL domains are converted into full-length antibody genes by linking, e.g., ligating, a nucleic acid molecule encoding a VH and/or VL domains to a nucleic acid molecule encoding a CH and/or CL region using standard molecular biological techniques. Nucleic acid molecules encoding the full-length heavy and/or light chains may then be expressed from a cell into which they have been introduced and the antibody isolated.

The nucleic acid molecules may be used to recombinantly express large quantities of antibodies. The nucleic acid molecules also may be used to produce chimeric antibodies, bi-specific antibodies, single chain antibodies, immunoadhesins, diabodies, mutated antibodies and antibody derivatives, as described herein.

Also described herein is a vector suitable for expressing one or both of the chains of an anti-PD-1 antibody or antigen-binding portion thereof, an anti-TIM-3 antibody or antigen-binding portion thereof, and/or an anti-LAG-3 antibody or antigen-binding portion thereof, as described herein. The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

In some embodiments, the vectors comprise nucleic acid molecules that encode the heavy chain, the light chain, or both the heavy and light chains, of an antibody described herein or an antigen-binding portion thereof. In some embodiments, the vectors comprise nucleic acid molecules encoding fusion proteins, modified antibodies, antibody fragments, and probes thereof.

In some embodiments, the anti-PD-1, anti-TIM-3, or anti-LAG-3 antibodies or antigen-binding portions thereof are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody coding sequence may be ligated into a vector such that transcriptional and translational control sequences within the vector serve their intended function of regulating the transcription and translation of the antibody coding sequence. The expression vector and expression control sequences may be chosen to be compatible with the expression host cell used. The antibody light chain coding sequence and the antibody heavy chain coding sequence can be inserted into separate vectors, and may be operatively linked to the same or different expression control sequences (e.g., promoters). In one embodiment, both coding sequences are inserted into the same expression vector, and may be operatively linked to the same expression control sequences (e.g., a common promoter), to separate identical expression control sequences (e.g., promoters), or to different expression control sequences (e.g., promoters). The antibody coding sequences may be inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can easily be inserted and expressed, as described above. The HC- and LC-encoding genes in such vectors may contain intron sequences that will result in enhanced overall antibody protein yields by stabilizing the related mRNA. The intron sequences are flanked by splice donor and splice acceptor sites, which determine where RNA splicing will occur. Location of intron sequences can be either in variable or constant regions of the antibody chains, or in both variable and constant regions when multiple introns are used. Polyadenylation and transcription termination may occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors may carry regulatory sequences that control the expression of the antibody chain genes in a host cell. It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing antibodies in plants, including a description of promoters and vectors, as well as transformation of plants, are known in the art. See, e.g., U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr-host cells with methotrexate selection/amplification), the neo gene (for G418 selection), and the glutamate synthetase gene.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

Host Cells and Methods of Antibody and Antibody Composition Production

Also described are methods for producing the combination therapies (e.g., compositions) of the invention. One embodiment relates to a method for producing antibodies as described herein, comprising providing recombinant host cells capable of expressing the antibodies, culturing said host cells under conditions suitable for expression of the antibodies, and isolating the resulting antibodies. Antibodies produced by such expression in such recombinant host cells are referred to herein as "recombinant antibodies." Also described are progeny cells of such host cells, and antibodies produced by same.

The term "recombinant host cell" (or simply "host cell"), as used herein, means a cell into which a recombinant expression vector has been introduced. The host cell may comprise, e.g., one or more vectors as described herein. The host cells may comprise, e.g., a nucleotide sequence encoding the heavy chain or an antigen-binding portion thereof, a nucleotide sequence encoding the light chain or an antigen-binding portion thereof, or both, of an anti-PD-1, anti-TIM-3, and/or anti-LAG-3 antibody or antigen-binding portion thereof as described herein. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Nucleic acid molecules encoding anti-PD-1, anti-TIM-3, and/or anti-LAG-3 antibodies or antigen-binding portions thereof and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455. Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NSO cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines.

Cell lines of particular preference are selected by determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., Nicotiana, Arabidopsis, duckweed, corn, wheat, potato, etc. Bacterial host cells include E. coli and Streptomyces species. Yeast host cells include Schizosaccharomyces pombe, Saccharomyces cerevisiae and Pichia pastoris.

Further, expression of antibodies or antigen-binding portions thereof as described herein from production cell lines can be enhanced using a number of known techniques. For example, the glutamine synthetase gene expression system (the GS system) is a common approach for enhancing expression under certain conditions. The GS system is discussed in whole or part in connection with EP Patents 0 216 846, 0 256 055, 0 323 997 and 0 338 841.

It is likely that antibodies expressed by different cell lines or in transgenic animals will have different glycosylation patterns from each other. However, all antibodies encoded by the nucleic acid molecules provided herein, or comprising the amino acid sequences provided herein, are part of the instant invention, regardless of the glycosylation state of the antibodies, and more generally, regardless of the presence or absence of post-translational modification(s).

In some embodiments, the invention relates to a method for producing an antibody composition comprising an anti-PD-1 antibody and an anti-TIM-3 antibody, the method comprising:
  providing first and second host cells, wherein the first host cell is capable of expressing an anti-PD-1 antibody as described herein and the second host cell is capable of expressing an anti-TIM-3 antibody as described herein,
  cultivating the first and second and host cells under conditions suitable for expression of the anti-PD-1 antibody and the anti-TIM-3 antibody, and
  isolating the resulting antibodies.

In some embodiments, the invention relates to a method for producing an antibody composition comprising an anti-PD-1 antibody and an anti-LAG-3 antibody, the method comprising:
  providing first and second host cells, wherein the first host cell is capable of expressing an anti-PD-1 antibody as described herein and the second host cell is capable of expressing an anti-LAG-3 antibody as described herein,
  cultivating the first and second host cells under conditions suitable for expression of the anti-PD-1 antibody and the anti-LAG-3 antibody, and
  isolating the resulting antibodies.

In some embodiments, the invention relates to a method for producing an antibody composition comprising an anti-TIM-3 antibody and an anti-LAG-3 antibody, the method comprising:
  providing first and second host cells, wherein the first host cell is capable of expressing an anti-TIM-3 antibody as described herein and the second host cell is capable of expressing an anti-LAG-3 antibody as described herein,
  cultivating the first and second host cells under conditions suitable for expression of the anti-TIM-3 antibody and the anti-LAG-3 antibody, and
  isolating the resulting antibodies.

In some embodiments, the invention relates to a method for producing an antibody composition comprising an anti-PD-1 antibody, an anti-TIM-3 antibody, and an anti-LAG-3 antibody, the method comprising:
  providing first, second, and third host cells, wherein the first host cell is capable of expressing an anti-PD-1 antibody as described herein, the second host cell is capable of expressing an anti-TIM-3 antibody as described herein, and the third host cell is capable of expressing an anti-LAG-3 antibody as described herein,
  cultivating the first, second, and third host cells under conditions suitable for expression of the anti-PD-1 antibody, the anti-TIM-3 antibody, and the anti-LAG-3 antibody, and
  isolating the resulting antibodies.

For production of an antibody composition of the invention, the antibodies directed to different targets may be produced separately, i.e., each antibody being produced in a separate bioreactor, or the individual antibodies may be produced together in a single bioreactor. If the antibody composition is produced in more than one bioreactor, the purified antibody composition can be obtained by pooling the antibodies obtained from individually purified supernatants from each bioreactor. Various approaches for production of a polyclonal antibody composition in multiple bioreactors, where the cell lines or antibody preparations are combined at a later point upstream or prior to or during downstream processing, are described in PCT Publication WO 2009/129814.

In the case of producing individual antibodies in a single bioreactor, this may be performed, e.g., as described in PCT Publication WO 2004/061104 or WO 2008/145133. The method described in WO 2004/061104 is based on site-specific integration of the antibody coding sequence into the genome of the individual host cells, while the method of WO 2008/145133 involves an alternative approach using random integration to produce antibodies in a single bioreactor.

Further information regarding methods suitable for preparing the antibody compositions of the invention may be found in PCT Publications WO 2012/059857 and WO 2013/164689.

The present invention also provides a polyclonal cell line that produces:
  at least one anti-PD-1 antibody or antigen-binding portion thereof as described herein and at least one anti-TIM-3 antibody or antigen-binding portion thereof as described herein;
  at least one anti-PD-1 antibody or antigen-binding portion thereof as described herein and at least one anti-LAG-3 antibody or antigen-binding portion thereof as described herein;
  at least one anti-TIM-3 antibody or antigen-binding portion thereof as described herein and at least one anti-LAG-3 antibody or antigen-binding portion thereof as described herein; or
  at least one anti-PD-1 antibody or antigen-binding portion thereof as described herein, at least one anti-TIM-3 antibody or antigen-binding portion thereof as described herein, and at least one anti-LAG-3 antibody or antigen-binding portion thereof as described herein.

The present invention also provides a method for producing the above polyclonal cell line, comprising providing host cells that each comprise a nucleotide sequence that encodes the heavy chain or an antigen-binding portion thereof and a nucleotide sequence that encodes the light chain or an antigen-binding portion thereof of at least one of the antibodies or portions produced by the polyclonal cell line.

The present invention also provide host cells comprising:
- a nucleotide sequence that encodes the heavy chain or an antigen-binding portion thereof, a nucleotide sequence that encodes the light chain or an antigen-binding portion thereof, or both, of an anti-PD-1 antibody as described herein, and a nucleotide sequence that encodes the heavy chain or an antigen-binding portion thereof, a nucleotide sequence that encodes the light chain or an antigen-binding portion thereof, or both, of an anti-TIM-3 antibody as described herein;
- a nucleotide sequence that encodes the heavy chain or an antigen-binding portion thereof, a nucleotide sequence that encodes the light chain or an antigen-binding portion thereof, or both, of an anti-PD-1 antibody as described herein; and a nucleotide sequence that encodes the heavy chain or an antigen-binding portion thereof, a nucleotide sequence that encodes the light chain or an antigen-binding portion thereof, or both, of an anti-LAG-3 antibody as described herein;
- a nucleotide sequence that encodes the heavy chain or an antigen-binding portion thereof, a nucleotide sequence that encodes the light chain or an antigen-binding portion thereof, or both, of an anti-TIM-3 antibody as described herein; and a nucleotide sequence that encodes the heavy chain or an antigen-binding portion thereof, a nucleotide sequence that encodes the light chain or an antigen-binding portion thereof, or both, of an anti-LAG-3 antibody as described herein; or
- a nucleotide sequence that encodes the heavy chain or an antigen-binding portion thereof, a nucleotide sequence that encodes the light chain or an antigen-binding portion thereof, or both, of an anti-PD-1 antibody as described herein; a nucleotide sequence that encodes the heavy chain or an antigen-binding portion thereof, a nucleotide sequence that encodes the light chain or an antigen-binding portion thereof, or both, of an anti-TIM-3 antibody as described herein; and a nucleotide sequence that encodes the heavy chain or an antigen-binding portion thereof, a nucleotide sequence that encodes the light chain or an antigen-binding portion thereof, or both, of an anti-LAG-3 antibody as described herein.

Pharmaceutical Compositions

Another aspect of the invention is a pharmaceutical composition comprising as active ingredients (e.g., as the sole active ingredients):
- at least one anti-PD-1 antibody or antigen-binding portion thereof as described herein and at least one anti-TIM-3 antibody or antigen-binding portion thereof as described herein;
- at least one anti-PD-1 antibody or antigen-binding portion thereof as described herein and at least one anti-LAG-3 antibody or antigen-binding portion thereof as described herein;
- at least one anti-TIM-3 antibody or antigen-binding portion thereof as described herein and at least one anti-LAG-3 antibody or antigen-binding portion thereof as described herein; or
- at least one anti-PD-1 antibody or antigen-binding portion thereof as described herein, at least one anti-TIM-3 antibody or antigen-binding portion thereof as described herein, and at least one anti-LAG-3 antibody or antigen-binding portion thereof as described herein.

In some aspects, the pharmaceutical composition comprises a multi-specific binding molecule (e.g., a multi-specific binding molecule that has the binding specificity of an anti-PD-1 antibody as described herein and an anti-TIM-3 or anti-LAG-3 antibody as described herein; or an anti-PD1 antibody, an anti-TIM-3 antibody, and an anti-LAG-3 antibody as described herein).

In some embodiments, the pharmaceutical composition may further comprise one or more additional antibodies that target one or more relevant cell surface receptors, e.g., one or more cancer-relevant receptors.

In some embodiments, the pharmaceutical composition is intended for amelioration, prevention, and/or treatment of a disorder, disease, or condition that improves, or slows down in its progression, by modulation of PD-1, TIM-3, and/or LAG-3. In some embodiments, the pharmaceutical composition is intended for amelioration, prevention, and/or treatment of cancer. In some embodiments, the pharmaceutical composition is intended for activation of the immune system.

The ratio between the antibodies of antigen-binding portions thereof in a pharmaceutical composition of the invention (or of individual antibodies or portions described herein being administered simultaneously, sequentially or separately) will often be such that the antibodies are administered in equal amounts, but this need not necessarily be the case. Thus, a composition of the invention comprising an anti-PD-1 antibody and an anti-TIM-3 antibody, an anti-PD-1 antibody and an anti-LAG-3 antibody, or an anti-TIM-3 antibody and an anti-LAG-3 antibody may contain said antibodies in approximately a 1:1 ratio. A composition of the invention comprising an anti-PD-1 antibody, an anti-TIM-3 antibody, and an anti-LAG-3 antibody may contain said antibodies in approximately a 1:1:1: ratio (i.e., in equal amounts). Depending on the characteristics of the individual antibodies, however, it may be desirable to use non-equal amounts of the different antibodies. Suitable ratios for the different antibodies in compositions of the invention may be determined as described in PCT Publication WO 2010/040356, which describes methods for identifying and selecting the optimal stoichiometric ratio between chemical entities in a combinatorial drug product, e.g. a polyclonal antibody composition, to obtain a combinatorial drug with optimal potency and efficacy.

Generally, the pharmaceutical compositions described herein are suitable to be administered as a formulation in association with one or more pharmaceutically acceptable excipient(s), e.g., as described below.

The term "excipient" is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP (good manufacturing practices) conditions.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the antibodies and antigen-binding portions described herein.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, and intrasynovial injection or infusions; and kidney dialytic infusion techniques. Regional perfusion is also contemplated. Particular embodiments include the intravenous and the subcutaneous routes.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the compositions in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin, and/or by using modified-release coatings (e.g., slow-release coatings).

Therapeutic Uses of Combination Therapies and Compositions of the Invention

In one aspect, the combination therapies and compositions of the invention are used to enhance or activate the immune system in a patient (e.g., a human) in need thereof. In some embodiments, the patient is immune-suppressed. In some embodiments, a physician can boost the anti-cancer activity of a patient's own immune system by administering a combination therapy or composition of the present invention, alone or in combination with other therapeutic agents (sequentially or concurrently). The combination therapy or composition modulates the activity of PD-1, TIM-3, and/or LAG-3 in immune cells, resulting in enhancement of anti-cancer immunity. In certain embodiments, the combination therapies and compositions of the invention are for use in the treatment of cancer, e.g., cancers that originate in tissues such as skin, lung, intestine, colon, ovary, brain, prostate, kidney, soft tissues, the hematopoietic system, head and neck, liver, bladder, breast, stomach, uterus and pancreas, and any cancers or other conditions which rely on PD-1, TIM-3, and/or LAG-3 activity and/or in which the patient expresses or overexpresses a ligand of any of these.

In some embodiments, cancers treated by the combination therapies and compositions of the invention may include, e.g., melanoma (e.g., advanced or metastatic melanoma), non-small cell lung cancer, head and neck squamous cell cancer, renal cell carcinoma, Hodgkin's lymphoma, non-Hodgkin's lymphoma, glioblastoma, glioma, squamous cell lung cancer, small-cell lung cancer, hepatocellular carcinoma, bladder cancer, upper urinary tract cancer, esophageal cancer, gastroesophageal junction cancer, gastric cancer, liver cancer, colon cancer, colorectal carcinoma, multiple myeloma, sarcomas, acute myeloid leukemia, chronic myeloid leukemia, myelodysplastic syndrome, nasopharyngeal cancer, chronic lymphocytic leukemia, acute lymphoblastic leukemia, small lymphocytic lymphoma, ovarian cancer, gastrointestinal cancer, primary peritoneal cancer, fallopian tube cancer, urothelial cancer, HTLV-associated T-cell leukemia/lymphoma, prostate cancer, genitourinary cancer, meningioma, adrenocortical cancer, gliosarcoma, fibrosarcoma, kidney cancer, breast cancer, pancreatic cancer, endometrial cancer, skin basal cell cancer, cancer of the appendix, biliary tract cancer, salivary gland cancer, advanced Merkel cell cancer, diffuse large B cell lymphoma, follicular lymphoma, mesothelioma, neuroendocrine tumors, urological cancer, bone cancer, thoracic cancer, respiratory tract cancer, adenoid cystic carcinoma, cervical cancer, astrocytoma, chordoma, neuroblastoma, oral cavity cancer, cutaneous squamous cell carcinoma, thyroid cancer, Kaposi sarcoma, anal cancer, gallbladder cancer, thymic cancer, uterine cancer, and solid tumors. The cancer may be, e.g., at an early, intermediate, advanced, or metastatic stage.

In particular embodiments, cancers treated by the combination therapies and compositions of the invention may include, e.g., melanoma (e.g., advanced melanoma, or unresectable or metastatic melanoma), non-small cell lung cancer (e.g., advanced non-small cell lung cancer), lung carcinoma, head and neck squamous cell carcinoma, glioblastoma (e.g., recurrent glioblastoma), gliosarcoma, Merkel-cell carcinoma, fibrosarcoma, ovarian cancer, bladder cancer, renal cell carcinoma, colorectal cancer, Hodgkin's lymphoma, non-Hodgkin's lymphoma, leukemia (e.g., acute myeloid leukemia), hematologic malignancies, solid tumors (e.g., advanced or metastatic solid tumors), MSI high tumors, HPV and HIV associated malignancies, and tumors with BRAC1 and BRAC2 mutations.

In certain embodiments, the pharmaceutical compositions of the invention are intended for treatment of an immune-mediated disorder such as psoriasis, systemic lupus erythematosis, MLS (sclerosis), Crohn's disease, diabetes mellitus, and/or colitis ulcerotis.

In some embodiments, the combination therapy or composition is for use in treating viral and/or parasitic infections, e.g., where the pathogens inhibit the host immune response. For example, the pathogen may be, e.g., HIV, hepatitis (A, B, or C), human papilloma virus (HPV), lymphocytic choriomeningitis virus (LCMV), adenovirus, flavivirus, echovirus, rhinovirus, coxsackie virus, cornovirus, respiratory syncytial virus, mumps virus, rotavirus, measles virus, rubella virus, parvovirus, vaccinia virus, human T-cell lymphotrophic virus (HTLV), human cytomegalovirus (HCMV), dengue virus, molluscum virus, poliovirus, rabies virus, John Cunningham (JC) virus, arboviral encephalitis virus, simian immunodeficiency virus (SIV), influenza, herpes, Giardia, malaria, *Leishmania, Staphylococcus aureus*, or *Pseudomonas aeruginosa*.

In some embodiments, the combination therapies and compositions of the invention may be used to treat a patient who is, or is at risk of being, immunocompromised (e.g., due to chemotherapeutic or radiation therapy).

In some embodiments, the combination therapies and compositions of the invention may be used for ex vivo activation and expansion of antigen-specific T cells.

In some embodiments, the patient may have been treated previously for a condition characterized by overexpression or overactivity of PD-1, TIM-3, and/or LAG-3 or any of their ligands (e.g., cancer or an immune disorder). For example, the patient may have been treated with one or more drugs targeting PD-1, TIM-3, and/or LAG-3 and may have acquired resistance to said drug(s).

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

"Therapeutically effective amount" refers to the amount of the therapeutic agent being administered that will relieve to some extent one or more of the symptoms of the disorder being treated. A therapeutically effective amount of an anti-cancer therapeutic may, for example, result in tumor shrinkage, increased survival, elimination of cancer cells, decreased disease progression, reversal of metastasis, or other clinical endpoints desired by healthcare professionals.

In some embodiments, the antibodies, antigen-binding portions, or multi-specific binding molecules in the combination therapy of the invention are administered in a single composition. In other embodiments, the antibodies, antigen-binding portions, or multi-specific binding molecules are administered in more than one composition. For example, a combination therapy comprising an anti-PD-1 antibody, an anti-TIM-3 antibody, and an anti-LAG-3 antibody may involve administration of a single composition comprising all three antibodies, a composition comprising two of the antibodies and a composition comprising one of the antibodies, or a separate composition for each antibody. In a case where there is more than one composition, the compositions can be administered simultaneously, sequentially, separately, or any combination thereof.

The combination therapies and compositions of the invention may be administered alone or in combination with one or more other drugs or antibodies (or as any combination thereof). The pharmaceutical compositions, methods and uses of the invention thus also encompass embodiments of combinations (co-administration) with other active agents, as detailed below.

As used herein, the terms "co-administration", "co-administered" and "in combination with," referring to the combination therapies or compositions of the invention with one or more other therapeutic agents, is intended to mean, and does refer to and include the following:
  simultaneous administration of such combination therapy (or a component thereof) or composition and therapeutic agent(s) to a patient in need of treatment, when such components are formulated together into a single dosage form which releases said components at substantially the same time to said patient,
  substantially simultaneous administration of such combination therapy (or a component thereof) or composition and therapeutic agent(s) to a patient in need of treatment, when such components are formulated apart from each other into separate dosage forms which are taken at substantially the same time by said patient, whereupon said components are released at substantially the same time to said patient,
  sequential administration of such combination therapy (or a component thereof) or composition and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination therapy (or a component thereof) or composition and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

The combination therapies and compositions of the invention may be administered without additional therapeutic treatments, i.e., as a stand-alone therapy (i.e., monotherapy). Alternatively, treatment with a combination therapy or composition of the invention may include at least one additional therapeutic treatment, e.g., another immunostimulatory agent, an anti-cancer agent, an anti-viral agent, or a vaccine (e.g., a tumor vaccine). In some embodiments, the combination therapy or composition may be co-administered or formulated with another medication/drug for the treatment of cancer. The additional therapeutic treatment may comprise, e.g., a chemotherapeutic, anti-neoplastic, or anti-angiogenic agent, a different anti-cancer antibody, and/or radiation therapy.

By combining the combination therapies and compositions of the invention with agents known to induce terminal differentiation of cancer cells, the effect may be improved further. Such compounds may, for example, be selected from the group consisting of retinoic acid, trans-retinoic acids, cis-retinoic acids, phenylbutyrate, nerve growth factor, dimethyl sulfoxide, active form vitamin D3, peroxisome proliferator-activated receptor gamma, 12-O-tetradecanoylphorbol 13-acetate, hexamethylene-bis-acetamide, transforming growth factor-beta, butyric acid, cyclic AMP, and vesnarinone. In some embodiments, the compound is selected from the group consisting of retinoic acid, phenylbutyrate, all-trans-retinoic acid and active form vitamin D.

Pharmaceutical articles comprising a combination therapy or composition of the invention and at least one other agent (e.g., a chemotherapeutic, anti-neoplastic, or anti-angiogenic agent) may be used as a combination treatment for simultaneous, separate or successive administration in cancer therapy. The other agent may be any agent suitable for treatment of the particular cancer in question, for example, an agent selected from the group consisting of alkylating agents, e.g., platinum derivatives such as cisplatin, carboplatin and/or oxaliplatin; plant alkoids, e.g., paclitaxel, docetaxel and/or irinotecan; antitumor antibiotics, e.g., doxorubicin (adriamycin), daunorubicin, epirubicin, idarubicin mitoxantrone, dactinomycin, bleomycin, actinomycin, luteomycin, and/or mitomycin; topoisomerase inhibitors such as topotecan; and/or antimetabolites, e.g., fluorouracil and/or other fluoropyrimidines. In some embodiments, the other agent is dacarbazine or gemcitabine.

A combination therapy or composition of the invention may also be used in combination with other anti-cancer therapies such as vaccines, cytokines, enzyme inhibitors, immunostimulatory compounds, and T cell therapies. In the case of a vaccine, it may, e.g., be a protein, peptide or DNA vaccine containing one or more antigens which are relevant for the cancer being treated, or a vaccine comprising dendritic cells along with an antigen. Suitable cytokines include, for example, IL-2, IFN-gamma and GM-CSF. An example of a type of enzyme inhibitor that has anti-cancer activity is an indoleamine-2,3-dioxygenase (IDO) inhibitor, for example 1-methyl-D-tryptophan (1-D-MT). Adoptive T cell therapy refers to various immunotherapy techniques that involve expanding or engineering patients' own T cells to recognize and attack their tumors.

It is also contemplated that a combination therapy or composition of the invention may be used in adjunctive therapy in connection with tyrosine kinase inhibitors. These are synthetic, mainly quinazoline-derived, low molecular weight molecules that interact with the intracellular tyrosine kinase domain of receptors and inhibit ligand-induced receptor phosphorylation by competing for the intracellular Mg-ATP binding site.

In some embodiments, the combination therapy or composition may be used in combination with another medication/drug that mediates immune system activation, including, but not limited to, an agent that modulates the expression or activity of A2AR, BTLA, B7-H3, B7-H4, CTLA-4, CD27, CD28, CD39, CD40, CD47, CD55, CD73, CD122, CD137, CD160, CGEN-15049, LY108, CHK1, CHK2, CTLA-3, CEACAM (e.g., CEACAM-1 and/or CEACAM-5), GAL9, GITR, HVEM, ICOS, IDO, KIR, LAIR1, NKG2A, OX40, PD-L1/PD-L2, LILRB2, CMTM6, TIGIT, TGFR-beta, TNFR2, VISTA and/or 2B4. In certain embodiments, the agent is an antibody or an antigen-binding fragment thereof that binds to one of the above molecules. In particular embodiments, the antibody or antigen-binding portion thereof, composition, or bi-specific binding molecule of the invention may be administered in combination with a CTLA-4 inhibitor (e.g., an anti-CTLA-4 antibody such as tremelimumab or ipilimumab). In one embodiment, the antibody or antigen-binding portion thereof, composition, or bi-specific binding molecule of the invention may be administered in combination with ipilimumab. It is also contemplated that the combination therapy or composition of the invention may be used in combination with a cytokine (e.g., IL-1, IL-2, IL-12, IL-15 or IL-21), an EGFR inhibitor, a VEGF inhibitor, etc.

In certain aspects, the combination therapies and compositions of the invention may be administered in combination with another inhibitor of the PD-1, TIM-3, or LAG-3 pathway, which may target PD-1, TIM-3, LAG-3, or one or more of ligands of any of these targets. Examples of such inhibitors include:

other anti-PD-1 antibodies and antibodies that target PD-1 ligands and/or co-receptors such as PD-L1 or PD-L2 (e.g., pembrolizumab and/or nivolumab);

other anti-TIM-3 antibodies and antibodies that target TIM-3 ligands and/or co-receptors such as galectin-9, HMGB-1, phosphatidylserine lipids, CEACAM1, LILRA1-6, or LILRB1-5 (e.g., MGB453, TSR-022, and/or LY3321367); and other anti-LAG-3 antibodies and antibodies that target LAG-3 ligands and/or co-receptors such as MHCII, Galectin-3, and LSECtin (e.g., BMS-986016, GSK2831781, REGN3767, BAP050 or BAP050-chi, or LAG525).

It is understood that the combination therapies and compositions of the invention may be used in a method of treatment as described herein, may be for use in a treatment as described herein, and/or may be for use in the manufacture of a medicament for a treatment as described herein. The invention also provides kits and articles of manufacture comprising the combination therapies or compositions of the invention as described herein.

Dose and Route of Administration

The combination therapies and compositions of the invention will be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the antibodies are being administered as a stand-alone treatment or in combination with one or more additional anti-cancer treatments.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen are adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied combination therapy. Further, the dosage regimen with the combination therapies and compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

It is contemplated that a suitable dose of an antibody in a combination therapy or composition of the invention will be in the range of 0.1-100 mg/kg, such as about 0.5-50 mg/kg, e.g., about 1-20 mg/kg. The antibody may for example be administered in a dosage of at least 0.25 mg/kg, e.g., at least 0.5 mg/kg, such as at least 1 mg/kg, e.g., at least 1.5 mg/kg, such as at least 2 mg/kg, e.g., at least 3 mg/kg, such as at least 4 mg/kg, e.g., at least 5 mg/kg; and e.g., up to at most 50 mg/kg, such as up to at the most 30 mg/kg, e.g., up to at the most 20 mg/kg, such as up to at the most 15 mg/kg. Administration will normally be repeated at suitable intervals, e.g., once every week, once every two weeks, once every three weeks, or once every four weeks, and for as long as deemed appropriate by the responsible doctor, who may optionally increase or decrease the dosage as necessary.

An effective amount for tumor therapy may be measured by its ability to stabilize disease progression and/or ameliorate symptoms in a patient, and preferably to reverse disease progression, e.g., by reducing tumor size. The ability of a combination therapy of the invention to inhibit cancer may be evaluated by in vitro assays, e.g., as described in the Examples, as well as in suitable animal models that are predictive of the efficacy in human tumors (see, e.g., the Examples). Suitable dosage regimens will be selected in order to provide an optimum therapeutic response in each particular situation, for example, administered as a single bolus or as a continuous infusion, and with possible adjustment of the dosage as indicated by the exigencies of each case.

Articles of Manufacture and Kits

The present invention also provides articles of manufacture comprising an anti-PD-1 antibody that competes for binding to human PD-1 with, or binds to the same epitope of human PD-1 as, an antibody selected from the group consisting of 12819.15384, 12748.15381, 12748.16124, 12865.15377, 12892.15378, 12796.15376, 12777.15382, 12760.15375 and 13112.15380; and an anti-TIM-3 antibody or an anti-LAG-3 antibody.

In some embodiments, the article of manufacture comprises:
  at least one anti-PD-1 antibody or antigen-binding portion thereof as described herein and at least one anti-TIM-3 antibody or antigen-binding portion thereof as described herein;
  at least one anti-PD-1 antibody or antigen-binding portion thereof as described herein and at least one anti-LAG-3 antibody or antigen-binding portion thereof as described herein;
  at least one anti-TIM-3 antibody or antigen-binding portion thereof as described herein and at least one anti-LAG-3 antibody or antigen-binding portion thereof as described herein; or
  at least one anti-PD-1 antibody or antigen-binding portion thereof as described herein, at least one anti-TIM-3 antibody or antigen-binding portion thereof as described herein, and at least one anti-LAG-3 antibody or antigen-binding portion thereof as described herein;
as well as methods for manufacturing said articles.

The present invention also provides kits comprising an anti-PD-1 antibody that competes for binding to human PD-1 with, or binds to the same epitope of human PD-1 as, an antibody selected from the group consisting of 12819.15384, 12748.15381, 12748.16124, 12865.15377, 12892.15378, 12796.15376, 12777.15382, 12760.15375 and 13112.15380; and an anti-TIM-3 antibody or an anti-LAG-3 antibody.

In some embodiments, the kit comprises:
- at least one anti-PD-1 antibody or antigen-binding portion thereof as described herein and at least one anti-TIM-3 antibody or antigen-binding portion thereof as described herein;
- at least one anti-PD-1 antibody or antigen-binding portion thereof as described herein and at least one anti-LAG-3 antibody or antigen-binding portion thereof as described herein;
- at least one anti-TIM-3 antibody or antigen-binding portion thereof as described herein and at least one anti-LAG-3 antibody or antigen-binding portion thereof as described herein; or
- at least one anti-PD-1 antibody or antigen-binding portion thereof as described herein, at least one anti-TIM-3 antibody or antigen-binding portion thereof as described herein, and at least one anti-LAG-3 antibody or antigen-binding portion thereof as described herein.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

In order that this invention may be better understood, the following examples are set forth. These examples are for purposes of illustration only and are not to be construed as limiting the scope of the invention in any manner.

EXAMPLES

Example 1: Enhanced In Vitro Activity of Combined PD-1/TIM-3 Targeting in One-Way MLR Assay This example demonstrates that combined targeting of PD-1 and TIM-3 using the anti-PD-1 antibody 12819 and the anti-TIM-3 antibody 15086.17145 enhances IFN-γ secretion in a one-way mixed lymphocyte reaction (MLR) assay.

In the one-way MLR assay, dendritic cells (DCs) and CD4$^+$ T-cells isolated from two different human healthy donors were co-cultured to induce an alloantigen specific reaction resulting in cytokine production and T-cell activation/proliferation. Dendritic cells (DCs) were differentiated from CD14$^+$ monocytes by 6 days of culture with 20 ng/ml granulocyte-macrophage colony-stimulating factor (GM-CSF) and 20 ng/ml interleukin-4 (IL-4) and mixed in a 1:10 ratio with CD4$^+$ T-cells isolated from peripheral blood mononuclear cells (PBMCs) from healthy human donor material. The indicated antibodies or antibody mixture were added to a final total concentration of 10 µg/mL. The antibody mixture contained a 1:1 ratio of anti-PD-1 and anti-TIM-3 antibodies. After 5 days of culture, supernatants were harvested and IFN-γ levels were determined using the Meso Scale electrochemiluminescence cytokine assay. Student's unpaired t-test was used for statistical analysis and Bonferroni correction was used to adjust for multiple comparisons. A corrected p-value <0.05 is considered statistically significant.

Figure 1:
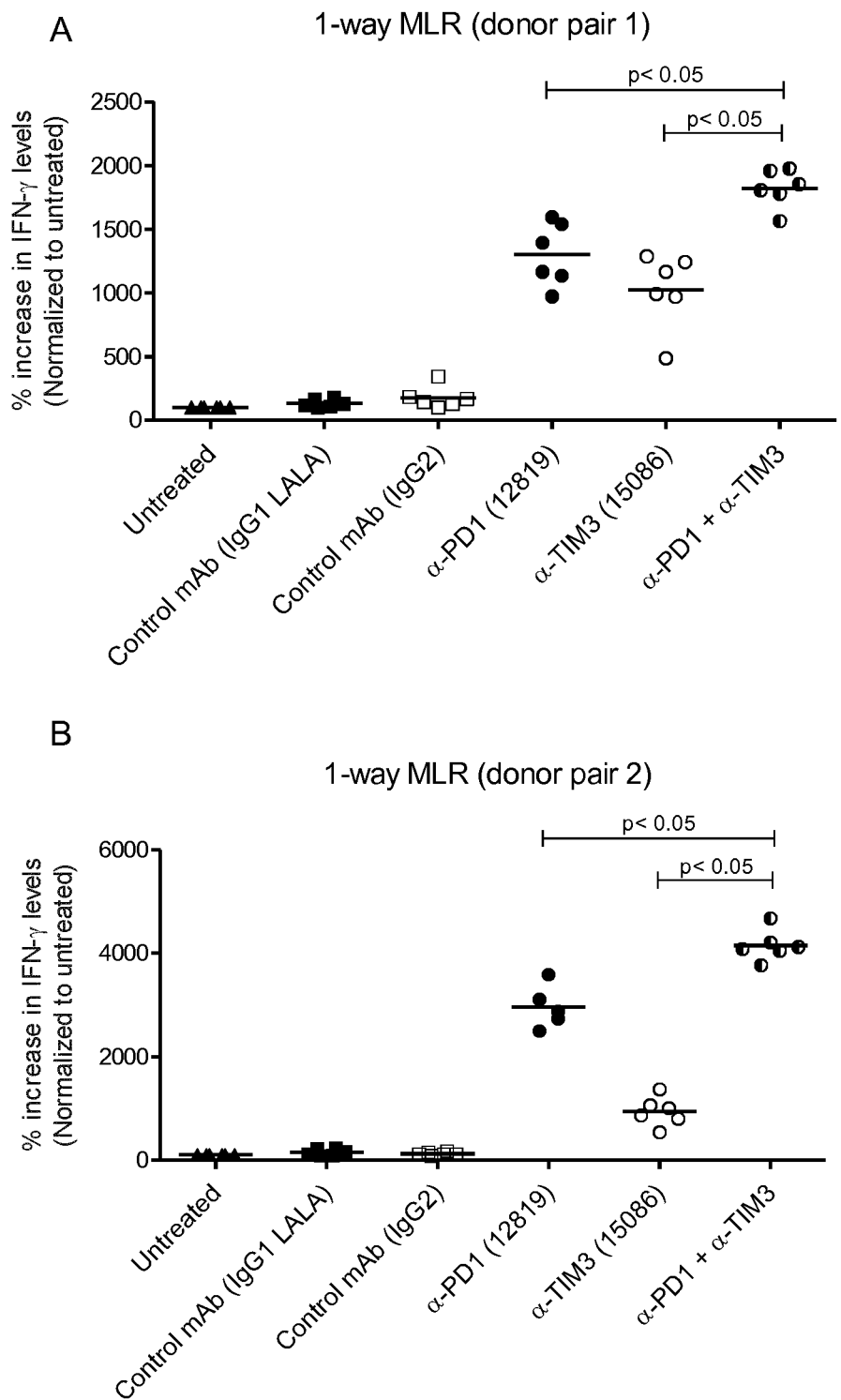
FIG. 1 is a set of graphs showing the percent increase in IFN-γ levels in three donor pairs (Panels A-C) after treatment with 10 μg/mL of control antibody (IgG1 LALA or IgG2), anti-PD-1 antibody 12819, anti-TIM-3 antibody 15086.17145, or a combination of antibodies 12819 and 15086.17145 at a 1:1 ratio, after 5 days of culture in a one-way MLR (mixed lymphocyte reaction) assay. Each dot in the graph represents a replicate and the mean is indicated by a horizontal bar.
Figure 1:
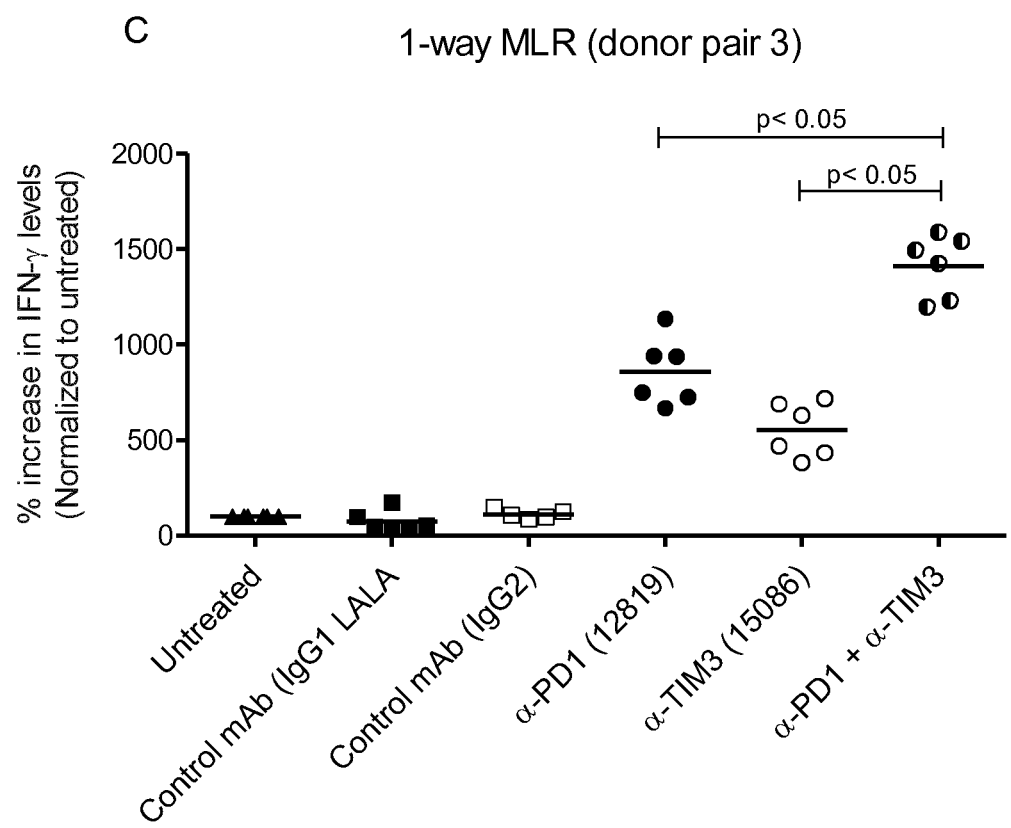

FIG. 1 shows the effect of anti-PD-1 and anti-TIM-3 antibodies on IFN-γ secretion in the one-way MLR assay in three independent donor-pairs. Both the anti-PD-1 (12819) and anti-TIM-3 (15086) antibodies were functional in the one-way MLR assay and increase IFN-γ secretion in all three donor pairs. Furthermore, the combination of anti-PD-1 and anti-TIM-3 antibodies shows enhanced activity by inducing a statistically significant increase in IFN-γ compared to the individual antibodies.

Example 2: Enhanced In Vitro Activity of Combined PD-1/TIM-3 Targeting in Two-Way MLR Assay This example demonstrates that combined targeting of PD-1 and TIM-3 using the anti-PD-1 antibody 12819 and the anti-TIM-3 antibody 15086.17145 enhances IFN-γ secretion in a two-way MLR assay.

In the two-way MLR assay, PBMCs from two different healthy human donors were co-cultured to induce an alloantigen specific reaction resulting in cytokine production and T-cell activation/proliferation. The PBMCs from the two different donors were mixed in a 1:1 ratio. The antibodies were tested at a final total antibody concentration of 10 µg/mL. After 5 days of culture, supernatants were harvested and IFN-γ levels were determined using the Meso Scale electrochemiluminescence cytokine assay. Student's unpaired t-test was used for statistical analysis and Bonferroni correction was used to adjust for multiple comparisons. A corrected p-value <0.05 is considered statistically significant.

Figure 2:
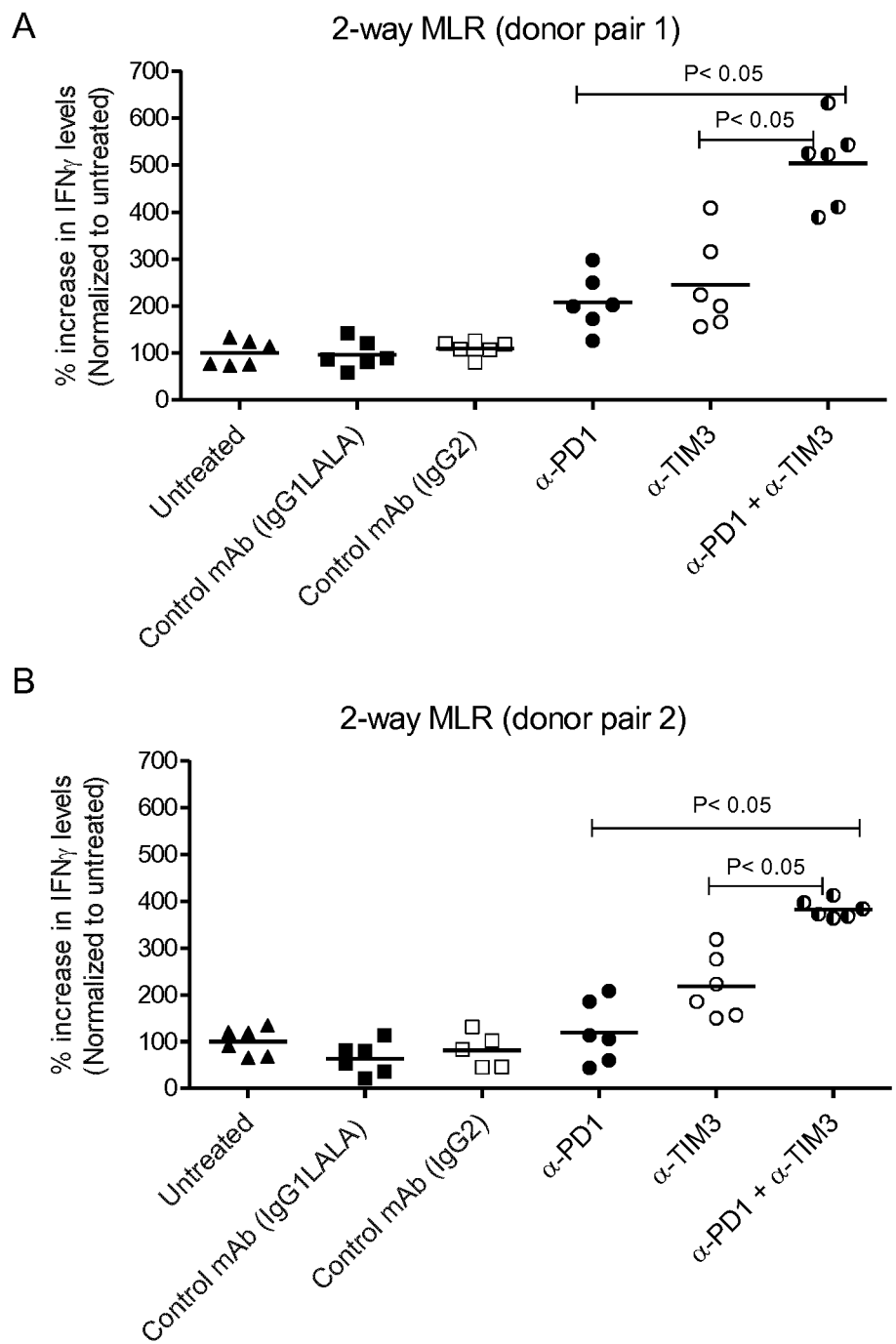
FIG. 2 is a set of graphs showing the percent increase in IFN-γ levels in three donor pairs (Panels A-C) after treatment with 10 μg/mL of control antibody (IgG1 LALA or IgG2), anti-PD-1 antibody 12819, anti-TIM-3 antibody 15086.17145, or a combination of antibodies 12819 and 15086.17145 at a 1:1 ratio, after 5 days of culture in a two-way MLR assay. Each dot in the graph represents a replicate and the mean is indicated by a horizontal bar.
Figure 2:
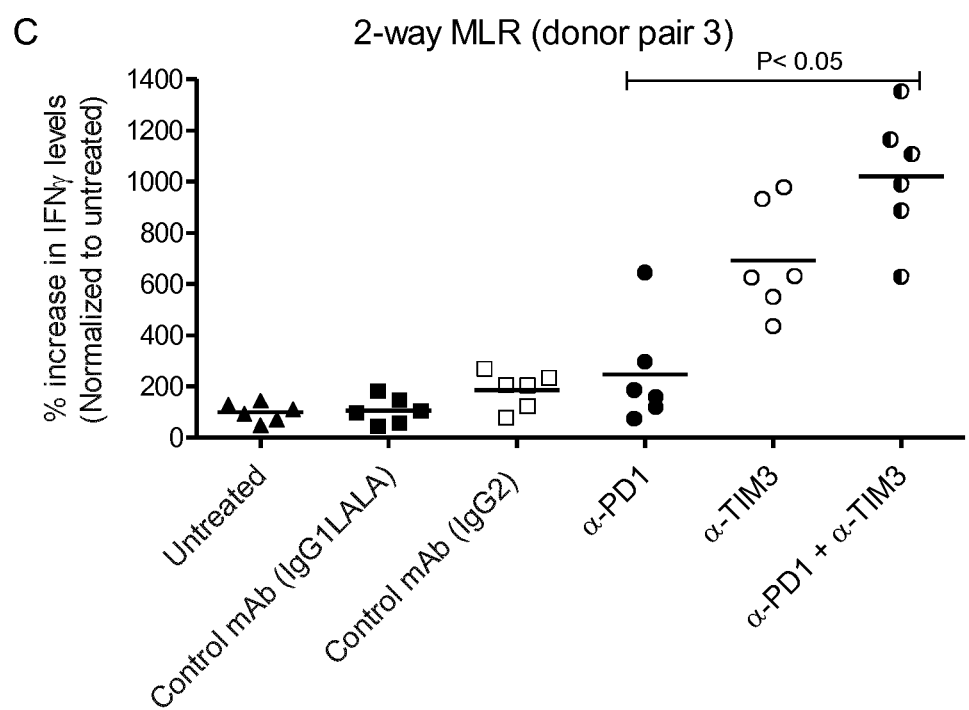

FIG. 2 shows the effect of anti-PD-1 and anti-TIM-3 antibodies on IFN-γ secretion in the two-way MLR assay in three independent human donor pairs. Anti-PD-1 and anti-TIM-3 antibodies both increased IFN-γ secretion in the two-way MLR assay. Additionally, the combination of anti-PD-1 and anti-TIM-3 antibodies showed enhanced activity by inducing increased IFN-γ secretion in comparison with the individual antibodies.

Example 3: Anti-TIM-3 Antibody Induces T-Cell Proliferation In Vitro in One-Way MLR Assay The ability of anti-TIM-3 antibody 15086.17145 to induce T-cell proliferation was investigated in the one-way MLR assay. The anti-TIM-3 antibody, a positive control antibody against PD-1 (12819), or a negative control IgG2 antibody were added to a final concentration of 25 µg/mL and incubated for 5 days prior to adding 1 µCi/well 3H-thymidine for an additional 18 hours. Cells were harvested, and 3H-thymidine incorporation determined by liquid scintillation counting (MicroBeta2).

Figure 3:
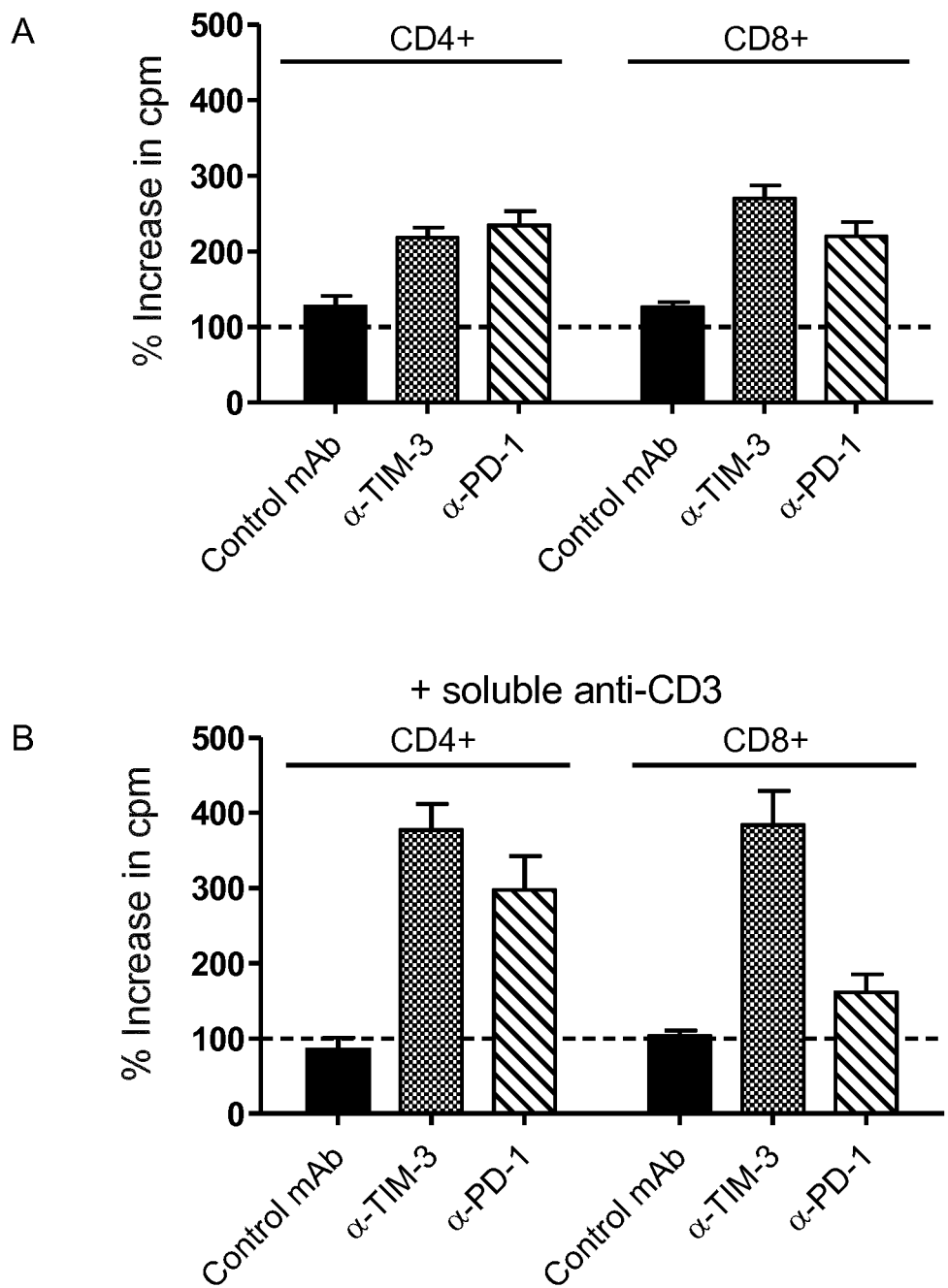
FIG. 3 is a pair of graphs showing the effect of anti-TIM-3 antibody 15086.17145 in comparison to positive control anti-PD-1 antibody 12819 on T-cell proliferation in the one-way MLR assay. The antibodies were added to a final concentration of 25 μg/mL and incubated without (Panel A)

As shown in FIG. 3, anti-TIM-3 antibody 15086.17145 induced proliferation of both CD4+ and CD8+ T-cells to a similar degree as the positive control antibody against PD-1 (Panel A). Addition of soluble anti-CD3 enhanced the proliferation induced by anti-TIM-3 antibody (Panel B).

Example 4: Anti-TIM-3 Antibody Induces IL-12p40 Secretion from Dendritic Cells

Monocyte derived dendritic cells were generated from healthy donor material as described previously in Example 1. The dendritic cells were incubated for 5 days with 10 µg/mL of anti-TIM-3 antibody 15086.17145 or a negative control IgG2 antibody, or without treatment, and IL-12p40 levels in the supernatants were determined using the standard ELISA cytokine assay.

As shown in FIG. 4, ligation of TIM-3 by anti-TIM-3 antibody 15086.17145 resulted in an increase in IL-12p40 secretion from dendritic cells.

Example 5: Anti-TIM-3 Antibody Induces Expression of Activation Markers in Dendritic Cells To further investigate the functional role of targeting TIM-3, expression levels of selected activation markers on monocyte derived dendritic cells were determined after treatment with anti-TIM-3 antibody 15086.17145.

Dendritic cells were treated with 25 µg/mL anti-TIM-3 antibody for 24 hours and gene expression of co-stimulatory molecules was determined using NanoString Technologies. Gene expression levels were normalized to 30 housekeeping genes with uniform expression. Data for selected relevant genes are presented as fold change relative to untreated control cells.

Gene expression analysis showed an upregulation of several activation markers and co-stimulatory molecules including MHC-II (HLA-DQB1 and HLA-DQA1), CD80 and CD86 (FIG. 5, Panel A). Increased cell surface expression of CD80 and CD86 upon treatment with anti-TIM-3 antibody 15086.17145 was validated using FACS analysis (FIG. 5, Panel B). The histogram overlays shown are representative of CD11c+dendritic cells, and numbers adjacent to the histograms denote MFI values.

Example 6: In Vivo Efficacy of Anti-TIM-3 Antibody 15086 on Human Lung PDX Tumor Growth This example shows the in vivo efficacy of anti-TIM-3 antibody 15086.17145 on a human lung patient-derived xenograft (PDX) tumor model in CD34$^+$ humanized NSG-SGM3 mice.

NSG-SGM3 mice were humanized using cord blood derived CD3$^+$ cells and engrafted in the right flank with patient-derived lung tumor fragments (LG1306). At tumor sizes between 50-150 mm$^3$, mice were randomized and treatment initiated. The mice received intraperitoneal injection of vehicle or anti-TIM-3 antibody 15086 with an initial dose of 10 mg/kg followed by 5 mg/kg 5×QSD. Tumors were measured three times weekly by caliper in two dimensions and tumor volume in mm$^3$ was calculated according to the formula: (width)$^2$×length×0.5. The grey area denotes the treatment period. Two-way ANOVA with Bonferroni's multiple comparisons test was applied to compare tumor volumes at each time-point between treatment groups. Data are presented as means±SEM, **p<0.01.

Treatment with anti-TIM-3 antibody 15086 resulted in a significant tumor growth inhibition in a CD34$^+$ humanized NSG-SGM3 mouse human lung PDX model (FIG. 6).

Example 7: Enhanced Effect of Combined PD-1/LAG-3, PD-1/TIM-3, or PD-1/TIM-3/LAG-3 Targeting in a PBMC+SEB Assay This example describes the enhanced effect of combining anti-PD-1 antibody 12819 with anti-LAG-3 antibody 15532 or anti-TIM-3 antibody 15086.17145 in the PBMC+SEB (Staphylococcal Enterotoxin B) assay.

SEB is a super-antigen that binds to MHC class II molecules and specific Vβ regions of T cell receptors (TCR) and drives non-specific stimulation of T-cells. This results in polyclonal T cell activation/proliferation and release of cytokines, including IL-2. Human PBMCs isolated from buffy coats from healthy donors were seeded in 384-well plates, and left untreated or treated with 10 ng/mL SEB and 10 µg/mL of the indicated single antibodies or antibody mixtures. Combinations of antibodies were 1:1 or 1:1:1 mixtures of the indicated antibodies. After 48 hours in a humidified incubator at 37° C., supernatants were removed and analyzed for IL-2 levels using an IL-2 ELISA kit (Life Technologies). Data are presented as average±SEM. Significant differences were tested using Student's t-test with Bonferroni correction.

FIG. 7 shows an increase in IL-2 secretion after treatment with a single anti-PD-1, anti-LAG-3 or anti-TIM-3 antibody, mixtures of two of the antibodies, or the mixture of all three antibodies. The data demonstrated that IL-2 levels were increased by single treatment with the anti-PD-1, anti-LAG-3 or anti-TIM-3 antibody, whereas IL-2 secretion was increased further by treatment with a combination of anti-PD-1 and anti-LAG-3 antibodies, or anti-PD-1 and anti-TIM-3 antibodies. The triple combination of anti-PD-1, anti-LAG-3, and anti-TIM-3 antibodies increased IL-2 secretion more than any of the two-antibody combinations.

Example 8: Enhanced In Vivo Efficacy of Combining Anti-PD-1 and Anti-LAG-3 Antibodies in Two Syngeneic Mouse Tumor Models This example demonstrates the in vivo efficacy of combining anti-PD-1 antibody 12819 with anti-LAG-3 antibody C9B7W (reactive with mouse LAG-3; BioXcell) or anti-LAG-3 antibody 15011 in two syngeneic mouse tumor models.

0.5×10$^6$ MC38 (colon carcinoma) or 5×10$^6$ ASB-XIV (lung carcinoma) cells were inoculated subcutaneously into the flank of 6-8 week old female BALB/cAnNRj (ASB-XIV) or C57BL/6 (MC38) mice, respectively. Tumors were measured three times weekly by caliper in two dimensions and tumor volume in mm$^3$ was calculated according to the formula: (width)$^2$×length×0.5. On day 5 (ASB-XIV) or day 13 (MC38) post-inoculation at an average tumor size of 30-50 mm$^3$, mice were randomized into four groups of ten animals and treatment was initiated. The mice were treated three times weekly with a total of six treatments by intraperitoneal injection of vehicle buffer, anti-PD-1 antibody 12819, anti-LAG-3 antibody C9B7W, anti-LAG-3 antibody 15011, or a combination of anti-PD-1 and anti-LAG-3 antibodies. The antibody treatments were administered at a dose of 10 mg/kg/target. Two-way ANOVA with Bonferroni's multiple comparisons test was applied to compare tumor volumes at each time-point between treatment groups. Statistical analyses were performed using GraphPad Prism version 5.0 (GraphPad Software, Inc.).

MC38 syngeneic tumors treated with monoclonal anti-PD-1 antibody 12819 displayed continuous tumor growth, albeit with slower growth kinetics than vehicle treated tumors (FIG. 8). No effect of treatment with anti-LAG-3 antibody C9B7W alone was observed. The combination of the anti-PD-1 antibody and the anti-LAG-3 antibody showed enhanced tumor growth inhibition compared to the anti-PD-1 treatment and significant tumor growth inhibition compared to vehicle treated tumors ($p<0.001$) (FIG. 8).

ASB-XIV syngeneic tumors treated with anti-PD-1 antibody 12819 showed delayed tumor growth compared to vehicle treated tumors (FIGS. 8 and 9). No effect of treatment with anti-LAG-3 antibody C9B7W alone was observed (FIG. 8), whereas anti-LAG-3 antibody 15011 significantly inhibited tumor growth compared to vehicle treatment ($p<0.05$) (FIG. 9). Combining the anti-PD-1 antibody and anti-LAG-3 antibody C9B7W significantly enhanced anti-tumor efficacy compared to vehicle treatment (FIG. 8). A significantly enhanced tumor inhibitory effect was also observed by a combination of the anti-PD-1 antibody and anti-LAG-3 antibody 15011 compared to single treatment with the anti-PD-1 antibody ($p<0.0001$) or the anti-LAG-3 antibody ($p<0.05$) (FIG. 9).

Example 9: Enhanced In Vivo Efficacy of Combining Anti-PD-1 and Anti-TIM-3 Antibodies in Two Syngeneic Mouse Tumor Models This example demonstrates the in vivo efficacy of combining anti-PD-1 antibody 12819 and anti-TIM-3 antibody 5D12 (reactive with mouse TIM-3; Anderson et al., Science 318:1141-43 (2007)) in two syngeneic mouse tumor models. $0.2 \times 10^6$ Sa1N (fibrosarcoma) or $5 \times 10^6$ ASB-XIV (lung carcinoma) cells were inoculated subcutaneously into the flank of 6-8 week old female NJ (Sa1N) and BALB/cAnNRj (ASB-XIV) mice, respectively. Tumors were measured three times weekly by caliper in two dimensions and tumor volume in mm$^3$ was calculated according to the formula: (width)$^2 \times$length$\times 0.5$. At an average tumor size of 60-110 mm$^3$, mice were randomized and treatment initiated. The mice were treated with a single dose (Sa1N), or treated three times weekly with a total of six treatments (ASB-XIV), by intraperitoneal injection of vehicle buffer, anti-PD-1 antibody 12819, and/or anti-TIM-3 antibody 5D12. The antibody treatments were administered at a dose of 10 mg/kg/target in mice with ASB-XIV tumors. Mice with Sa1N tumors were dosed with anti-PD-1 and anti-TIM-3 antibodies at 1 mg/kg and 10 mg/kg, respectively. Two-way ANOVA with Bonferroni's multiple comparisons test was applied to compare tumor volumes at each time-point between treatment groups. Statistical analyses were performed using GraphPad Prism version 5.0 (GraphPad Software, Inc.).

On day 6 post-inoculation of ASB-XIV tumor cells, at an average tumor size of 56 mm$^3$, mice were randomized into four groups of ten animals and treatment was initiated. Treatment with anti-PD-1 antibody 12819 delayed tumor growth, whereas treatment with anti-TIM-3 antibody 5D12 had no effect on tumor growth compared to vehicle treatment. A pronounced tumor inhibitory effect was seen by combining the anti-PD-1 antibody with the anti-TIM-3 antibody, compared to single treatment with either antibody ($p<0.001$) (FIG. 10).

On day 13 post-inoculation of Sa1N tumor cells, at an average tumor size of 110 mm$^3$, mice were randomized into four groups of ten animals and dosed with a single treatment of antibodies. The results showed an initial tumor growth delay from single antibody treatment with anti-PD-1 antibody 12819 or anti-TIM-3 antibody 5D12. An enhanced anti-tumor effect was observed by combining the anti-PD-1 antibody with the anti-TIM-3 antibody, compared to single antibody treatment. The combination treatment also significantly inhibited tumor growth compared to vehicle treatment ($p<0.0001$) (FIG. 10).

Example 10: In Vivo Efficacy of Combining Anti-PD-1 and Anti-TIM-3 Antibodies in a Human Xenograft Tumor Model This example demonstrates enhanced in vivo efficacy of combining anti-PD-1 antibody 12819 with anti-TIM-3 antibody 15086.17145 in a human xenograft tumor model, where A375 cells (human melanoma) were engrafted in mice reconstituted with human PBMCs.

Human PBMCs were interperitoneally injected into NOG (Donor 1 and Donor 2) or NOG-EXL (hGM-CSF/hIL-3-NOG) (Donor 3) mice one day prior to subcutaneous engraftment of the human A375 melanoma cells. Treatment was initiated on the day of PBMC injection and the mice were treated three times weekly with a total of six treatments by intraperitoneal injection of vehicle buffer, anti-PD-1 antibody 12819, anti-TIM-3 antibody 15086.17145, ora combination of the anti-PD-1 and anti-TIM-3 antibodies. The antibody treatments were administered at a dose of 10 mg/kg/target. Tumors were measured three times weekly by caliper in two dimensions and tumor volume in mm$^3$ was calculated per the formula: (width)$^2 \times$length$\times 0.5$. Two-way ANOVA with Bonferroni's multiple comparisons test was applied to compare tumor volumes at each time-point between treatment groups. Statistical analyses were performed using GraphPad Prism version 5.0 (GraphPad Software, Inc.).

As shown in FIG. 11, treatment with the combination of the anti-PD-1 and anti-TIM-3 antibodies resulted in significant (and synergistic, in at least Donor 3) tumor growth delay ($p<0.05$ and $p<0.01$), whereas single antibody treatment (anti-PD-1 or anti-TIM-3) showed limited effect on tumor growth compared to the vehicle treated group.

Example 11: Combined PD-1 and TIM-3 Targeting Leads to Increased Survival in Mice Co-Engrafted with Human Immune and Tumor Cells This example demonstrates the in vivo efficacy of combining anti-PD-1 antibody 12819 with anti-TIM-3 antibody 15086.17145 in mouse models of human tumors.

$2 \times 10^6$ A375 (melanoma) cells were mixed with $2 \times 10^6$ human PBMC and inoculated subcutaneously into the flank of 6-8 week old female NOD-scid mice. At the time of cell inoculation, treatment was initiated. The mice were treated three times weekly with a total of six treatments by intraperitoneal injection of vehicle buffer, anti-PD-1 antibody 12819, anti-TIM-3 antibody 15086.17145, or a combination of anti-PD-1 and anti-TIM-3. The antibody treatments were administered at a dose of 10 mg/kg for each antibody. Tumors were measured three times weekly by caliper in two dimensions and tumor volume in mm³ was calculated according to the formula: (width)²×length×0.5.

Survival was defined as having a tumor size <400 mm³. The results showed an increase in survival of mice treated with a dual combination of anti-PD-1 and anti-TIM-3 antibodies compared to any single antibody treatment (FIG. 12, Panels A-E)).

Example 12: Combined PD-1, LAG-3, and TIM-3 Targeting Leads to Increased Survival in a Syngeneic Mouse Tumor Model This example demonstrates the in vivo efficacy of combining anti-PD-1 antibody 12819 with anti-LAG-3 antibody C9B7W and anti-TIM-3 antibody 5D12 in a syngeneic mouse tumor model.

5×10⁶ ASB-XIV (lung carcinoma) cells were inoculated subcutaneously into the flank of 6-8 week old female BALB/cAnNRj mice. Tumors were measured three times weekly by caliper in two dimensions and tumor volume in mm³ was calculated according to the formula: (width)²×length×0.5. On day 5 post-inoculation, at an average tumor size of 50 mm³, mice were randomized into seven groups of ten animals and treatment was initiated. The mice were treated three times weekly with a total of six treatments by intraperitoneal injection of vehicle buffer, anti-PD-1 antibody 12819, anti-LAG-3 antibody C9B7W, anti-TIM-3 antibody 5D12, or a combination of anti-PD-1 and anti-LAG-3, anti-PD-1 and anti-TIM-3, or anti-PD-1, anti-LAG-3, and anti-TIM-3 antibodies. The antibody treatments were administered at a dose of 10 mg/kg for each antibody.

Survival was defined as having a tumor size <400 mm³. The results showed increased survival of mice treated with a triple combination of anti-PD-1, anti-LAG-3 and anti-TIM-3 antibodies compared to any single or dual antibody treatment (FIG. 13, Panels A-H).

TABLE 1

Antibody Sequence Identifiers

| Target | Ab | DNA VH | DNA VL | Protein VH | Protein VL | H-CDR1 | H-CDR2 | H-CDR3 | L-CDR1 | L-CDR2 | L-CDR3 |
|---|---|---|---|---|---|---|---|---|---|---|---|
| TIM-3 | 15086.15086 | 1 | 2 | 3 | 4 | 8 | 9 | 10 | 11 | 12 | 13 |
| | 15086.16837 | 5 | 6 | 7 | | | | | | | |
| | 15086.17145 | | | | | | | | | | |
| | 15086.17144 | | | | | | | | | | |
| | 15105 | 14 | 15 | 16 | 17 | 18 | 19 | 20 | 21 | 22 | 23 |
| | 15107 | 24 | 25 | 26 | 27 | 28 | 29 | 30 | 31 | 32 | 33 |
| | 15109 | 34 | 35 | 36 | 37 | 38 | 39 | 40 | 41 | 42 | 43 |
| | 15174 | 44 | 45 | 46 | 47 | 48 | 49 | 50 | 51 | 52 | 53 |
| | 15175 | 54 | 55 | 56 | 57 | 58 | 59 | 60 | 61 | 62 | 63 |
| | 15260 | 64 | 65 | 66 | 67 | 68 | 69 | 70 | 71 | 72 | 73 |
| | 15284 | 74 | 75 | 76 | 77 | 78 | 79 | 80 | 81 | 82 | 83 |
| | 15299 | 84 | 85 | 86 | 87 | 88 | 89 | 90 | 91 | 92 | 93 |
| | 15353 | 94 | 95 | 96 | 97 | 98 | 99 | 100 | 101 | 102 | 103 |
| | 15354 | 104 | 105 | 106 | 107 | 108 | 109 | 110 | 111 | 112 | 113 |
| | 17244 | 114 | 115 | 116 | 117 | 118 | 119 | 120 | 121 | 122 | 123 |
| | 17245 | 124 | 125 | 126 | 127 | 128 | 129 | 130 | 131 | 132 | 133 |
| | 19324 | 134 | 135 | 136 | 137 | 138 | 139 | 140 | 141 | 142 | 143 |
| | 19416 | 144 | 145 | 146 | 147 | 148 | 149 | 150 | 151 | 152 | 153 |
| | 19568 | 154 | 155 | 156 | 157 | 158 | 159 | 160 | 161 | 162 | 163 |
| | 20131 | 164 | 165 | 166 | 167 | 168 | 169 | 170 | 171 | 172 | 173 |
| | 20185 | 174 | 175 | 176 | 177 | 178 | 179 | 180 | 181 | 182 | 183 |
| | 20293 | 184 | 185 | 186 | 187 | 188 | 189 | 190 | 191 | 192 | 193 |
| | 20300 | 194 | 195 | 196 | 197 | 198 | 199 | 200 | 201 | 202 | 203 |
| | 20362 | 204 | 205 | 206 | 207 | 208 | 209 | 210 | 211 | 212 | 213 |
| | 20621 | 214 | 215 | 216 | 217 | 218 | 219 | 220 | 221 | 222 | 223 |
| PD-1 | 12819.15384 | 224 | 225 | 226 | 227 | 228 | 229 | 230 | 231 | 232 | 233 |
| | 12748.15381 | 234 | 235 | 236 | 237 | 238 | 239 | 240 | 241 | 242 | 243 |
| | 12865.15377 | 244 | 245 | 246 | 247 | 248 | 249 | 250 | 251 | 252 | 253 |
| | 12892.15378 | 254 | 255 | 256 | 257 | 258 | 259 | 260 | 261 | 262 | 263 |
| | 12796.15376 | 264 | 265 | 266 | 267 | 268 | 269 | 270 | 271 | 272 | 273 |
| | 12777.15382 | 274 | 275 | 276 | 277 | 278 | 279 | 280 | 281 | 282 | 283 |
| | 12760.15375 | 284 | 285 | 286 | 287 | 288 | 289 | 290 | 291 | 292 | 293 |
| | 13112.15380 | 294 | 295 | 296 | 297 | 298 | 299 | 300 | 301 | 302 | 303 |
| | 12748.16124 | 234 | 391 | 236 | 392 | 238 | 239 | 240 | 393 | 394 | 395 |
| LAG-3 | 15646 | 304 | 305 | 306 | 307 | 308 | 309 | 310 | 311 | 312 | 313 |
| | 15532 | 314 | 315 | 316 | 317 | 318 | 319 | 320 | 321 | 322 | 323 |
| | 15723 | 324 | 325 | 326 | 327 | 328 | 329 | 330 | 331 | 332 | 333 |
| | 15595 | 334 | 335 | 336 | 337 | 338 | 339 | 340 | 341 | 342 | 343 |
| | 15431 | 344 | 345 | 346 | 347 | 348 | 349 | 350 | 351 | 352 | 353 |
| | 15572 | 354 | 355 | 356 | 357 | 358 | 359 | 360 | 361 | 362 | 363 |
| | 15011 | 364 | 365 | 366 | 367 | 368 | 369 | 370 | 371 | 372 | 373 |

TABLE 2

Constant Region Sequences

| SEQ ID NO | Description | Sequence |
|---|---|---|
| 374 | IgG1 heavy chain constant region protein sequence | ASTKGPSVFPLAPSSKSTSGGTAALGCLVKDYFPEPVTVSWNSGALTSGVHTFPAVLQSSGLYSLSSVVTVPSS SLGTQTYICNVNHKPSNTKVDKRVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPIEKTISKA KGQPREPQVYTLPPSREEMTKNQVSLTCLVKGFYPSDIAVEWESNGQPENNYKTTPPVLDSDGSFFLYSKLTVD KSRWQQGNVFSCSVMHEALHNHYTQKSLSLSPGK |
| 375 | IgG1-LALA heavy chain constant region protein sequence | ASTKGPSVFPLAPSSKSTSGGTAALGCLVKDYFPEPVTVSWNSGALTSGVHTFPAVLQSSGLYSLSSVVTVPSS SLGTQTYICNVNHKPSNTKVDKRVEPKSCDKTHTCPPCPAPEAAGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPIEKTISKA KGQPREPQVYTLPPSREEMTKNQVSLTCLVKGFYPSDIAVEWESNGQPENNYKTTPPVLDSDGSFFLYSKLTVD KSRWQQGNVFSCSVMHEALHNHYTQKSLSLSPGK |
| 376 | IgG4 (S228P) heavy chain constant region protein sequence | ASTKGPSVFPLAPCSRSTSESTAALGCLVKDYFPEPVTVSWNSGALTSGVHTFPAVLQSSGLYSLSSVVTVPSS SLGTKTYTCNVDHKPSNTKVDKRVESKYGPPCPPCPAPEFLGGPSVFLFPPKPKDTLMISRTPEVTCVVVDVSQ EDPEVQFNWYVDGVEVHNAKTKPREEQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNYKTTPPVLDSDGSFFLYSRLTVDKSR WQEGNVFSCSVMHEALHNHYTQKSLSLSLGK |
| 377 | IgG2 heavy chain constant region protein sequence | ASTKGPSVFPLAPCSRSTSESTAALGCLVKDYFPEPVTVSWNSGALTSGVHTFPAVLQSSGLYSLSSVVTVPSS NFGTQTYTCNVDHKPSNTKVDKTVERKCCVECPPCPAPPVAGPSVFLFPPKPKDTLMISRTPEVTCVVVDVSHE DPEVQFNWYVDGVEVHNAKTKPREEQFNSTFRVVSVLTVVHQDWLNGKEYKCKVSNKGLPAPIEKTISKTKGQP REPQVYTLPPSREEMTKNQVSLTCLVKGFYPSDIAVEWESNGQPENNYKTTPPMLDSDGSFFLYSKLTVDKSRW QQGNVFSCSVMHEALHNHYTQKSLSLSPGK |
| 378 | Kappa light chain constant region protein sequence | RTVAAPSVFIFPPSDEQLKSGTASVVCLLNNFYPREAKVQWKVDNALQSGNSQESVTEQDSKDSTYSLSSTLTL SKADYEKHKVYACEVTHQGLSSPVTKSFNRGEC |
| 379 | Lambda light chain constant region protein sequence | GQPKANPTVTLFPPSSEELQANKATLVCLISDFYPGAVTVAWKADGSPVKAGVETTKPSKQSNNKYAASSYLSL TPEQWKSHRSYSCQVTHEGSTVEKTVAPTECS |
| 380 | IgG1-LALA heavy chain constant region DNA sequence excluding introns | GCCTCCACCAAGGGCCCATCGGTCTTCCCCCTGGCACCCTCCTCCAAGAGCACCTCTGGGGGCACAGCGGCCCT GGGCTGCCTGGTCAAGGACTACTTCCCCGAACCGGTGACGGTGTCGTGGAACTCAGGCGCCCTGACCAGCGGCG TGCACACCTTCCCGGCTGTCCTACAGTCCTCAGGACTCTACTCCCTCAGCAGCGTGGTGACCGTGCCCTCCAGC AGCTTGGGCACCCAGACCTACATCTGCAACGTGAATCACAAGCCCAGCAACACCAAGGTGGACAAGAGAGTTGA GCCCAAATCTTGTGACAAAACTCACACATGCCCACCGTGCCCAGCACCTGAAGCCGCCGGGGGACCGTCAGTCT TCCTCTTCCCCCCAAAACCCAAGGACACCCTCATGATCTCCCGGACCCCTGAGGTCACATGCGTGGTGGTGGAC GTGAGCCACGAAGACCCTGAGGTCAAGTTCAACTGGTACGTGGACGGCGTGGAGGTGCATAATGCCAAGACAAA GCCGCGGGAGGAGCAGTACAACAGCACGTACCGTGTGGTCAGCGTCCTCACCGTCCTGCACCAGGACTGGCTGA ATGGCAAGGAGTACAAGTGCAAGGTCTCCAACAAAGCCCTCCCAGCCCCCATCGAGAAAACCATCTCCAAAGCC AAAGGGCAGCCCCGAGAACCACAGGTGTACACCCTGCCCCCATCCCGGGAGGAGATGACCAAGAACCAGGTCAG CCTGACCTGCCTGGTCAAAGGCTTCTATCCCAGCGACATCGCCGTGGAGTGGGAGAGCAATGGGCAGCCGGAGA ACAACTACAAGACCACGCCTCCCGTGCTGGACTCCGACGGCTCCTTCTTCCTCTATAGCAAGCTCACCGTGGAC AAGAGCAGGTGGCAGCAGGGGAACGTCTTCTCATGCTCCGTGATGCATGAGGCTCTGCACAACCACTACACGCA GAAGAGCCTCTCCCTGTCCCCGGGTAAA |
| 381 | IgG1-LALA heavy chain constant region DNA sequence including introns | GCCTCCACCAAGGGCCCATCGGTCTTCCCCCTGGCACCCTCCTCCAAGAGCACCTCTGGGGGCACAGCGGCCCT GGGCTGCCTGGTCAAGGACTACTTCCCCGAACCGGTGACGGTGTCGTGGAACTCAGGCGCCCTGACCAGCGGCG TGCACACCTTCCCGGCTGTCCTACAGTCCTCAGGACTCTACTCCCTCAGCAGCGTGGTGACCGTGCCCTCCAGC AGCTTGGGCACCCAGACCTACATCTGCAACGTGAATCACAAGCCCAGCAACACCAAGGTGGACAAGAGAGTTGG TGAGAGGCCAGCACAGGGAGGGAGGGTGTCTGCTGGAAGCCAGGCTCAGCGCTCCTGCCTGGACGCATCCCGGC TATGCAGTCCCAGTCCAGGGCAGCAAGGCAGGCCCCGTCTGCCTCTTCACCCGGAGGCCTCTGCCCGCCCCACT CATGCTCAGGGAGAGGTCTTCTGGCTTTTTCCCCAGGCTCTGGGCAGGCACAGGCTAGGTGCCCCTAACCCAG GCCCTGCACACAAAGGGGCAGGTGCTGGGCTCAGACCTGCCAAGAGCCATATCCGGGAGGACCCTGCCCCTGAC CTAAGCCCACCCCAAAGGCCAAACTCTCCACTCCCTCAGCTCGGACACCTTCTCTCCTCCCAGATTCCAGTAAC TCCCAATCTTCTCTCTGCAGAGCCCAAATCTTGTGACAAAACTCACACATGCCCACCGTGCCCAGGTAAGCCAG CCCAGGCCTCGCCCTCCAGCTCAAGGCGGGACAGGTGCCCTAGAGTAGCCTGCATCCAGGGACAGGCCCCAGCC GGGTGCTGACACGTCCACCTCCATCTCTTCCTCAGCACCTGAAgccgccGGGGGACCGTCAGTCTTCCTCTTCC CCCCAAAACCCAAGGACACCCTCATGATCTCCCGGACCCCTGAGGTCACATGCGTGGTGGTGGACGTGAGCCAC GAAGACCCTGAGGTCAAGTTCAACTGGTACGTGGACGGCGTGGAGGTGCATAATGCCAAGACAAAGCCGCGGGA GGAGCAGTACAACAGCACGTACCGTGTGGTCAGCGTCCTCACCGTCCTGCACCAGGACTGGCTGAATGGCAAGG AGTACAAGTGCAAGGTCTCCAACAAAGCCCTCCCAGCCCCCATCGAGAAAACCATCTCCAAAGCCAAAGGTGGG ACCCGTGGGGTGCGAGGGCCACATGGACAGAGGCCGGCTCGGCCCACCCTCTGCCCTGAGAGTGACCGCTGTAC CAACCTCTGTCCCTACAGGGCAGCCCCGAGAACCACAGGTGTACACCCTGCCCCCATCCCGGGAGGAGATGACC AAGAACCAGGTCAGCCTGACCTGCCTGGTCAAAGGCTTCTATCCCAGCGACATCGCCGTGGAGTGGGAGAGCAA TGGGCAGCCGGAGAACAACTACAAGACCACGCCTCCCGTGCTGGACTCCGACGGCTCCTTCTTCCTCTATAGCA AGCTCACCGTGGACAAGAGCAGGTGGCAGCAGGGGAACGTCTTCTCATGCTCCGTGATGCATGAGGCTCTGCAC AACCACTACACGCAGAAGAGCCTCTCCCTGTCCCCGGGTAAA |
| 382 | IgG4 (S228P) heavy chain constant region DNA sequence excluding introns | GCTTCCACCAAGGGCCCATCGGTCTTCCCCCTGGCGCCCTGCTCCAGGAGCACCTCCGAGAGCACAGCCGCCCT GGGCTGCCTGGTCAAGGACTACTTCCCCGAACCGGTGACGGTGTCGTGGAACTCAGGCGCCCTGACCAGCGGCG TGCACACCTTCCCGGCTGTCCTACAGTCCTCAGGACTCTACTCCCTCAGCAGCGTGGTGACCGTGCCCTCCAGC AGCTTGGGCACGAAGACCTACACCTGCAACGTAGATCACAAGCCCAGCAACACCAAGGTGGACAAGAGAGTTGA |

TABLE 2-continued

Constant Region Sequences

| SEQ ID NO | Description | Sequence |
|---|---|---|
| | | GTCCAAATATGGTCCCCCATGCCCAcCATGCCCAGCACCTGAGTTCCTGGGGGGACCATCAGTCTTCCTGTTCC CCCCAAAACCCAAGGACACTCTCATGATCTCCCGGACCCCTGAGGTCACGTGCGTGGTGGTGGACGTGAGCCAG GAAGACCCCGAGGTCCAGTTCAACTGGTACGTGGATGGCGTGGAGGTGCATAATGCCAAGACAAAGCCGCGGGA GGAGCAGTTCAACAGCACGTACCGTGTGGTCAGCGTCCTCACCGTCCTGCACCAGGACTGGCTGAACGGCAAGG AGTACAAGTGCAAGGTCTCCAACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAGAACCAGGTCAGCCTGACCTG CCTGGTCAAAGGCTTCTACCCCAGCGACATCGCCGTGGAGTGGGAGAGCAATGGGCAGCCGGAGAACAACTACA AGACCACGCCTCCCGTGCTGGACTCCGACGGCTCCTTCTTCCTCTACAGCAGGCTCACCGTGGACAAGAGCAGG TGGCAGGAGGGGAATGTCTTCTCATGCTCCGTGATGCATGAGGCTCTGCACAACCACTACACACAGAAGAGCCT CTCCCTGTCTCTGGGTAAA |
| 383 | IgG4 (S228P) heavy chain constant region DNA sequence including introns | GCTTCCACCAAGGGCCCATCGGTCTTCCCCCTGGCGCCCTGCTCCAGGAGCACCTCCGAGAGCACAGCCGCCCT GGGCTGCCTGGTCAAGGACTACTTCCCCGAACCGGTGACGGTGTCGTGGAACTCAGGCGCCCTGACCAGCGGCG TGCACACCTTCCCGGCTGTCCTACAGTCCTCAGGACTCTACTCCCTCAGCAGCGTGGTGACCGTGCCCTCCAGC AGCTTGGGCACGAAGACCTACACCTGCAACGTAGATCACAAGCCCAGCAACACCAAGGTGGACAAGAGAGTTGG TGAGAGGCCAGCACAGGGAGGGAGGGTGTCTGCTGGAAGCCAGGCTCAGCCCTCCTGCCTGGACGCACCCCGGC TGTGCAGCCCCAGCCCAGGGCAGCAAGGCAGGCCCCATCTGTCTCCTCACCCGGAGGCCTCTGACCACCCCACT CATGCTCAGGGAGAGGGTCTTCTGGATTTTTCCACCAGGCTCCGGGCAGCCACAGGCTGGATGCCCCTACCCCA GGCCCTGAgCATACAGGGGCAGGTGCTGCGCTCAGACCTGCCAAGAGCCATATCCGGGAGGACCCTGCCCCTGA CCTAAGCCCACCCCAAAGGCCAAACTCTCCACTCCCTCAGCTCAGACACCTTCTCTCCTCCCAGATCTGAGTAA CTCCCAATCTTCTCTCTGCAGAGTCCAAATATGGTCCCCCATGCCCAcCATGCCCAGGTAAGCCAACCCAGGCC TCGCCCTCCAGCTCAAGGCGGGACAGGTGCCCTAGAGTAGCCTGCATCCAGGGACAGGCCCCAGCCGGGTGCTG ACGCATCCACCTCCATCTCTTCCTCAGCACCTGAGTTCCTGGGGGGACCATCAGTCTTCCTGTTCCCCCCAAAA CCCAAGGACACTCTCATGATCTCCCGACCCCTGAGGTCACGTGCGTGGTGGTGGACGTGAGCCAGGAAGACCC CGAGGTCCAGTTCAACTGGTACGTGGATGGCGTGGAGGTGCATAATGCCAAGACAAAGCCGCGGGAGGAGCAGT TCAACAGCACGTACCGTGTGGTCAGCGTCCTCACCGTCCTGCACCAGGACTGGCTGAACGGCAAGGAGTACAAG TGCAAGGTCTCCAACAAAGGCCTCCCGTCCTCCATCGAGAAAACCATCTCCAAAGCCAAAGGTGGGACCCACGG GGTGCGAGGGCACATGGACAGAGGTCAGCTCGGCCCACCCTCTGCCCTGGGAGTGACCGCTGTGCCAACCTCT GTCCCTACAGGGCAGCCCCGAGAGCCACAGGTGTACACCCTGCCCCCATCCCAGGAGGAGATGACCAAGAACCA GGTCAGCCTGACCTGCCTGGTCAAAGGCTTCTACCCCAGCGACATCGCCGTGGAGTGGGAGAGCAATGGGCAGC CGGAGAACAACTACAAGACCACGCCTCCCGTGCTGGACTCCGACGGCTCCTTCTTCCTCTACAGCAGGCTCACC GTGGACAAGAGCAGGTGGCAGGAGGGGAATGTCTTCTCATGCTCCGTGATGCATGAGGCTCTGCACAACCACTA CACACAGAAGAGCCTCTCCCTGTCTCTGGGTAAA |
| 384 | IgG2 heavy chain constant region DNA sequence excluding introns | GCCTCCACCAAGGGCCCATCGGTCTTCCCCCTGGCGCCCTGCTCCAGGAGCACCTCCGAGAGCACAGCCGCCCT GGGCTGCCTGGTCAAGGACTACTTCCCCGAACCGGTGACGGTGTCGTGGAACTCAGGCGCTCTGACCAGCGGCG TGCACACCTTCCCAGCTGTCCTACAGTCCTCAGGACTCTACTCCCTCAGCAGCGTGGTGACCGTGCCCTCCAGC AACTTCGGCACCCAGACCTACACCTGCAACGTAGATCACAAGCCCAGCAACACCAAGGTGGACAAGACAGTTGA GCGCAAATGTTGTGTCGAGTGCCCACCGTGCCCAGCACCACCTGTGCAGGACCGTCAGTCTTCCTCTTCCCCC CAAAACCCAAGGACACCCTCATGATCTCCCGGACCCCTGAGGTCACGTGCGTGGTGGTGGACGTGAGCCACGAA GACCCCGAGGTCCAGTTCAACTGGTACGTGGACGGCGTGGAGGTGCATAATGCCAAGACAAAGCCACGGGAGGA GCAGTTCAACAGCACGTTCCGTGTGGTCAGCGTCCTCACCGTTGTGCACCAGGACTGGCTGAACGGCAAGGAGT ACAAGTGCAAGGTCTCCAACAAAGCCCTCCCAGCCCCCATCGAGAAAACCATCTCCAAAACCAAAGGGCAGCCC CGAGAACCACAGGTGTACACCCTGCCCCCATCCCGGGAGGAGATGACCAAGAACCAGGTCAGCCTGACCTGCCT GGTCAAAGGCTTCTACCCCAGCGACATCGCCGTGGAGTGGGAGAGCAATGGGCAGCCGGAGAACAACTACAAGA CCACACCTCCCATGCTGGACTCCGACGGCTCCTTCTTCCTCTACAGCAAGCTCACCGTGGACAAGAGCAGGTGG CAGCAGGGGAACGTCTTCTCATGCTCCGTGATGCATGAGGCTCTGCACAACCACTACACGCAGAAGAGCCTCTC CCTGTCTCCGGGTAAA |
| 385 | IgG2 heavy chain constant region DNA sequence including introns | GCCTCCACCAAGGGCCCATCGGTCTTCCCCCTGGCGCCCTGCTCCAGGAGCACCTCCGAGAGCACAGCCGCCCT GGGCTGCCTGGTCAAGGACTACTTCCCCGAACCGGTGACGGTGTCGTGGAACTCAGGCGCTCTGACCAGCGGCG TGCACACCTTCCCAGCTGTCCTACAGTCCTCAGGACTCTACTCCCTCAGCAGCGTGGTGACCGTGCCCTCCAGC AACTTCGGCACCCAGACCTACACCTGCAACGTAGATCACAAGCCCAGCAACACCAAGGTGGACAAGACAGTTGG TGAGAGGCCAGCTCAGGGAGGGAGGGTGTCTGCTGGAAGCCAGGCTCAGCCCTCCTGCCTGGACGCACCCCGGC TGTGCAGCCCCAGCCCAGGGCAGCAAGGCAGGCCCCATCTGTCTCCTCACCCGGAGGCCTCTGCCCGCCCCACT CATGCTCAGGGAGAGGGTCTTCTGGCTTTTTCCACCAGGCTCCAGGCAGGCACAGGCTGGGTGCCCCTACCCCA GGCCCTTCACACACAGGGGCAGGTGCTTGGCTCAGACCTGCCAAAAGCCATATCGGGAGGACCCTGCCCCTGA CCTAAGCCCACCCCAAAGGCCAAACTGTCCACTCCCTCAGCTCGGACACCTTCTCTCCTCCCAGATCCGAGTAA CTCCCAATCTTCTCTCTGCAGAGCGCAAATGTTGTGTCGAGTGCCCACCGTGCCCAGGTAAGCCAGCCCAGGCC TCGCCCTCCAGCTCAAGGCGGGACAGGTGCCCTAGAGTAGCCTGCATCCAGGGACAGGCCCCAGCCTGGGTGCTG ACACGTCCACCTCCATCTCTTCCTCAGCACCACCTGTGGCAGGACCGTCAGTCTTCCTCTTCCCCCCAAACCC AAGGACACCCTCATGATCTCCCGGACCCCTGAGGTCACGTGCGTGGTGGTGGACGTGAGCCACGAAGACCCCGA GGTCCAGTTCAACTGGTACGTGGACGGCGTGGAGGTGCATAATGCCAAGACAAAGCCACGGGAGGAGCAGTTCA ACAGCACGTTCCGTGTGGTCAGCGTCCTCACCGTTGTGCACCAGGACTGGCTGAACGGCAAGGAGTACAAGTGC AAGGTCTCCAACAAAGCCCTCCCAGCCCCCATCGAGAAAACCATCTCCAAAACCAAAGGGCAGCCCCGCGGGGT ATGAGGGCCACATGGACAGAGGCCGGCTCGGCCCACCCTCTGCCCTGGGAGTGACCGCTGTGCCAACCTCTGTC CCTACAGGGCAGCCCCGAGAACCACAGGTGTACACCCTGCCCCCATCCCGGGAGGAGATGACCAAGAACCAGGT CAGCCTGACCTGCCTGGTCAAAGGCTTCTACCCCAGCGACATCGCCGTGGAGTGGGAGAGCAATGGGCAGCCGG AGAACAACTACAAGACCACACCTCCCATGCTGGACTCCGACGGCTCCTTCTTCCTCTACAGCAAGCTCACCGTG GACAAGAGCAGGTGGCAGCAGGGGAACGTCTTCTCATGCTCCGTGATGCATGAGGCTCTGCACAACCACTACAC GCAGAAGAGCCTCTCCCTGTCTCCGGGTAAA |

TABLE 2-continued

Constant Region Sequences

| SEQ ID NO | Description | Sequence |
|---|---|---|
| 386 | Kappa light chain constant region DNA sequence | CGTACGGTGGCTGCACCATCTGTCTTCATCTTCCCGCCATCTGATGAGCAGTTGAAATCTGGAACTGCCTCTGT<br>TGTGTGCCTGCTGAATAACTTCTATCCCAGAGAGGCCAAAGTACAGTGGAAGGTGGATAACGCCCTCCAATCGG<br>GTAACTCCCAGGAGAGTGTCACAGAGCAGGACAGCAAGGACAGCACCTACAGCCTCAGCAGCACCCTGACGCTG<br>AGCAAAGCAGACTACGAGAAACACAAAGTCTACGCCTGCGAAGTCACCCATCAGGGCCTGAGCTCGCCCGTCAC<br>AAAGAGCTTCAACAGGGGAGAGTGT |
| 387 | Lambda light chain constant region DNA sequence | CCTAGGTCAGCCCAAGGCCAACCCCACTGTCACTCTGTTCCCGCCCTCCTCTGAGGAGCTCCAAGCCAACAAGG<br>CCACACTAGTGTGTCTGATCAGTGACTTCTACCCGGGAGCTGTGACAGTGGCCTGGAAGGCAGATGGCAGCCCC<br>GTCAAGGCGGGAGTGGAGACCACCAAACCCTCCAAACAGAGCAACAACAAGTACGCGGCCAGCAGCTACCTGAG<br>CCTGACGCCCGAGCAGTGGAAGTCCCACAGAAGCTACAGCTGCCAGGTCACGCATGAAGGGAGCACCGTGGAGA<br>AGACAGTGGCCCCTACAGAATGTTCATAA |

TABLE 3

Target Protein Sequences

| Protein | Amino Acid Sequence |
|---|---|
| Human PD-1<br>UniProt Q15116<br>(SEQ ID NO: 388) | MQIPQAPWPVVWAVLQLGWRPGWFLDSPDRPWNPPTFSPALLVVTEGDNATFTCSFSNTS<br>ESFVLNWYRMSPSNQTDKLAAFPEDRSQPGQDCRFRVTQLPNGRDFHMSVVRARRNDSGT<br>YLCGAISLAPKAQIKESLRAELRVTERRAEVPTAHPSPSPRPAGQFQTLVVGVVGGLLGS<br>LVLLVWVLAVICSRAARGTIGARRTGQPLKEDPSAVPVFSVDYGELDFQWREKTPEPPVP<br>CVPEQTEYATIVFPSGMGTSSPARRGSADGPRSAQPLRPEDGHCSWPL |
| Human TIM-3<br>UniProt Q8TDQ0<br>(SEQ ID NO: 389) | MFSHLPFDCVLLLLLLLTRSSEVEYRAEVGQNAYLPCFYTPAAPGNLVPVCWGKGACPV<br>FECGNVVLRTDERDVNYWTSRYWLNGDFRKGDVSLTIENVTLADSGIYCCRIQIPGIMND<br>EKFNLKLVIKPAKVTPAPTRQRDFTAAFPRMLTTRGHGPAETQTLGSLPDINLTQISTLA<br>NELRDSRLANDLRDSGATIRIGIYIGAGICAGLALALIFGALIFKWYSHSKEKIQNLSLI<br>SLANLPPSGLANAVAEGIRSEENIYTIEENVYEVEEPNEYYCYVSSRQQPSQPLGCRFAM<br>P |
| Human LAG-3<br>UniProt P18627<br>(SEQ ID NO: 390) | MWEAQFLGLLFLQPLWVAPVKPLQPGAEVPVVWAQEGAPAQLPCSPTIPLQDLSLLRRAG<br>VTWQHQPDSGPPAAAPGHPLAPGPHPAAPSSWGPRPRRYTVLSVGPGGLRSGRLPLQPRV<br>QLDERGRQRGDFSLWLRPARRADAGEYRAAVHLRDRALSCRLRLRLGQASMTASPPGSLR<br>ASDWVILNCSFSRPDRPASVHWFRNRGQGRVPVRESPHHHLAESFLFLPQVSPMDSGPWG<br>CILTYRDGFNVSIMYNLTVLGLEPPTPLTVYAGAGSRVGLPCRLPAGVGTRSFLTAKWTP<br>PGGGPDLLVTGDNGDFTLRLEDVSQAQAGTYTCHIHLQEQQLNATVTLAIITVTPKSFGS<br>PGSLGKLLCEVTPVSGQERFVWSSLDTPSQRSFSGPWLEAQEAQLLSQPWQCQLYQGERL<br>LGAAVYFTELSSPGAQRSGRAPGALPAGHLLLFLILGVLSLLLLVTGAFGFHLWRRQWRP<br>RRFSALEQGIHPPQAQSKIEELEQEPEPEPEPEPEPEPEPEPEPEQL |

TABLE 4

Anti-TIM-3 antibody heavy and light chain variable domain nucleotide sequences

| Ab | Sequence (5' to 3') |
|---|---|
| 15086.<br>15086 VH | CAGGTGCAGCTACAGCAGTCGGGCCCAGGACTGGTGAAGCCTTCACAGACCCTGTCC<br>CTCACCTGCACTGTCTCTGGTGGCTCCATCAGCAGTGGTGGTTACTACTGGAGTTGG<br>ACCCGTCAGCACCCAGGGATGGGCCTGGAGTGGATTGGATACATCTCTTACAGTGGG<br>AGTATCTATTACACTCCGTCCCTCAAGAGTCGACTTACCATATCAGTGGACACGTCT<br>AAGAACCAGTTCTCCCTGAAGCTGAGCTCTGTGACTGCCGCGGACACGGCCGTATAT<br>TACTGTGCGAGTTTGGATTCCTGGGGATCTAACCGTGACTACTGGGGCCAGGGAACC<br>CTGGTCACCGTCTCGAGT<br>(SEQ ID NO: 1) |
| 15086.<br>15086 VL | GAAATTGTGTTGACGCAGTCTCCAGCCACCCTGTCTTTGTCTCCAGGGGAAAGAGCC<br>ACCCTCTCCTGCAGGGCCAGTCAGAGTGTTAGCAGCTACTTAGCCTGGTACCAACAG<br>AAACCTGGCCAGGCTCCCAGGCTCCTCATCTATGATGCATCCAACAGGGCCACTGGC<br>ATCCCAGCCAGGTTCAGTGGCAGTGGGTCTGGGACAGACTTCACTCTCACCATCAGC<br>AGCCTAGAGCCTGAAGATTTTGCAGTTTATTACTGTCAGCAGCGTAGCAACTGGCCG<br>CTCACTTTCGGCGGAGGGACCAAGGTGGAGATTAAG<br>(SEQ ID NO: 2) |
| 15086.<br>16837/<br>15086. | CAGGTGCAGCTGCAGGAGAGTGGCCCCGGACTGGTCAAGCCTTCACAGACTCTGAGC<br>CTGACCTGCACAGTGTCTGGCGGAAGTATCAGCTCCGGGGGTTACTATTGGAGCTGG<br>ACCCGACAGCACCCAGGAATGGGTCTGGAATGGATCGGGTACATTTCATATAGCGGC |

TABLE 4-continued

Anti-TIM-3 antibody heavy and light chain variable domain nucleotide sequences

| Ab | Sequence (5' to 3') |
|---|---|
| 17145/<br>15086.<br>17144 VH | TCCATCTACTATACACCCTCACTGAAAAGCAGGCTGACCATTTCCGTGGACACATCT<br>AAGAACCAGTTCAGCCTGAAACTGTCTAGTGTGACAGCCGCTGATACTGCAGTCTAC<br>TATTGTGCCTCCCTGGACTCTTGGGGCAGTAATAGAGATTACTGGGGCCAGGGAACT<br>CTGGTCACCGTCTCGAGT<br>(SEQ ID NO: 5) |
| 15086.<br>16837/<br>15086.<br>17145/<br>15086.<br>17144 VL | GAGATCGTGCTGACTCAGTCCCCAGCCACCCTGTCACTGAGCCCAGGAGAACGAGCA<br>ACCCTGTCTTGCAGGGCCTCCCAGTCTGTCAGCTCCTACCTGGCTTGGTATCAGCAG<br>AAGCCCGGGCAGGCACCTCGACTGCTGATCTACGACGCCAGTAACAGAGCTACCGGT<br>ATTCCCGCCCGCTTCAGTGGTTCAGGCAGCGGAACAGACTTTACCCTGACAATCTCT<br>AGTCTGGAGCCTGAAGATTTCGCCGTGTACTATTGTCAGCAGAGGTCTAATTGGCCA<br>CTGACATTTGGCGGAGGGACTAAGGTCGAGATCAAG<br>(SEQ ID NO: 6) |
| 15105 VH | CAGGTCACCTTGAAGGAGTGGGGCGCAGGACTGTTGAGGCCCTCGGAGACCCTGTCC<br>CTCACCTGCGCTGTCTATGGTGGGTCCTTCAGTGGTTACTACTGGAGCTGGATCCGC<br>CAGCCCCCAGGGAAGGGGCTGGAGTGGATAGGGGAAATCAATCATAGTGGAAGCACC<br>AACTACAACCCGTCCCTCAAGAGTCGAGTCACCATATCAGTAGACGCGACCAAGAAA<br>CAATTCTCCCTGAAGCTGACCTCTGTGACCGCCGCGGACACGGCTGTGTATTACTGT<br>GCGAGATATTGGGAGCTCCCTGACTACTGGGGCCAGGGCACCCTGGTCACCGTCTCG<br>AGT<br>(SEQ ID NO: 14) |
| 15105 VL | GACATCCAGTTGACCCAGTCTCCATCCTCCCTGTCTGCATCTGTAGGAGACAGAGTC<br>ACCATCACTTGCCGGGCAAGTCAGGGCATTAGAAATGATTTAGGCTGGTATCAGCAG<br>AAACCAGGGAAAGCCCCTAAGCGCCTGATCTATGCTGCATCCAGTTTGCAAAGTGGG<br>GTCCCATCAAGGTTCAGCGGCAGTGGATCTGGGACAGAATTCACTCTCACAATCAGC<br>AGCCTGCAGCCTGAAGATTTTGCAACTTATTACTGTCTACAGCATAATAGTTACCCT<br>CCGACGTTCGGCCAAGGGACCAAGGTGGAAATCAAG<br>(SEQ ID NO: 15) |
| 15107 VH | CAGATGCAGCTGGTGCAGTGGGGCGCAGGACTGTTGAAGCCTTCGGAGACCCTGTCC<br>CTCACCTGCGCTGTCTATGGTGGGTCCTTCAGTGGTTACTACTGGAGCTGGATCCGC<br>CAGCCCCCAGGGAAGGGGCTGGAGTGGATTGGGGAAATCAATCATAGTGGAAGCACC<br>AACTACAACCCGTCCCTCAAGAGTCGAGTCACCATGTCAGTTGACACGTCCAAGCAC<br>CAGTTCTCCCTGAAGCTGAGCTCTGTGACCGCCGCGGACACGGCTGTGTATTACTGT<br>GCGAGATGGTGGGAGCTTCCTGACTACTGGGGCCAGGGAACCCTGGTCACCGTCTCG<br>AGT<br>(SEQ ID NO: 24) |
| 15107 VL | GAAATTGTGTTGACGCAGTCTCCATCCTCCCTGTCTGCATCTGTAGGAGACAGAGTC<br>ACCATCACTTGCCGGGCAAGTCAGGGCATTAGAAATGATTTAGGCTGGTATCAGCAG<br>AAACCAGGGAAAGCCCCTAAGCGCCTGATCTATGCTGCATCCAGTTTGCAAAGTGGG<br>GTCCCATCAAGGTTCAGCGGCAGTGGATCTGGGACAGAATTCACTCTCACAATCAGC<br>AGCCTGCAGCCTGAAGATTTTGCAACTTATTACTGTCTACAGCATAATAGTTACCCG<br>TGGACGTTCGGCCAAGGGACCAAGGTGGAAATCAAG<br>(SEQ ID NO: 25) |
| 15109 VH | CAGATGCAGCTGGTGCAATGGGGCGCAGGACTGTTGAAGCCTTCGGAGACCCTGTCC<br>CTCACCTGCGCTGTCTATGGTGGGTCCTTCAGTGGTTACTACTGGAGCTGGATCCGC<br>CAGCCCCCAGGGAAGGGGCTGGAGTGGATTGGGGAAATCAATCATAGTGGAAGCACC<br>AACTACAACCCGTCCCTCAAGAGTCGAGTCACCATATCAGTAGACACGTCCAAGAAC<br>CAGTTCTCCCTGAAGCTGAGCTCTGTGACCGCCGCGGACACGGCTGTGTATTACTGT<br>GCGAGGTTTTACTATGCTCCGAACTTTGACTACTGGGGCCAGGGCACCCTGGTCACC<br>GTCTCGAGT<br>(SEQ ID NO: 34) |
| 15109 VL | GAAATTGTGTTGACGCAGTCTCCTTCCACCCTGTCTGCATCTGTAGGAGACAGAGTC<br>ACCATCACTTGCCGGGCCAGTCAGAGTATTAGTAGCTGGTTGGCCTGGTATCAGCAG<br>AAACCAGGGACAGCCCCTAAGCTCCTGATCTATAAGGCGTCTAGTTTAGAAAGTGGG<br>GTCCCATCAAGGTTCAGCGGCAGTGGATCTGGGACAGAATTCACTCTCACCATCAGC<br>AGCCTGCAGCCTGATGATTTTGCAACTTATTACTGCCAACAGTATAATAGTTATTCC<br>ACTTTCGGCGGAGGGACCAAGGTGGAGATCAAA<br>(SEQ ID NO: 35) |
| 15174 VH | CAGGTGCAGCTGCAGCAGTCGGGCCCAGGACTGGTGAAGCCTTCGGAGACCCTGTCC<br>CTCACCTGCACTGTCTCTGGTGGCTCCATCAGCAGTAGTAATTACTACTGGGGCTGG<br>ATCCGCCAGCCCCCAGGGAAGGGGCTGGAGTGGATTGGGAGTATCTATTATAGTGGG<br>AACACCTACTACAACCCGTCCCTCAAGAGTCGAGTCACCATATCCGTAGACACGTCC<br>AAGAACCAGTTCTCCCTGAAGCTGAGTTCTGTGACCGCCGCAGACACGGCTGTGTAT<br>TACTGTGCGAGACAGACAGTGGCTGGCCCCCTCTTTGACTACTGGGGCCAGGGAACC<br>CTGGTCACCGTCTCGAGT<br>(SEQ ID NO: 44) |

TABLE 4-continued

Anti-TIM-3 antibody heavy and light chain variable domain nucleotide sequences

| Ab | Sequence (5' to 3') |
|---|---|
| 15174 VL | GAAATTGTGATGACGCAGTCTCCTTCCACCCTGTCTGCATCTGTAGGAGACAGAGTC<br>ACCATCACTTGCCGGGCCAGTCAGAGTATTAGTAGCTGGTTGGCCTGGTATCAGCAG<br>AAACCAGGGAAAGCCCCTAAGGTCCTGATCTATAAGGCGTCTAGTTTAGAAAGTGGG<br>GTCCCATCAAGGTTCAGCGGCAGTGGATCTGGGACAGAACTCACTCTCACCATCAGC<br>AGCCTGCAGCCTGATGATTTTGCAACTTATTACTGCCAACAGTATAATAGTTATTCA<br>TTCACTTTCGGCCCTGGGACCAAAGTGGATATCAAG<br>(SEQ ID NO: 45) |
| 15175 VH | CAGGTCCAGCTGGTGCAATCTGGGGCTGAGGTGAAGAAGCCTGGGGCCTCAGTGAAG<br>GTCTCCTGCAAGGCTGCTGGATACACCTTAACCGGCTACTATATGCACTGGGTGCGA<br>CAGGCCCCTGGACAAGGCCTTGAGTGGATGGGACGGATCAACCCTAACAGTGGTGGC<br>TCAAACAATGCACAGAAGTTTCAGGGCAGGGTCACCATGACCAGGGACACGTCCATC<br>AGCACAGCCTACATGGAGCTGAGCAGGCTGAGATCTGACGACACGGCCGTGTATTAC<br>TGTGCGAGAGAGGGTCCCCTGTATAGCAGTGGCTGGTACGAGGGTGCTTTTGATATC<br>TGGGGCCAAGGGACAATGGTCACCGTCTCGAGT<br>(SEQ ID NO: 54) |
| 15175 VL | GAAATTGTGATGACGCAGTCTCCTTCCACCCTGTCTGCATCTGTAGGAGACAGAGTC<br>ACCATCACTTGCCGGGCCAGTCAGAGTATTAGTAGTTGGTTGGCCTGGTATCAGCAG<br>AAACCAGGGAAAGCCCCTAAGCTCCTGATCTATAAGGCGTCTAGTTTAGAAAGTGGG<br>GTCCCATCAAGGTTCAGCGGCAGTGGATCTGGGACAGAATTCACTCTCACCATCAGC<br>AGCCTGCAGCCTGATGATTTTGCAACTTATTACTGCCAACAGTATAATAGTTATTCT<br>CCGGGGCTCACTTTCGGCGGAGGGACCAAGGTGGAGATCAAG<br>(SEQ ID NO: 55) |
| 15260 VH | CAGATGCAGCTACAGCAGTCAGGTCCAGGACTGGTGAAGCCCTCGCAGACCCTCTCA<br>CTCACCTGTGCCATCTCCGGGGACAGTGTCTCTAGCAACAGTGCTGCTTGGAACTGG<br>ATCAGGCAGTCCCCATCGAGAGGCCTTGAGTGGCTGGGAAGGACATACTACAGGTCC<br>AAGTGGTATTCTGCTTTTGCAGTATCTGTGAAAAGTCGAATAACCATCAACCCAGAC<br>ACATCCAAGAACCAGTTCTCCCTGCAGCTGAACTCTGTGACTCCCGAGGACACGGCT<br>GTGTATTACTGTGCAAGAGAGGGTAGCAGTGGCTGGTACGGATACGTCCACCACTGG<br>GGCCAGGGCACCCTGGTCACCGTCTCGAGT<br>(SEQ ID NO: 64) |
| 15260 VL | GAAATTGTGTTGACGCAGTCTCCAGCTTCCCTGTCTGTATCTCTGGGAGAAACTGTC<br>ACCATCGAATGTCGAGCAAGTGAGGACATTTACAATGGTTTAGCATGGTATCAGCAG<br>AAGCCAGGGAAATCTCCTCAGCTCCTGATCTATAATGCAAATAGCTTGCATACTGGG<br>GTCCCATCACGGTTCAGTGGCAGTGGATCTGGTACACAGTATTCTCTCAAGATAAAC<br>AGCCTGCAATCTGAAGATGTCGCAAGTTATTTCTGTCAACAGTATTACGATTATCCT<br>CCGACGTTCGGCCAAGGGACCAAGGTGGAAATCAAA<br>(SEQ ID NO: 65) |
| 15284 VH | CAGGTGCAGCTGCAGGAGTCGGGCCCAGGACTGGTGAAGCCTTCGGAGACCCTGTCC<br>CTCACCTGCACTGTCTCTGGTGGCTCCTTCAGCAGTAGTAGTTACTACTGGGGCTGG<br>ATCCGCCAGCCCCCTGGGAAGGGGCTGGAGTGGATTGGGATCTTCTATTATAGTGGG<br>ACCACCTACTACAACCCGTCCCTCAAGAGTCGAGTCACCATATCCGCACACACGTCC<br>AAGAGCCAGTTCTCCCTGAAGCTGAGCTCTGTGACCGCCGCAGACACGGCTGTGTAT<br>TACTGTGCGAGAGGGGGAGAATATTTTGACCGGTTACTCCCCTTTGACTACTGGGGC<br>CAGGGAACCCTGGTCACCGTCTCGAGT<br>(SEQ ID NO: 74) |
| 15284 VL | GAAATTGTGATGACGCAGTCTCCATCCTTCCTGTCTGCATCTGTAGGAGACAGAGTC<br>ACCATCACTTGCCGGGCCAGTCAGGGCATTAGCAGTTATTTAGCCTGGTATCAGCAA<br>AAACCAGGGAAAGCCCCTAAGCTCCTGATCTATGCTGCATCCACTTTGGAAAGTGGG<br>GTCCCATCAAGGTTCAGCGGCAGTGGATCTGGGACAGAATTCACTCTCACAATCAGC<br>AGCCTGCAGCCTGAAGATTTTGCAACTTATTACTGTCAACAGCTTAATAGTTACCCA<br>TTCACTTTCGGCCCTGGGACCAAAGTGGATATCAAA<br>(SEQ ID NO: 75) |
| 15299 VH | CAGGTGCAGCTGGTGGAGTCTGGGGGAGGCTTGGTACAGCCGGGGGGTCCCTGAGA<br>CTCTCCTGTACAGCCTCTGGATTCACCTTTAGCAGCTATGCCATGAGCTGGGTCCGC<br>CAGGCTCCAGGGAAGGGGCTGGAGTGGGTCTCAGCTATTGGTGGTAGTGGTGGTAGC<br>ACATACTACGCAGACTCCGTGAAGGGCCGGTTCACCATCTCCAGAGACAATTCCAAG<br>AACACGCTGTATCTGCAAATGAACAGCCTGAGAGCCGAGGACACGGCCGTATATTAC<br>TGTGTGAAAGATGGGGCAGGAGGCTTTGACTACTGGGGCCAGGGAACCCTGGTCACC<br>GTCTCGAGT<br>(SEQ ID NO: 84) |
| 15299 VL | GATATTGTGATGACGCAGTCTTCATCCTCCCTGTCTGCATCTGTAGGAGACAGAGTC<br>ACCATCACTTGCCGGGCAAGTCAGGGCATTATAAATCATTTAGGCTGGTATCAGCAT<br>AAACCAGGGAAAGCCCCTAATCGCCTAATCTATGCTGCATCCAGTTTGCAAAGTGGG |

TABLE 4-continued

Anti-TIM-3 antibody heavy and light chain variable domain nucleotide sequences

| Ab | Sequence (5' to 3') |
|---|---|
| | GTCCCATCAAGGTTCAGCGGCAGTGGATCTGGGACAGAATTCACTCTCACAATCAGC<br>AGCCTGCAGCCTGAAGATTTTGCAACTTATTACTGTCTACGGCATAATAGTTACCCT<br>CCGACGTTCGGCCAAGGGACCAAGGTGGAAATCAAG<br>(SEQ ID NO: 85) |
| 15353 VH | CAGGTGCAGCTACAGCAGTCGGGCCCAGGACTGGTGAAGCCTTCACAGACCCTGTCC<br>CTCACCTGCACTGTCTCTGGTGGCTCCATCAACAGTGGTGGTCACTACTGGAGCTGG<br>ATCCGCCAGCACCCAGGGAGGGCCTGGAGTGGATTGGGTACATCTATTACAGTGGG<br>AGCATCTACTACAACCCGTCCCTCAAGAGTCGACTTACCATATCAGTAGACACGTCT<br>AAGAACCAGTTCTCCCTGAAGCTGAGCTCTGTGACTGCCGCGGACACGGCCGTGTAT<br>TACTGTGCGAGTTATTACTATGCCAGTAGTGGTGATGCTTTTGATATCTGGGGCCAA<br>GGGACAATGGTCACCGTCTCGAGT<br>(SEQ ID NO: 94) |
| 15353 VL | GAAACGACACTCACGCAGTCTCCAGCCACCCTGTCTTTGTCTCCAGGGGAAAGAGCC<br>ACCCTCTCCTGCAGGGCCAGTCAGAGTGTTAGCAGCTACTTAGCCTGGTACCAACAG<br>AAACCTGGCCAGGCTCCCAGGCTCCTCATCTATGATGCATCCAACAGGGCCACTGGC<br>ATCCCAGCCAGGTTCAGTGGCAGTGGGTCTGGGACAGACTTCACTCTCACCATCAGC<br>AGCCTAGAGCCTGAAGATTTTGCAGTTTATTACTGTCAGCAGCGTAGCAACTGGCCT<br>CCGACGTTCGGCCAAGGGACCAAGGTGGAAATCAAA<br>(SEQ ID NO: 95) |
| 15354 VH | CAGGTGCAGCTGCAGGAGTCTGGGGGAGGCTTGGTACAGCCGGGGGGGTCCCTGAGA<br>CTCTCCTGTACAGCCTCTGGATTCACCTTTAGTAATTATGCCATGAGCTGGGTCCGC<br>CAGGCTCCAGGGAAGGGGCTGGAGTGGGTCTCAGCTATTAGTGGTCGTGGTGGTAGC<br>ACATTCTTCGCAGACTCCGTGAAGGGCCGGTTCACCATCTCCAGAGACAATTCCAAG<br>AGCACGCTGTATCTGCAAACGAACAGCCTGAGAGCCGAGGACACGGCCGTATATTAC<br>TGTGCGAAAGGGGGCCCGTTGTATAACTGGAACGACGGTGATGGTTTTGATATCTGG<br>GGCCAAGGGACCACGGTCACAGTCTCGAGT<br>(SEQ ID NO: 104) |
| 15354 VL | GAAATTGTGTTGACGCAGTCTCCAGCCACCCTGTCTGTGTCTCCAGGGGAAAGAGCC<br>ACCCTCTCCTGCAGGGCCAGTCAGAGTGTTAGCAGCAACTTAGCCTGGTACCAGCAG<br>AAACCTGGCCAGGCTCCCAGGCTCCTCATCTATGGTGCATCCACCAGGGCCACTGGT<br>ATCCCAGCCAGGTTCAGTGGCACTGGGTCTGGGACAGAGTTCACTCTCACCATCAGC<br>AGCCTGCAGTCTGAAGATTTTGCACTTTATTACTGTCAGCAGTATGATAACTGGCCT<br>CCGTGGACGTTCGGCCAAGGGACCAAGGTGGAAATCAAA<br>(SEQ ID NO: 105) |
| 17244 VH | CAGGTGCAGCTGCAGGAGTCTGGGGGAGGCTTGGTCAAGCCTGGAGGGTCCCTGAGA<br>CTCTCCTGTGCAGCCTCTGGATTCACCTTCAGTGACTACTACATGACCTGGATCCGC<br>CAGGCTCCAGGGAAGGGGCTGGAGTGGATTTCATACATTAGTGGTGGTGGTGGTTCC<br>ATATACTACGCAGACTCTGTGAAGGGCCGATTCACCATCTCCAGGGACAACGCCAAG<br>AACTCACTGTATCTGCAAATGAACAGCCTGAGAGCCGAGGACACGGCCGTTTATTTC<br>TGTGCGAGAGGGAACTGGGGATCGGCGGCTCTTGATATCTGGGGCCAAGGGACAATG<br>GTCACGGTCTCGAGT<br>(SEQ ID NO: 114) |
| 17244 VL | GAAATTGTGTTGACGCAGTCTCCATCCTCACTGTCTGCATCTGTAGGAGACAGAGTC<br>ACCATCACTTGTCGGGCGAGTCAGGGCATTAACAATTATTTAGCCTGGTTTCAGCAG<br>AAACCAGGGAGAGCCCCTAAGTCCCTGATCTATGCTGCATCCAGTTTGCAAAGTGGG<br>GTCCCATCGAAGTTCAGCGGCAGTGGATCTGGGACAGATTTCACTCTCACCATCAGC<br>AGCCTGCAGCCTGAAGATTTTGCAACTTATTACTGCCAACAGTATAATAGTTACCCT<br>CCAACTCTCGGCCCTGGGACCAACGTGGATATCAAA<br>(SEQ ID NO: 115) |
| 17245 VH | CAGGTGCAGCTGGTGGAGTCTGGGGGAGGCTTGGTACAGCCGGGGGGGTCCCTGAGA<br>CTCTCCTGTACAGCCTCTGGATTCACCTTTAGCAGCTATGCCATGAGCTGGGTCCGC<br>CAGGCTCCAGGGAAGGGGCTGGAGTGGGTCTCAGCTATTGGTGGTAGTGGTGGTAGC<br>GCATACTACGCAGACTCCGTGAAGGGCCGGTTCACCATCTCCAGAGACAATTCCAAG<br>AACACGCTGTATCTGCAAATGAACAGCCTGAGAGCCGAGGACACGGCCGTATATTAC<br>TGTGTGAAAGATGGGGCAGGAGGCTTTGACTACTGGGGCCAGGGCACCCTGGTCACC<br>GTCTCGAGT<br>(SEQ ID NO: 124) |
| 17245 VL | GACATCCAGTTGACCCAGTCCCCATCCTCCCTGTCTGCATCTGTAGGAGACAGAGTC<br>ACCATCACTTGCCGGGCAAGTCAGGGCATTAGAAATCATTTAGGCTGGTATCAGCAG<br>AAACCAGGGAAAGCCCCTAAGCGCCTAATCTATGCTGCATCCAGTTTGCAAAGTGGG<br>GTCCCATCAAGGTTCAGCGGCAGTGGATCTGGGACAGAATTCACTCTCACAATCAGC<br>AGCCTGCAGCCTGAAGATTTTGCAACTTATTACTGTCTACAGCATAATAGTTACCCT<br>CCGACGTTCGGCCAAGGGACCAAGGTGGAAATCAAG<br>(SEQ ID NO: 125) |
| 19324 VH | CAGATGCAGCTACAGCAGTCTGGGGGAGGCTTGGTACAGCCGGGGGGGTCCCTGAGA<br>CTCTCCTGTGCAGCCTCTGGATTCACCGTTAGCAGCTATGCCATGAGCTGGGTCCGC |

TABLE 4-continued

Anti-TIM-3 antibody heavy and light chain variable domain nucleotide sequences

| Ab | Sequence (5' to 3') |
|---|---|
| | CAGGCTCTAGGGAAGGGGCTGGAGTGGGTCTCAGGTATTAGTGGTAGTGGTGGTAGC<br>ACATACTACGCAGACTCCGTGAAGGGCCGGTTCACCATCTCCAGAGACAATTCCAAG<br>AATACGCTGTATCTGCAAATGAACAGCCTGAGAGCCGAGGACACGGCCGTATATTAC<br>TGTGCGAAGATAGTGGGAGCTACCCACTTTGACTACTGGGGCCAGGGAACCCTGGTC<br>ACGGTCTCGAGT<br>(SEQ ID NO: 134) |
| 19324 VL | GAAATTGTGATGACACAGTCTCCAGACTCCCTGGCTGTGTCTCTGGGCGAGAGGGCC<br>ACCATCAACTGCAAGTCCAGCCAGAGTGTTTTATACAGCTCCAACAATAAGAACTAC<br>TTAGCTTGGTACCAGCAGAAACCAGGACAGCCTCCTAAGCTGCTCATTTACTGGGCA<br>TCTACCCGGGAATCCGGGGTCCCTGACCGATTCAGTGGCAGCGGGTCTGGGACAGAT<br>TTCACTCTCACCATCAGCAGCCTGCAGGCTGAAGATGTGGCAGTTTATTACTGTCAG<br>CAATATTATAGTGGTCCGATCACCTTCGGCCAAGGGACACGACTGGAGATTAAG<br>(SEQ ID NO: 135) |
| 19416 VH | CAGGTGCAGCTGGTGGAGTCGGGCCCAGGACTGGTGAAGCCTTCACAGACCCTGTCC<br>CTCACCTGCACTGTCTCTGGTGGCTCCATCAACAGTGGTGGTTACTACTGGAGCTGG<br>ATCCGCCAGCACCCAGGGAAGGGCCTGGAGTGGATTGGGTACATCTATTACAGTGGG<br>AGCATCTACTACAACCCGTCCCTCAGGAGTCGACTTACCATATCAGTAGACACGTCT<br>AAGAACCAGTTCTCCCTGAAGCTGAGCTCTGTGACTGCCGCGGACACGGCCGTTTAT<br>TACTGTGCGACTCCTTATTACTATGGTTCGGGGAGTTATGGGGACTACTGGGGCCAG<br>GGCACCCTGGTCACTGTCTCGAGT<br>(SEQ ID NO: 144) |
| 19416 VL | GACATCCAGATGACCCAGTCTCCAGCCACCCTGTCTTTGTCTCCAGGGGAAAGAGCC<br>ACCCTCTCCTGCAGGGCCAGTCAGAGTGTTAACAACTACTTAGCCTGGTACCAACAG<br>AAACCTGGCCAGGCTCCCAGGCTCCTCATCTATGATGCATCCAACAGGGCCACTGGC<br>ATCCCAGCCAGGTTCAGTGGCAGTGGGTCTGGGACAGACTTCACTCTCACCATCAGC<br>AGCCTAGAGCCTGAAGATTTTGCAGTTTATTACTGTCAGCAGCGTAGCAACTGGCCC<br>ATCACCTTCGGCCAAGGGACACGACTGGAGATTAAA<br>(SEQ ID NO: 145) |
| 19568 VH | CAGATGCAGCTGCAGGAGTCGGGCCCAGGACTGGTGAAGCCTTCTCAGACCCTGTCC<br>CTCACCTGCACTGTGTCTGGTGGCTCCATCAGCAGTGTTGGTTACTACTGGAACTGG<br>ATCCGCCAGCACCCAGGGAAGGGCCTGGAGTTCATTGGGTACATCTATTACAGTGGG<br>AGCATCTACTACAATCCGTCCCTCAAGAGTCGAGTTACCATATCCGTAGACACGTCT<br>AAGAACCAGTTCTCCCTGAAGCTGAGCTCTGTGACTGCCGCGGACACGGCCCTATAT<br>TACTGTGCGAGCGTCGGTATAGTGGGAGCCTCCTACTTTGAGTACTGGGGCCAGGGA<br>ACCCTGGTCACAGTCTCGAGT<br>(SEQ ID NO: 154) |
| 19568 VL | GAAATTGTGATGACACAGTCTCCAGCCACCCTGTCTTTGTCTCCAGGGGAAAGAGCC<br>ACCCTCTCCTGCAGGGCCAGTCAGAGTGTTAGCAGCTACTTAGCCTGGTACCAACAG<br>AAACCTGGCCAGGCTCCCAGGCTCCTCATCTATGATGCATCCAACAGGGCCACTGGC<br>ATCCCAGCCAGGTTCAGTGGCAGTGGGTCTGGGACAGACTTCACTCTCACCATCAGC<br>AGCCTAGAGCCTGAAGATTTTGCAGTTTATTACTGTCAGCAGCGTAGCAACTGGCCT<br>ATCACCTTCGGCCAAGGGACACGACTGGAGATCAAG<br>(SEQ ID NO: 155) |
| 20131 VH | CAGGTGCAGCTACAGCAGTCTGGGGGAGGCTTGGTACAGCCTGGGGGGTCCCTGAGA<br>CTCTCCTGTGCAGCCTCTGGATTCACCTTAAGCAGCTATGCCATGAGCTGGGTCCGC<br>CAGGCTCCAGGGAAGGGGCTGGAGTGGGTCTCAGGTATTAGTGGTAGTGGTGGTAGC<br>ACATACAACGCAGACTCCGTGAAGGGCCGGTTCACCATCTCCAGAGACAATTCCAAG<br>AACACGCTGTTTCTGCAAATGAACAGCCTGAGAGCCGAGGACACGGCCGTATATTAC<br>TGTGCGAAAATTTTTGGGTCCTACTACTTTGACTACTGGGGCCAGGGAACCCTGGTC<br>ACAGTCTCGAGT<br>(SEQ ID NO: 164) |
| 20131 VL | GAAATTGTGATGACACAGTCTCCAGACTCCCTGGCTGTGTCTCTGGGCGAGAGGGCC<br>ACCATCAACTGCAAGTCCAGCCAGAGTGTTTTATACAGCTCCAACAATAAGAACTAC<br>TTAGCTTGGTACCAGCAGAAACCAGGACAGCCTCCTAAGCTGCTCATTTACTGGACA<br>TCTACCCGGGAATCCGGGGTCCCTAACCGATTCAGTGGCAGCGGGTCTGGGACAGAT<br>TTCACTCTCACCATCAGCAGCCTGCAGGCTGAAGATGTGGCAGTTTATTACTGTCAG<br>CAATATTATAGTGGTCCTCCGACGTTCGGCCAAGGGACCAAGGTGGAAATCAAA<br>(SEQ ID NO: 165) |
| 20185 VH | CAGGTGCAGCTGGTGGAGTCTGGGGGAGGCTTGGTTCGGCCTGGGGGGTCCCTGAGA<br>CTCTCCTGTGCAGTCTCTGGATTCACCTTTAGCAGCTATGCCATGAGCTGGGTCCGC<br>CAGGCTCCAGGGAAGGGGCTGGAGTGGGTCTCAGGTATTAGTGGTAGTGGTGGTAGC<br>ACATACAACGCAGACTCCGTGAAGGGCCGGTTCACCATCTCCAGAGACAATTCCAAG<br>AACACGCTGTATCTTCAAATGAACAGCCTGAGAGCCGAGGACACGGCCGTATATTAC<br>TGTGCGAAAATTTTTGGGTCCTACTACTTTGACTACTGGGGCCAGGGAACCCTGGTC<br>ACCGTCTCGAGT<br>(SEQ ID NO: 174) |

TABLE 4-continued

Anti-TIM-3 antibody heavy and light chain variable domain nucleotide sequences

| Ab | Sequence (5' to 3') |
|---|---|
| 20185 VL | GAAATTGTGATGACACAGTCTCCAGACTCCCTGGCTGTGTCTCTGGGCGAGAGGGCC<br>ACCATCAACTGCAAGTCCAGCCAGAGTGTTTTATACAGCTCCAATAATAAGAACTAC<br>TTAGCTTGGTACCAGCAGAAATCAGGACAGCCTCCTAAGCTGCTCATTTACTGGGCA<br>TCTACCCGGGAATCCGGGGTCCCTGACCGATTCAGTGGCAGCGGGTCTGGGACAGAT<br>TTCACTCTCACCATCAGCAGCCTGCAGGCTGAAGATGTGGCAGTTTATTACTGTCAG<br>CAATATTATAGTGGTCCACCGACGTTCGGCCAAGGGACCAAGGTGGAAATCAAA<br>(SEQ ID NO: 175) |
| 20293 VH | ACGTGACAGGGCGCGCCCAGGTCCAGCTGCAGGAGAGCGGTCCCGGACTGGTGAAGC<br>CATCCCAGACACTGAGCCTGACTTGTACTGTGAGCGGCGGTAGCATCTCCAGCGGCG<br>GCTACTATTGGTCCTGGATCAGGCAGCACCCAGGCAAGGGCCTGGAGTGGATCGGCT<br>ACATCTACTATAGCGGCTCTATCTACTATAACCCTTCCCTGAAGAGCCGGGTGACCA<br>TCTCTGTGGACACATCCAAGAATCAGTTCTATCTGAAGCTGTCTTCCGTGACCGCCG<br>CTGATACAGCCGTGTACTATTGCGCCTCACTGATGGTCTGGGGGGTCATGGGCGATT<br>ACTGGGGGCAGGGCACACTGGTCACAGTCTCGAGT<br>(SEQ ID NO: 184) |
| 20293 VL | GAGATTGTGCTGACCCAGTCTCCCGCCACCCTGTCTCTGAGTCCTGGCGAGAGAGCC<br>ACCCTGAGCTGCAGAGCCTCTCAGTCCGTGTCCAGCTATCTGGCCTGGTATCAGCAG<br>AAGCCCGGCCAGGCTCCCCGGCTGCTGATCTACGATGCCTCCAATAGAGCCACCGGC<br>ATCCCTGCCAGATTCTCCGGCTCTGGCTCTGGCACCGACTTTACCCTGACCATCTCC<br>AGCCTGGAACCCGAGGACTTCGCCGTGTACTACTGCCAGCAGCGGTCCGACTGGCCT<br>CCTACATTTGGCCAAGGCACCAAGGTGGAAATCAAG<br>(SEQ ID NO: 185) |
| 20300 VH | CAGGTCCAGCTACAGCAGTCTGGGGGAGGCTTGGTTCATCCTGGGGGGTCCCTAAGA<br>CTCTCCTGTGCAGCCTCTGGATTCACCGTTGACACCTATGCCATGACCTGGGTCCGC<br>CAGGCTCCAGGGAAGGGGCTGGAGTGGGTCTCAGGTATTAGCGGTAGTGGTGGTAGC<br>ACATACTACGCAGACTCCGTGAAGGGCCGGTTCACCATCTCCAGAGACAACTCCAAG<br>AACACGCTGTATCTGCAAATGAACAGCCTGAGAGACGAGGACACGGCCGTATATTAC<br>TGTGCGAAGATAGTGGGAGTTACCCACTTTGACTACTGGGGCCAGGGCACCCTGGTC<br>ACGGTCTCGAGT<br>(SEQ ID NO: 194) |
| 20300 VL | GAAATTGTGATGACGCAGTCTCCAGACTCCCTGGCTGTGTCTCTGGGCGAGAGGGCC<br>ACCATCAACTGCAAGTCCAGCCAGAGTGTTTTATACAGGTCCAACAATAAGAACTAT<br>TTAGCTTGGTACCAGCAGAAACCAGGACAGCCTCCTAAGCTGCTCATTTACTGGGCA<br>TCTACCCGGGAATCCGGGTCCCTGACCGATTCAGTGGCAGCGGGTCTGGGACAGAT<br>TTCACTCTCACCATCAGCAGCCTGCAGGCTGAAGATGTGGCAGTTTATTACTGTCAG<br>CAATATTATAGTGGTCCGATCACCTTCGGCCAAGGGACACGACTGGAGATTAAG<br>(SEQ ID NO: 195) |
| 20362 VH | CAGGTCACCTTGAAGGAGTCGGGCCCAGGACTGGTGAAGCCTTCACAGACCCTGTCC<br>CTCACCTGCACTGTCTCTGGTGGCTCCATCAGCAGTGGTGGTCATTACTGGAGCTGG<br>ATCCGCCAGCACCCAGGGAAGGGCCTGGAGTGGATTGGGTACATCTCTTACAGTGGG<br>AGCACCTACTACAACCCGTCCCTCAAGAGTCGACTTACCATATCAGTAGACACGTCT<br>AAGAACCAGTTCTCCCTGAAGCTGAGCTCTGTGACTGCCGCGGACACGGCCGTGTAT<br>TACTGTGCGACCGCGTATTACGATATTTTGACTGGTTACCCTTTTGACTACTGGGGC<br>CAGGGAACCCTGGTCACGGTCTCGAGT<br>(SEQ ID NO: 204) |
| 20362 VL | GAAATTGTGATGACACAGTCTCCAGCCACCCTGTCTTTGTCTCCAGGGGAAAGAGCC<br>ACCCTCTCCTGCAGGGCCAGTCAGAGTGTTAGCAGCTACTTAGCCTGGTACCAACAG<br>AAACCTGGCCAGGCTCCCAGGCTCCTCATCTATGATGCATCCAGACAGGGCCACTGGC<br>ATCCCAGCCAGGTTCAGTGGCAGTGGGTCTGGGACAGACTTCACTCTCACCATCAGC<br>AGCCTAGAGCCTGAAGATTTTGCAGTTTATTACTGTCAGCAGCGTAGCAACTGGCCG<br>ATCACCTTCGGCCAAGGGACACGACTGGAGATCAAG<br>(SEQ ID NO: 205) |
| 20621 VH | CAGGTGCAGCTACAGCAGTCGGGCCCAGGACTGGTGAAGCCTTCACAGACCCTGTCC<br>CTCACCTGCACTGTCTCTGGTGGCTCCATCAGCAGTGGTGGTTACTACTGGAGCTGG<br>ATCCGCCAGCACCCAGGGAAGGGCCTGGAGTGGATTGGGTACATCTCTTATAGTGGG<br>AGTATCTACTACAACCCGTCCCTCAAGAGTCGAGTTACCATATCAGTAGACACGTCT<br>AAGAACCAGTTCTCCCTGAAGCTGAGCTCTGTGACTGCCACGGACACGGCCGTGTAT<br>TACTGTGCGACCGCGTATTACGATCTTTTGACTGGTTACCCTTTTGACTACTGGGGC<br>CAGGGAACCCTGGTCACGGTCTCGAGT<br>(SEQ ID NO: 214) |
| 20621 VL | GAAATTGTGATGACGCAGTCTCCAGCCACCCTGTCTTTGTCTCCAGGGGAAAGAGCC<br>ACCCTCTCCTGCAGGGCCAGTCAGAGTGTTAGCAGCTACTTAGCCTGGTACCAACAG<br>AAACCTGGCCAGGCTCCCAGGCTCCTCATCTATGATGCATCCAACAGGGCCACTGGC |

TABLE 4-continued

Anti-TIM-3 antibody heavy and light chain variable domain nucleotide sequences

| Ab | Sequence (5' to 3') |
|---|---|
| | ATCCCAGCCAGGTTCAGTGGCAGTGGGTCTGGGACAGACTTCACTCTCACCATCAGC<br>AGCCTAGAGCCTGAAGATTTTGCAGTTTATTACTGTCAGCAGCGTAGCAACTGGCCG<br>ATCACCTTCGGCCAAGGGACACGACTGGAGATTAAG<br>(SEQ ID NO: 215) |

TABLE 5

Anti-TIM-3 antibody heavy and light chain variable domain amino acid sequences

| Ab | Sequence (N-terminal to C-terminal) |
|---|---|
| 15086.15086<br>VH | QVQLQQSGPGLVKPSQTLSLTCTVS*GGSISSGGYY*WSWTRQHPGMGLEWIGY*I<br>SYSGSI*YYTPSLKSRLTISVDTSKNQFSLKLSSVTAADTAVYY*CASLDSWGSN<br>RDYW*GQGTLVTVSS<br>(SEQ ID NO: 3) |
| 15086.16837<br>15086.17145<br>15086.17144<br>VH | QVQLQESGPGLVKPSQTLSLTCTVS*GGSISSGGYY*WSWTRQHPGMGLEWIGY*I<br>SYSGSI*YYTPSLKSRLTISVDTSKNQFSLKLSSVTAADTAVYY*CASLDSWGSN<br>RDYW*GQGTLVTVSS<br>(SEQ ID NO: 7) |
| 15086.15086<br>15086.16837<br>15086.17145<br>15086.17144<br>VL | EIVLTQSPATLSLSPGERATLSCRAS*QSVSSY*LAWYQQKPGQAPRLLIY*DASN<br>RATGIPARFSGSGSGTDFTLTISSLEPEDFAVYY*CQQRSNWPLTF***GGGTKVEI<br>K<br>(SEQ ID NO: 4) |
| 15105 VH | QVTLKEWGAGLLRPSETLSLTCAVY*GGSFSGYY*WSWIRQPPGKGLEWIGE*INH<br>SGST*NYNPSLKSRVTISVDATKKQFSLKLTSVTAADTAVYY*CARYWELPDYW*G<br>QGTLVTVSS<br>(SEQ ID NO: 16) |
| 15105 VL | DIQLTQSPSSLSASVGDRVTITCRAS*QGIRND*LGWYQQKPGKAPKRLIY*AAS*S<br>LQSGVPSRFSGSGSGTEFTLTISSLQPEDFATYY*CLQHNSYPPTF*GQGTKVEI<br>K<br>(SEQ ID NO: 17) |
| 15107 VH | QMQLVQWGAGLLKPSETLSLTCAVY*GGSFSGYY*WSWIRQPPGKGLEWIGE*INH<br>SGST*NYNPSLKSRVTMSVDTSKHQFSLKLSSVTAADTAVYY*CARWWELPDYW*G<br>QGTLVTVSS<br>(SEQ ID NO: 26) |
| 15107 VL | EIVLTQSPSSLSASVGDRVTITCRAS*QGIRND*LGWYQQKPGKAPKRLIY*AAS*S<br>LQSGVPSRFSGSGSGTEFTLTISSLQPEDFATYY*CLQHNSYPWTF*GQGTKVEI<br>K<br>(SEQ ID NO: 27) |
| 15109 VH | QMQLVQWGAGLLKPSETLSLTCAVY*GGSFSGYY*WSWIRQPPGKGLEWIGE*INH<br>SGST*NYNPSLKSRVTISVDTSKNQFSLKLSSVTAADTAVYY*CARFYYAPNFDY<br>W*WGQGTLVTVSS<br>(SEQ ID NO: 36) |
| 15109 VL | EIVLTQSPSTLSASVGDRVTITCRAS*QSISSW*LAWYQQKPGTAPKLLIY*KAS*S<br>LESGVPSRFSGSGSGTEFTLTISSLQPDDFATYY*CQQYNSYSTF*GGGTKVEIK<br>(SEQ ID NO: 37) |
| 15174 VH | QVQLQQSGPGLVKPSETLSLTCTVS*GGSISSSNYY*WGWIRQPPGKGLEWIGS*I<br>YYSGNT*YYNPSLKSRVTISVDTSKNQFSLKLSSVTAADTAVYY*CARQTVAGPL<br>FDYW*GQGTLVTVSS<br>(SEQ ID NO: 46) |
| 15174 VL | EIVMTQSPSTLSASVGDRVTITCRAS*QSISSW*LAWYQQKPGKAPKVLIY*KAS*S<br>LESGVPSRFSGSGSGTELTLTISSLQPDDFATYY*CQQYNSYSFTF*GPGTKVDI<br>K<br>(SEQ ID NO: 47) |
| 15175 VH | QVQLVQSGAEVKKPGASVKVSCKAA*GYTLTGYY*MHWVRQAPGQGLEWMGR*INP<br>NSGGS*NNAQKFQGRVTMTRDTSISTAYMELSRLSDDTAVYY*CAREGPLYSSG<br>WYEGAFDIW*GQGTMVTVSS<br>(SEQ ID NO: 56) |

TABLE 5-continued

Anti-TIM-3 antibody heavy and light chain variable domain amino acid sequences

| Ab | Sequence (N-terminal to C-terminal) |
|---|---|
| 15175 VL | EIVMTQSPSTLSASVGDRVTITCRAS*QSISSW*LAWYQQKPGKAPKLLIY*KAS*S LESGVPSRFSGSGSGTEFTLTISSLQPDDFATYY*CQQYNSYSPGLTF*GGGTKV EIK<br>(SEQ ID NO: 57) |
| 15260 VH | QMQLQQSGPGLVKPSQTLSLTCAIS*GDSVSSNSAA*WNWIRQSPSRGLEWLGR*T YYRSKWYS*AFAVSVKSRITINPDTSKNQFSLQLNSVTPEDTAVYY*CAREGSSG WYGYVHHW*GQGTLVTVSS<br>(SEQ ID NO: 66) |
| 15260 VL | EIVLTQSPASLSVSLGETVTIECRAS*EDIYNG*LAWYQQKPGKSPQLLIY*NAN*S LHTGVPSRFSGSGSGTQYSLKINSLQSEDVASYF*CQQYYDYPPTF*GQGTKVEI K<br>(SEQ ID NO: 67) |
| 15284 VH | QVQLQESGPGLVKPSETLSLTCTVS*GGSFSSSSYY*WGWIRQPPGKGLEWIGI*F YYSGTT*YYNPSLKSRVTISAHTSKSQFSLKLSSVTAADTAVYY*CARGGEYFDR LLPFDYW*GQGTLVTVSS<br>(SEQ ID NO: 76) |
| 15284 VL | EIVMTQSPSFLSASVGDRVTITCRAS*QGISSY*LAWYQQKPGKAPKLLIY*AAS*T LESGVPSRFSGSGSGTEFTLTISSLQPEDFATYY*CQQLNSYPFTF*GPGTKVDI K<br>(SEQ ID NO: 77) |
| 15299 VH | QVQLVESGGGLVQPGGSLRLSCTAS*GFTFSSYA*MSWVRQAPGKGLEWVSA*IGG SGGST*YYADSVKGRFTISRDNSKNTLYLQMNSLRAEDTAVYY*CVKDGAGGFDY W*GQGTLVTVSS<br>(SEQ ID NO: 86) |
| 15299 VL | DIVMTQSSSSLSASVGDRVTITCRAS*QGIINH*LGWYQHKPGKAPNRLIY*AAS*S LQSGVPSRFSGSGSGTEFTLTISSLQPEDFATYYCLRHNS*YPPTF*GQGTKVEI K<br>(SEQ ID NO: 87) |
| 15353 VH | QVQLQQSGPGLVKPSQTLSLTCTVS*GGSINSGGHY*WSWIRQHPGRGLEWIGY*I YYSGSI*YYNPSLKSRLTISVDTSKNQFSLKLSSVTAADTAVYY*CASYYASSG DAFDIW*GQGTMVTVSS<br>(SEQ ID NO: 96) |
| 15353 VL | ETTLTQSPATLSLSPGERATLSCRAS*QSVSSY*LAWYQQKPGQAPRLLIY*DAS*N RATGIPARFSGSGSGTDFTLTISSLEPEDFAVYY*CQQRSNWPPTF*GQGTKVEI K<br>(SEQ ID NO: 97) |
| 15354 VH | QVQLQESGGGLVQPGGSLRLSCTAS*GFTFSNYA*MSWVRQAPGKGLEWVSA*ISG RGGST*FFADSVKGRFTISRDNSKSTLYLQTNSLRAEDTAVYY*CAKGGPLYNWN DGDGFDIW*GQGTTVTVSS<br>(SEQ ID NO: 106) |
| 15354 VL | EIVLTQSPATLSVSPGERATLSCRAS*QSVSSN*LAWYQQKPGQAPRLLIY*GAS*T RATGIPARFSGTGSGTEFTLTISSLQSEDFALYY*CQQYDNWPPWTF*GQGTKVE IK<br>(SEQ ID NO: 107) |
| 17244 VH | QVQLQESGGGLVKPGGSLRLSCAAS*GFTFSDYY*MTWIRQAPGKGLEW*ISYISG GGGSI*YYADSVKGRFTISRDNAKNSLYLQMNSLRAEDTAVYF*CARGNWGSAAL DIW*GQGTMVTVSS<br>(SEQ ID NO: 116) |
| 17244 VL | EIVLTQSPSSLSASVGDRVTITCRAS*QGINNY*LAWFQQKPGRAPKSLIY*AAS*S LQSGVPSKFSGSGSGTDFTLTISSLQPEDFATYY*CQQYNSYPPTL*GPGTNVDI K<br>(SEQ ID NO: 117) |
| 17245 VH | QVQLVESGGGLVQPGGSLRLSCTAS*GFTFSSYA*MSWVRQAPGKGLEWVSA*IGG SGGSA*YYADSVKGRFTISRDNSKNTLYLQMNSLRAEDTAVYY*CVKDGAGGFDY W*GQGTLVTVSS<br>(SEQ ID NO: 126) |
| 17245 VL | DIQLTQSPSSLSASVGDRVTITCRAS*QGIRNH*LGWYQQKPGKAPKRLIY*AAS*S LQSGVPSRFSGSGSGTEFTLTISSLQPEDFATYY*CLQHNSYPPTF*GQGTKVEI K<br>(SEQ ID NO: 127) |

TABLE 5-continued

Anti-TIM-3 antibody heavy and light chain variable domain amino acid sequences

| Ab | Sequence (N-terminal to C-terminal) |
|---|---|
| 19324 VH | QMQLQQSGGGLVQPGGSLRLSCAAS*GFTVSSYA*MSWVRQALGKGLEWVSG*ISG SGGST*YYADSVKGRFTISRDNSKNTLYLMNSLRAEDTAVYY*CAKIVGATHFD YW*GQGTLVTVSS<br>(SEQ ID NO: 136) |
| 19324 VL | EIVMTQSPDSLAVSLGERATINCKSS*QSVLYSSNNKNY*LAWYQQKPGQPPKLL IY*WAS*TRESGVPDRFSGSGSGTDFTLTISSLQAEDVAVYY*CQQYYSGPITF*GQ GTRLEIK<br>(SEQ ID NO: 137) |
| 19416 VH | QVQLVESGPGLVKPSQTLSLTCTVS*GGSINSGGYY*WSWIRQHPGKGLEWIGY*I YYSGSI*YYNPSLRSRLTISVDTSKNQFSLKLSSVTAADTAVYY*CATPYYYGSG SYGDYW*GQGTLVTVSS<br>(SEQ ID NO: 146) |
| 19416 VL | DIQMTQSPATLSLSPGERATLSCRAS*QSVNNY*LAWYQQKPGQAPRLLIY*DAS*N RATGIPARFSGSGSGTDFTLTISSLEPEDFAVYY*CQQRSNWPITF*GQGTRLEI K<br>(SEQ ID NO: 147) |
| 19568 VH | QMQLQESGPGLVKPSQTLSLTCTVS*GGSISSVGYY*WNWIRQHPGKGLEFIGY*I YYSGSI*YYNPSLKSRVTISVDTSKNQFSLKLSSVTAADTALYY*CASVGIVGAS YFEYW*GQGTLVTVSS<br>(SEQ ID NO: 156) |
| 19568 VL | EIVMTQSPATLSLSPGERATLSCRAS*QSVSSY*LAWYQQKPGQAPRLLIY*DAS*N RATGIPARFSGSGSGTDFTLTISSLEPEDFAVYY*CQQRSNWPITF*GQGTRLEI K<br>(SEQ ID NO: 157) |
| 20131 VH | QVQLQQSGGGLVQPGGSLRLSCAAS*GFTLSSYA*MSWVRQAPGKGLEWVSG*ISG SGGST*YNADSVKGRFTISRDNSKNTLFLQMNSLRAEDTAVYY*CAKIFGSYYFD YW*GQGTLVTVSS<br>(SEQ ID NO: 166) |
| 20131 VL | EIVMTQSPDSLAVSLGERATINCKSS*QSVLYSSNNKNY*LAWYQQKPGQPPKLL IY*WTS*TRESGVPNRFSGSGSGTDFTLTISSLQAEDVAVYY*CQQYYSGPPTF*GQ GTKVEIK<br>(SEQ ID NO: 167) |
| 20185 VH | QVQLVESGGGLVRPGGSLRLSCAVS*GFTFSSYA*MSWVRQAPGKGLEWVSG*ISG SGGST*YNADSVKGRFTISRDNSKNTLYLMNSLRAEDTAVYY*CAKIFGSYYFD YW*GQGTLVTVSS<br>(SEQ ID NO: 176) |
| 20185 VL | EIVMTQSPDSLAVSLGERATINCKSS*QSVLYSSNNKNY*LAWYQQKSGQPPKLL IY*WAS*TRESGVPDRFSGSGSGTDFTLTISSLQAEDVAVYY*CQQYYSGPPTF*GQ GTKVEIK<br>(SEQ ID NO: 177) |
| 20293 VH | QVQLQESGPGLVKPSQTLSLTCTVS*GGSISSGGYY*WSWIRQHPGKGLEWIGYI YYSGSI*YYNPSLKSRVTISVDTSKNQFYLKLSSVTAADTAVYY*CASLMVWGVM GDYW***GQGTLVTVSS<br>(SEQ ID NO: 186) |
| 20293 VL | EIVLTQSPATLSLSPGERATLSCRAS*QSVSSY*LAWYQQKPGQAPRLLIY*DAS*N RATGIPARFSGSGSGTDFTLTISSLEPEDFAVYY*CQQRSDWPPTF*GQGTKVEI K<br>(SEQ ID NO: 187) |
| 20300 VH | QVQLQQSGGGLVHPGGSLRLSCAAS*GFTVDTYA*MTWVRQAPGKGLEWVSG*ISG SGGST*YYADSVKGRFTISRDNSKNTLYLQMNSLRDEDTAVYY*CAKIVGVTHFD*GQGTLVTVSS<br>(SEQ ID NO: 196) |
| 20300 VL | EIVMTQSPDSLAVSLGERATINCKSS*QSVIYRSNNKNY*LAWYQQKPGQPPKLL IY*WAS*TRESGVPDRFSGSGSGTDFTLTISSLQAEDVAVYY*CQQYYSGPITF*GQ GTRLEIK<br>(SEQ ID NO: 197) |
| 20362 VH | QVTLKESGPGLVKPSQTLSLTCTVS*GGSISSGGHY*WSWIRQHPGKGLEWIGY*I SYSGST*YYNPSLKSRLTISVDTSKNQFSLKLSSVTAADTAVYY*CATAYYDILT*GYPFDYWGQGTLVTVSS<br>(SEQ ID NO: 206) |

TABLE 5-continued

Anti-TIM-3 antibody heavy and light chain variable domain amino acid sequences

| Ab | Sequence (N-terminal to C-terminal) |
|---|---|
| 20362 VL | EIVMTQSPATLSLSPGERATLSCRAS*QSVSSY*LAWYQQKPGQAPRLLIY*DAS*DRATGIPARFSGSGSGTDFTLTISSLEPEDFAVYY*CQQRSNWPITF*GQGTRLEIK<br>(SEQ ID NO: 207) |
| 20621 VH | QVQLQQSGPGLVKPSQTLSLTCTVS*GGSISSGGYY*WSWIRQHPGKGLEWIGY*ISYSGSI*YYNPSLKSRVTISVDTSKNQFSLKLSSVTATDTAVYY*CATAYYDLLTGYPFDYW*GQGTLVTVSS<br>(SEQ ID NO: 216) |
| 20621 VL | EIVMTQSPATLSLSPGERATLSCRAS*QSVSSY*LAWYQQKPGQAPRLLIY*DAS*NRATGIPARFSGSGSGTDFTLTISSLEPEDFAVYY*CQQRSNWPITF*GQGTRLEIK<br>(SEQ ID NO: 217) |

(CDRs are bolded and italicized)

TABLE 6

Anti-PD-1 antibody heavy and light chain variable domain nucleotide sequences

| Ab | Sequence (5' to 3') |
|---|---|
| 12819.15384 VH | GGCGCGCCGAGGTGCAGCTGCTGGAATCTGGAGGAGGACTGGTCCAGCCAGGTGGATCCCTGCGACTGAGCTGCGCCGCTTCTGGATTCACCTTTACAAGATACGACATGGTGTGGGTCCGCCAGGCACCAGGAAAGGGACTGGAGTGGGTGGCTGGTATCGGCGATAGTAACAAGATGACCCGCTACGCACCTGCCGTCAAAGGGAGGGCAACAATTAGTCGGGACAACTCAAAGAATACTCTGTATCTGCAGATGAATTCCCTGCGAGCTGAGGATACAGCAGTGTACTATTGTGCCAAAGGTAGCTGCATCGCCTGTTGGGACGAAGCTGGCCGTATTGATGCATGGGGACAGGGGACTCTGGTGACCGTCTCGAG<br>(SEQ ID NO: 224) |
| 12819.15384 VL | GCTAGCCTCTTACGAGCTGACTCAGGACCCTGCAGTGAGTGTCGCCCTGGGCCAGACAGTGAGAATCACTTGCTCCGGCGGAGGGAGCTACGATGGTTCCAGCTACTATGGCTGGTATCAGCAGAAGCCAGGACAGGCACCTGTGACCGTCATCTATAACAATAACAATAGGCCATCTGACATTCCCGATCGGTTCAGTGGATCTAGTTCAGGGAACACAGCTTCTCTGACCATTACAGGAGCCCAGGCTGAGGACGAAGCAGATTACTATTGTGGGTCATACGACAGGCCAGAAACAAATTCCGATTATGTGGGAATGTTTGGTAGCGGCACTAAAGTCACCGTCCTAGG<br>(SEQ ID NO: 225) |
| 12748.15381<br>12748.16124 VH | GGCGCGCCGAGGTGCAGCTGCTGGAAAGCGGAGGAGGACTGGTCCAGCCAGGTGGATCTCTGCGACTGAGTTGCGCCGCTTCAGGCTTCACATTTTCTGACTACGCCATGAACTGGGTGAGGCAGGCTCCTGGCAAGGGACTGGAGTGGGTCGCAGGAATCGGGAACGATGGAAGTTACACTAATTATGGAGCAGCCGTGAAGGGGAGAGCTACTATTTCCCGCGACAACAGCAAAAATACCCTGTACCTGCAGATGAACTCACTGAGAGCTGAAGATACCGCAGTGTACTATTGTGCCTCTGACATCAGGAGTCGGAATGATTGCTCCTATTTCCTGGGAGGGTGTTCCAGCGGCTTTATTGACGTGTGGGGTCAGGGCACCCTGGTCACAGTCTCGAG<br>(SEQ ID NO: 234) |
| 12748.15381 VL | GCTAGCCTCTTACGAGCTGACCCAGGACCCAGCAGTGTCCGTCGCCCTGGGCCAGACAGTGAGAATCACTTGCTCCGGCGGATCCAGCTACAGCTATGGGTGGTTCCAGCAGAAGCCCGGTCAGGCCCCTGTGACCGTCATCTATGAAAGTAACAATAGGCCATCAGACATTCCCGATCGGTTTTCTGGCTCTAGTTCAGGAAACACAGCTAGTCTGACCATCACAGGGGCCCAGGCTGAGGACGAAGCTGATTACTATTGTGGCAATGCAGATTCCAGCTCTGGAATTTTCGGGTCCGGTACTAAAGTCACCGTCCTAGG<br>(SEQ ID NO: 235) |
| 12865.15377 VH | GGCGCGCCGAGGTGCAGCTGCTGGAATCCGGAGGAGGACTGGTCCAGCCAGGTGGATCCCTGCGACTGAGCTGCGCCGCTTCTGGATTCGACTTTAGCGATCACGGGATGCAGTGGGTGAGACAGGCACCAGGCAAGGGACTGGAGTACGTGGGTGTCATCGGACACCACAGGCCGCTATACATACTATGCACCTGCCGTCAAGGGCAGGGCTACCATTAGTCGGGACAACTCAAAAAATACACTGTACCTGCAGATGAACTCTCTGAGGGCTGAAGATACTGCAGTGTACTATTGCGCCAAAACTACCTGCTGGGAGGGTACCTGTGCAATACCGTCGGAAGTATCGATGCTTGGGGACAGGGGACACTGGTGACTGTCTCGAG<br>(SEQ ID NO: 244) |

TABLE 6-continued

Anti-PD-1 antibody heavy and light chain variable domain nucleotide sequences

| Ab | Sequence (5' to 3') |
|---|---|
| 12865.15377 VL | GCTAGCCTCCTACGAGCTGACTCAGGACCCAGCAGTGAGCGTCGCCCTGGGCC<br>AGACAGTGAGAATCACTTGCTCTGGCGGAGGGTCCAGCTCTTACTATGGTTGG<br>TACCAGCAGAAGCCCGGCCAGGCTCCTGTGACCGTCATCTATGACGATACAAA<br>CAGGCCAAGTGGAATTCCCGATCGGTTCTCAGGTAGTTCATCCGGCAATACAG<br>CTTCTCTGACCATCACAGGGGCCCAGGCTGAGGACGAAGCAGATTACTATTGT<br>GGTGGCTATGAAGGAAGCTCTCACGCCGGGATTTTTGGAAGTGGGACTAAAGT<br>CACCGTCCTAGG<br>(SEQ ID NO: 245) |
| 12892.15378 VH | GGCGCGCCGAGGTGCAGCTGCTGGAAAGTGGAGGAGGACTGGTCCAGCCAGGT<br>GGAAGCCTGAGACTGTCTTGCGCCGCTAGTGGCTTCGACTTTTCCAGCTACAC<br>CATGCAGTGGGTGAGGCAGGCACCAGGCAAGGGACTGGAGTGGGTGGGCGTCA<br>TCTCTAGTACTGGAGGGTCTACCGGATACGGGCCTGCTGTGAAGGGAAGGGCA<br>ACAATTTCACGGGATAACTCCAAAAATACTCTGTATCTGCAGATGAACAGCCT<br>GAGGGCAGAAGACACAGCCGTGTACTATTGCGTGAAATCAATCTCCGGAGATG<br>CCTGGTCTGTGGACGGGCTGGATGCTTGGGGTCAGGGCACCCTGGTCACAGTC<br>TCGAG<br>(SEQ ID NO: 254) |
| 12892.15378 VL | GCTAGCCTCATACGAGCTGACCCAGGACCCAGCAGTGTCCGTCGCCCTGGGAC<br>AGACAGTGAGAATCACTTGCTCCGGAGGAGGATCCGCCTACGGTTGGTATCAG<br>CAGAAGCCCGGCCAGGCACCTGTGACCGTCATCTACTATAACAATCAGAGGCC<br>ATCTGGCATTCCCGACCGGTTCAGTGGATCCAGCTCTGGGAACACAGCAAGTC<br>TGACCATCACAGGCGCCCAGGCTGAGGACGAAGCCGATTACTATTGTGGAAGC<br>TATGATAGTTCAGCTGTGGGGATTTTTGGTTCTGGCACTAAAGTCACCGTCCT<br>AGG<br>(SEQ ID NO: 255) |
| 12796.15376 VH | GGCGCGCCGAGGTGCAGCTGCTGGAAAGTGGAGGAGGACTGGTCCAGCCAGGT<br>GGAAGCCTGAGACTGTCTTGCGCCGCTAGTGGCTTCGACTTTTCCAGCTACAC<br>CATGCAGTGGGTGAGGCAGGCACCAGGCAAGGGACTGGAGTGGGTGGGCGTCA<br>TCTCTAGTACTGGAGGGTCTACCGGATACGGGCCTGCTGTGAAGGGAAGGGCA<br>ACAATTTCACGGGATAACTCCAAAAATACTCTGTATCTGCAGATGAACAGCCT<br>GAGGGCAGAAGACACAGCCGTGTACTATTGCGTGAAATCAGTCTCCGGAGATG<br>CCTGGTCTGTGGACGGGCTGGATGCTTGGGGTCAGGGCACCCTGGTCACAGTC<br>TCGAG<br>(SEQ ID NO: 264) |
| 12796.15376 VL | GCTAGCCTCATACGAGCTGACCCAGGACCCAGCAGTGTCCGTCGCCCTGGGCC<br>AGACAGTGAGAATCACTTGCTCCGGAGGAGGATCCGCCTACGGTTGGTATCAG<br>CAGAAGCCCGGCCAGGCACCTGTGACCGTCATCTACTATAACAATCAGAGGCC<br>ATCTGACATTCCCGATCGGTTCAGTGGATCCAGCTCTGGGAACACAGCAAGTC<br>TGACCATCACAGGCGCCCAGGCTGAGGACGAAGCCGATTACTATTGTGGAAGC<br>TATGATAGTTCAGCTGTGGGGATTTTTGGTTCTGGCACTAAAGTCACCGTCCT<br>AGG<br>(SEQ ID NO: 265) |
| 12777.15382 VH | GGCGCGCCGAGGTGCAGCTGCTGGAATCCGGAGGAGGACTGGTCCAGCCAGGT<br>GGAAGCCTGCGACTGTCTTGCGCCGCTAGTGGATTCGACTTTTCCAGCTACGG<br>AATGCAGTGGGTGAGGCAGGCACCAGGCAAGGGACTGGAGTGGGTGGGCGTCA<br>TCTCTGGAAGTGGGATTACCACACTGTACGCACCTGCCGTCAAGGGAAGGGCT<br>ACTATCTCACGGGACAACTCTAAAAATACAGTGTATCTGCAGATGAACTCCCT<br>GAGAGCTGAAGATACCGCAGTCTACTATTGTACACGCTCACCCTCCATCACAG<br>ACGGCTGGACTTATGGAGGGGCCTGGATTGATGCTTGGGGTCAGGGCACTCTG<br>GTGACCGTCTCGAG<br>(SEQ ID NO: 274) |
| 12777.15382 VL | GCTAGCCAGCTACGAGCTGACCCAGGACCCAGCAGTGTCCGTCGCCCTGGGCC<br>AGACAGTGAGAATCACTTGCAGTGGCGGAGATGGGTCATACGGTTGGTTCCAG<br>CAGAAGCCCGGACAGGCCCCTGTGACCGTCATCTATGACAACGATAATAGGCC<br>ATCTGACATTCCCGATCGGTTTAGTGGCTCCAGCTCTGGAAACACAGCTTCTC<br>TGACCATCACAGGGGCCCAGGCTGAGGACGAAGCTGATTACTATTGTGGCAAT<br>GCAGACCTGTCCGGGGGTATTTTCGGCAGCGGAACTAAAGTCACCGTCCTAGG<br>(SEQ ID NO: 275) |
| 12760.15375 VH | GGCGCGCCGAGGTGCAGCTGCTGGAATCTGGAGGAGGACTGGTCCAGCCAGGT<br>GGATCCCTGAGACTGAGCTGCGCCGCTTCTGGATTCACCTTTAGTACATTCAA<br>CATGGTGTGGGTCAGGCAGGCACCTGGAAAGGGACTGGAGTACGTGGCTGAAA<br>TCTCCAGCGACGGCTCTTTTACATGGTATGCAACTGCCGTCAAGGGCAGGGCC<br>ACCATTAGTCGGGATAACTCAAAAAATACAGTGTACCTGCAGATGAATTCCCT<br>GAGGGCTGAGGACACCGCAGTCTACTATTGCGCAAAATCCGATTGTTCTAGTT<br>CATACTATGGATATAGCTGTATCGGGATCATTGACGCTTGGGGTCAGGGCACT<br>CTGGTGACCGTCTCGAG<br>(SEQ ID NO: 284) |

TABLE 6-continued

Anti-PD-1 antibody heavy and light chain variable domain nucleotide sequences

| Ab | Sequence (5' to 3') |
|---|---|
| 12760.15375 VL | GCTAGCCTCCTATGAGCTGACCCAGGACCCAGCAGTGAGCGTCGCCCTGGGCC<br>AGACAGTGAGAATCACTTGCTCCGGCGGAATTAGCGACGATGGCTCTTACTAT<br>TACGGATGGTTCCAGCAGAAGCCCGGACAGGCCCCTGTGACCGTCATCTATAT<br>TAACGACAGGCGGCCAAGTAATATCCCCGATAGGTTTTCAGGGTCCAGCTCTG<br>GTAACACAGCTTCTCTGACCATTACAGGGGCCCAGGCTGAGGACGAAGCTGAT<br>TATTACTGTGGCTCTTACGATAGTTCAGCAGGGGTGGGTATCTTCGGCAGTGG<br>AACTAAAGTCACCGTCCTAGG<br>(SEQ ID NO: 285) |
| 13112.15380 VH | GGCGCGCCGAGGTGCAGCTGCTGGAAAGTGGAGGAGGACTGGTCCAGCCAGGT<br>GGATCACTGAGACTGTCCTGCGCCGCCTCCGGCTTCACCTTTTCCAGCTACAA<br>CATGTTCTGGGTGCGCCAGGCACCAGGAAAGGGACTGGAGTTTGTCGCTGAAA<br>TCTCTGGTAGTAATACTGGAAGCCGAACCTGGTACGCACCTGCCGTGAAGGGC<br>AGGGCTACAATTTCTCGGGACAACAGTAAAAATACTCTGTATCTGCAGATGAA<br>CTCTCTGAGGGCTGAGGATACAGCAGTGTACTATTGTGCAAAATCAATCTACG<br>GAGGGTATTGCGCCGGTGGCTATTCCTGTGGTGTGGGCCTGATTGACGCATGG<br>GGACAGGGGACCCTGGTCACAGTCTCGAG<br>(SEQ ID NO: 294) |
| 13112.15380 VL | GCTAGCCTCATACGAGCTGACCCAGGACCCAGCAGTGTCCGTCGCCCTGGGCC<br>AGACAGTGAGAATCACTTGCAGTGGCGGATCCAGCGATTACTATGGGTGGTTC<br>CAGCAGAAGCCCGGTCAGGCCCCTGTGACCGTCATCTACTATAACAACAAGAG<br>GCCATCTGACATTCCCGATCGGTTTAGTGGCTCTAGTTCAGGAAACACAGCCT<br>CCCTGACCATTACAGGGGCCCAGGCTGAGGACGAAGCTGATTACTATTGTGGC<br>AATGCAGACTCCAGCGTGGGAGTCTTCGGGTCTGGTACTAAGGTGACCGTCCT<br>AGG<br>(SEQ ID NO: 295) |
| 12748.16124 VL | GCTAGCCTCTTACGAGCTGACTCAGCCACCTTCCGTGTCCGTGTCCCCAGGAC<br>AGACCGCAAGAATCACATGCAGTGGCGGATCCAGCTACTCATATGGGTGGTTC<br>CAGCAGAAGCCTGGTCAGGCCCCCGTGACAGTCATCTATGAGAGCAACAATAG<br>GCCTTCTGACATTCCAGAACGGTTTAGTGGCTCTAGTTCAGGAACCACAGTGA<br>CTCTGACCATCAGCGGGGTCCAGGCCGAGGACGAAGCTGATTACTATTGTGGC<br>AACGCTGATTCCAGCTCTGGAATTTTCGGGTCCGGTACAAAAGTGACTGTCCT<br>AGG<br>(SEQ ID NO: 391) |

TABLE 7

Anti-PD-1 antibody heavy and light chain variable domain amino acid sequences

| Ab | Sequence (N-terminal to C-terminal) |
|---|---|
| 12819.15384 VH | EVQLLESGGGLVQPGGSLRLSCAASGFTFTRYDMVWVRQAPGKGLEWVAGIGD<br>SNKMTRYAPAVKGRATISRDNSKNTLYLQMNSLRAEDTAVYYCAKGSCIACWD<br>EAGRIDAWGQGTLVTVSS<br>(SEQ ID NO: 226) |
| 12819.15384 VL | SYELTQDPAVSVALGQTVRITCSGGGSYDGSSYYGWYQQKPGQAPVTVIYNNN<br>NRPSDIPDRFSGSSSGNTASLTITGAQAEDEADYYCGSYDRPETNSDYVGMFG<br>SGTKVTVL<br>(SEQ ID NO: 227) |
| 12748.15381<br>12748.16124 VH | EVQLLESGGGLVQPGGSLRLSCAASGFTFSDYAMNWVRQAPGKGLEWVAGIGN<br>DGSYTNYGAAVKGRATISRDNSKNTLYLQMNSLRAEDTAVYYCASDIRSRNDC<br>SYFLGGCSSGFIDVWGQGTLVTVSS<br>(SEQ ID NO: 236) |
| 12748.15381 VL | SYELTQDPAVSVALGQTVRITCSGGSSYSYGWFQQKPGQAPVTVIYESNNRPS<br>DIPDRFSGSSSGNTASLTITGAQAEDEADYYCGNADSSSGIFGSGTKVTVL<br>(SEQ ID NO: 237) |
| 12865.15377 VH | EVQLLESGGGLVQPGGSLRLSCAASGFDFSDHGMQWVRQAPGKGLEYVGVIDT<br>TGRYTYYAPAVKGRATISRDNSKNTLYLQMNSLRAEDTAVYYCAKTTCVGGYL<br>CNTVGSIDAWGQGTLVTVSS<br>(SEQ ID NO: 246) |

TABLE 7-continued

Anti-PD-1 antibody heavy and light chain variable domain amino acid sequences

| Ab | Sequence (N-terminal to C-terminal) |
|---|---|
| 12865.15377 VL | SYELTQDPAVSVALGQTVRITCSGG*GSSSY*YGWYQQKPGQAPVTVIY*DDT*NRPSGIPDRFSGSSSGNTASLTITGAQAEDEADYY*CGGYEGSSHAGIF*GSGTKVTVL<br>(SEQ ID NO: 247) |
| 12892.15378 VH | EVQLLESGGGLVQPGGSLRLSCAAS*GFDFSSYT*MQWVRQAPGKGLEWVGV*ISSTGGST*GYGPAVKGRATISRDNSKNTLYLQMNSLRAEDTAVYY*CVKSISGDAWSVDGLDAW*GQGTLVTVSS<br>(SEQ ID NO: 256) |
| 12892.15378 VL | SYELTQDPAVSVALGQTVRITCSGG*GSA*YGWYQQKPGQAPVTVIY*YNN*QRPSGIPDRFSGSSSGNTASLTITGAQAEDEADYY*CGSYDSSAVGIF*GSGTKVTVL<br>(SEQ ID NO: 257) |
| 12796.15376 VH | EVQLLESGGGLVQPGGSLRLSCAAS*GFDFSSYT*MQWVRQAPGKGLEWVGV*ISSTGGST*GYGPAVKGRATISRDNSKNTLYLQMNSLRAEDTAVYY*CVKSVSGDAWSVDGLDAW*GQGTLVTVSS<br>(SEQ ID NO: 266) |
| 12796.15376 VL | SYELTQDPAVSVALGQTVRITCSGG*GSA*YGWYQQKPGQAPVTVIY*YNN*QRPSDIPDRFSGSSSGNTASLTITGAQAEDEADYY*CGSYDSSAVGIF*GSGTKVTVL<br>(SEQ ID NO: 267) |
| 12777.15382 VH | EVQLLESGGGLVQPGGSLRLSCAAS*GFDFSSYG*MQWVRQAPGKGLEWVGV*ISGSGITT*LYAPAVKGRATISRDNSKNTVYLQMNSLRAEDTAVYY*CTRSPSITDGWTYGAWIDAW*GQGTLVTVSS<br>(SEQ ID NO: 276) |
| 12777.15382 VL | SYELTQDPAVSVALGQTVRITCSGG*DGS*YGWFQQKPGQAPVTVIY*DND*NRPSDIPDRFSGSSSGNTASLTITGAQAEDEADYY*CGNADLSGGIF*GSGTKVTVL<br>(SEQ ID NO: 277) |
| 12760.15375 VH | EVQLLESGGGLVQPGGSLRLSCAAS*GFTFSSYN*MVWVRQAPGKGLEYVAEISS*DGSFT*WYATAVKGRATISRDNSKNTVYLQMNSLRAEDTAVYY*CAKSDCSSSYYGYSCIGIIDAW*GQGTLVTVSS<br>(SEQ ID NO: 286) |
| 12760.15375 VL | SYELTQDPAVSVALGQTVRITCSGG*ISDDGSYY*YGWFQQKPGQAPVTVIY*IND*RRPSNIPDRFSGSSSGNTASLTITGAQAEDEADYY*CGNASSAGVGIF*GSGTKVTVL<br>(SEQ ID NO: 287) |
| 13112.15380 VH | EVQLLESGGGLVQPGGSLRLSCAAS*GFTFSSYN*MFWVRQAPGKGLEFVAE*ISGSNTGSRT*WYAPAVKGRATISRDNSKNTLYLQMNSLRAEDTAVYY*CAKSIYGGYCAGGYSCGVGLIDAW*GQGTLVTVSS<br>(SEQ ID NO: 296) |
| 13112.15380 VL | SYELTQDPAVSVALGQTVRITCSGG*SSDY*YGWFQQKPGQAPVTVIY*YNN*KRPSDIPDRFSGSSSGNTASLTITGAQAEDEADYY*CGNADSSVGVF*GSGTKVTVL<br>(SEQ ID NO: 297) |
| 12748.16124 VL | SYELTQPPSVSVSPGQTARITCSGG*SSYS*YGWFQQKPGQAPVTVIY*ESN*NRPSDIPERFSGSSSGTTVTLTISGVQAEDEADYY*CGNADSSSGIF*GSGTKVTVL<br>(SEQ ID NO: 392) |

(CDRs are bolded and italicized)

TABLE 8

Anti-LAG-3 antibody heavy and light chain variable domain nucleotide sequences

| Ab | Sequence (5' to 3') |
|---|---|
| 15646 VH | CAGGTGCAGCTGCAGCAGTGGGGTGCCGGTCTGCTGAAGCCTTCTGAAACTCTGTCTCTGACTTGTGCCGTCTATGGTGGATCATTCAGCGGCTACTATTGGTCCTGGATCAGGCAGCCCCCTGGCAAGGGCCTGGAGTGGATCGGCGAGATCAACCACCGGGGCTCTACCAACTACAATCCCTCTCTGAAGAGCAGGGTGACCATCTCCGTGGACACATCTAAGAATCAGTTCAGCCTGAAGCTGAGCTCCGTGACCGCCGCTGATACAGCCGTGTACTATTGCACAAGGGGGGAGGAATGGGAGTCACTGTTCTTTGATTACTGGGGCAGGGGACACTGGTCACAGTCTCGAGT<br>(SEQ ID NO: 304) |

TABLE 8-continued

Anti-LAG-3 antibody heavy and light chain variable domain nucleotide sequences

| Ab | Sequence (5' to 3') |
|---|---|

15646 VL GAAATCGTCCTGACCCAGTCCCCCGCCACCCTGAGCCTGAGCCCCGGAGAAAGAGC
CACCCTGTCCTGCCGAGCAAGCCAGTCCATCAGCTCCTATCTCGCCTGGTATCAGC
AGAAACCAGGCCAGGCTCCCCGGCTGCTGATCTACGGCGCCTCCAACAGAGCTACA
GGAATCCCAGCCCGCTTCAGCGGCTCCGGCTCTGGCACAGACTTTACCCTGACAAT
CTCTAGCCTGGAGCCTGAGGATTTCGCCGTGTACTATTGCCAGCAGAGATCTAATT
GGCCACTGACATTCGGCGGCGGCACACGGGTGGAGATCAAG
(SEQ ID NO: 305)

15532 VH CAGGTTCAGCTGCAGCAGTGGGGCGCCGGCCTGCTGAGACCAAGCGAGACCCTGTC
CCTGACATGCGCCGTGTATGGCGAGAGCTTCTCCGGCTATTACTGGAACTGGATCC
GGCAGCCTCCCGGCAAGGGCCTGGAGTGGATCGGCGAGATCAATCACTCCGGCTCC
ACCAATTACAACCCATCCCTGAAGTCTCGGGTGACAATCAGCGTGGATACAAGCAA
GACCCAGTTCAGCCTGAAGCTGAGCTCCGTGACAGCTGCCGATACCGCCGTGTATT
ACTGCGCCAGAGGCTGGGACCTGCTGGATTGGAATGACTACTGGAATGAGTACTGG
GGCCAGGGGACCCTGGTGACCGTCTCGAGT
(SEQ ID NO: 314)

15532 VL GAGATCGTGCTGACCCAGTCCCCTGCCACCCTGTCTCTGTCCCCTGGCGAGCGGGC
CACCCTGTCCTGTAGAGCTTCTCAGTCCGTGTCTTCCTACCTGGCTTGGTACCAGC
AGAAGCCAGGACAGGCCCCAAGACTGCTGATCTATGACGCTTCCAATCGGGCTACC
GGCATCCCAGCTCGCTTTAGCGGCTCCGGCTCCGGCACCGACTTCACCCTGACAAT
CAGCTCCCTGGAGCCAGAGGATTTTGCCGTGTATTACTGTCAGCAGAGGTCCAATT
GGCCACTGACATTTGGCGGCGGCACAAAGGTTGAGATCAAG
(SEQ ID NO: 315)

15723 VH CAGGTTCAGCTGCAGCAGTGGGGCGCTGGCCTGCTGAAGCCCTCTGAGACCCTGTC
TCTGACCTGTGCCGTGTATGGCGGCAGCTTCTCCGGCTATTACTGGAACTGGATCC
GCCAGCCCCCCGGCAAGGGCCTGGAGTGGATCGGCGAGATCAACCACTCCGGCTCT
ACCAACTACAATCCTTCTCTGAAGTCCAGGGTGACAATCAGCGTGGACACCAGCAA
GAACCAGTTTAGCCTGAAGCTGTCCAGCGTGACAGCTGCCGATACAGCCGTGTATT
ACTGCGCCAGAGGCGAGGATTGGGGCGAGAGCTTCTTTGATTACTGGGGCCAGGGG
ACCCTGGTGACCGTCTCGAGT
(SEQ ID NO: 324)

15723 VL GAGATCGTGCTGACCCAGTCCCCTGCCACCCTGTCTCTGTCCCCTGGCGAGCGGGC
CACCCTGAGCTGTCGGGCCTCCCAGTCCGTGAGCTCCTACCTGGCTTGGTATCAGC
AGAAGCCAGGACAGGCCCCAAGACTGCTGATCTACGCCGCTTCCAATCGGGCCACC
GGCATCCCCGCCAGATTTTCCGGCTCTGGCTCCGGCACCGATTTCACCCTGACAAT
CAGCTCCCTGGAGCCAGAGGACTTCGCCGTGTACTACTGCCAGCAGAGGTCTAATT
GGCCACTGACATTTGGCGGCGGCACCAAGGTTGAGATCAAG
(SEQ ID NO: 325)

15595 VH CAGGTTCAGCTGGTGCAGTCCGGCGCTGAGGTGAAGAAGCCTGGAGCTTCTGTGAA
GGTTTCCTGTAAGGTTTCCGGCTATAGCCTGACCGAGATCTCTATGCACTGGGTAC
GGCAAGCCCCCGGCAAGGGCCTGGAGTGGATGGGCGGCTTTGACCCAGAGGATGGC
GAGACCATCTACGCTCAGAGGTTTCAGGGGCGCGTGATCATGACCGAGGATACCAG
CACCGATACCGCCTACATGGAGCTGTCCAGCCTGAGATCCGAGGATACCGCCGTGT
ATTACTGCGCTACTGGTGGCTGGGGCCCCAATTGGTTCGATCCTTGGGGCCAGGGG
ACCCTGGTGACCGTCTCGAGT
(SEQ ID NO: 334)

15595 VL GACATCCAGATGACACAGTCTCCTTCCTCTGTGAGCGCCTCTGTGGGCGACCGCGT
GACCATCACATGCCGCGCTTCCCAGGGGATCTCTTCCTGGCTGGCTTGGTACCAGC
AGAAGCCCGGCAAGGCCCCCAAGCTGCTGATCTATGCTGCCAGCAGCCTGCAGTCC
GGCGTGCCTTCCAGGTTTAGCGGCTCCGGCTCCGGCACCGACTTTACACTGACAAT
CAGCTCCCTGCAGCCCGAGGATTTTGCCACCTATTACTGTCAGCAGGCGAATTCCT
TCCCTTTTACATTCGGCCCTGGCACCAAGGTTGATATCAAG
(SEQ ID NO: 335)

15431 VH CAGGTTCAGCTGCAGCAGTCCGGCCCCGGCCTGGTGAAGCCAAGCCAGACCCTGTC
TCTGACATGCGCCATCTCCGGCGACAGCGTGTCCTCTAACTCCGCCGCTTGGAATT
GGATCCGGCAGTCTCCATCCAGAGGCCTGGAGTGGCTGGGCAGAACCTATTACCGG
TCCAAGTGGTACAACGATTATGCCGTGTCCGTGAAGAGCAGAATCACCATCAACCC
TGATACCAGCAAGAACCAGTTCAGCCTGCAGCTGAATTCCGTGACCCCAGAGGATA
CAGCCGTGTATTACTGTGCTAGGGACGATGATTGGAATGACTTCGATTACTGGGGC
CAGGGGACCCTGGTGACAGTCTCGAGT
(SEQ ID NO: 344)

15431 VL GAGATCGTGCTGACCCAGTCCCCAGCTACACTGTCCCTGTCTCCCGGCGAGCGGGC
CACCCTGAGCTGTAGAGCTTCCCAGTCCGTGTCTTCCTATCTGGCTTGGTATCAGC
AGAAGCCAGGACAGGCCCCAAGGCTGCTGATCTACGACGCCTCCAATAGAGCCACC

TABLE 8-continued

Anti-LAG-3 antibody heavy and light chain variable domain nucleotide sequences

| Ab | Sequence (5' to 3') |
|---|---|
| | GGCATCCCAGCTAGATTTTCTGGCTCCGGCTCCGGCACCGATTTCACACTGACCAT<br>CTCTAGCCTGGAGCCAGAGGATTTTGCTGTATATTACTGCCAGCAGCGCAGCAACT<br>GGCCCCTGACATTTGGCGGCGGCACCAAGGTTGAGATCAAG<br>(SEQ ID NO: 345) |
| 15572 VH | CAGCTGCAGCTGCAGGAAAGCGGCCCCGGCCTGGTGAAGCCCTCTGAGACCCTGTC<br>CCTGACATGCACCGTGAGCGGCGATTCCATCAGCTCTTCCAGCTATTACTGGGGCT<br>GGATCCGGCAGCCCCCCGGCAAGGGCCTGGAGTGGATCGGCAGCATCTTCTACTCC<br>GGCAATACATATTATAATCCTTCTCTGAAGAGCAGGGTGACAATCAGCGTGGATAC<br>CTCCAAGAATCAGTTTAGCCTGAAGCTGAGCTCCGTGACAGCTGCCGATACAGCCG<br>TGTATTACTGCGCTAGGGAGGACGATTTTCTGACCGATTATTACGGCGCTTTCGAC<br>ATCTGGGGCCAGGGGACAATGGTGACAGTCTCGAGT<br>(SEQ ID NO: 354) |
| 15572 VL | GATATCCAGATGACCCAGTCTCCAAGCACCCTGAGCGCCTCTGTGGGCGATCGGGT<br>GACCATCACATGTCGGGCTTCTCAGTCCATCAGCAGCTGGCTGGCTTGGTATCAGC<br>AGAAGCCCGGCAAGGCCCCAAAGCTGCTGATCTACAAGGCCTCTTCCAGCGAGAGC<br>GGCGTGCCATCCAGGTTTAGCGGCTCCGGCTCCGGCACCGAGTTTACCCTGACCAT<br>CTCTTCCCTGCAGCCCGATGACTTTGCCACCTACTACTGTCAGCAGTACAATTCCT<br>ATCTGACATTCGGCGGCGGCACCAAGGTTGAGATCAAG<br>(SEQ ID NO: 355) |
| 15011 VH | GAGGTGCAGCTGCTGGAATCCGGAGGAGGACTGGTCCAGCCAGGTGGATCCCTGCG<br>ACTGAGCTGCGCCGCTTCTGGCTTCGACTTTAGAAGCTACGCAATGATGTGGGTCC<br>GCCAGGCACCAGGAAAGGGACTGGAGTGGGTGGGAGGGATCAACGGTGAAGTCGGT<br>GGCTCTAATACATACTATGCACCTGCCGTCAAGGGAAGGGCTACTATTAGTCGGGA<br>CAACTCAAAAAATACCCTGTATCTGCAAATGAACAGTCTGAGGGCCGAGGATACCG<br>CCGTGTACTATTGCGTGAAAGGTGCTGGCGCATGCGGCATCTGTAATGACGATATT<br>GATGCATGGGGACAGGGGACCCTGGTGACAGTCTCGAGT<br>(SEQ ID NO: 364) |
| 15011 VL | AGTTATGAGCTGACTCAGGACCCAGCAGTGTCAGTCGCCCTGGGCCAGACAGTGAG<br>AATCACTTGCAGTGGGGCTGGTTCATATGCAGGCTCCTACTATTACGGATGGCACC<br>AGCAGAAGCCCGGACAGGCACCTGTGACAGTCATCTACGACAACGATAAAAGGCCA<br>AGCAATATTCCCGACCGGTTCTCTGGGTCCAGCTCTGGTAACACCGCCTCCCTGAC<br>CATTACTGGGGCCCAGGCTGAGGACGAAGCTGATTATTACTGTGGCTCTACAAACG<br>ATAATGACGATGGCGGACTGTTTGGCTCCGGAACTAAGGTCACCGTCCTA<br>(SEQ ID NO: 365) |

TABLE 9

Anti-LAG-3 antibody heavy and light chain variable domain amino acid sequences

| Ab | Sequence (N-terminal to C-terminal) |
|---|---|
| 15646 VH | QVQLQQWGAGLLKPSETLSLTCAVY*GGSFSGYY*WSWIRQPPGKGLEWIG*EINHRGST*<br>NYNPSLKSRVTISVDTSKNQFSLKLSSVTAADTAVYY*CTRGEEW*GQGTL<br>VTVSS<br>(SEQ ID NO: 306) |
| 15646 VL | EIVLTQSPATLSLSPGERATLSCRAS*QSISSY*LAWYQQKPGQAPRLLIY*GAS*NRATG<br>IPARFSGSGSGTDFTLTISSLEPEDFAVYY*CQQRSNWPLTF*SNWPLTFGGGTRVEIK<br>(SEQ ID NO: 307) |
| 15532 VH | QVQLQQWGAGLLRPSETLSLTCAVY*GESFSGYY*WNWIRQPPGKGLEWIG*EINHSGST*<br>NYNPSLKSRVTISVDTSKTQFSLKLSSVTAADTAVYY*CARGWDLLDWNDYWNEYW*GQ<br>GTLVTVSS<br>(SEQ ID NO: 316) |
| 15532 VL | EIVLTQSPATLSLSPGERATLSCRAS*QSVSSY*LAWYQQKPGQAPRLLIY*DAS*NRATG<br>IPARFSGSGSGTDFTLTISSLEPEDFAVYY*CQQRSNWPLTF*GGGTKVEIK<br>(SEQ ID NO: 317) |
| 15723 VH | QVQLQQWGAGLLKPSETLSLTCAVY*GGSFSGYY*WNWIRQPPGKGLEWIG*EINHSGST*<br>NYNPSLKSRVTISVDTSKNQFSLKLSSVTAADTAVYY*CARGEDWGESFFDYW*GQGTL<br>VTVSS<br>(SEQ ID NO: 326) |
| 15723 VL | EIVLTQSPATLSLSPGERATLSCRAS*QSVSSY*LAWYQQKPGQAPRLLIY*AAS*NRATG<br>IPARFSGSGSGTDFTLTISSLEPEDFAVYY*CQQRSNWPLTF*GGGTKVEIK<br>(SEQ ID NO: 327) |

TABLE 9-continued

Anti-LAG-3 antibody heavy and light chain variable
domain amino acid sequences

| Ab | Sequence (N-terminal to C-terminal) |
|---|---|
| 15595 VH | QVQLVQSGAEVKKPGASVKVSCKVS*GYSLTEIS*MHWVRQAPGKGLEWMGG*FDPEDGE* *TI*YAQRFQGRVIMTEDTSTDTAYMELSSLRSEDTAVYY*CATGGWGPNWFDPW*GQGTL VTVSS<br>(SEQ ID NO: 336) |
| 15595 VL | DIQMTQSPSSVSASVGDRVTITCRAS*QGISSW*LAWYQQKPGKAPKLLIY*AAS*SLQSG VPSRFSGSGSGTDFTLTISSLQPEDFATYY*CQQ**A*NSFPFTF***GPGTKVDIK<br>(SEQ ID NO: 337) |
| 15431 VH | QVQLQQSGPGLVKPSQTLSLTCAIS*GDSVSSNSA*AWNWIRQSPSRGLEWLGR*TYYRS* *KW*YNDYAVSVKSRITINPDTSKNQFSLQLNSVTPEDTAVYY*CARDDDWNDFDYW*GQG TLVTVSS<br>(SEQ ID NO: 346) |
| 15431 VL | EIVLTQSPATLSLSPGERATLSCRAS*QSVSSY*LAWYQQKPGQAPRLLIY*DAS*NRATG IPARFSGSGSGTDFTLTISSLEPEDFAVYY*CQQRSNWPLTF*GGGTKVEIK<br>(SEQ ID NO: 347) |
| 15572 VH | QLQLQESGPGLVKPSETLSLTCTVS*GDSISSSSYY*WGWIRQPPGKGLEWIGS*IFYSG* *NT*YYNPSLKSRVTISVDTSKNQFSLKLSSVTAADTAVYY*CAREDDFLTDYYGAFDIW* GQGTMVTVSS<br>(SEQ ID NO: 356) |
| 15572 VL | DIQMTQSPSTLSASVGDRVTITCRAS*QSISSW*LAWYQQKPGKAPKLLIY*KAS*SSESG VPSRFSGSGSGTEFTLTISSLQPDDFATYY*CQQYNSYLTF*GGGTKVEIK<br>(SEQ ID NO: 357) |
| 15011 VH | EVQLLESGGGLVQPGGSLRLSCAAS*GFDFRSYA*MMWVRQAPGKGLEWVGG*INGEVGG* *SNT*YYAPAVKGRATISRDNSKNTLYLQMNSLRAEDTAVYY*CVKGAGACGICNDDIDA* *W*GQGTLVTVSS<br>(SEQ ID NO: 366) |
| 15011 VL | SYELTQDPAVSVALGQTVRITCSGA*GSYAGSY*YYGWHQQKPGQAPVTVIY*DND*KRPS NIPDRFSGSSSGNTASLTITGAQAEDEADYY*CGSTNDNDDGGLF*GSGTKVTVL<br>(SEQ ID NO: 367) |

(CDRs are bolded and italicized)

The invention claimed is:

1. A method of enhancing immunity in a human patient in need thereof, comprising administering to the patient pembrolizumab or nivolumab in combination with an anti-TIM-3 antibody or an antigen-binding portion thereof that comprises:
   a) H-CDR1-3 and L-CDR1-3 that comprise the amino acid sequences of SEQ ID NOs: 8-13, respectively;
   b) a heavy chain variable domain (VH) and a light chain variable domain (VL) that comprise the amino acid sequences of SEQ ID NOs: 7 and 4, respectively; or
   c) a heavy chain (HC) that comprises the amino acid sequences of SEQ ID NOs: 7 and 377 and a light chain (LC) that comprises the amino acid sequences of SEQ ID NOs: 4 and 378.

2. The method of claim 1, wherein the patient has cancer.

3. The method of claim 2, wherein the cancer is selected from the group consisting of leukemia, Hodgkin's lymphoma, non-Hodgkin's lymphoma, myeloma, melanoma, non-small cell lung cancer, bladder cancer, gallbladder cancer, head and neck squamous cell carcinoma, esophageal cancer, gastroesophageal cancer, gastric cancer, ovarian cancer, colorectal cancer, renal cell carcinoma, pancreatic cancer, Merkel cell carcinoma, fibrosarcoma, gliosarcoma, mesothelioma, biliary tract cancer, and glioblastoma.

4. The method of claim 1, further comprising administering to the patient radiation therapy, a chemotherapeutic agent, an anti-neoplastic agent, or an anti-angiogenic agent.

5. The method of claim 1, further comprising administering irinotecan to the patient.

6. A method of enhancing immunity in a human patient in need thereof, comprising administering to the patient an anti-PD-1 antibody or an antigen-binding portion thereof and an anti-TIM-3 antibody or an antigen-binding portion thereof, wherein
I) the anti-PD-1 antibody comprises:
   a) heavy chain complementarity-determining regions (H-CDR) 1-3 and light chain complementarity-determining regions (L-CDR) 1-3 comprising the amino acid sequences of SEQ ID NOs: 228-233, respectively;
   b) a heavy chain variable domain (VH) and a light chain variable domain (VL) comprising the amino acid sequences of SEQ ID NOs: 226 and 227, respectively; or
   c) a heavy chain (HC) and a light chain (LC) comprising the amino acid sequences of SEQ ID NOs: 226 and 375, and SEQ ID NOs: 227 and 379, respectively; and
II) the anti-TIM-3 antibody comprises:
   a) H-CDR1-3 and L-CDR1-3 comprising the amino acid sequences of SEQ ID NOs: 8-13, respectively;
   b) a VH and a VL comprising the amino acid sequences of SEQ ID NOs: 7 and 4, respectively; or
   c) an HC and an LC comprising the amino acid sequences of SEQ ID NOs: 7 and 377; and SEQ ID NOs: 4 and 378; respectively.

7. The method of claim 6, wherein the patient has cancer.

8. The method of claim 7, wherein the cancer is selected from the group consisting of leukemia, Hodgkin's lymphoma, non-Hodgkin's lymphoma, myeloma, melanoma, non-small cell lung cancer, bladder cancer, gallbladder cancer, head and neck squamous cell carcinoma, esophageal cancer, gastroesophageal cancer, gastric cancer, ovarian cancer, colorectal cancer, renal cell carcinoma, pancreatic cancer, Merkel cell carcinoma, fibrosarcoma, gliosarcoma, mesothelioma, biliary tract cancer, and glioblastoma.

9. The method of claim 6, further comprising administering to the patient radiation therapy, a chemotherapeutic agent, an anti-neoplastic agent, or an anti-angiogenic agent.

10. The method of claim 6, further comprising administering irinotecan to the patient.

11. A method of treating cancer in a human patient, comprising administering to the patient pembrolizumab; an anti-TIM-3 antibody comprising an HC that comprises the amino acid sequences of SEQ ID NOs: 7 and 377 and an LC that comprises the amino acid sequences of SEQ ID NOs: 4 and 378; and irinotecan.

12. The method of claim 11, wherein the cancer is selected from the group consisting of leukemia, Hodgkin's lymphoma, non-Hodgkin's lymphoma, myeloma, melanoma, non-small cell lung cancer, bladder cancer, gallbladder cancer, head and neck squamous cell carcinoma, esophageal cancer, gastroesophageal cancer, gastric cancer, ovarian cancer, colorectal cancer, renal cell carcinoma, pancreatic cancer, Merkel cell carcinoma, fibrosarcoma, gliosarcoma, mesothelioma, biliary tract cancer, and glioblastoma.

13. The method of claim 11, further comprising administering to the patient radiation therapy, a chemotherapeutic agent, an anti-neoplastic agent, or an anti-angiogenic agent.

14. A method of treating cancer in a human patient, comprising administering to the patient nivolumab; an anti-TIM-3 antibody comprising an HC that comprises the amino acid sequences of SEQ ID NOs: 7 and 377 and an LC that comprises the amino acid sequences of SEQ ID NOs: 4 and 378; and irinotecan.

15. The method of claim 14, wherein the cancer is selected from the group consisting of leukemia, Hodgkin's lymphoma, non-Hodgkin's lymphoma, myeloma, melanoma, non-small cell lung cancer, bladder cancer, gallbladder cancer, head and neck squamous cell carcinoma, esophageal cancer, gastroesophageal cancer, gastric cancer, ovarian cancer, colorectal cancer, renal cell carcinoma, pancreatic cancer, Merkel cell carcinoma, fibrosarcoma, gliosarcoma, mesothelioma, biliary tract cancer, and glioblastoma.

16. The method of claim 14, further comprising administering to the patient radiation therapy, a chemotherapeutic agent, an anti-neoplastic agent, or an anti-angiogenic agent.

\* \* \* \* \*

UNITED STATES PATENT AND TRADEMARK OFFICE
CERTIFICATE OF CORRECTION

| | |
|---|---|
| PATENT NO. | : 11,939,380 B2 |
| APPLICATION NO. | : 16/500918 |
| DATED | : March 26, 2024 |
| INVENTOR(S) | : Lindsted et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 810 days.

Signed and Sealed this
Eighth Day of October, 2024

Katherine Kelly Vidal
*Director of the United States Patent and Trademark Office*

SEQUENCE LISTING

<160> NUMBER OF SEQ ID NOS: 397

<210> SEQ ID NO 1
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
caggtgcagc tacagcagtc gggcccagga ctggtgaagc cttcacagac cctgtccctc      60
acctgcactg tctctggtgg ctccatcagc agtggtggtt actactggag ttggaccccgt    120 cagcacccag ggatgggcct ggagtggatt ggatacatct cttacagtgg gagtatctat    180
tacactccgt ccctcaagag tcgacttacc atatcagtgg acacgtctaa gaaccagttc    240
tccctgaagc tgagctctgt gactgccgcg gacacggccg tatattactg tgcgagtttg    300
gattcctggg gatctaaccg tgactactgg ggccagggaa ccctggtcac cgtctcgagt    360

<210> SEQ ID NO 2
<211> LENGTH: 321
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 2
gaaattgtgt tgacgcagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggccgctcac tttcggcgga   300
gggaccaagg tggagattaa g                                             321

<210> SEQ ID NO 3
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3
```

Gln Val Gln Leu Gln Gln Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Thr Arg Gln His Pro Gly Met Gly Leu Glu
        35                  40                  45

Trp Ile Gly Tyr Ile Ser Tyr Ser Gly Ser Ile Tyr Tyr Thr Pro Ser
    50                  55                  60

Leu Lys Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Ser Leu Asp Ser Trp Gly Ser Asn Arg Asp Tyr Trp Gly Gln
        100                 105                 110

Gly Thr Leu Val Thr Val Ser Ser
    115                 120

```
<210> SEQ ID NO 4
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105

<210> SEQ ID NO 5
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
caggtgcagc tgcaggagag tggccccgga ctggtcaagc cttcacagac tctgagcctg      60
acctgcacag tgtctggcgg aagtatcagc tccgggggtt actattggag ctggacccga     120
cagcacccag gaatgggtct ggaatggatc gggtacattt catatagcgg ctccatctac     180
tatacaccct cactgaaaag caggctgacc atttccgtgg acacatctaa gaaccagttc     240
agcctgaaac tgtctagtgt gacagccgct gatactgcag tctactattg tgcctccctg     300
gactcttggg gcagtaatag agattactgg ggccagggaa ctctggtcac cgtctcgagt     360

<210> SEQ ID NO 6
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
gagatcgtgc tgactcagtc cccagccacc ctgtcactga gcccaggaga acgagcaacc      60
ctgtcttgca gggcctccca gtctgtcagc tcctacctgg cttggtatca gcagaagccc     120
gggcaggcac ctcgactgct gatctacgac gccagtaaca gagctaccgg tattcccgcc     180
cgcttcagtg gttcaggcag cggaacagac tttaccctga caatctctag tctggagcct     240
gaagatttcg ccgtgtacta ttgtcagcag aggtctaatt ggccactgac atttggcgga     300
gggactaagg tcgagatcaa g                                               321

<210> SEQ ID NO 7
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
                 20                  25                  30

Gly Tyr Tyr Trp Ser Trp Thr Arg Gln His Pro Gly Met Gly Leu Glu
             35                  40                  45
```

Trp Ile Gly Tyr Ile Ser Tyr Ser Gly Ser Ile Tyr Tyr Thr Pro Ser
    50                  55                  60

Leu Lys Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Leu Asp Ser Trp Gly Ser Asn Arg Asp Tyr Trp Gly Gln
            100                 105                 110

Gly Thr Leu Val Thr Val Ser Ser
        115                 120

<210> SEQ ID NO 8
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Gly Ser Ile Ser Ser Gly Gly Tyr Tyr
1               5                   10

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ile Ser Tyr Ser Gly Ser Ile
1               5

<210> SEQ ID NO 10
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Cys Ala Ser Leu Asp Ser Trp Gly Ser Asn Arg Asp Tyr Trp
1               5                   10

<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gln Ser Val Ser Ser Tyr
1               5

<210> SEQ ID NO 12
<211> LENGTH: 3

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Ala Ser
1

<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Cys Gln Gln Arg Ser Asn Trp Pro Leu Thr Phe
1               5                   10

<210> SEQ ID NO 14
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
caggtcacct tgaaggagtg gggcgcagga ctgttgaggc cctcggagac cctgtccctc      60
acctgcgctg tctatggtgg gtccttcagt ggttactact ggagctggat ccgccagccc     120
ccagggaagg ggctggagtg gatagggaa atcaatcata gtggaagcac caactacaac     180
ccgtccctca agagtcgagt caccatatca gtagacgcga ccaagaaaca attctccctg     240
aagctgacct ctgtgaccgc cgcggacacg gctgtgtatt actgtgcgag atattgggag     300
ctccctgact actggggcca gggcaccctg gtcaccgtct cgagt                    345

<210> SEQ ID NO 15
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
gacatccagt tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt accctccgac gttcggccaa     300
gggaccaagg tggaaatcaa g                                              321

<210> SEQ ID NO 16
<211> LENGTH: 115
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

```
Gln Val Thr Leu Lys Glu Trp Gly Ala Gly Leu Leu Arg Pro Ser Glu
1               5                   10                  15
Thr Leu Ser Leu Thr Cys Ala Val Tyr Gly Gly Ser Phe Ser Gly Tyr
            20                  25                  30
Tyr Trp Ser Trp Ile Arg Gln Pro Pro Gly Lys Gly Leu Glu Trp Ile
        35                  40                  45
Gly Glu Ile Asn His Ser Gly Ser Thr Asn Tyr Asn Pro Ser Leu Lys
    50                  55                  60
Ser Arg Val Thr Ile Ser Val Asp Ala Thr Lys Lys Gln Phe Ser Leu
65                  70                  75                  80
Lys Leu Thr Ser Val Thr Ala Ala Asp Thr Ala Val Tyr Tyr Cys Ala
                85                  90                  95
Arg Tyr Trp Glu Leu Pro Asp Tyr Trp Gly Gln Gly Thr Leu Val Thr
            100                 105                 110
Val Ser Ser
        115
```

<210> SEQ ID NO 17
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

```
Asp Ile Gln Leu Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Pro
                85                  90                  95
Thr Phe Gly Gln Gly Thr Lys Val Glu Ile Lys
            100                 105
```

<210> SEQ ID NO 18
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 18

```
Gly Gly Ser Phe Ser Gly Tyr Tyr
1               5
```

```
<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ile Asn His Ser Gly Ser Thr
1               5

<210> SEQ ID NO 20
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Cys Ala Arg Tyr Trp Glu Leu Pro Asp Tyr Trp
1               5                   10

<210> SEQ ID NO 21
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln Gly Ile Arg Asn Asp
1               5

<210> SEQ ID NO 22
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ala Ala Ser
1

<210> SEQ ID NO 23
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Cys Leu Gln His Asn Ser Tyr Pro Pro Thr Phe
1               5                   10

<210> SEQ ID NO 24
<211> LENGTH: 345
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
cagatgcagc tggtgcagtg gggcgcagga ctgttgaagc cttcggagac cctgtccctc    60
acctgcgctg tctatggtgg gtccttcagt ggttactact ggagctggat ccgccagccc   120
ccagggaagg gctggagtg gattggggaa atcaatcata gtggaagcac caactacaac    180
ccgtccctca agagtcgagt caccatgtca gttgacacgt ccaagcacca gttctccctg   240
aagctgagct ctgtgaccgc cgcggacacg gctgtgtatt actgtgcgag atggtgggag   300
cttcctgact actggggcca gggaaccctg gtcaccgtct cgagt                   345

<210> SEQ ID NO 25
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
gaaattgtgt tgacgcagtc tccatcctcc ctgtctgcat ctgtaggaga cagagtcacc    60
atcacttgcc gggcaagtca gggcattaga aatgatttag ctggtatca gcagaaacca   120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgtggac gttcggccaa   300
gggaccaagg tggaaatcaa g                                             321

<210> SEQ ID NO 26
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gln Met Gln Leu Val Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Met Ser Val Asp Thr Ser Lys His Gln Phe Ser Leu
65                  70                  75                  80

Lys Leu Ser Ser Val Thr Ala Ala Asp Thr Ala Val Tyr Tyr Cys Ala
                85                  90                  95
```

-continued

Arg Trp Trp Glu Leu Pro Asp Tyr Trp Gly Gln Gly Thr Leu Val Thr
            100                 105                 110

Val Ser Ser
        115

<210> SEQ ID NO 27
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 28
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Gly Ser Phe Ser Gly Tyr Tyr
1               5

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ile Asn His Ser Gly Ser Thr
1               5

<210> SEQ ID NO 30
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 30

Cys Ala Arg Trp Trp Glu Leu Pro Asp Tyr Trp
1               5                   10

<210> SEQ ID NO 31
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gln Gly Ile Arg Asn Asp
1               5

<210> SEQ ID NO 32
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ala Ala Ser
1

<210> SEQ ID NO 33
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Cys Leu Gln His Asn Ser Tyr Pro Trp Thr Phe
1               5                   10

<210> SEQ ID NO 34
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34
cagatgcagc tggtgcaatg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattggggaa atcaatcata gtggaagcac caactacaac     180
ccgtccctca agagtcgagt caccatatca gtagacacgt ccaagaacca gttctccctg     240
aagctgagct ctgtgaccgc cgcggacacg gctgtgtatt actgtgcgag gttttactat     300
gctccgaact ttgactactg gggccagggc accctggtca ccgtctcgag t              351

<210> SEQ ID NO 35
<211> LENGTH: 318
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
gaaattgtgt tgacgcagtc tccttccacc ctgtctgcat ctgtaggaga cagagtcacc      60
atcacttgcc gggccagtca gagtattagt agctggttgg cctggtatca gcagaaacca     120
gggacagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attccacttt cggcggaggg     300
accaaggtgg agatcaaa                                                   318

<210> SEQ ID NO 36
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Gln Met Gln Leu Val Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Phe Tyr Tyr Ala Pro Asn Phe Asp Tyr Trp Gly Gln Gly Thr Leu
            100                 105                 110

Val Thr Val Ser Ser
        115

<210> SEQ ID NO 37
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Glu Ile Val Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Thr Ala Pro Lys Leu Leu Ile
        35                  40                  45

Tyr Lys Ala Ser Ser Leu Glu Ser Gly Val Pro Ser Arg Phe Ser Gly
    50                  55                  60
```

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Thr
                85                  90                  95

Phe Gly Gly Gly Thr Lys Val Glu Ile Lys
            100                 105

<210> SEQ ID NO 38
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gly Gly Ser Phe Ser Gly Tyr Tyr
1               5

<210> SEQ ID NO 39
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Ile Asn His Ser Gly Ser Thr
1               5

<210> SEQ ID NO 40
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Cys Ala Arg Phe Tyr Tyr Ala Pro Asn Phe Asp Tyr Trp
1               5                   10

<210> SEQ ID NO 41
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gln Ser Ile Ser Ser Trp
1               5

<210> SEQ ID NO 42
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Lys Ala Ser
1

<210> SEQ ID NO 43
<211> LENGTH: 10
<212> TYPE: PRT
<213> ORGANIZM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Cys Gln Gln Tyr Asn Ser Tyr Ser Thr Phe
1               5                   10

<210> SEQ ID NO 44
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44
caggtgcagc tgcagcagtc gggcccagga ctggtgaagc cttcggagac cctgtccctc      60
acctgcactg tctctggtgg ctccatcagc agtagtaatt actactgggg ctggatccgc     120
cagcccccag ggaaggggct ggagtggatt gggagtatct attatagtgg gaacacctac     180
tacaacccgt ccctcaagag tcgagtcacc atatccgtag acacgtccaa gaaccagttc     240
tccctgaagc tgagttctgt gaccgccgca gacacggctg tgtattactg tgcgagacag     300
acagtggctg ccccctcttt gactactggg gccagggaa ccctggtcac cgtctcgagt      360

<210> SEQ ID NO 45
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
gaaattgtga tgacgcagtc tccttccacc ctgtctgcat ctgtaggaga cagagtcacc      60
atcacttgcc gggccagtca gagtattagt agctggttgg cctggtatca gcagaaacca     120
gggaaagccc ctaaggtcct gatctataag gcgtctagtt tagaaagtgg ggtcccatca     180
aggttcagcg gcagtggatc tgggacagaa ctcactctca ccatcagcag cctgcagcct     240
gatgattttg caacttatta ctgccaacag tataatagtt attcattcac tttcggccct     300
gggaccaaag tggatatcaa g                                               321

<210> SEQ ID NO 46
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

<400> SEQUENCE: 46

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Tyr Trp Gly Trp Ile Arg Gln Pro Pro Gly Lys Gly Leu Glu
        35                  40                  45

Trp Ile Gly Ser Ile Tyr Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Thr Val Ala Gly Pro Leu Phe Asp Tyr Trp Gly Gln
            100                 105                 110

Gly Thr Leu Val Thr Val Ser Ser
        115                 120

<210> SEQ ID NO 47
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Glu Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Leu Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Thr Phe Gly Pro Gly Thr Lys Val Asp Ile Lys
            100                 105

<210> SEQ ID NO 48
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Gly Ser Ile Ser Ser Ser Asn Tyr Tyr
1               5                   10

<210> SEQ ID NO 49
<211> LENGTH: 7
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 49

Ile Tyr Tyr Ser Gly Asn Thr
1               5

<210> SEQ ID NO 50
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Cys Ala Arg Gln Thr Val Ala Gly Pro Leu Phe Asp Tyr Trp
1               5                   10

<210> SEQ ID NO 51
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gln Ser Ile Ser Ser Trp
1               5

<210> SEQ ID NO 52
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Lys Ala Ser
1

<210> SEQ ID NO 53
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Cys Gln Gln Tyr Asn Ser Tyr Ser Phe Thr Phe
1               5                   10

<210> SEQ ID NO 54
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 54

```
caggtccagc tggtgcaatc tggggctgag gtgaagaagc ctggggcctc agtgaaggtc    60
tcctgcaagg ctgctggata caccttaacc ggctactata tgcactgggt gcgacaggcc   120
cctggacaag gccttgagtg gatgggacgg atcaaccctc acagtggtgg ctcaaacaat   180
gcacagaagt ttcagggcag ggtcaccatg accagggaca cgtccatcag cacagcctac   240
atggagctga gcaggctgag atctgacgac acggccgtgt attactgtgc gagagaggggt   300
cccctgtata gcagtggctg gtacgagggt gcttttgata tctggggcca agggacaatg   360
gtcaccgtct cgagt                                                    375
```

<210> SEQ ID NO 55
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55

```
gaaattgtga tgacgcagtc tccttccacc ctgtctgcat ctgtaggaga cagagtcacc    60
atcacttgcc gggccagtca gagtattagt agttggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attctccggg gctcactttc   300
ggcggaggga ccaaggtgga gatcaag                                       327
```

<210> SEQ ID NO 56
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

```
Gln Val Gln Leu Val Gln Ser Gly Ala Glu Val Lys Lys Pro Gly Ala
1               5                   10                  15

Ser Val Lys Val Ser Cys Lys Ala Ala Gly Tyr Thr Leu Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Ser Asn Asn Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Pro Leu Tyr Ser Ser Gly Trp Tyr Glu Gly Ala Phe
            100                 105                 110

Asp Ile Trp Gly Gln Gly Thr Met Val Thr Val Ser Ser
        115                 120                 125
```

<210> SEQ ID NO 57

```
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Glu Ile Val Met Thr Gln Ser Pro Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Pro
                85                  90                  95

Gly Leu Thr Phe Gly Gly Gly Thr Lys Val Glu Ile Lys
            100                 105

<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Tyr Thr Leu Thr Gly Tyr Tyr
1               5

<210> SEQ ID NO 59
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Ile Asn Pro Asn Ser Gly Gly Ser
1               5

<210> SEQ ID NO 60
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Cys Ala Arg Glu Gly Pro Leu Tyr Ser Ser Gly Trp Tyr Glu Gly Ala
1               5                   10                  15

Phe Asp Ile Trp
            20
```

```
<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gln Ser Ile Ser Ser Trp
1               5

<210> SEQ ID NO 62
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Lys Ala Ser
1

<210> SEQ ID NO 63
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Cys Gln Gln Tyr Asn Ser Tyr Ser Pro Gly Leu Thr Phe
1               5                  10

<210> SEQ ID NO 64
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64
cagatgcagc tacagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
tctgcttttg cagtatctgt gaaaagtcga ataaccatca cccagacaca tccaagaac     240 cagttctccc tgcagctgaa ctctgtgact cccgaggaca cggctgtgta ttactgtgca     300
agagagggta gcagtggctg gtacggatac gtccaccact ggggccaggg caccctggtc     360
accgtctcga gt                                                         372

<210> SEQ ID NO 65
<211> LENGTH: 321
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic polynucleotide"

<400> SEQUENCE: 65

```
gaaattgtgt tgacgcagtc tccagcttcc ctgtctgtat ctctgggaga aactgtcacc    60
atcgaatgtc gagcaagtga ggacatttac aatggtttag catggtatca gcagaagcca   120
gggaaatctc ctcagctcct gatctataat gcaaatagct tgcatactgg ggtcccatca   180
cggttcagtg gcagtggatc tggtacacag tattctctca agataaacag cctgcaatct   240
gaagatgtcg caagttattt ctgtcaacag tattacgatt atcctccgac gttcggccaa   300
gggaccaagg tggaaatcaa a                                             321
```

<210> SEQ ID NO 66
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Gln Met Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Ser Ala Phe Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Gly Ser Ser Gly Trp Tyr Gly Tyr Val His
            100                 105                 110

His Trp Gly Gln Gly Thr Leu Val Thr Val Ser Ser
        115                 120

<210> SEQ ID NO 67
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Glu Ile Val Leu Thr Gln Ser Pro Ala Ser Leu Ser Val Ser Leu Gly
1               5                   10                  15

Glu Thr Val Thr Ile Glu Cys Arg Ala Ser Glu Asp Ile Tyr Asn Gly
            20                  25                  30

Leu Ala Trp Tyr Gln Gln Lys Pro Gly Lys Ser Pro Gln Leu Leu Ile
        35                  40                  45

Tyr Asn Ala Asn Ser Leu His Thr Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys Gln Gln Tyr Tyr Asp Tyr Pro Pro
            85                  90                  95

Thr Phe Gly Gln Gly Thr Lys Val Glu Ile Lys
            100                 105

<210> SEQ ID NO 68
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Gly Asp Ser Val Ser Ser Asn Ser Ala Ala
1               5                   10

<210> SEQ ID NO 69
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Thr Tyr Tyr Arg Ser Lys Trp Tyr Ser
1               5

<210> SEQ ID NO 70
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Cys Ala Arg Glu Gly Ser Ser Gly Trp Tyr Gly Tyr Val His His Trp
1               5                   10                  15

<210> SEQ ID NO 71
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Glu Asp Ile Tyr Asn Gly
1               5

<210> SEQ ID NO 72
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Asn Ala Asn
1

<210> SEQ ID NO 73
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Cys Gln Gln Tyr Tyr Asp Tyr Pro Pro Thr Phe
1               5                   10

<210> SEQ ID NO 74
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
caggtgcagc tgcaggagtc gggcccagga ctggtgaagc cttcggagac cctgtccctc      60
acctgcactg tctctggtgg ctccttcagc agtagtagtt actactgggg ctggatccgc     120 cagcccctg ggaaggggct ggagtggatt gggatcttct attatagtgg gaccacctac      180
tacaacccgt ccctcaagag tcgagtcacc atatccgcac acacgtccaa gagccagttc     240
tccctgaagc tgagctctgt gaccgccgca gacacggctg tgtattactg tgcgagaggg     300
ggagaatatt ttgaccggtt actccccttt gactactggg gccagggaac cctggtcacc     360
gtctcgagt                                                              369

<210> SEQ ID NO 75
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
gaaattgtga tgacgcagtc tccatccttc ctgtctgcat ctgtaggaga cagagtcacc      60
atcacttgcc gggccagtca gggcattagc agttatttag cctggtatca gcaaaaacca     120
gggaaagccc ctaagctcct gatctatgct gcatccactt tggaaagtgg ggtcccatca     180
aggttcagcg gcagtggatc tgggacagaa ttcactctca caatcagcag cctgcagcct     240
gaagattttg caacttatta ctgtcaacag cttaatagtt acccattcac tttcggccct     300
gggaccaaag tggatatcaa a                                                321

<210> SEQ ID NO 76
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 76

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ile Phe Tyr Tyr Ser Gly Thr Thr Tyr Tyr Asn Pro Ser
    50                  55                  60

Leu Lys Ser Arg Val Thr Ile Ser Ala His Thr Ser Lys Ser Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gly Glu Tyr Phe Asp Arg Leu Leu Pro Phe Asp Tyr
            100                 105                 110

Trp Gly Gln Gly Thr Leu Val Thr Val Ser Ser
        115                 120

<210> SEQ ID NO 77
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 77

Glu Ile Val Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Phe
                85                  90                  95

Thr Phe Gly Pro Gly Thr Lys Val Asp Ile Lys
            100                 105

<210> SEQ ID NO 78
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 78

Gly Gly Ser Phe Ser Ser Ser Ser Tyr Tyr
1               5                   10

<210> SEQ ID NO 79

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Phe Tyr Tyr Ser Gly Thr Thr
1               5

<210> SEQ ID NO 80
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Cys Ala Arg Gly Gly Glu Tyr Phe Asp Arg Leu Leu Pro Phe Asp Tyr
1               5                   10                  15

Trp

<210> SEQ ID NO 81
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Gln Gly Ile Ser Ser Tyr
1               5

<210> SEQ ID NO 82
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Ala Ala Ser
1

<210> SEQ ID NO 83
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Cys Gln Gln Leu Asn Ser Tyr Pro Phe Thr Phe
1               5                   10

<210> SEQ ID NO 84
<211> LENGTH: 351
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84
caggtgcagc tggtggagtc tgggggaggc ttggtacagc cggggggtc cctgagactc      60
tcctgtacag cctctggatt cacctttagc agctatgcca tgagctgggt ccgccaggct     120
ccagggaagg ggctggagtg ggtctcagct attggtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgt gaaagatggg     300
gcaggaggct ttgactactg gggccaggga accctggtca ccgtctcgag t              351

<210> SEQ ID NO 85
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
gatattgtga tgacgcagtc ttcatcctcc ctgtctgcat ctgtaggaga cagagtcacc      60
atcacttgcc gggcaagtca gggcattata aatcatttag gctggtatca gcataaacca     120
gggaaagccc ctaatcgcct aatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacgg cataatagtt accctccgac gttcggccaa     300
gggaccaagg tggaaatcaa g                                                321

<210> SEQ ID NO 86
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86
```

Gln Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Gly Ala Gly Gly Phe Asp Tyr Trp Gly Gln Gly Thr Leu
            100                 105                 110

Val Thr Val Ser Ser
            115

```
<210> SEQ ID NO 87
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Asp Ile Val Met Thr Gln Ser Ser Ser Leu Ser Ala Ser Val Gly
1               5                   10                  15

Asp Arg Val Thr Ile Thr Cys Arg Ala Ser Gln Gly Ile Ile Asn His
            20                  25                  30

Leu Gly Trp Tyr Gln His Lys Pro Gly Lys Ala Pro Asn Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Arg His Asn Ser Tyr Pro Pro
                85                  90                  95

Thr Phe Gly Gln Gly Thr Lys Val Glu Ile Lys
            100                 105

<210> SEQ ID NO 88
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Gly Phe Thr Phe Ser Ser Tyr Ala
1               5

<210> SEQ ID NO 89
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Ile Gly Gly Ser Gly Gly Ser Thr
1               5

<210> SEQ ID NO 90
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Cys Val Lys Asp Gly Ala Gly Gly Phe Asp Tyr Trp
1               5                   10
```

<210> SEQ ID NO 91
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 91

Gln Gly Ile Ile Asn His
1               5

<210> SEQ ID NO 92
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 92

Ala Ala Ser
1

<210> SEQ ID NO 93
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 93

Tyr Pro Pro Thr Phe
1               5

<210> SEQ ID NO 94
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 94
caggtgcagc tacagcagtc gggcccagga ctggtgaagc cttcacagac cctgtccctc      60
acctgcactg tctctggtgg ctccatcaac agtggtggtc actactggag ctggatccgc     120
cagcacccag ggaggggcct ggagtggatt gggtacatct attacagtgg gagcatctac     180
tacaacccgt ccctcaagag tcgacttacc atatcagtag acacgtctaa gaaccagttc     240
tccctgaagc tgagctctgt gactgccgcg gacacggccg tgtattactg tgcgagttat     300
tactatgcca gtagtggtga tgcttttgat atctggggcc aagggacaat ggtcaccgtc     360
tcgagt                                                                366

<210> SEQ ID NO 95
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95
gaaacgacac tcacgcagtc tccagccacc ctgtctttgt ctccagggga aagagccacc      60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccgac gttcggccaa    300
gggaccaagg tggaaatcaa a                                              321

<210> SEQ ID NO 96
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Gln Val Gln Leu Gln Gln Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Gly His Tyr Trp Ser Trp Ile Arg Gln His Pro Gly Arg Gly Leu Glu
        35                  40                  45

Trp Ile Gly Tyr Ile Tyr Tyr Ser Gly Ser Ile Tyr Tyr Asn Pro Ser
    50                  55                  60

Leu Lys Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Tyr Tyr Tyr Ala Ser Ser Gly Asp Ala Phe Asp Ile Trp
            100                 105                 110

Gly Gln Gly Thr Met Val Thr Val Ser Ser
        115                 120

<210> SEQ ID NO 97
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Glu Thr Thr Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 98
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gly Gly Ser Ile Asn Ser Gly Gly His Tyr
1               5                   10

<210> SEQ ID NO 99
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Ile Tyr Tyr Ser Gly Ser Ile
1               5

<210> SEQ ID NO 100
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Cys Ala Ser Tyr Tyr Tyr Ala Ser Ser Gly Asp Ala Phe Asp Ile Trp
1               5                   10                  15

<210> SEQ ID NO 101
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gln Ser Val Ser Ser Tyr
1               5

<210> SEQ ID NO 102
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Asp Ala Ser
1

<210> SEQ ID NO 103
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Cys Gln Gln Arg Ser Asn Trp Pro Pro Thr Phe
1               5                   10

<210> SEQ ID NO 104
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104
caggtgcagc tgcaggagtc tgggggaggc ttggtacagc cggggggtc cctgagactc      60 tcctgtacag cctctggatt cacctttagt aattatgcca tgagctgggt ccgccaggct    120
ccagggaagg ggctggagtg gtctcagct attagtggtc gtggtggtag cacattcttc    180
gcagactccg tgaagggccg gttcaccatc tccagadaca attccaagag cacgctgtat    240
ctgcaaacga cagcctgag agccgaggac acggccgtat attactgtgc gaaggggggc    300
ccgttgtata actggaacga cggtgatggt tttgatatct ggggccaagg gaccacggtc    360
acagtctcga gt                                                        372

<210> SEQ ID NO 105
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 105
gaaattgtgt tgacgcagtc tccagccacc ctgtctgtgt ctccagggga aagagccacc      60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcactgggtc tgggacagag ttcactctca ccatcagcag cctgcagtct    240
gaagattttg cactttatta ctgtcagcag tatgataact ggcctccgtg acgttcggc     300 caagggacca aggtggaaat caaa                                            324

<210> SEQ ID NO 106
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Gly Ser Thr Phe Phe Ala Asp Ser Val
    50                  55                  60

Lys Gly Arg Phe Thr Ile Ser Arg Asp Asn Ser Lys Ser Thr Leu Tyr
65                  70                  75                  80

Leu Gln Thr Asn Ser Leu Arg Ala Glu Asp Thr Ala Val Tyr Tyr Cys
                85                  90                  95

Ala Lys Gly Gly Pro Leu Tyr Asn Trp Asn Asp Gly Asp Gly Phe Asp
            100                 105                 110

Ile Trp Gly Gln Gly Thr Thr Val Thr Val Ser Ser
        115                 120

<210> SEQ ID NO 107
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Thr Gly Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asp Asn Trp Pro Pro
                85                  90                  95

Trp Thr Phe Gly Gln Gly Thr Lys Val Glu Ile Lys
            100                 105

<210> SEQ ID NO 108
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Gly Phe Thr Phe Ser Asn Tyr Ala
1               5

<210> SEQ ID NO 109

```
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Ile Ser Gly Arg Gly Gly Ser Thr
1               5

<210> SEQ ID NO 110
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Cys Ala Lys Gly Gly Pro Leu Tyr Asn Trp Asn Asp Gly Asp Gly Phe
1               5                   10                  15

Asp Ile Trp

<210> SEQ ID NO 111
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Gln Ser Val Ser Ser Asn
1               5

<210> SEQ ID NO 112
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Gly Ala Ser
1

<210> SEQ ID NO 113
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Cys Gln Gln Tyr Asp Asn Trp Pro Pro Trp Thr Phe
1               5                   10

<210> SEQ ID NO 114
<211> LENGTH: 357
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 114

```
caggtgcagc tgcaggagtc tgggggaggc ttggtcaagc ctggagggtc cctgagactc      60
tcctgtgcag cctctggatt caccttcagt gactactaca tgacctggat ccgccaggct     120
ccagggaagg ggctggagtg gatttcatac attagtggtg gtggtggttc catatactac     180
gcagactctg tgaagggccg attcaccatc tccagggaca cgccaagaa ctcactgtat      240
ctgcaaatga acagcctgag agccgaggac acggccgttt atttctgtgc gagagggaac     300
tggggatcgg cggctcttga tatctggggc caagggacaa tggtcacggt ctcgagt       357
```

<210> SEQ ID NO 115
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115

```
gaaattgtgt tgacgcagtc tccatcctca ctgtctgcat ctgtaggaga cagagtcacc      60
atcacttgtc gggcgagtca gggcattaac aattatttag cctggtttca gcagaaacca     120
gggagagccc ctaagtccct gatctatgct gcatccagtt tgcaaagtgg ggtcccatcg     180
aagttcagcg gcagtggatc tgggacagat ttcactctca ccatcagcag cctgcagcct     240
gaagattttg caacttatta ctgccaacag tataatagtt accctccaac tctcggccct     300
gggaccaacg tggatatcaa a                                             321
```

<210> SEQ ID NO 116
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 116

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Ile
        35                  40                  45

Ser Tyr Ile Ser Gly Gly Gly Gly Ser Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Gly Asn Trp Gly Ser Ala Ala Leu Asp Ile Trp Gly Gln Gly
            100                 105                 110

Thr Met Val Thr Val Ser Ser
        115
```

<210> SEQ ID NO 117
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 117

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Arg Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Leu Gly Pro Gly Thr Asn Val Asp Ile Lys
            100                 105

<210> SEQ ID NO 118
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 118

Gly Phe Thr Phe Ser Asp Tyr Tyr
1               5

<210> SEQ ID NO 119
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 119

Ile Ser Tyr Ile Ser Gly Gly Gly Gly Ser Ile
1               5                   10

<210> SEQ ID NO 120
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 120

Cys Ala Arg Gly Asn Trp Gly Ser Ala Ala Leu Asp Ile Trp
1               5                   10

<210> SEQ ID NO 121
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 121

Gln Gly Ile Asn Asn Tyr
1               5

<210> SEQ ID NO 122
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 122

Ala Ala Ser
1

<210> SEQ ID NO 123
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 123

Cys Gln Gln Tyr Asn Ser Tyr Pro Pro Thr Leu
1               5                   10

<210> SEQ ID NO 124
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 124
caggtgcagc tggtggagtc tgggggaggc ttggtacagc cggggggggtc cctgagactc      60 tcctgtacag cctctggatt caccttttagc agctatgcca tgagctgggt ccgccaggct    120
ccagggaagg ggctggagtg ggtctcagct attggtggta gtggtggtag cgcatactac    180
gcagactccg tgaagggccg gttcaccatc tccagagaca attccaagaa cacgctgtat    240
ctgcaaatga acagcctgag agccgaggac acggccgtat attactgtgt gaaagatggg    300
gcaggaggct ttgactactg gggccagggc accctggtca ccgtctcgag t             351

<210> SEQ ID NO 125
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 125

```
gacatccagt tgacccagtc cccatcctcc ctgtctgcat ctgtaggaga cagagtcacc    60
atcacttgcc gggcaagtca gggcattaga aatcatttag ctggtatca gcagaaacca   120 gggaaagccc ctaagcgcct aatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt accctccgac gttcggccaa   300
gggaccaagg tggaaatcaa g                                             321
```

<210> SEQ ID NO 126
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 126

```
Gln Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Gly Ala Gly Gly Phe Asp Tyr Trp Gly Gln Gly Thr Leu
            100                 105                 110

Val Thr Val Ser Ser
        115
```

<210> SEQ ID NO 127
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 127

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn His
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95
```

```
Thr Phe Gly Gln Gly Thr Lys Val Glu Ile Lys
            100                 105
```

<210> SEQ ID NO 128
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

```
Gly Phe Thr Phe Ser Ser Tyr Ala
1               5
```

<210> SEQ ID NO 129
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

```
Ile Gly Gly Ser Gly Gly Ser Ala
1               5
```

<210> SEQ ID NO 130
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

```
Cys Val Lys Asp Gly Ala Gly Gly Phe Asp Tyr Trp
1               5                   10
```

<210> SEQ ID NO 131
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

```
Gln Gly Ile Arg Asn His
1               5
```

<210> SEQ ID NO 132
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

```
Ala Ala Ser
1
```

<210> SEQ ID NO 133
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Cys Leu Gln His Asn Ser Tyr Pro Pro Thr Phe
1               5                   10

<210> SEQ ID NO 134
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 134
cagatgcagc tacagcagtc tgggggaggc ttggtacagc cggggggtc cctgagactc     60 tcctgtgcag cctctggatt caccgttagc agctatgcca tgagctgggt ccgccaggct    120
ctagggaagg ggctggagtg ggtctcaggt attagtggta gtggtggtag cacatactac    180
gcagactccg tgaagggccg gttcaccatc tccagagaca attccaagaa tacgctgtat    240
ctgcaaatga acagcctgag agccgaggac acggccgtat attactgtgc gaagatagtg    300
ggagctaccc actttgacta ctggggccag ggaaccctgg tcacggtctc gagt          354

<210> SEQ ID NO 135
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 135
gaaattgtga tgacacagtc tccagactcc ctggctgtgt ctctgggcga gagggccacc     60
atcaactgca gtccagcca gagtgttta tacagctcca acaataagaa ctacttagct      120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtggt    300
ccgatcacct tcggccaagg gacacgactg gagattaag                            339

<210> SEQ ID NO 136
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Gln Met Gln Leu Gln Gln Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Ala Met Ser Trp Val Arg Gln Ala Leu Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Val Gly Ala Thr His Phe Asp Tyr Trp Gly Gln Gly Thr
            100                 105                 110

Leu Val Thr Val Ser Ser
            115

<210> SEQ ID NO 137
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Gly Pro Ile Thr Phe Gly Gln Gly Thr Arg Leu Glu Ile
            100                 105                 110

Lys

<210> SEQ ID NO 138
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Gly Phe Thr Val Ser Ser Tyr Ala
1               5

<210> SEQ ID NO 139
<211> LENGTH: 8
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 139

Ile Ser Gly Ser Gly Gly Ser Thr
1               5

<210> SEQ ID NO 140
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Cys Ala Lys Ile Val Gly Ala Thr His Phe Asp Tyr Trp
1               5                   10

<210> SEQ ID NO 141
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Gln Ser Val Leu Tyr Ser Ser Asn Asn Lys Asn Tyr
1               5                   10

<210> SEQ ID NO 142
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Trp Ala Ser
1

<210> SEQ ID NO 143
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Cys Gln Gln Tyr Tyr Ser Gly Pro Ile Thr Phe
1               5                   10

<210> SEQ ID NO 144
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 144

```
caggtgcagc tggtggagtc gggcccagga ctggtgaagc cttcacagac cctgtccctc    60
acctgcactg tctctggtgg ctccatcaac agtggtggtt actactggag ctggatccgc   120
cagcacccag ggaagggcct ggagtggatt gggtacatct attacagtgg gagcatctac   180
tacaacccgt ccctcaggag tcgacttacc atatcagtag acacgtctaa gaaccagttc   240
tccctgaagc tgagctctgt gactgccgcg gacacggccg tttattactg tgcgactcct   300
tattactatg gttcggggag ttatggggac tactggggcc agggcaccct ggtcactgtc   360
tcgagt                                                               366
```

<210> SEQ ID NO 145
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 145

```
gacatccaga tgacccagtc tccagccacc ctgtctttgt ctccagggga aagagccacc    60
ctctcctgca gggccagtca gagtgttaac aactacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcccatcac cttcggccaa   300
gggacacgac tggagattaa a                                              321
```

<210> SEQ ID NO 146
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 146

```
Gln Val Gln Leu Val Glu Ser Gly Pro Gly Leu Val Lys Pro Ser Gln
 1               5                  10                  15
Thr Leu Ser Leu Thr Cys Thr Val Ser Gly Gly Ser Ile Asn Ser Gly
            20                  25                  30
Gly Tyr Tyr Trp Ser Trp Ile Arg Gln His Pro Gly Lys Gly Leu Glu
        35                  40                  45
Trp Ile Gly Tyr Ile Tyr Tyr Ser Gly Ser Ile Tyr Tyr Asn Pro Ser
    50                  55                  60
Leu Arg Ser Arg Leu Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Thr Pro Tyr Tyr Gly Ser Gly Ser Tyr Gly Asp Tyr Trp
               100                 105                 110
Gly Gln Gly Thr Leu Val Thr Val Ser Ser
       115                 120
```

<210> SEQ ID NO 147

```
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147
```

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Asn Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

```
<210> SEQ ID NO 148
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148
```

Gly Gly Ser Ile Asn Ser Gly Gly Tyr Tyr
1               5                   10

```
<210> SEQ ID NO 149
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149
```

Ile Tyr Tyr Ser Gly Ser Ile
1               5

```
<210> SEQ ID NO 150
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150
```

Cys Ala Thr Pro Tyr Tyr Tyr Gly Ser Gly Ser Tyr Gly Asp Tyr Trp
1               5                   10                  15

```
<210> SEQ ID NO 151
<211> LENGTH: 6
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Gln Ser Val Asn Asn Tyr
1               5

<210> SEQ ID NO 152
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Asp Ala Ser
1

<210> SEQ ID NO 153
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Cys Gln Gln Arg Ser Asn Trp Pro Ile Thr Phe
1               5                   10

<210> SEQ ID NO 154
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 154
cagatgcagc tgcaggagtc gggcccagga ctggtgaagc cttctcagac cctgtccctc      60
acctgcactg tgtctggtgg ctccatcagc agtgttggtt actactggaa ctggatccgc     120
cagcacccag ggaagggcct ggagttcatt gggtacatct attacagtgg gagcatctac     180
tacaatccgt ccctcaagag tcgagttacc atatccgtag acacgtctaa gaaccagttc     240
tccctgaagc tgagctctgt gactgccgcg gacacggccc tatattactg tgcgagcgtc     300
ggtatagtgg gagcctccta ctttgagtac tggggccagg gaaccctggt cacagtctcg     360
agt                                                                    363

<210> SEQ ID NO 155
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 155

```
gaaattgtga tgacacagtc tccagccacc ctgtctttgt ctccagggga aagagccacc      60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctatcac cttcggccaa    300
gggacacgac tggagatcaa g                                              321
```

<210> SEQ ID NO 156
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 156

```
Gln Met Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Val
            20                  25                  30

Gly Tyr Tyr Trp Asn Trp Ile Arg Gln His Pro Gly Lys Gly Leu Glu
        35                  40                  45

Phe Ile Gly Tyr Ile Tyr Tyr Ser Gly Ser Ile Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Leu Tyr Tyr
                85                  90                  95

Cys Ala Ser Val Gly Ile Val Gly Ala Ser Tyr Phe Glu Tyr Trp Gly
            100                 105                 110

Gln Gly Thr Leu Val Thr Val Ser Ser
        115                 120
```

<210> SEQ ID NO 157
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 157

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 158
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Gly Gly Ser Ile Ser Ser Val Gly Tyr Tyr
1               5                   10

<210> SEQ ID NO 159
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Ile Tyr Tyr Ser Gly Ser Ile
1               5

<210> SEQ ID NO 160
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Cys Ala Ser Val Gly Ile Val Gly Ala Ser Tyr Phe Glu Tyr Trp
1               5                   10                  15

<210> SEQ ID NO 161
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Gln Ser Val Ser Ser Tyr
1               5

<210> SEQ ID NO 162
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

Asp Ala Ser
1

<210> SEQ ID NO 163
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Cys Gln Gln Arg Ser Asn Trp Pro Ile Thr Phe
1               5                   10

<210> SEQ ID NO 164
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 164
caggtgcagc tacagcagtc tggggggaggc ttggtacagc ctggggggtc cctgagactc      60
tcctgtgcag cctctggatt caccttaagc agctatgcca tgagctgggt ccgccaggct     120
ccagggaagg ggctggagtg ggtctcaggt attagtggta gtggtggtag cacatacaac     180
gcagactccg tgaagggccg gttcaccatc tccagagaca attccaagaa cacgctgttt     240
ctgcaaatga acagcctgag agccgaggac acggccgtat attactgtgc gaaaattttt     300
gggtcctact actttgacta ctggggccag ggaaccctgg tcacagtctc gagt           354

<210> SEQ ID NO 165
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 165
gaaattgtga tgacacagtc tccagactcc ctggctgtgt ctctgggcga gagggccacc      60
atcaactgca gtccagcca gagtgtttta tacagctcca acaataagaa ctacttagct     120
tggtaccagc agaaaccagg acagcctcct aagctgctca tttactggac atctacccgg     180
gaatccgggg tccctaaccg attcagtggc agcgggtctg ggacagattt cactctcacc     240
atcagcagcc tgcaggctga agatgtggca gtttattact gtcagcaata ttatagtggt     300
cctccgacgt tcggccaagg gaccaaggtg gaaatcaaa                             339

<210> SEQ ID NO 166
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 166

Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Asn Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Ile Phe Gly Ser Tyr Tyr Phe Asp Tyr Trp Gly Gln Gly Thr
            100                 105                 110

Leu Val Thr Val Ser Ser
        115

<210> SEQ ID NO 167
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Thr Ser Thr Arg Glu Ser Gly Val
    50                  55                  60

Pro Asn Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Gly Pro Pro Thr Phe Gly Gln Gly Thr Lys Val Glu Ile
            100                 105                 110

Lys

<210> SEQ ID NO 168
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Gly Phe Thr Leu Ser Ser Tyr Ala
1               5

<210> SEQ ID NO 169
<211> LENGTH: 8

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Ile Ser Gly Ser Gly Gly Ser Thr
1               5

<210> SEQ ID NO 170
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Cys Ala Lys Ile Phe Gly Ser Tyr Tyr Phe Asp Tyr Trp
1               5                   10

<210> SEQ ID NO 171
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Gln Ser Val Leu Tyr Ser Ser Asn Asn Lys Asn Tyr
1               5                   10

<210> SEQ ID NO 172
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Trp Thr Ser
1

<210> SEQ ID NO 173
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Cys Gln Gln Tyr Tyr Ser Gly Pro Pro Thr Phe
1               5                   10

<210> SEQ ID NO 174
<211> LENGTH: 354
<212> TYPE: DNA
<213> ORGANISM: Artificial Sequence
<220> FEATURE:
<221> NAME/KEY: source
```

<223> OTHER INFORMATION: /note="Description of Artificial Sequence:
    Synthetic polynucleotide"

<400> SEQUENCE: 174

```
caggtgcagc tggtggagtc tgggggaggc ttggttcggc ctggggggtc cctgagactc    60
tcctgtgcag tctctggatt cacctttagc agctatgcca tgagctgggt ccgccaggct   120
ccagggaagg ggctggagtg ggtctcaggt attagtggta gtggtggtag cacatacaac   180
gcagactccg tgaagggccg gttcaccatc tccagagaca attccaagaa cacgctgtat   240
cttcaaatga acagcctgag agccgaggac acggccgtat attactgtgc gaaaattttt   300
gggtcctact actttgacta ctggggccag ggaaccctgg tcaccgtctc gagt         354
```

<210> SEQ ID NO 175
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 175

```
gaaattgtga tgacacagtc tccagactcc ctggctgtgt ctctgggcga gagggccacc    60
atcaactgca gtccagccag agtgttttta tacagctcca ataataagaa ctacttagct   120
tggtaccagc agaaatcagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtggt   300
ccaccgacgt tcggccaagg gaccaaggtg gaaatcaaa                          339
```

<210> SEQ ID NO 176
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 176

```
Gln Val Gln Leu Val Glu Ser Gly Gly Gly Leu Val Arg Pro Gly Gly
 1               5                  10                  15

Ser Leu Arg Leu Ser Cys Ala Val Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Asn Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Phe Gly Ser Tyr Tyr Phe Asp Tyr Trp Gly Gln Gly Thr
            100                 105                 110

Leu Val Thr Val Ser Ser
        115
```

<210> SEQ ID NO 177

```
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 177

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Ser Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Gly Pro Pro Thr Phe Gly Gln Gly Thr Lys Val Glu Ile
            100                 105                 110

Lys

<210> SEQ ID NO 178
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Gly Phe Thr Phe Ser Ser Tyr Ala
1               5

<210> SEQ ID NO 179
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Ile Ser Gly Ser Gly Gly Ser Thr
1               5

<210> SEQ ID NO 180
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Cys Ala Lys Ile Phe Gly Ser Tyr Tyr Phe Asp Tyr Trp
1               5                   10
```

```
<210> SEQ ID NO 181
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Gln Ser Val Leu Tyr Ser Ser Asn Asn Lys Asn Tyr
1               5                   10

<210> SEQ ID NO 182
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Trp Ala Ser
1

<210> SEQ ID NO 183
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Cys Gln Gln Tyr Tyr Ser Gly Pro Pro Thr Phe
1               5                   10

<210> SEQ ID NO 184
<211> LENGTH: 377
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184
acgtgacagg gcgcgcccag gtccagctgc aggagagcgg tcccggactg gtgaagccat      60
cccagacact gagcctgact tgtactgtga gcggcggtag catctccagc ggcggctact     120
attggtcctg gatcaggcag cacccaggca agggcctgga gtggatcggc tacatctact     180
atagcggctc tatctactat aaccccttccc tgaagagccg ggtgaccatc tctgtggaca     240
catccaagaa tcagttctat ctgaagctgt cttccgtgac cgccgctgat acagccgtgt     300
actattgcgc ctcactgatg gtctgggggg tcatgggcga ttactggggg cagggcacac     360
tggtcacagt ctcgagt                                                    377

<210> SEQ ID NO 185
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 185

```
gagattgtgc tgacccagtc tcccgccacc ctgtctctga gtcctggcga gagagccacc    60
ctgagctgca gagcctctca gtccgtgtcc agctatctgg cctggtatca gcagaagccc   120
ggccaggctc cccggctgct gatctacgat gcctccaata gagccaccgg catccctgcc   180
agattctccg gctctggctc tggcaccgac tttaccctga ccatctccag cctggaaccc   240
gaggacttcg ccgtgtacta ctgccagcag cggtccgact ggcctcctac atttggccaa   300
ggcaccaagg tggaaatcaa g                                             321
```

<210> SEQ ID NO 186
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 186

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Ile Tyr Tyr Asn Pro Ser
    50                  55                  60

Leu Lys Ser Arg Val Thr Ile Ser Val Asp Thr Ser Lys Asn Gln Phe
65                  70                  75                  80

Tyr Leu Lys Leu Ser Ser Val Thr Ala Ala Asp Thr Ala Val Tyr Tyr
                85                  90                  95

Cys Ala Ser Leu Met Val Trp Gly Val Met Gly Asp Tyr Trp Gly Gln
            100                 105                 110

Gly Thr Leu Val Thr Val Ser Ser
        115                 120
```

<210> SEQ ID NO 187
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 187

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Arg Ser Asp Trp Pro Pro
                85                  90                  95

Thr Phe Gly Gln Gly Thr Lys Val Glu Ile Lys
            100                 105

<210> SEQ ID NO 188
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Gly Gly Ser Ile Ser Ser Gly Gly Tyr Tyr
1               5                   10

<210> SEQ ID NO 189
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Ile Tyr Tyr Ser Gly Ser Ile
1               5

<210> SEQ ID NO 190
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Cys Ala Ser Leu Met Val Trp Gly Val Met Gly Asp Tyr Trp
1               5                   10

<210> SEQ ID NO 191
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Gln Ser Val Ser Ser Tyr
1               5

<210> SEQ ID NO 192
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Asp Ala Ser
1

<210> SEQ ID NO 193
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Cys Gln Gln Arg Ser Asp Trp Pro Pro Thr Phe
1               5                   10

<210> SEQ ID NO 194
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 194
caggtccagc tacagcagtc tgggggaggc ttggttcatc ctgggggtc cctaagactc      60 tcctgtgcag cctctggatt caccgttgac acctatgcca tgacctgggt ccgccaggct     120
ccagggaagg ggctggagtg ggtctcaggt attagcggta gtggtggtag cacatactac     180
gcagactccg tgaagggccg gttcaccatc tccagagaca actccaagaa cacgctgtat     240
ctgcaaatga acagcctgag agacgaggac acggccgtat attactgtgc gaagatagtg     300
ggagttaccc actttgacta ctggggccag ggcaccctgg tcacggtctc gagt            354

<210> SEQ ID NO 195
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 195
gaaattgtga tgacgcagtc tccagactcc ctggctgtgt ctctgggcga gagggccacc      60
atcaactgca gtccagcca gagtgtttta tacaggtcca acaataagaa ctatttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtggt     300
ccgatcacct tcggccaagg gacacgactg gagattaag                            339

<210> SEQ ID NO 196
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 196

Gln Val Gln Leu Gln Gln Ser Gly Gly Gly Leu Val His Pro Gly Gly
1               5                   10                  15

Ser Leu Arg Leu Ser Cys Ala Ala Ser Gly Phe Thr Val Asp Thr Tyr
            20                  25                  30

Ala Met Thr Trp Val Arg Gln Ala Pro Gly Lys Gly Leu Glu Trp Val
        35                  40                  45

Ser Gly Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Lys Ile Val Gly Val Thr His Phe Asp Tyr Trp Gly Gln Gly Thr
            100                 105                 110

Leu Val Thr Val Ser Ser
        115

<210> SEQ ID NO 197
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 197

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Gly Pro Ile Thr Phe Gly Gln Gly Thr Arg Leu Glu Ile
            100                 105                 110

Lys

<210> SEQ ID NO 198
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Gly Phe Thr Val Asp Thr Tyr Ala
1               5

<210> SEQ ID NO 199
<211> LENGTH: 8

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Ile Ser Gly Ser Gly Gly Ser Thr
1               5

<210> SEQ ID NO 200
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Cys Ala Lys Ile Val Gly Val Thr His Phe Asp Tyr Trp
1               5                   10

<210> SEQ ID NO 201
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Gln Ser Val Leu Tyr Arg Ser Asn Asn Lys Asn Tyr
1               5                   10

<210> SEQ ID NO 202
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Trp Ala Ser
1

<210> SEQ ID NO 203
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Cys Gln Gln Tyr Tyr Ser Gly Pro Ile Thr Phe
1               5                   10

<210> SEQ ID NO 204
<211> LENGTH: 369
<212> TYPE: DNA
<213> ORGANISM: Artificial Sequence
<220> FEATURE:
<221> NAME/KEY: source
```

<223> OTHER INFORMATION: /note="Description of Artificial Sequence:
Synthetic polynucleotide"

<400> SEQUENCE: 204

```
caggtcacct tgaaggagtc gggcccagga ctggtgaagc cttcacagac cctgtccctc     60
acctgcactg tctctggtgg ctccatcagc agtggtggtc attactggag ctggatccgc    120
cagcacccag ggaagggcct ggagtggatt gggtacatct cttacagtgg gagcacctac    180
tacaacccgt ccctcaagag tcgacttacc atatcagtag acacgtctaa gaaccagttc    240
tccctgaagc tgagctctgt gactgccgcg gacacggccg tgtattactg cgaccgcg     300
tattacgata ttttgactgg ttacccttt gactactggg gccagggaac cctggtcacg    360
gtctcgagt                                                            369
```

<210> SEQ ID NO 205
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 205

```
gaaattgtga tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccgaca gggccactgg catcccagcc    180
aggttcagtg gcagtgggtc tgggacagac ttcactctca ccatcagcag cctagagcct    240
gaagattttg cagtttatta ctgtcagcag cgtagcaact ggccgatcac cttcggccaa    300
gggacacgac tggagatcaa g                                              321
```

<210> SEQ ID NO 206
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 206

```
Gln Val Thr Leu Lys Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly His Tyr Trp Ser Trp Ile Arg Gln His Pro Gly Lys Gly Leu Glu
        35                  40                  45

Trp Ile Gly Tyr Ile Ser Tyr Ser Gly Ser Thr Tyr Tyr Asn Pro Ser
    50                  55                  60

Leu Lys Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Thr Ala Tyr Tyr Asp Ile Leu Thr Gly Tyr Pro Phe Asp Tyr
            100                 105                 110

Trp Gly Gln Gly Thr Leu Val Thr Val Ser Ser
        115                 120
```

<210> SEQ ID NO 207
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 207

Glu Ile Val Met Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asp Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Ile
                85                  90                  95
Thr Phe Gly Gln Gly Thr Arg Leu Glu Ile Lys
            100                 105

<210> SEQ ID NO 208
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 208

Gly Gly Ser Ile Ser Ser Gly Gly His Tyr
1               5                   10

<210> SEQ ID NO 209
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 209

Ile Ser Tyr Ser Gly Ser Thr
1               5

<210> SEQ ID NO 210
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 210

Cys Ala Thr Ala Tyr Tyr Asp Ile Leu Thr Gly Tyr Pro Phe Asp Tyr
1               5                   10                  15
Trp

<210> SEQ ID NO 211
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 211

Gln Ser Val Ser Ser Tyr
1               5

<210> SEQ ID NO 212
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 212

Asp Ala Ser
1

<210> SEQ ID NO 213
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 213

Cys Gln Gln Arg Ser Asn Trp Pro Ile Thr Phe
1               5                   10

<210> SEQ ID NO 214
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 214
caggtgcagc tacagcagtc gggcccagga ctggtgaagc cttcacagac cctgtccctc     60
acctgcactg tctctggtgg ctccatcagc agtggtggtt actactggag ctggatccgc    120
cagcacccag ggaagggcct ggagtggatt gggtacatct cttatagtgg gagtatctac    180
tacaacccgt ccctcaagag tcgagttacc atatcagtag acacgtctaa gaaccagttc    240
tccctgaagc tgagctctgt gactgccacg gacacggccg tgtattactg tgcgaccgcg    300
tattacgatc ttttgactgg ttacccttt gactactggg gccagggaac cctggtcacg    360
gtctcgagt                                                            369

<210> SEQ ID NO 215
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 215
gaaattgtga tgacgcagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggccgatcac cttcggccaa   300
gggacacgac tggagattaa g                                             321

<210> SEQ ID NO 216
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 216

Gln Val Gln Leu Gln Gln Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Ser Tyr Ser Gly Ser Ile Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Thr Asp Thr Ala Val Tyr Tyr
                85                  90                  95

Cys Ala Thr Ala Tyr Tyr Asp Leu Leu Thr Gly Tyr Pro Phe Asp Tyr
            100                 105                 110

Trp Gly Gln Gly Thr Leu Val Thr Val Ser Ser
        115                 120

<210> SEQ ID NO 217
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 217

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

```
Glu Asp Phe Ala Val Tyr Tyr Cys Gln Gln Arg Ser Asn Trp Pro Ile
                85                  90                  95
Thr Phe Gly Gln Gly Thr Arg Leu Glu Ile Lys
            100                 105
```

<210> SEQ ID NO 218
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 218

```
Gly Gly Ser Ile Ser Ser Gly Gly Tyr Tyr
1               5                   10
```

<210> SEQ ID NO 219
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 219

```
Ile Ser Tyr Ser Gly Ser Ile
1               5
```

<210> SEQ ID NO 220
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 220

```
Cys Ala Thr Ala Tyr Tyr Asp Leu Leu Thr Gly Tyr Pro Phe Asp Tyr
1               5                   10                  15
Trp
```

<210> SEQ ID NO 221
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 221

```
Gln Ser Val Ser Ser Tyr
1               5
```

<210> SEQ ID NO 222
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 222

Asp Ala Ser
1

<210> SEQ ID NO 223
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Cys Gln Gln Arg Ser Asn Trp Pro Ile Thr Phe
1               5                   10

<210> SEQ ID NO 224
<211> LENGTH: 379
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 224
ggcgcgccga ggtgcagctg ctggaatctg gaggaggact ggtccagcca ggtggatccc      60
tgcgactgag ctgcgccgct tctggattca cctttacaag atacgacatg gtgtgggtcc     120
gccaggcacc aggaaaggga ctggagtggg tggctggtat cggcgatagt aacaagatga     180
cccgctacgc acctgccgtc aagggaggg caacaattag tcggacaac tcaaagaata       240 ctctgtatct gcagatgaat tccctgcgag ctgaggatac agcagtgtac tattgtgcca     300
aaggtagctg catcgcctgt gggacgaag ctggccgtat tgatgcatgg ggacagggga      360
ctctggtgac cgtctcgag                                                   379

<210> SEQ ID NO 225
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 225
gctagcctct tacgagctga ctcaggaccc tgcagtgagt gtcgccctgg gccagacagt      60
gagaatcact tgctccggcg gagggagcta cgatggttcc agctactatg ctggtatca     120 gcagaagcca ggacaggcac ctgtgaccgt catctataac aataacaata ggccatctga     180
cattcccgat cggttcagtg gatctagttc agggaacaca gcttctctga ccattacagg     240
agcccaggct gaggacgaag cagattacta ttgtgggtca tacgacaggc cagaaacaaa     300
ttccgattat gtgggaatgt tggtagcgg cactaaagtc accgtcctag g               351

<210> SEQ ID NO 226
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 226

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Asp Met Val Trp Val Arg Gln Ala Pro Gly Lys Gly Leu Glu Trp Val
        35                  40                  45

Ala Gly Ile Gly Asp Ser Asn Lys Met Thr Arg Tyr Ala Pro Ala Val
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Cys Ile Ala Cys Trp Asp Glu Ala Gly Arg Ile Asp
            100                 105                 110

Ala Trp Gly Gln Gly Thr Leu Val Thr Val Ser Ser
            115                 120

<210> SEQ ID NO 227
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 227

Ser Tyr Glu Leu Thr Gln Asp Pro Ala Val Ser Val Ala Leu Gly Gln
1               5                   10                  15

Thr Val Arg Ile Thr Cys Ser Gly Gly Ser Tyr Asp Gly Ser Ser
            20                  25                  30

Tyr Tyr Gly Trp Tyr Gln Gln Lys Pro Gly Gln Ala Pro Val Thr Val
            35                  40                  45

Ile Tyr Asn Asn Asn Arg Pro Ser Asp Ile Pro Asp Arg Phe Ser
    50                  55                  60

Gly Ser Ser Ser Gly Asn Thr Ala Ser Leu Thr Ile Thr Gly Ala Gln
65                  70                  75                  80

Ala Glu Asp Glu Ala Asp Tyr Tyr Cys Gly Ser Tyr Asp Arg Pro Glu
                85                  90                  95

Thr Asn Ser Asp Tyr Val Gly Met Phe Gly Ser Gly Thr Lys Val Thr
            100                 105                 110

Val Leu

<210> SEQ ID NO 228
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Gly Phe Thr Phe Thr Arg Tyr Asp
1               5

<210> SEQ ID NO 229

```
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Ile Gly Asp Ser Asn Lys Met Thr
1               5

<210> SEQ ID NO 230
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Cys Ala Lys Gly Ser Cys Ile Ala Cys Trp Asp Glu Ala Gly Arg Ile
1               5                   10                  15

Asp Ala Trp

<210> SEQ ID NO 231
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Gly Ser Tyr Asp Gly Ser Ser Tyr
1               5

<210> SEQ ID NO 232
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Asn Asn Asn
1

<210> SEQ ID NO 233
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Cys Gly Ser Tyr Asp Arg Pro Glu Thr Asn Ser Asp Tyr Val Gly Met
1               5                   10                  15

Phe

<210> SEQ ID NO 234
```

<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 234

```
ggcgcgccga ggtgcagctg ctggaaagcg gaggaggact ggtccagcca ggtggatctc    60
tgcgactgag ttgcgccgct tcaggcttca cattttctga ctacgccatg aactgggtga   120
ggcaggctcc tggcaaggga ctggagtggg tcgcaggaat cgggaacgat ggaagttaca   180
ctaattatgg agcagccgtg aaggggagag ctactatttc ccgcgacaac agcaaaaata   240
ccctgtacct gcagatgaac tcactgagag ctgaagatac cgcagtgtac tattgtgcct   300
ctgacatcag gagtcggaat gattgctcct atttcctggg agggtgttcc agcggcttta   360
ttgacgtgtg gggtcagggc accctggtca cagtctcgag                          400
```

<210> SEQ ID NO 235
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 235

```
gctagcctct tacgagctga cccaggaccc agcagtgtcc gtcgccctgg gccagacagt    60
gagaatcact tgctccggcg gatccagcta cagctatggg tggttccagc agaagcccgg   120
tcaggcccct gtgaccgtca tctatgaaag taacaatagg ccatcagaca ttcccgatcg   180
gttttctggc tctagttcag gaaacacagc tagtctgacc atcacagggg cccaggctga   240
ggacgaagct gattactatt gtggcaatgc agattccagc tctggaattt tcgggtccgg   300
tactaaagtc accgtcctag g                                              321
```

<210> SEQ ID NO 236
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 236

```
Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Asp Tyr
            20                  25                  30

Ala Met Asn Trp Val Arg Gln Ala Pro Gly Lys Gly Leu Glu Trp Val
        35                  40                  45

Ala Gly Ile Gly Asn Asp Gly Ser Tyr Thr Asn Tyr Gly Ala Ala Val
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Ala Ser Asp Ile Arg Ser Arg Asn Asp Cys Ser Tyr Phe Leu Gly Gly
            100                 105                 110

Cys Ser Ser Gly Phe Ile Asp Val Trp Gly Gln Gly Thr Leu Val Thr
        115                 120                 125

Val Ser Ser
    130

<210> SEQ ID NO 237
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 237

Ser Tyr Glu Leu Thr Gln Asp Pro Ala Val Ser Val Ala Leu Gly Gln
1               5                   10                  15

Thr Val Arg Ile Thr Cys Ser Gly Gly Ser Ser Tyr Ser Tyr Gly Trp
            20                  25                  30

Phe Gln Gln Lys Pro Gly Gln Ala Pro Val Thr Val Ile Tyr Glu Ser
        35                  40                  45

Asn Asn Arg Pro Ser Asp Ile Pro Asp Arg Phe Ser Gly Ser Ser Ser
    50                  55                  60

Gly Asn Thr Ala Ser Leu Thr Ile Thr Gly Ala Gln Ala Glu Asp Glu
65                  70                  75                  80

Ala Asp Tyr Tyr Cys Gly Asn Ala Asp Ser Ser Ser Gly Ile Phe Gly
                85                  90                  95

Ser Gly Thr Lys Val Thr Val Leu
            100

<210> SEQ ID NO 238
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Gly Phe Thr Phe Ser Asp Tyr Ala
1               5

<210> SEQ ID NO 239
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Ile Gly Asn Asp Gly Ser Tyr Thr
1               5

<210> SEQ ID NO 240
<211> LENGTH: 26
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 240

Cys Ala Ser Asp Ile Arg Ser Arg Asn Asp Cys Ser Tyr Phe Leu Gly
1               5                   10                  15

Gly Cys Ser Ser Gly Phe Ile Asp Val Trp
            20                  25

<210> SEQ ID NO 241
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Ser Ser Tyr Ser
1

<210> SEQ ID NO 242
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Glu Ser Asn
1

<210> SEQ ID NO 243
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Cys Gly Asn Ala Asp Ser Ser Ser Gly Ile Phe
1               5                   10

<210> SEQ ID NO 244
<211> LENGTH: 385
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 244
ggcgcgccga ggtgcagctg ctggaatccg gaggaggact ggtccagcca ggtggatccc      60
tgcgactgag ctgcgccgct tctgattcg actttagcga tcacgggatg cagtgggtga     120
gacaggcacc aggcaaggga ctggagtacg tgggtgtcat cgacaccaca ggccgctata    180
catactatgc acctgccgtc aagggcaggg ctaccattag tcggacaac tcaaaaaata     240 cactgtacct gcagatgaac tctctgaggg ctgaagatac tgcagtgtac tattgcgcca    300
```

```
aaactacctg cgtgggaggg tacctgtgca ataccgtcgg aagtatcgat gcttggggac    360
aggggacact ggtgactgtc tcgag                                         385
```

<210> SEQ ID NO 245
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 245

```
gctagcctcc tacgagctga ctcaggaccc agcagtgagc gtcgccctgg gccagacagt     60
gagaatcact tgctctggcg gagggtccag ctcttactat ggttggtacc agcagaagcc    120
cggccaggct cctgtgaccg tcatctatga cgatacaaac aggccaagtg gaattcccga    180
tcggttctca ggtagttcat ccggcaatac agcttctctg accatcacag gggcccaggc    240
tgaggacgaa gcagattact attgtggtgg ctatgaagga agctctcacg ccgggatttt    300
tggaagtggg actaaagtca ccgtcctagg                                     330
```

<210> SEQ ID NO 246
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 246

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Asp His
            20                  25                  30

Gly Met Gln Trp Val Arg Gln Ala Pro Gly Lys Gly Leu Glu Tyr Val
        35                  40                  45

Gly Val Ile Asp Thr Thr Gly Arg Tyr Thr Tyr Tyr Ala Pro Ala Val
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Thr Cys Val Gly Gly Tyr Leu Cys Asn Thr Val Gly Ser
            100                 105                 110

Ile Asp Ala Trp Gly Gln Gly Thr Leu Val Thr Val Ser Ser
        115                 120                 125
```

<210> SEQ ID NO 247
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 247

```
Ser Tyr Glu Leu Thr Gln Asp Pro Ala Val Ser Val Ala Leu Gly Gln
1               5                   10                  15
```

```
Thr Val Arg Ile Thr Cys Ser Gly Gly Ser Ser Tyr Tyr Gly
            20                  25                  30

Trp Tyr Gln Gln Lys Pro Gly Gln Ala Pro Val Thr Val Ile Tyr Asp
        35                  40                  45

Asp Thr Asn Arg Pro Ser Gly Ile Pro Asp Arg Phe Ser Gly Ser Ser
        50                  55                  60

Ser Gly Asn Thr Ala Ser Leu Thr Ile Thr Gly Ala Gln Ala Glu Asp
65                  70                  75                  80

Glu Ala Asp Tyr Tyr Cys Gly Tyr Glu Gly Ser Ser His Ala Gly
                85                  90                  95

Ile Phe Gly Ser Gly Thr Lys Val Thr Val Leu
            100                 105
```

<210> SEQ ID NO 248
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 248

```
Gly Phe Asp Phe Ser Asp His Gly
1               5
```

<210> SEQ ID NO 249
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

```
Ile Asp Thr Thr Gly Arg Tyr Thr
1               5
```

<210> SEQ ID NO 250
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

```
Cys Ala Lys Thr Thr Cys Val Gly Gly Tyr Leu Cys Asn Thr Val Gly
1               5                   10                  15

Ser Ile Asp Ala Trp
            20
```

<210> SEQ ID NO 251
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Gly Ser Ser Ser Tyr
1               5

<210> SEQ ID NO 252
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Asp Asp Thr
1

<210> SEQ ID NO 253
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Cys Gly Gly Tyr Glu Gly Ser Ser His Ala Gly Ile Phe
1               5                   10

<210> SEQ ID NO 254
<211> LENGTH: 376
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 254
ggcgcgccga ggtgcagctg ctggaaagtg gaggaggact ggtccagcca ggtggaagcc      60
tgagactgtc ttgcgccgct agtggcttcg acttttccag ctacaccatg cagtgggtga     120
ggcaggcacc aggcaaggga ctggagtggg tgggcgtcat ctctagtact ggagggtcta     180
ccggatacgg gcctgctgtg aagggaaggg caacaatttc acgggataac tccaaaaata     240
ctctgtatct gcagatgaac agcctgaggg cagaagacac agccgtgtac tattgcgtga     300
aatcaatctc cggagatgcc tggtctgtgg acgggctgga tgcttggggt cagggcaccc     360
tggtcacagt ctcgag                                                     376

<210> SEQ ID NO 255
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 255
gctagcctca tacgagctga cccaggaccc agcagtgtcc gtcgccctgg gacagacagt      60
gagaatcact tgctccggag gaggatccgc ctacggttgg tatcagcaga gcccggcca     120 ggcacctgtg accgtcatct actataacaa tcagaggcca tctggcattc ccgaccggtt     180

-continued

```
cagtggatcc agctctggga acacagcaag tctgaccatc acaggcgccc aggctgagga     240
cgaagccgat tactattgtg gaagctatga tagttcagct gtggggattt ttggttctgg     300
cactaaagtc accgtcctag g                                                321
```

<210> SEQ ID NO 256
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 256

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Asp Phe Ser Ser Tyr
            20                  25                  30

Thr Met Gln Trp Val Arg Gln Ala Pro Gly Lys Gly Leu Glu Trp Val
        35                  40                  45

Gly Val Ile Ser Ser Thr Gly Gly Ser Thr Gly Tyr Gly Pro Ala Val
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Ser Ile Ser Gly Asp Ala Trp Ser Val Asp Gly Leu Asp Ala
            100                 105                 110

Trp Gly Gln Gly Thr Leu Val Thr Val Ser Ser
        115                 120
```

<210> SEQ ID NO 257
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 257

```
Ser Tyr Glu Leu Thr Gln Asp Pro Ala Val Ser Val Ala Leu Gly Gln
 1               5                  10                  15

Thr Val Arg Ile Thr Cys Ser Gly Gly Ser Ala Tyr Gly Trp Tyr
            20                  25                  30

Gln Gln Lys Pro Gly Gln Ala Pro Val Thr Val Ile Tyr Tyr Asn Asn
        35                  40                  45

Gln Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ser Tyr Asp Ser Ser Ala Val Gly Ile Phe Gly
                85                  90                  95

Ser Gly Thr Lys Val Thr Val Leu
            100
```

<210> SEQ ID NO 258
<211> LENGTH: 8

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 258

Gly Phe Asp Phe Ser Ser Tyr Thr
1               5

<210> SEQ ID NO 259
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 259

Ile Ser Ser Thr Gly Gly Ser Thr
1               5

<210> SEQ ID NO 260
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Cys Val Lys Ser Ile Ser Gly Asp Ala Trp Ser Val Asp Gly Leu Asp
1               5                   10                  15

Ala Trp

<210> SEQ ID NO 261
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Gly Ser Ala
1

<210> SEQ ID NO 262
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Tyr Asn Asn
1

<210> SEQ ID NO 263
<211> LENGTH: 12
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic peptide"

<400> SEQUENCE: 263

Cys Gly Ser Tyr Asp Ser Ser Ala Val Gly Ile Phe
1               5                   10

<210> SEQ ID NO 264
<211> LENGTH: 376
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 264

```
ggcgcgccga ggtgcagctg ctggaaagtg gaggaggact ggtccagcca ggtggaagcc      60
tgagactgtc ttgcgccgct agtggcttcg acttttccag ctacaccatg cagtgggtga     120
ggcaggcacc aggcaaggga ctggagtggg tgggcgtcat ctctagtact ggagggtcta     180
ccggatacgg gcctgctgtg aagggaaggg caacaatttc acgggataac tccaaaaata     240
ctctgtatct gcagatgaac agcctgaggg cagaagacac agccgtgtac tattgcgtga     300
aatcagtctc cggagatgcc tggtctgtgg acgggctgga tgcttggggt cagggcaccc     360
tggtcacagt ctcgag                                                     376
```

<210> SEQ ID NO 265
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 265

```
gctagcctca tacgagctga cccaggaccc agcagtgtcc gtcgccctgg gccagacagt      60
gagaatcact tgctccggag gaggatccgc ctacggttgg tatcagcaga gcccggcca     120
ggcacctgtg accgtcatct actataacaa tcagaggcca tctgacattc ccgatcggtt     180
cagtggatcc agctctggga acacagcaag tctgaccatc acaggcgccc aggctgagga     240
cgaagccgat tactattgtg gaagctatga tagttcagct gtggggattt ttggttctgg     300
cactaaagtc accgtcctag g                                               321
```

<210> SEQ ID NO 266
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 266

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Tyr
            20                  25                  30

```
Thr Met Gln Trp Val Arg Gln Ala Pro Gly Lys Gly Leu Glu Trp Val
            35                  40                  45

Gly Val Ile Ser Ser Thr Gly Gly Ser Thr Gly Tyr Gly Pro Ala Val
        50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Ser Val Ser Gly Asp Ala Trp Ser Val Asp Gly Leu Asp Ala
                100                 105                 110

Trp Gly Gln Gly Thr Leu Val Thr Val Ser Ser
            115                 120
```

```
<210> SEQ ID NO 267
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 267

Ser Tyr Glu Leu Thr Gln Asp Pro Ala Val Ser Val Ala Leu Gly Gln
1               5                   10                  15

Thr Val Arg Ile Thr Cys Ser Gly Gly Ser Ala Tyr Gly Trp Tyr
            20                  25                  30

Gln Gln Lys Pro Gly Gln Ala Pro Val Thr Val Ile Tyr Tyr Asn Asn
            35                  40                  45

Gln Arg Pro Ser Asp Ile Pro Asp Arg Phe Ser Gly Ser Ser Ser Gly
        50                  55                  60

Asn Thr Ala Ser Leu Thr Ile Thr Gly Ala Gln Ala Glu Asp Glu Ala
65                  70                  75                  80

Asp Tyr Tyr Cys Gly Ser Tyr Asp Ser Ser Ala Val Gly Ile Phe Gly
                85                  90                  95

Ser Gly Thr Lys Val Thr Val Leu
            100
```

```
<210> SEQ ID NO 268
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Gly Phe Asp Phe Ser Ser Tyr Thr
1               5
```

```
<210> SEQ ID NO 269
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 269

Ile Ser Ser Thr Gly Gly Ser Thr
1               5

<210> SEQ ID NO 270
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 270

Cys Val Lys Ser Val Ser Gly Asp Ala Trp Ser Val Asp Gly Leu Asp
1               5                   10                  15

Ala Trp

<210> SEQ ID NO 271
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 271

Gly Ser Ala
1

<210> SEQ ID NO 272
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 272

Tyr Asn Asn
1

<210> SEQ ID NO 273
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273

Cys Gly Ser Tyr Asp Ser Ser Ala Val Gly Ile Phe
1               5                   10

<210> SEQ ID NO 274
<211> LENGTH: 385
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 274

```
ggcgcgccga ggtgcagctg ctggaatccg gaggaggact ggtccagcca ggtggaagcc      60
tgcgactgtc ttgcgccgct agtggattcg acttttccag ctacggaatg cagtgggtga     120
ggcaggcacc aggcaaggga ctggagtggg tgggcgtcat ctctggaagt gggattacca     180
cactgtacgc acctgccgtc aagggaaggg ctactatctc acgggacaac tctaaaaata     240
cagtgtatct gcagatgaac tccctgagag ctgaagatac cgcagtctac tattgtacac     300
gctcaccctc catcacagac ggctggactt atggaggggc ctggattgat gcttggggtc     360
agggcactct ggtgaccgtc tcgag                                           385
```

<210> SEQ ID NO 275
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 275

```
gctagccagc tacgagctga cccaggaccc agcagtgtcc gtcgccctgg gccagacagt      60
gagaatcact tgcagtggcg gagatgggtc atacggttgg ttccagcaga agcccggaca     120
ggcccctgtg accgtcatct atgacaacga taataggcca tctgacattc ccgatcggtt     180
tagtggctcc agctctggaa acacagcttc tctgaccatc acaggggccc aggctgagga     240
cgaagctgat tactattgtg caatgcaga cctgtccggg ggtattttcg gcagcggaac     300
taaagtcacc gtcctagg                                                  318
```

<210> SEQ ID NO 276
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 276

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Tyr
            20                  25                  30

Gly Met Gln Trp Val Arg Gln Ala Pro Gly Lys Gly Leu Glu Trp Val
        35                  40                  45

Gly Val Ile Ser Gly Ser Gly Ile Thr Thr Leu Tyr Ala Pro Ala Val
    50                  55                  60

Lys Gly Arg Ala Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Thr Arg Ser Pro Ser Ile Thr Asp Gly Trp Thr Tyr Gly Gly Ala Trp
            100                 105                 110

Ile Asp Ala Trp Gly Gln Gly Thr Leu Val Thr Val Ser Ser
        115                 120                 125
```

<210> SEQ ID NO 277

-continued

```
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 277

Ser Tyr Glu Leu Thr Gln Asp Pro Ala Val Ser Val Ala Leu Gly Gln
1               5                  10                  15

Thr Val Arg Ile Thr Cys Ser Gly Gly Asp Gly Ser Tyr Gly Trp Phe
            20                  25                  30

Gln Gln Lys Pro Gly Gln Ala Pro Val Thr Val Ile Tyr Asp Asn Asp
        35                  40                  45

Asn Arg Pro Ser Asp Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Asn Ala Asp Leu Ser Gly Ile Phe Gly Ser
                85                  90                  95

Gly Thr Lys Val Thr Val Leu
            100

<210> SEQ ID NO 278
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Gly Phe Asp Phe Ser Ser Tyr Gly
1               5

<210> SEQ ID NO 279
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Ile Ser Gly Ser Gly Ile Thr Thr
1               5

<210> SEQ ID NO 280
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

Cys Thr Arg Ser Pro Ser Ile Thr Asp Gly Trp Thr Tyr Gly Gly Ala
1               5                  10                  15

Trp Ile Asp Ala Trp
            20
```

```
<210> SEQ ID NO 281
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Asp Gly Ser
1

<210> SEQ ID NO 282
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Asp Asn Asp
1

<210> SEQ ID NO 283
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Cys Gly Asn Ala Asp Leu Ser Gly Gly Ile Phe
1               5                   10

<210> SEQ ID NO 284
<211> LENGTH: 388
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 284
ggcgcgccga ggtgcagctg ctggaatctg gaggaggact ggtccagcca ggtggatccc      60
tgagactgag ctgcgccgct tctggattca cctttagtac attcaacatg gtgtgggtca     120
ggcaggcacc tggaaaggga ctggagtacg tggctgaaat ctccagcgac ggctctttta     180
catggtatgc aactgccgtc aagggcaggg ccaccattag tcgggataac tcaaaaaata     240
cagtgtacct gcagatgaat ccctgagggc tgaggacac cgcagtctac tattgcgcaa      300
aatccgattg ttctagttca tactatggat atagctgtat cgggatcatt gacgcttggg     360
gtcagggcac tctggtgacc gtctcgag                                         388

<210> SEQ ID NO 285
<211> LENGTH: 339
<212> TYPE: DNA
<213> ORGANISM: Artificial Sequence
<220> FEATURE:
<221> NAME/KEY: source
```

<223> OTHER INFORMATION: /note="Description of Artificial Sequence:
Synthetic polynucleotide"

<400> SEQUENCE: 285

```
gctagcctcc tatgagctga cccaggaccc agcagtgagc gtcgccctgg gccagacagt    60
gagaatcact tgctccggcg gaattagcga cgatggctct tactattacg gatggttcca   120
gcagaagccc ggacaggccc ctgtgaccgt catctatatt aacgacaggc ggccaagtaa   180
tatccccgat aggttttcag gtccagctc tggtaacaca gcttctctga ccattacagg   240
ggcccaggct gaggacgaag ctgattatta ctgtggctct tacgatagtt cagcaggggt   300
gggtatcttc ggcagtggaa ctaaagtcac cgtcctagg                          339
```

<210> SEQ ID NO 286
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 286

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Asn Met Val Trp Val Arg Gln Ala Pro Gly Lys Gly Leu Glu Tyr Val
        35                  40                  45

Ala Glu Ile Ser Ser Asp Gly Ser Phe Thr Trp Tyr Ala Thr Ala Val
    50                  55                  60

Lys Gly Arg Ala Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
            85                  90                  95

Ala Lys Ser Asp Cys Ser Ser Ser Tyr Tyr Gly Tyr Ser Cys Ile Gly
        100                 105                 110

Ile Ile Asp Ala Trp Gly Gln Gly Thr Leu Val Thr Val Ser Ser
    115                 120                 125
```

<210> SEQ ID NO 287
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 287

```
Ser Tyr Glu Leu Thr Gln Asp Pro Ala Val Ser Val Ala Leu Gly Gln
1               5                   10                  15

Thr Val Arg Ile Thr Cys Ser Gly Gly Ile Ser Asp Asp Gly Ser Tyr
            20                  25                  30

Tyr Tyr Gly Trp Phe Gln Gln Lys Pro Gly Gln Ala Pro Val Thr Val
        35                  40                  45

Ile Tyr Ile Asn Asp Arg Arg Pro Ser Asn Ile Pro Asp Arg Phe Ser
    50                  55                  60

Gly Ser Ser Ser Gly Asn Thr Ala Ser Leu Thr Ile Thr Gly Ala Gln
65                  70                  75                  80
```

Ala Glu Asp Glu Ala Asp Tyr Tyr Cys Gly Ser Tyr Asp Ser Ser Ala
            85                  90                  95

Gly Val Gly Ile Phe Gly Ser Gly Thr Lys Val Thr Val Leu
            100                 105                 110

<210> SEQ ID NO 288
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Gly Phe Thr Phe Ser Thr Phe Asn
1               5

<210> SEQ ID NO 289
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

Ile Ser Ser Asp Gly Ser Phe Thr
1               5

<210> SEQ ID NO 290
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 290

Cys Ala Lys Ser Asp Cys Ser Ser Ser Tyr Tyr Gly Tyr Ser Cys Ile
1               5                   10                  15

Gly Ile Ile Asp Ala Trp
            20

<210> SEQ ID NO 291
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Ile Ser Asp Asp Gly Ser Tyr Tyr
1               5

<210> SEQ ID NO 292
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Ile Asn Asp
1

<210> SEQ ID NO 293
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Cys Gly Ser Tyr Asp Ser Ser Ala Gly Val Gly Ile Phe
1               5                   10

<210> SEQ ID NO 294
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 294

| | | | | | | |
|---|---|---|---|---|---|---|
| ggcgcgccga | ggtgcagctg | ctggaaagtg | gaggaggact | ggtccagcca | ggtggatcac | 60 |
| tgagactgtc | ctgcgccgcc | tccggcttca | ccttttccag | ctacaacatg | ttctgggtgc | 120 |
| gccaggcacc | aggaaaggga | ctggagtttg | tcgctgaaat | ctctggtagt | aatactggaa | 180 |
| gccgaacctg | gtacgcacct | gccgtgaagg | cagggctac | aatttctcgg | gacaacagta | 240 |
| aaaatactct | gtatctgcag | atgaactctc | tgagggctga | ggatacagca | gtgtactatt | 300 |
| gtgcaaaatc | aatctacgga | gggtattgcg | ccggtggcta | ttcctgtggt | gtgggcctga | 360 |
| ttgacgcatg | gggacagggg | accctggtca | cagtctcgag | | | 400 |

<210> SEQ ID NO 295
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 295

| | | | | | | |
|---|---|---|---|---|---|---|
| gctagcctca | tacgagctga | cccaggaccc | agcagtgtcc | gtcgccctgg | gccagacagt | 60 |
| gagaatcact | tgcagtggcg | gatccagcga | ttactatggg | tggttccagc | agaagcccgg | 120 |
| tcaggcccct | gtgaccgtca | tctactataa | caacaagagg | ccatctgaca | ttcccgatcg | 180 |
| gtttagtggc | tctagttcag | gaaacacagc | ctccctgacc | attacagggg | cccaggctga | 240 |
| ggacgaagct | gattactatt | gtggcaatgc | agactccagc | gtgggagtct | tcgggtctgg | 300 |
| tactaaggtg | accgtcctag | g | | | | 321 |

<210> SEQ ID NO 296
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 296

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asn Met Phe Trp Val Arg Gln Ala Pro Gly Lys Gly Leu Glu Phe Val
        35                  40                  45

Ala Glu Ile Ser Gly Ser Asn Thr Gly Ser Arg Thr Trp Tyr Ala Pro
    50                  55                  60

Ala Val Lys Gly Arg Ala Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Ile Tyr Gly Gly Tyr Cys Ala Gly Gly Tyr Ser
            100                 105                 110

Cys Gly Val Gly Leu Ile Asp Ala Trp Gly Gln Gly Thr Leu Val Thr
        115                 120                 125

Val Ser Ser
    130

<210> SEQ ID NO 297
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 297

Ser Tyr Glu Leu Thr Gln Asp Pro Ala Val Ser Val Ala Leu Gly Gln
1               5                   10                  15

Thr Val Arg Ile Thr Cys Ser Gly Gly Ser Ser Asp Tyr Tyr Gly Trp
            20                  25                  30

Phe Gln Gln Lys Pro Gly Gln Ala Pro Val Thr Val Ile Tyr Tyr Asn
        35                  40                  45

Asn Lys Arg Pro Ser Asp Ile Pro Asp Arg Phe Ser Gly Ser Ser Ser
    50                  55                  60

Gly Asn Thr Ala Ser Leu Thr Ile Thr Gly Ala Gln Ala Glu Asp Glu
65                  70                  75                  80

Ala Asp Tyr Tyr Cys Gly Asn Ala Asp Ser Ser Val Gly Val Phe Gly
                85                  90                  95

Ser Gly Thr Lys Val Thr Val Leu
            100

<210> SEQ ID NO 298
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 298

Gly Phe Thr Phe Ser Ser Tyr Asn
1               5

-continued

```
<210> SEQ ID NO 299
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Ile Ser Gly Ser Asn Thr Gly Ser Arg Thr
1               5                   10

<210> SEQ ID NO 300
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Cys Ala Lys Ser Ile Tyr Gly Gly Tyr Cys Ala Gly Gly Tyr Ser Cys
1               5                   10                  15

Gly Val Gly Leu Ile Asp Ala Trp
            20

<210> SEQ ID NO 301
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Ser Ser Asp Tyr
1

<210> SEQ ID NO 302
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

Tyr Asn Asn
1

<210> SEQ ID NO 303
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Cys Gly Asn Ala Asp Ser Ser Val Gly Val Phe
1               5                   10
```

<210> SEQ ID NO 304
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 304

```
caggtgcagc tgcagcagtg gggtgccggt ctgctgaagc cttctgaaac tctgtctctg      60
acttgtgccg tctatggtgg atcattcagc ggctactatt ggtcctggat caggcagccc     120
cctggcaagg gcctggagtg gatcggcgag atcaaccacc ggggctctac caactacaat     180
ccctctctga agagcagggt gaccatctcc gtggacacat ctaagaatca gttcagcctg     240
aagctgagct ccgtgaccgc cgctgataca gccgtgtact attgcacaag gggggaggaa     300
tgggagtcac tgttctttga ttactggggg caggggacac tggtcacagt ctcgagt       357
```

<210> SEQ ID NO 305
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 305

```
gaaatcgtcc tgacccagtc ccccgccacc ctgagcctga gccccggaga aagagccacc      60
ctgtcctgcc gagcaagcca gtccatcagc tcctatctcg cctggtatca gcagaaacca     120
ggccaggctc cccggctgct gatctacggc gcctccaaca gagctacagg aatcccagcc     180
cgcttcagcg gctccggctc tggcacagac tttaccctga caatctctag cctggagcct     240
gaggatttcg ccgtgtacta ttgccagcag agatctaatt ggccactgac attcggcggc     300
ggcacacggg tggagatcaa g                                                321
```

<210> SEQ ID NO 306
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 306

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95
```

```
Arg Gly Glu Glu Trp Glu Ser Leu Phe Phe Asp Tyr Trp Gly Gln Gly
                100                 105                 110

Thr Leu Val Thr Val Ser Ser
        115

<210> SEQ ID NO 307
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 307

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Arg Val Glu Ile Lys
            100                 105

<210> SEQ ID NO 308
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Gly Gly Ser Phe Ser Gly Tyr Tyr
1               5

<210> SEQ ID NO 309
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Ile Asn His Arg Gly Ser Thr
1               5

<210> SEQ ID NO 310
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 310

Cys Thr Arg Gly Glu Glu Trp Glu Ser Leu Phe Phe Asp Tyr Trp
1               5                   10                  15

<210> SEQ ID NO 311
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Gln Ser Ile Ser Ser Tyr
1               5

<210> SEQ ID NO 312
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Gly Ala Ser
1

<210> SEQ ID NO 313
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Cys Gln Gln Arg Ser Asn Trp Pro Leu Thr Phe
1               5                   10

<210> SEQ ID NO 314
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 314
caggttcagc tgcagcagtg gggcgccggc ctgctgagac caagcgagac cctgtccctg      60
acatgcgccg tgtatggcga gagcttctcc ggctattact ggaactggat ccggcagcct     120
cccggcaagg gcctggagtg gatcggcgag atcaatcact ccggctccac caattacaac     180
ccatccctga gtctcgggt gacaatcagc gtggatacaa gcaagaccca gttcagcctg     240
aagctgagct ccgtgacagc tgccgatacc gccgtgtatt actgcgccag aggctgggac     300
ctgctggatt ggaatgacta ctggaatgag tactggggcc aggggaccct ggtgaccgtc     360
tcgagt                                                                366

<210> SEQ ID NO 315

<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 315

```
gagatcgtgc tgacccagtc ccctgccacc ctgtctctgt ccctggcga gcgggccacc    60
ctgtcctgta gagcttctca gtccgtgtct tcctacctgg cttggtacca gcagaagcca   120
ggacaggccc caagactgct gatctatgac gcttccaatc gggctaccgg catcccagct   180
cgctttagcg gctccggctc cggcaccgac ttcaccctga caatcagctc cctggagcca   240
gaggattttg ccgtgtatta ctgtcagcag aggtccaatt ggccactgac atttggcggc   300
ggcacaaagg ttgagatcaa g                                             321
```

<210> SEQ ID NO 316
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 316

Gln Val Gln Leu Gln Gln Trp Gly Ala Gly Leu Leu Arg Pro Ser Glu
1               5                   10                  15

Thr Leu Ser Leu Thr Cys Ala Val Tyr Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Thr Gln Phe Ser Leu
65                  70                  75                  80

Lys Leu Ser Ser Val Thr Ala Ala Asp Thr Ala Val Tyr Tyr Cys Ala
                85                  90                  95

Arg Gly Trp Asp Leu Leu Asp Trp Asn Asp Tyr Trp Asn Glu Tyr Trp
            100                 105                 110

Gly Gln Gly Thr Leu Val Thr Val Ser Ser
        115                 120

<210> SEQ ID NO 317
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 317

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

```
Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
                100                 105

<210> SEQ ID NO 318
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

Gly Glu Ser Phe Ser Gly Tyr Tyr
1               5

<210> SEQ ID NO 319
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

Ile Asn His Ser Gly Ser Thr
1               5

<210> SEQ ID NO 320
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

Cys Ala Arg Gly Trp Asp Leu Leu Asp Trp Asn Asp Tyr Trp Asn Glu
1               5                   10                  15

Tyr Trp

<210> SEQ ID NO 321
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

Gln Ser Val Ser Ser Tyr
1               5

<210> SEQ ID NO 322
<211> LENGTH: 3
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 322

Asp Ala Ser
1

<210> SEQ ID NO 323
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 323

Cys Gln Gln Arg Ser Asn Trp Pro Leu Thr Phe
1               5                   10

<210> SEQ ID NO 324
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 324
caggttcagc tgcagcagtg gggcgctggc ctgctgaagc cctctgagac cctgtctctg      60
acctgtgccg tgtatggcgg cagcttctcc ggctattact ggaactggat ccgccagccc     120
cccggcaagg gcctggagtg gatcggcgag atcaaccact ccggctctac caactacaat     180
ccttctctga gtccagggt gacaatcagc gtggacacca gcaagaacca gtttagcctg     240
aagctgtcca gcgtgacagc tgccgataca gccgtgtatt actgcgccag aggcgaggat     300
tggggcgaga gcttctttga ttactggggc caggggaccc tggtgaccgt ctcgagt        357

<210> SEQ ID NO 325
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 325
gagatcgtgc tgacccagtc ccctgccacc ctgtctctgt ccctggcga gcgggccacc      60 ctgagctgtc gggcctccca gtccgtgagc tcctacctgg cttggtatca gcagaagcca    120
ggacaggccc caagactgct gatctacgcc gcttccaatc gggccaccgg catccccgcc    180
agattttccg gctctggctc cggcaccgat ttcaccctga caatcagctc cctggagcca    240
gaggacttcg ccgtgtacta ctgccagcag aggtctaatt ggccactgac atttggcggc    300
ggcaccaagg ttgagatcaa g                                               321

<210> SEQ ID NO 326
<211> LENGTH: 119
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 326

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Glu Asp Trp Gly Glu Ser Phe Phe Asp Tyr Trp Gly Gln Gly
            100                 105                 110

Thr Leu Val Thr Val Ser Ser
        115

<210> SEQ ID NO 327
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 327

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Ala Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 328
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 328

Gly Gly Ser Phe Ser Gly Tyr Tyr
1               5
```

```
<210> SEQ ID NO 329
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 329

Ile Asn His Ser Gly Ser Thr
1               5

<210> SEQ ID NO 330
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Cys Ala Arg Gly Glu Asp Trp Gly Glu Ser Phe Phe Asp Tyr Trp
1               5                   10                  15

<210> SEQ ID NO 331
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 331

Gln Ser Val Ser Ser Tyr
1               5

<210> SEQ ID NO 332
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Ala Ala Ser
1

<210> SEQ ID NO 333
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 333

Cys Gln Gln Arg Ser Asn Trp Pro Leu Thr Phe
1               5                   10

<210> SEQ ID NO 334
<211> LENGTH: 357
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 334
caggttcagc tggtgcagtc cggcgctgag gtgaagaagc ctggagcttc tgtgaaggtt        60
tcctgtaagg tttccggcta tagcctgacc gagatctcta tgcactgggt acggcaagcc       120
cccggcaagg gcctggagtg gatgggcggc tttgacccag aggatggcga gaccatctac       180
gctcagaggt tcaggggcg cgtgatcatg accgaggata ccagcaccga taccgcctac        240
atggagctgt ccagcctgag atccgaggat accgccgtgt attactgcgc tactggtggc       300
tggggcccca attggttcga tccttgggc caggggaccc tggtgaccgt ctcgagt          357

<210> SEQ ID NO 335
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 335
gacatccaga tgacacagtc tccttcctct gtgagcgcct ctgtgggcga ccgcgtgacc        60
atcacatgcc gcgcttccca ggggatctct tcctggctgg cttggtacca gcagaagccc       120
ggcaaggccc ccaagctgct gatctatgct gccagcagcc tgcagtccgg cgtgccttcc       180
aggtttagcg gctccggctc cggcaccgac tttacactga caatcagctc cctgcagccc       240
gaggattttg ccacctatta ctgtcagcag gcgaattcct tccttttac attcggccct        300 ggcaccaagg ttgatatcaa g                                                 321

<210> SEQ ID NO 336
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 336

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ser Leu Thr Glu Ile
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Arg Phe
        50                  55                  60

Gln Gly Arg Val Ile Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Trp Gly Pro Asn Trp Phe Asp Pro Trp Gly Gln Gly
            100                 105                 110

Thr Leu Val Thr Val Ser Ser
        115
```

```
<210> SEQ ID NO 337
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 337

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 338
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 338

Gly Tyr Ser Leu Thr Glu Ile Ser
1               5

<210> SEQ ID NO 339
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 339

Phe Asp Pro Glu Asp Gly Glu Thr
1               5

<210> SEQ ID NO 340
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 340

Cys Ala Thr Gly Gly Trp Gly Pro Asn Trp Phe Asp Pro Trp
1               5                   10
```

<210> SEQ ID NO 341
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 341

Gln Gly Ile Ser Ser Trp
1               5

<210> SEQ ID NO 342
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Ala Ala Ser
1

<210> SEQ ID NO 343
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 343

Cys Gln Gln Ala Asn Ser Phe Pro Phe Thr Phe
1               5                   10

<210> SEQ ID NO 344
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 344
caggttcagc tgcagcagtc cggccccggc ctggtgaagc caagccagac cctgtctctg      60
acatgcgcca tctccggcga cagcgtgtcc tctaactccg ccgcttggaa ttggatccgg     120
cagtctccat ccagaggcct ggagtggctg ggcagaacct attaccgtc caagtggtac      180 aacgattatg ccgtgtccgt gaagagcaga atcaccatca accctgatac cagcaagaac     240
cagttcagcc tgcagctgaa ttccgtgacc ccagaggata cagccgtgta ttactgtgct     300
agggacgatg attggaatga cttcgattac tggggccagg ggaccctggt gacagtctcg     360
agt                                                                   363

<210> SEQ ID NO 345
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 345

```
gagatcgtgc tgacccagtc cccagctaca ctgtccctgt ctcccggcga gcgggccacc     60
ctgagctgta gagcttccca gtccgtgtct tcctatctgg cttggtatca gcagaagcca    120
ggacaggccc caaggctgct gatctacgac gcctccaata gagccaccgg catcccagct    180
agatttctg ctccggctc cggcaccgat ttcacactga ccatctctag cctggagcca     240
gaggattttg ctgtatatta ctgccagcag cgcagcaact ggccccctgac atttggcggc    300
ggcaccaagg ttgagatcaa g                                              321
```

<210> SEQ ID NO 346
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 346

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Asp Asp Trp Asn Asp Phe Asp Tyr Trp Gly
            100                 105                 110

Gln Gly Thr Leu Val Thr Val Ser Ser
        115                 120
```

<210> SEQ ID NO 347
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 347

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Arg Ser Asn Trp Pro Leu
            85                  90                  95

Thr Phe Gly Gly Gly Thr Lys Val Glu Ile Lys
            100                 105

<210> SEQ ID NO 348
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Gly Asp Ser Val Ser Ser Asn Ser Ala
1               5

<210> SEQ ID NO 349
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Thr Tyr Tyr Arg Ser Lys Trp
1               5

<210> SEQ ID NO 350
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Cys Ala Arg Asp Asp Asp Trp Asn Asp Phe Asp Tyr Trp
1               5                   10

<210> SEQ ID NO 351
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Gln Ser Val Ser Ser Tyr
1               5

<210> SEQ ID NO 352
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 352

Asp Ala Ser
1

<210> SEQ ID NO 353
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 353

Cys Gln Gln Arg Ser Asn Trp Pro Leu Thr Phe
1               5                   10

<210> SEQ ID NO 354
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 354
cagctgcagc tgcaggaaag cggccccggc ctggtgaagc cctctgagac cctgtccctg      60
acatgcaccg tgagcggcga ttccatcagc tcttccagct attactgggg ctggatccgg     120
cagccccccg gcaagggcct ggagtggatc ggcagcatct tctactccgg caatacatat     180
tataatcctt ctctgaagag cagggtgaca atcagcgtgg ataccctcca gaatcagttt     240
agcctgaagc tgagctccgt gacagctgcc gatacagccg tgtattactg cgctagggag     300
gacgattttc tgaccgatta ttacggcgct ttcgacatct ggggccaggg gacaatggtg     360
acagtctcga gt                                                        372

<210> SEQ ID NO 355
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 355
gatatccaga tgacccagtc tccaagcacc ctgagcgcct ctgtgggcga tcgggtgacc      60
atcacatgtc gggcttctca gtccatcagc agctggctgg cttggtatca gcagaagccc     120
ggcaaggccc caaagctgct gatctacaag gcctcttcca gcgagagcgg cgtgccatcc     180
aggtttagcg gctccggctc cggcaccgag tttaccctga ccatctcttc cctgcagccc     240
gatgactttg ccacctacta ctgtcagcag tacaattcct atctgacatt cggcggcggc     300
accaaggttg agatcaag                                                  318

<210> SEQ ID NO 356
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 356

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Phe Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Asp Phe Leu Thr Asp Tyr Tyr Gly Ala Phe Asp
            100                 105                 110

Ile Trp Gly Gln Gly Thr Met Val Thr Val Ser Ser
        115                 120

<210> SEQ ID NO 357
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 357

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Ser Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Leu Thr
                85                  90                  95

Phe Gly Gly Gly Thr Lys Val Glu Ile Lys
            100                 105

<210> SEQ ID NO 358
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 358

Gly Asp Ser Ile Ser Ser Ser Ser Tyr Tyr
1               5                   10

<210> SEQ ID NO 359

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 359

Ile Phe Tyr Ser Gly Asn Thr
1               5

<210> SEQ ID NO 360
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 360

Cys Ala Arg Glu Asp Asp Phe Leu Thr Asp Tyr Tyr Gly Ala Phe Asp
1               5                   10                  15

Ile Trp

<210> SEQ ID NO 361
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

Gln Ser Ile Ser Ser Trp
1               5

<210> SEQ ID NO 362
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Lys Ala Ser
1

<210> SEQ ID NO 363
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 363

Cys Gln Gln Tyr Asn Ser Tyr Leu Thr Phe
1               5                   10

<210> SEQ ID NO 364
<211> LENGTH: 375
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 364

```
gaggtgcagc tgctggaatc cggaggagga ctggtccagc caggtggatc cctgcgactg      60
agctgcgccg cttctggctt cgactttaga agctacgcaa tgatgtgggt ccgccaggca     120
ccaggaaagg gactggagtg ggtgggaggg atcaacggtg aagtcggtgg ctctaataca     180
tactatgcac ctgccgtcaa gggaagggct actattagtc gggacaactc aaaaaatacc     240
ctgtatctgc aaatgaacag tctgagggcc gaggatacccg ccgtgtacta ttgcgtgaaa     300
ggtgctggcg catgcggcat ctgtaatgac gatattgatg catggggaca ggggaccctg     360
gtgacagtct cgagt                                                      375
```

<210> SEQ ID NO 365
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 365

```
agttatgagc tgactcagga cccagcagtg tcagtcgccc tgggccagac agtgagaatc      60
acttgcagtg gggctggttc atatgcaggc tcctactatt acggatggca ccagcagaag     120
cccggacagg cacctgtgac agtcatctac gacaacgata aaaggccaag caatattccc     180
gaccggttct ctgggtccag ctctggtaac accgcctccc tgaccattac tgggggccag     240
gctgaggacg aagctgatta ttactgtggc tctacaaacg ataatgacga tggcggactg     300
tttggctccg gaactaaggt caccgtccta                                      330
```

<210> SEQ ID NO 366
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 366

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Arg Ser Tyr
            20                  25                  30

Ala Met Met Trp Val Arg Gln Ala Pro Gly Lys Gly Leu Glu Trp Val
        35                  40                  45

Gly Gly Ile Asn Gly Glu Val Gly Gly Ser Asn Thr Tyr Tyr Ala Pro
    50                  55                  60

Ala Val Lys Gly Arg Ala Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Lys Gly Ala Gly Ala Cys Gly Ile Cys Asn Asp Asp Ile
            100                 105                 110
```

Asp Ala Trp Gly Gln Gly Thr Leu Val Thr Val Ser Ser
            115                 120                 125

<210> SEQ ID NO 367
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 367

Ser Tyr Glu Leu Thr Gln Asp Pro Ala Val Ser Val Ala Leu Gly Gln
1               5                   10                  15

Thr Val Arg Ile Thr Cys Ser Gly Ala Gly Ser Tyr Ala Gly Ser Tyr
            20                  25                  30

Tyr Tyr Gly Trp His Gln Gln Lys Pro Gly Gln Ala Pro Val Thr Val
        35                  40                  45

Ile Tyr Asp Asn Asp Lys Arg Pro Ser Asn Ile Pro Asp Arg Phe Ser
50                  55                  60

Gly Ser Ser Ser Gly Asn Thr Ala Ser Leu Thr Ile Thr Gly Ala Gln
65                  70                  75                  80

Ala Glu Asp Glu Ala Asp Tyr Tyr Cys Gly Ser Thr Asn Asp Asn Asp
                85                  90                  95

Asp Gly Gly Leu Phe Gly Ser Gly Thr Lys Val Thr Val Leu
            100                 105                 110

<210> SEQ ID NO 368
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 368

Gly Phe Asp Phe Arg Ser Tyr Ala
1               5

<210> SEQ ID NO 369
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 369

Ile Asn Gly Glu Val Gly Gly Ser Asn Thr
1               5                   10

<210> SEQ ID NO 370
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

<400> SEQUENCE: 370

Cys Val Lys Gly Ala Gly Ala Cys Gly Ile Cys Asn Asp Asp Ile Asp
1               5                   10                  15

Ala Trp

<210> SEQ ID NO 371
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 371

Gly Ser Tyr Ala Gly Ser Tyr
1               5

<210> SEQ ID NO 372
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 372

Asp Asn Asp
1

<210> SEQ ID NO 373
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 373

Cys Gly Ser Thr Asn Asp Asn Asp Asp Gly Gly Leu Phe
1               5                   10

<210> SEQ ID NO 374
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 374

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 375
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 375

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

-continued

```
Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 376
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 376

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
            100                 105                 110
```

```
Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 377
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 377

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125
```

-continued

```
Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 378
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 378

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 379
<211> LENGTH: 106
<212> TYPE: PRT
<213> ORGANISM: Artificial Sequence
<220> FEATURE:
<221> NAME/KEY: source
```

<223> OTHER INFORMATION: /note="Description of Artificial Sequence:
Synthetic polypeptide"

<400> SEQUENCE: 379

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 380
<211> LENGTH: 990
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 380
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaagc cgccggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc catcgagaaa accatctcc     660 aaagccaaag gcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc cccgggtaaa                                      990

<210> SEQ ID NO 381
<211> LENGTH: 1596
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 381

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttggtgag     300
aggccagcac agggagggag ggtgtctgct ggaagccagg ctcagcgctc ctgcctggac     360
gcatcccggc tatgcagtcc cagtccaggg cagcaaggca ggccccgtct gcctcttcac     420
ccggaggcct ctgcccgccc cactcatgct caggagagag gtcttctggc tttttcccca     480
ggctctgggc aggcacaggc taggtgcccc taacccaggc cctgcacaca aaggggcagg     540
tgctgggctc agacctgcca agagccatat ccgggaggac cctgccctg acctaagccc      600
accccaaagg ccaaactctc cactccctca gctcggacac cttctctcct cccagattcc     660
agtaactccc aatcttctct ctgcagagcc caaatcttgt gacaaaactc acacatgccc     720
accgtgccca ggtaagccag cccaggcctc gccctccagc tcaaggcggg acaggtgccc     780
tagagtagcc tgcatccagg acaggcccc agcgggtgc tgacacgtcc acctccatct       840
cttcctcagc acctgaagcc gccggggac cgtcagtctt cctcttcccc ccaaaaccca      900
aggacaccct catgatctcc cggacccctg aggtcacatg cgtggtggtg gacgtgagcc     960
acgaagaccc tgaggtcaag ttcaactggt acgtggacgg cgtggaggtg cataatgcca    1020
agacaaagcc gcgggaggag cagtacaaca gcacgtaccg tgtggtcagc gtcctcaccg    1080
tcctgcacca ggactggctg aatggcaagg agtacaagtg caaggtctcc aacaaagccc    1140
tcccagcccc catcgagaaa accatctcca aagccaaagg tgggacccgt ggggtgcgag    1200
ggccacatgg acagaggccg gctcggccca ccctctgccc tgagagtgac cgctgtacca    1260
acctctgtcc ctacagggca gccccgagaa ccacaggtgt acaccctgcc cccatcccgg    1320
gaggagatga ccaagaacca ggtcagcctg acctgcctgg tcaaaggctt ctatcccagc    1380
gacatcgccg tggagtggga gagcaatggg cagccggaga caactacaa gaccacgcct     1440
cccgtgctgg actccgacgg ctccttcttc ctctatagca agctcaccgt ggacaagagc    1500
aggtggcagc aggggaacgt cttctcatgc tccgtgatgc atgaggctct gcacaaccac    1560
tacacgcaga gagcctctc cctgtccccg ggtaaa                              1596
```

<210> SEQ ID NO 382
<211> LENGTH: 981
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 382

```
gcttccacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
```

| | |
|---|---|
| tacacctgca acgtagatca caagcccagc aacaccaagg tggacaagag agttgagtcc | 300 |
| aaatatggtc ccccatgccc accatgccca gcacctgagt tcctgggggg accatcagtc | 360 |
| ttcctgttcc cccaaaacc caaggacact ctcatgatct cccggacccc tgaggtcacg | 420 |
| tgcgtggtgg tggacgtgag ccaggaagac cccgaggtcc agttcaactg gtacgtggat | 480 |
| ggcgtggagg tgcataatgc caagacaaag ccgcgggagg agcagttcaa cagcacgtac | 540 |
| cgtgtggtca gcgtcctcac cgtcctgcac caggactggc tgaacggcaa ggagtacaag | 600 |
| tgcaaggtct ccaacaaagg cctcccgtcc tccatcgaga aaaccatctc aaagccaaa | 660 |
| gggcagcccc gagagccaca ggtgtacacc ctgcccccat cccaggagga gatgaccaag | 720 |
| aaccaggtca gcctgacctg cctggtcaaa ggcttctacc ccagcgacat cgccgtggag | 780 |
| tgggagagca atgggcagcc ggagaacaac tacaagacca cgcctcccgt gctggactcc | 840 |
| gacggctcct tcttcctcta cagcaggctc accgtggaca agagcaggtg gcaggagggg | 900 |
| aatgtcttct catgctccgt gatgcatgag gctctgcaca accactacac acagaagagc | 960 |
| ctctccctgt ctctgggtaa a | 981 |

<210> SEQ ID NO 383
<211> LENGTH: 1588
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 383

| | |
|---|---|
| gcttccacca agggcccatc ggtcttcccc ctggcgccct gctccaggag cacctccgag | 60 |
| agcacagccg ccctgggctg cctggtcaag gactacttcc ccgaaccggt gacggtgtcg | 120 |
| tggaactcag gcgccctgac cagcggcgtg cacaccttcc cggctgtcct acagtcctca | 180 |
| ggactctact ccctcagcag cgtggtgacc gtgccctcca gcagcttggg cacgaagacc | 240 |
| tacacctgca acgtagatca caagcccagc aacaccaagg tggacaagag agttggtgag | 300 |
| aggccagcac agggagggag ggtgtctgct ggaagccagg ctcagccctc ctgcctggac | 360 |
| gcaccccggc tgtgcagccc cagcccaggg cagcaaggca ggccccatct gtctcctcac | 420 |
| ccggaggcct ctgaccaccc cactcatgct caggagagg tcttctgga ttttccacc | 480 |
| aggctccggg cagccacagg ctggatgccc ctaccccagg ccctgagcat acaggggcag | 540 |
| gtgctgcgct cagacctgcc aagagccata tccggagga ccctgcccct gacctaagcc | 600 |
| caccccaaag gccaaactct ccactccctc agctcagaca ccttctctcc tcccagatct | 660 |
| gagtaactcc caatcttctc tctgcagagt ccaaatatgg tccccatgcc caccatgcc | 720 |
| caggtaagcc aacccaggcc tcgccctcca gctcaaggcg ggacaggtgc cctagagtag | 780 |
| cctgcatcca gggacaggcc ccagccgggt gctgacgcat ccacctccat ctcttcctca | 840 |
| gcacctgagt tcctggggg accatcagtc ttcctgttcc cccaaaacc caaggacact | 900 |
| ctcatgatct cccggacccc tgaggtcacg tgcgtggtgg tggacgtgag ccaggaagac | 960 |
| cccgaggtcc agttcaactg gtacgtggat ggcgtggagg tgcataatgc caagacaaag | 1020 |
| ccgcgggagg agcagttcaa cagcacgtac cgtgtggtca gcgtcctcac cgtcctgcac | 1080 |
| caggactggc tgaacggcaa ggagtacaag tgcaaggtct ccaacaaagg cctcccgtcc | 1140 |
| tccatcgaga aaaccatctc aaagccaaa ggtgggaccc acggggtgcg agggccacat | 1200 |
| ggacagaggt cagctcggcc caccctctgc cctgggagtg accgctgtgc caacctctgt | 1260 |

| | |
|---|---|
| ccctacaggg cagccccgag agccacaggt gtacaccctg cccccatccc aggaggagat | 1320 |
| gaccaagaac caggtcagcc tgacctgcct ggtcaaaggc ttctacccca gcgacatcgc | 1380 |
| cgtggagtgg gagagcaatg ggcagccgga gaacaactac aagaccacgc ctcccgtgct | 1440 |
| ggactccgac ggctccttct tcctctacag caggctcacc gtggacaaga gcaggtggca | 1500 |
| ggagggaat gtcttctcat gctccgtgat gcatgaggct ctgcacaacc actacacaca | 1560 |
| gaagagcctc tccctgtctc tgggtaaa | 1588 |

<210> SEQ ID NO 384
<211> LENGTH: 978
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 384

| | |
|---|---|
| gcctccacca agggcccatc ggtcttcccc ctggcgccct gctccaggag cacctccgag | 60 |
| agcacagccg ccctgggctg cctggtcaag gactacttcc ccgaaccggt gacggtgtcg | 120 |
| tggaactcag gcgctctgac cagcggcgtg cacaccttcc cagctgtcct acagtcctca | 180 |
| ggactctact ccctcagcag cgtggtgacc gtgccctcca gcaacttcgg cacccagacc | 240 |
| tacacctgca acgtagatca caagcccagc aacaccaagg tggacaagac agttgagcgc | 300 |
| aaatgttgtg tcgagtgccc accgtgccca gcaccacctg tggcaggacc gtcagtcttc | 360 |
| ctcttccccc caaaacccaa ggacaccctc atgatctccc ggacccctga ggtcacgtgc | 420 |
| gtggtggtgg acgtgagcca cgaagacccc gaggtccagt tcaactggta cgtggacggc | 480 |
| gtggaggtgc ataatgccaa gacaaagcca cgggaggagc agttcaacag cacgttccgt | 540 |
| gtggtcagcg tcctcaccgt tgtgcaccag gactggctga acggcaagga gtacaagtgc | 600 |
| aaggtctcca acaaaggcct cccagccccc atcgagaaaa ccatctccaa aaccaaaggg | 660 |
| cagccccgag aaccacaggt gtacaccctg cccccatccc gggaggagat gaccaagaac | 720 |
| caggtcagcc tgacctgcct ggtcaaaggc ttctacccca gcgacatcgc cgtggagtgg | 780 |
| gagagcaatg ggcagccgga gaacaactac aagaccacac ctcccatgct ggactccgac | 840 |
| ggctccttct tcctctacag caagctcacc gtggacaaga gcaggtggca gcagggaac | 900 |
| gtcttctcat gctccgtgat gcatgaggct ctgcacaacc actacacgca gaagagcctc | 960 |
| tccctgtctc cgggtaaa | 978 |

<210> SEQ ID NO 385
<211> LENGTH: 1585
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 385

| | |
|---|---|
| gcctccacca agggcccatc ggtcttcccc ctggcgccct gctccaggag cacctccgag | 60 |
| agcacagccg ccctgggctg cctggtcaag gactacttcc ccgaaccggt gacggtgtcg | 120 |
| tggaactcag gcgctctgac cagcggcgtg cacaccttcc cagctgtcct acagtcctca | 180 |
| ggactctact ccctcagcag cgtggtgacc gtgccctcca gcaacttcgg cacccagacc | 240 |

```
tacacctgca acgtagatca caagcccagc aacaccaagg tggacaagac agttggtgag    300
aggccagctc agggagggag ggtgtctgct ggaagccagg ctcagccctc ctgcctggac    360
gcaccccggc tgtgcagccc cagcccaggg cagcaaggca ggccccatct gtctcctcac    420
ccggaggcct ctgcccgccc cactcatgct caggagagag gtcttctggc ttttccacc     480 aggctccagg caggcacagg ctgggtgccc ctaccccagg cccttcacac acaggggcag    540
gtgcttggct cagacctgcc aaaagccata tccgggagga ccctgcccct gacctaagcc    600
gaccccaaag gccaaactgt ccactccctc agctcggaca ccttctctcc tcccagatcc    660
gagtaactcc caatcttctc tctgcagagc gcaaatgttg tgtcgagtgc ccaccgtgcc    720
caggtaagcc agcccaggcc tcgccctcca gctcaaggcg ggacaggtgc cctagagtag    780
cctgcatcca gggacaggcc ccagctgggt gctgacacgt ccacctccat ctcttcctca    840
gcaccacctg tggcaggacc gtcagtcttc ctcttccccc caaaacccaa ggacaccctc    900
atgatctccc ggacccctga ggtcacgtgc gtggtggtgg acgtgagcca cgaagacccc    960
gaggtccagt tcaactggta cgtggacggc gtggaggtgc ataatgccaa gacaaagcca   1020
cgggaggagc agttcaacag cacgttccgt gtggtcagcg tcctcaccgt tgtgcaccag   1080
gactggctga acggcaagga gtacaagtgc aaggtctcca acaaaggcct cccagccccc   1140
atcgagaaaa ccatctccaa aaccaaaggt gggacccgcg gggtatgagg gccacatgga   1200
cagaggccgc tcggcccac cctctgccct gggagtgacc gctgtgccaa cctctgtccc    1260
tacagggcag ccccgagaac cacaggtgta caccctgccc ccatcccggg aggagatgac    1320
caagaaccag gtcagcctga cctgcctggt caaaggcttc tacccagcg acatcgccgt    1380 ggagtgggag agcaatgggc agccggagaa caactacaag accacacctc ccatgctgga    1440
ctccgacggc tccttcttcc tctacagcaa gctcaccgtg gacaagagca ggtggcagca    1500
ggggaacgtc ttctcatgct ccgtgatgca tgaggctctg cacaaccact acacgcagaa    1560
gagcctctcc ctgtctccgg gtaaa                                         1585

<210> SEQ ID NO 386
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 386
cgtacggtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                             321

<210> SEQ ID NO 387
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 387

```
cctaggtcag cccaaggcca accccactgt cactctgttc ccgccctcct ctgaggagct    60
ccaagccaac aaggccacac tagtgtgtct gatcagtgac ttctacccgg gagctgtgac   120
agtggcctgg aaggcagatg gcagccccgt caaggcggga gtggagacca ccaaaccctc   180
caaacagagc aacaacaagt acgcggccag cagctacctg agcctgacgc cgagcagtg    240
gaagtcccac agaagctaca gctgccaggt cacgcatgaa gggagcaccg tggagaagac   300
agtggcccct acagaatgtt cataa                                         325
```

<210> SEQ ID NO 388
<211> LENGTH: 288
<212> TYPE: PRT
<213> ORGANISM: Homo sapiens

<400> SEQUENCE: 388

```
Met Gln Ile Pro Gln Ala Pro Trp Pro Val Val Trp Ala Val Leu Gln
  1               5                  10                  15
Leu Gly Trp Arg Pro Gly Trp Phe Leu Asp Ser Pro Asp Arg Pro Trp
             20                  25                  30
Asn Pro Pro Thr Phe Ser Pro Ala Leu Leu Val Val Thr Glu Gly Asp
         35                  40                  45
Asn Ala Thr Phe Thr Cys Ser Phe Ser Asn Thr Ser Glu Ser Phe Val
     50                  55                  60
Leu Asn Trp Tyr Arg Met Ser Pro Ser Asn Gln Thr Asp Lys Leu Ala
 65                  70                  75                  80
Ala Phe Pro Glu Asp Arg Ser Gln Pro Gly Gln Asp Cys Arg Phe Arg
                 85                  90                  95
Val Thr Gln Leu Pro Asn Gly Arg Asp Phe His Met Ser Val Val Arg
            100                 105                 110
Ala Arg Arg Asn Asp Ser Gly Thr Tyr Leu Cys Gly Ala Ile Ser Leu
        115                 120                 125
Ala Pro Lys Ala Gln Ile Lys Glu Ser Leu Arg Ala Glu Leu Arg Val
    130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Leu Val Val Gly Val Val Gly Gly
                165                 170                 175
Leu Leu Gly Ser Leu Val Leu Leu Val Trp Val Leu Ala Val Ile Cys
            180                 185                 190
Ser Arg Ala Ala Arg Gly Thr Ile Gly Ala Arg Arg Thr Gly Gln Pro
        195                 200                 205
Leu Lys Glu Asp Pro Ser Ala Val Pro Val Phe Ser Val Asp Tyr Gly
    210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
        275                 280                 285
```

<210> SEQ ID NO 389

```
<211> LENGTH: 301
<212> TYPE: PRT
<213> ORGANISM: Homo sapiens

<400> SEQUENCE: 389

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
290                 295                 300

<210> SEQ ID NO 390
<211> LENGTH: 525
<212> TYPE: PRT
<213> ORGANISM: Homo sapiens

<400> SEQUENCE: 390

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45
```

```
Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Ala Asp Ala
        130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
                180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
                260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
                340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
    450                 455                 460
```

```
Val Thr Gly Ala Phe Gly Phe His Leu Trp Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
        515                 520                 525

<210> SEQ ID NO 391
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 391
gctagcctct tacgagctga ctcagccacc ttccgtgtcc gtgtcccag  gacagaccgc     60 aagaatcaca tgcagtggcg gatccagcta ctcatatggg tggttccagc agaagcctgg   120
tcaggccccc gtgacagtca tctatgagag caacaatagg ccttctgaca ttccagaacg   180
gtttagtggc tctagttcag gaaccacagt gactctgacc atcagcgggg tccaggccga   240
ggacgaagct gattactatt gtggcaacgc tgattccagc tctggaattt tcgggtccgg   300
tacaaaagtg actgtcctag g                                             321

<210> SEQ ID NO 392
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 392

Ser Tyr Glu Leu Thr Gln Pro Pro Ser Val Ser Val Ser Pro Gly Gln
1               5                   10                  15

Thr Ala Arg Ile Thr Cys Ser Gly Ser Ser Tyr Ser Tyr Gly Trp
            20                  25                  30

Phe Gln Gln Lys Pro Gly Gln Ala Pro Val Thr Val Ile Tyr Glu Ser
                35                  40                  45

Asn Asn Arg Pro Ser Asp Ile Pro Glu Arg Phe Ser Gly Ser Ser Ser
        50                  55                  60

Gly Thr Val Thr Leu Thr Ile Ser Gly Val Gln Ala Glu Asp Glu
65                  70                  75                  80

Ala Asp Tyr Tyr Cys Gly Asn Ala Asp Ser Ser Ser Gly Ile Phe Gly
                85                  90                  95

Ser Gly Thr Lys Val Thr Val Leu
            100

<210> SEQ ID NO 393
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 393

Ser Ser Tyr Ser
1

<210> SEQ ID NO 394
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 394

Glu Ser Asn
1

<210> SEQ ID NO 395
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 395

Cys Gly Asn Ala Asp Ser Ser Ser Gly Ile Phe
1               5                   10

<210> SEQ ID NO 396
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 396

Gly Gly Gly Gly Ser Gly Gly Gly Gly Ser Gly Gly Gly Gly Ser
1               5                   10                  15

<210> SEQ ID NO 397
<211> LENGTH: 6
<212> TYPE: PRT
<213> ORGANISM: Homo sapiens

<400> SEQUENCE: 397

Lys Ile Glu Glu Leu Glu
1               5
```